(12) United States Patent
Gillespie

(10) Patent No.: US 9,073,881 B2
(45) Date of Patent: Jul. 7, 2015

(54) BENZOIC ACID DERIVATIVES

(75) Inventor: Paul Gillespie, Westfield, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 159 days.

(21) Appl. No.: 13/603,602

(22) Filed: Sep. 5, 2012

(65) Prior Publication Data

US 2013/0079346 A1   Mar. 28, 2013

Related U.S. Application Data

(60) Provisional application No. 61/538,240, filed on Sep. 23, 2011.

(51) Int. Cl.

| A61K 31/426 | (2006.01) |
|---|---|
| A61K 31/496 | (2006.01) |
| A61K 31/506 | (2006.01) |
| C07D 417/10 | (2006.01) |
| A61K 31/4439 | (2006.01) |
| C07D 417/04 | (2006.01) |
| C07D 277/30 | (2006.01) |
| A61K 31/427 | (2006.01) |
| A61K 31/5377 | (2006.01) |
| A61K 31/454 | (2006.01) |
| C07D 277/34 | (2006.01) |
| C07D 417/08 | (2006.01) |
| C07D 417/12 | (2006.01) |
| C07D 277/38 | (2006.01) |

(52) U.S. Cl.
CPC ............ *C07D 277/34* (2013.01); *C07D 417/04* (2013.01); *C07D 417/08* (2013.01); *C07D 417/12* (2013.01); *C07D 277/38* (2013.01)

(58) Field of Classification Search
CPC . A61K 31/426; A61K 31/496; A61K 31/506; A61K 31/4439; A61K 31/5377; A61K 31/454; A61K 31/427; C07D 417/10; C07D 417/04; C07D 277/30

USPC ......... 514/236.8, 254.02, 256, 326, 342, 365; 544/133, 333, 369; 546/209, 269.7; 548/204

See application file for complete search history.

(56) References Cited

FOREIGN PATENT DOCUMENTS

| WO | 2006/078942 | 7/2006 |
|---|---|---|
| WO | 2007/118149 | 10/2007 |

OTHER PUBLICATIONS

Fan et al., Neoplasia 12:346-356 ( 2010).
(International Search Report for PCT/EP2012/068188 Nov. 19, 2012).
Yefidoff-Freedman et al., Chemical Abstract MEDI-94 (Aug. 22-26, 2010).
Hoeffer et al., Proc. Natl. Acad. Sci. USA 108:3383-3388 ( 2011).
Kabha et al., Chemical Abstract MEDI 28 (Aug. 22-26, 2010).
Mahalingam et al., Chemical Abstract MEDI-479 (Aug. 22-26, 2010).
Takrouri et al., Chemical Abstract MEDI 78 (Aug. 22-26, 2010).
Moerke et al., Cell 128:257-267 ( 2007).

*Primary Examiner* — Kendra D Carter
*Assistant Examiner* — Jason A Deck

(57) ABSTRACT

There are disclosed are compounds of the formula:

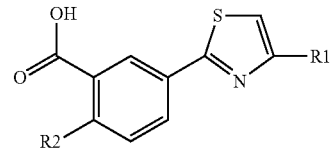

wherein R1 and R2 are as disclosed herein,
which are eIF4E inhibitors useful in the treatment of cancers. Also disclosed are compositions comprising the compounds, as well as methods of treating cancer using the compounds.

21 Claims, No Drawings

BENZOIC ACID DERIVATIVES

PRIORITY TO RELATED APPLICATION(S)

This application claims the benefit of U.S. Provisional Application No. 61/538,240, filed Sep. 23, 2011, which is hereby incorporated by reference in its entirety.

FIELD OF INVENTION

The present invention relates to compounds that inhibit eIF4E.

BACKGROUND OF THE INVENTION

Many disease states are characterized by uncontrolled proliferation and differentiation of cells. These disease states encompass a variety of cell types and maladies such as cancer, atherosclerosis, and restenosis.

The term cancer is used to describe a class of diseases characterized principally by uncontrolled cell growth. Cancer is currently one of the leading causes of death in the world, and is projected to become the leading cause of death in the next few years. By 2030, it is projected that there will be more than 20 million new cancer diagnoses per annum, with at least 13 million deaths.

There are many different forms of cancer, and many of these types require different forms of treatment. The current main forms of treatment for cancer include surgery, radiation therapy, bone marrow transplantation, immunotherapy, anti-angiogenic therapy, and treatment with cytotoxic agents (commonly known as chemotherapy). A large number of cytotoxic agents have been used for the treatment of cancer over the last 70 years, including nitrogen mustards such as chloromethine and estramustine; anthracyclines such as doxorubicin, daunorubicin, and idarubicin; platinum-containing compounds such as cisplatin, carboplatin and oxaliplatin; antimetabolites such as dacarbazine, capecitabine, fludarabine, 5-fluorouracil, gemcitabine, methotrexate, and pemetrexed; topoisomerase inhibitors such as topotecan and irinotecan; inhibitors of tubulin polymerization such as vinblastine and vincristine; and inhibitors of tubulin depolymerization such as paclitaxel and docetaxel.

Although many anti-cancer agents are known and have achieved considerable success as therapeutic agents for the treatment of a variety of cancers, there is still a significant unmet need for new therapies for cancer.

Eukaryotic initiation factor 4E (eIF4E) is a 24 kDa protein that plays a key role in the initiation of translation of mRNA. At the initiation of mRNA translation, eIF4E binds to the 7-methylguanosine cap at the 5' end of mRNAs, and forms a complex (called eIF4F) with the scaffolding protein eIF4G and the helicase eIF4A. The formation of this complex is required for the initiation of cap-dependent translation and therefore the binding of eIF4E to eIF4G is a critical event in this process.

eIF4E has been identified as a promising target in the field of oncology because of a number of pieces of data that implicate it in transformation and tumorigenesis.

Two small molecule inhibitors of the eIF4E-eIF4G interaction have been disclosed by Gerhard Wagner and colleagues (Moerke, N. J. et al. *Cell* 2007, 128, 257-267). These inhibitors have the formulae i and ii. Rigidified analogues of the compound of formula ii were disclosed by the Wagner group at the 240th National Meeting of the American Chemical Society (Aug. 22-26, 2010) (see MEDI-28, MEDI-78, MEDI-94, and MEDI-479, which have been abstracted in Chemical Abstracts as AN 2010:1011638, AN 2010:1011687, AN 2010:1011703, AN 2010:1012083, respectively). The activity of the compound of formula ii has been demonstrated in vivo in a rat model of fear consolidation, which depends on the formation of the eIF4F complex (Hoeffer, C. A. et al. *Proc. Nat. Acad. Sci. USA* 2011, 108, 3383-3388). In another study, the compound of formula ii, when combined with the apoptosis-inducing protein TRAIL, inhibited the eIF4E/eIF4G interaction and also inhibited the growth and induced apoptosis in human lung cancer cells. However, further experiments using siRNA suggest that the augmentation of TRAIL activity by 4EGI-1 is independent of cap-dependent translation (Fan, S. et al. *Neoplasia* 2010, 12, 346-356).

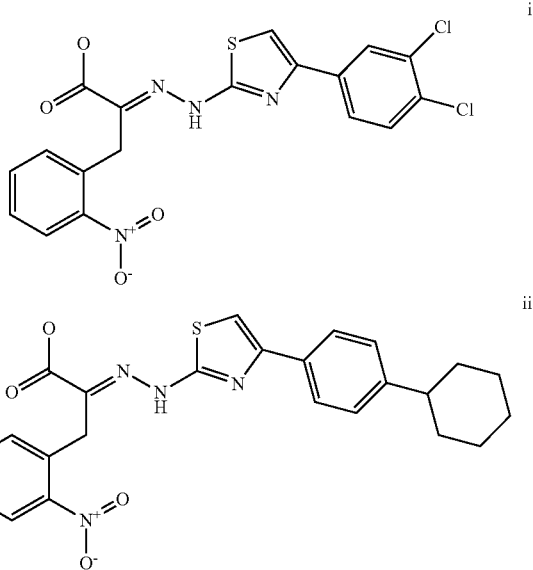

SUMMARY OF THE INVENTION

The present invention provides eIF4E-inhibitory compounds of Formula I, as set forth below:

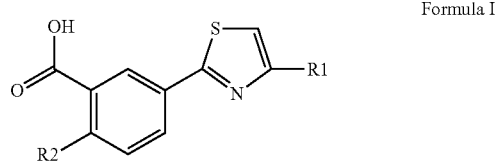

Formula I wherein R1 and R2 are as described herein.

DETAILED DESCRIPTION OF THE INVENTION

The present invention provides eIF4E-inhibitory compounds of Formula I:

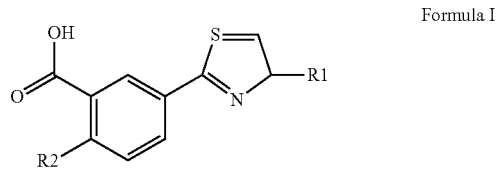

Formula I wherein R1 is selected from the group consisting of

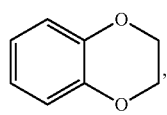

bromothienyl, thienyl, pyridyl, phenyl optionally substituted with one or two members selected from the group consisting of fluoro, chloro, bromo, methyl, methoxy, difluoromethoxy, trifluoromethyl, trifluoromethoxy, —S(O)$_2$-methyl, and cyano;

wherein R2 is selected from the group consisting of thienyl optionally substituted by a member selected from the group consisting of methyl, acetyl, and chloro;

pyridyl optionally substituted by one or two members selected from the group consisting of amido, methoxy, methyl, fluoro, chloro, and cyano;

pyrimidinyl optionally substituted with a member selected from the group consisting of ethoxy, methoxy, hydroxy, and isopropyl; and phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH, —C(O)—X1, wherein X1 is a member selected from the group consisting of

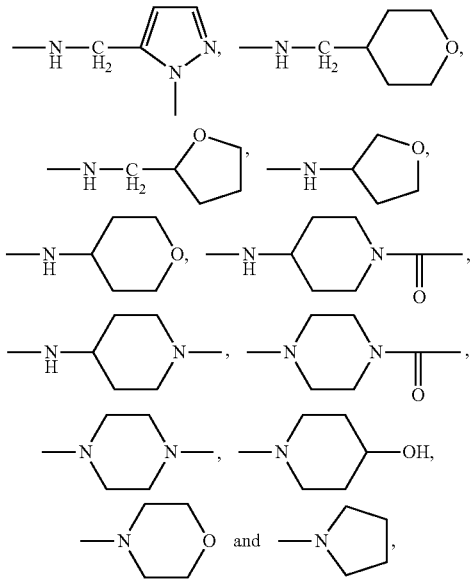

and

—NH—X2, wherein X2 is a member selected from the group consisting of —CH(CH3)-phenyl and —(CH2)n-X4, wherein n is 1, 2 or 3 and X4 is a member selected from the group consisting of —N(methyl)$_2$, —N(ethyl)$_2$, pyridyl, thienyl, morpholinyl, and phenyl optionally substituted with a member selected from the group consisting of methyl, methoxy, fluoro, and trifluoromethyl; and a pharmaceutically acceptable salt thereof.

In another aspect, the invention is directed to compounds of formula I, wherein R1 is selected from the group consisting of

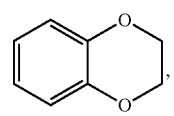

bromothienyl, thienyl, pyridyl, phenyl optionally substituted with one or two members selected from the group consisting of fluoro, chloro, bromo, methyl, methoxy, difluoromethoxy, trifluoromethyl, trifluoromethoxy, and cyano;

wherein R2 is selected from the group consisting of:

thienyl optionally substituted by a member selected from the group consisting of methyl, acetyl, and chloro;

pyridyl optionally substituted by one or two members selected from the group consisting of amido, methoxy, methyl, fluoro, chloro, and cyano;

pyrimidinyl optionally substituted with a member selected from the group consisting of ethoxy, methoxy, hydroxy, and isopropyl; and phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH, —C(O)—X1, wherein X1 is a member selected from the group consisting of

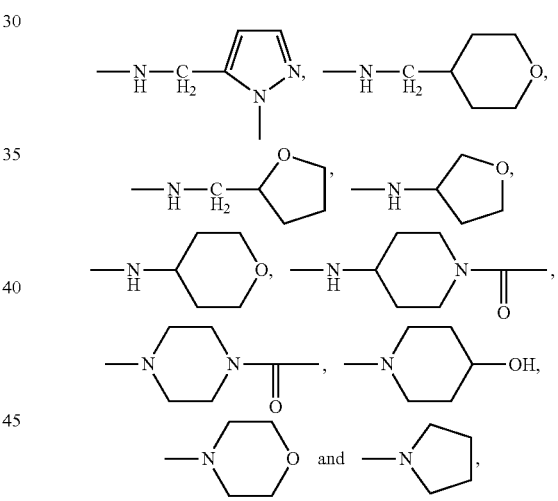

and —NH—X2, wherein X2 is a member selected from the group consisting of —CH(CH3)-phenyl and —(CH2)n-X4, wherein n is 1 or 2 and X4 is a member selected from the group consisting of pyridyl, thienyl, and phenyl optionally substituted with a member selected from the group consisting of methyl, methoxy, fluoro, and trifluoromethyl and a pharmaceutically acceptable salt thereof.

In another aspect, the invention is directed to compounds of Formula I where R1 is phenyl optionally substituted with one or two members selected from the group consisting of fluoro, chloro, bromo, methyl, methoxy, difluoromethoxy, trifluoromethyl, trifluoromethoxy, and cyano.

In another aspect, the invention is directed to compounds of Formula I wherein R2 is phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl and nitro.

In another aspect, the invention is directed to compounds of Formula I wherein R2 is phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH, —C(O)—X1, wherein X1 is a member selected from the group consisting of

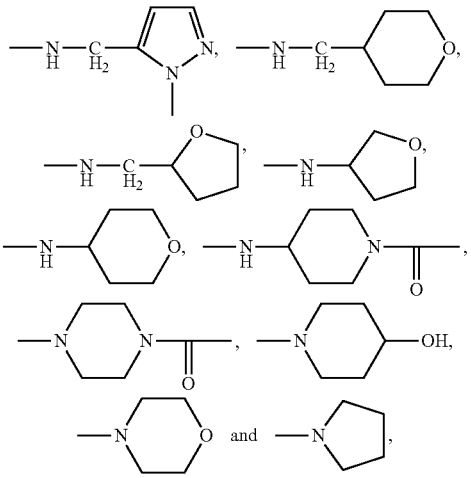

and —NH—X2, wherein X2 is a member selected from the group consisting of —CH(CH3)-phenyl and —(CH2)n-X4, wherein n is 1 or 2 and X4 is a member selected from the group consisting of pyridyl, thienyl, and phenyl optionally substituted with a member selected from the group consisting of methyl, methoxy, fluoro, and trifluoromethyl.

In another aspect, the invention is directed to compounds of Formula I where R1 is dichlorophenyl and R2 is phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH, —C(O)—X1, wherein X1 is a member consisting of

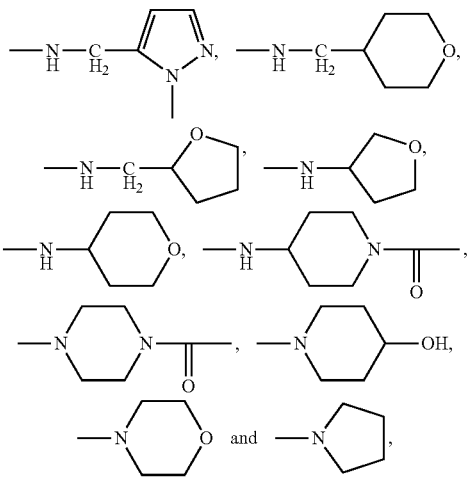

and —NH—X2, where X2 is a member selected from the group consisting of —CH(CH3)-phenyl and —(CH2)n-X4, where n is 1 or 2 and X4 is a member selected from the group consisting of pyridyl, thienyl, and phenyl optionally substituted with a member selected from the group consisting of methyl, methoxy, fluoro, and trifluoromethyl.

In another aspect, the invention is directed to compounds of Formula I where R1 is selected from the group consisting of

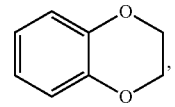

bromothienyl, thienyl, and pyridyl.

In another aspect, the invention is directed to compounds of Formula I where R1 is dichlorophenyl.

In another aspect, the invention is directed to compounds of Formula I where R1 is 3,4-dichlorophenyl.

In another aspect, the invention is directed to compounds of Formula I where R1 is 2,3-Dihydro-benzo[1,4]dioxin-6-yl, 2,4-Dichloro-phenyl, 2,4-Difluoro-phenyl, 2,4-Dimethyl-phenyl, 2,5-Dichloro-phenyl, 2,6-Difluoro-phenyl, 2-Chloro-phenyl, 2-Fluoro-4-methoxy-phenyl, 2-Fluoro-phenyl, 2-Methoxy-phenyl, 2-trifluoromethyl-phenyl, 3,4-Dichloro-phenyl, 3,4-Difluoro-phenyl, 3,5-Bis-trifluoromethyl-phenyl, 3,5-Difluoro-phenyl, 3-Bromo-phenyl, 3-Chloro-4-fluoro-phenyl, 3-Chloro-phenyl, 3-Cyano-phenyl, 3-Fluoro-phenyl, 3-Methoxy-phenyl, 3-trifluoromethyl-phenyl, 4-Bromo-phenyl, 4-Chloro-3-methyl-phenyl, 4-Chloro-phenyl, 4-Cyano-phenyl, 4-Difluoromethoxy-phenyl, 4-Fluoro-phenyl, 4-Methanesulfonyl-phenyl, 4-Methoxy-phenyl, 4-p-tolyl-, 4-pyridin-2-yl-, 4-pyridin-3-yl-, 4-pyridin-4-yl-, 4-thiophen-2-yl-, 4-thiophen-3-yl-, 4-thiophen-3-yl-, 4-trifluoromethoxy-phenyl, 4-trifluoromethyl-phenyl or 5-Bromo-thiophen-2-yl.

In another aspect, the invention is directed to compounds of Formula I where R2 is selected from the group consisting of: thienyl optionally substituted by a member selected from the group consisting of methyl, acetyl, and chloro; pyridyl optionally substituted by one or two members selected from the group consisting of amido, methoxy, methyl, fluoro, chloro, and cyano and pyrimidinyl optionally substituted with a member selected from the group consisting of ethoxy, methoxy, hydroxy, and isopropyl.

In yet another aspect, the invention is directed to compounds of Formula I where R2 is nitrophenyl.

In yet another aspect, the invention is directed to compounds of Formula I where R2 is 2-nitrophenyl.

In yet another aspect, the invention is directed to compounds of Formula I where R2 is 2-(2-Acetyl-thiophen-3-yl)-phenyl, 2-(2-Carbamoyl-pyridin-3-yl)-, 2-(2-Chloro-thiophen-3-yl)-, 2-(2-ethoxy-pyrimidin-5-yl)-, 2-(2-hydroxy-pyrimidin-5-yl)-, 2-(2-methoxy-pyridin-3-yl)-, 2-(2-methoxy-pyrimidin-5-yl)-, 2-(2-methyl-pyridin-3-yl)-, 2-(3-Chloro-thiophen-2-yl)-, 2-(3-methyl-pyridin-4-yl)-, 2-(4-isopropyl-pyrimidin-5-yl)-, 2-(4-methyl-thiophen-3-yl)-, 2-(5-Chloro-pyridin-3-yl)-, 2-(5-fluoro-pyridin-2-yl)-, 2-(6-Cyano-pyridin-2-yl)-, 2-(6-methoxy-pyridin-2-yl)-, 2',3',5'-Trichloro-phenyl, 2',3',5'-trifluoro-phenyl, 2',3'-Dichloro-phenyl, 2',3'-difluoro-phenyl, 2',4'-bis-trifluoromethyl-phenyl, 2',4'-Dichloro-phenyl, 2',4'-difluoro-phenyl, 2',5'-Dichloro-phenyl, 2',5'-difluoro-phenyl, 2'-Acetyl-phenyl, 2'-Carbamoyl-phenyl, 2'-chloro-2'-fluoro-phenyl, 2'-chloro-3'-trifluoromethyl-phenyl, 2'-chloro-4'-ethoxy-phenyl, 2'-chloro-4'-fluoro-phenyl, 2'-chloro-4'-methoxy-phenyl, 2'-chloro-4'-methyl-phenyl, 2'-chloro-4'-trifluoromethyl-phenyl, 2'-Chloro-5'-cyano-phenyl, 2'-chloro-5'-fluoro-phenyl, 2'-chloro-5'-hydroxy-phenyl, 2'-chloro-5'-methoxy-phenyl, 2'-chloro-5'-methyl-phenyl, 2'-chloro-5'-trifluoromethoxy-phenyl, 2'-chloro-5'-trifluoromethyl-phenyl, 2'-Cyano-phenyl, 2'-fluoro-4'-carboxy-phenyl, 2'-fluoro-phenyl, 2'-formyl-5'-methyl-phenyl, 2'-formyl-phenyl, 2'-methoxy-6'-chloro-phenyl, 2'-methoxy-phenyl, 2'-methyl-4'-cyano-phenyl, 2'-methyl-phenyl, 2'-nitro-5'-trifluoromethyl-phenyl, 2'-nitro-phenyl, 2-pyridin-3-yl-, 2-pyridin-4-yl-, 2-pyrimidin-5-yl-, 3'-Acetyl-phenyl, 3'-Chloro-4'-cyano-phenyl, 3'-Cyano-phenyl, 3'-methoxy-phenyl, 3'-nitro-phenyl, 4'-(1-Acetyl-piperidin-4-ylcarbamoyl)-phenyl, 4'-(1-methyl-piperidin-4-ylcarbamoyl)-phenyl, 4'-(1-phenyl-ethylcarbamoyl)-phenyl, 4'-(2-dimethylamino-ethylcarbamoyl)-phenyl, 4'-(2-fluoro-benzylcarbamoyl)-phenyl, 4'-(2-morpholin-4-yl-ethylcarbamoyl)-phenyl, 4'-(2-pyridin-3-yl-ethylcarbamoyl)-phenyl, 4'-(3-diethylamino-propylcarbamoyl)-phenyl, 4'-(3-dimethylamino-propylcarbamoyl)-phenyl, 4'-(3-fluoro-benzylcarbamoyl)-phenyl, 4'-(3-methoxy-benzylcarbamoyl)-phenyl, 4'-(3-methyl-benzylcarbamoyl)-phenyl, 4'-(3-morpholin-4-yl-propylcarbamoyl)-phenyl, 4'-(3-trifluoromethyl-benzylcarbamoyl)-phenyl, 4'-(4-Acetyl-piperazine-1-carbonyl)-phenyl, 4'-(4-fluoro-benzylcarbamoyl)-phenyl, 4'-(4-hydroxy-piperidine-1-carbonyl)-phenyl, 4'-(4-methoxy-benzylcarbamoyl)-phenyl, 4'-(4-methyl-piperazine-1-carbonyl)-phenyl, 4'-(morpholine-4-carbonyl)-phenyl, 4'-(pyrrolidine-1-carbonyl)-phenyl, 4'-(tetrahydro-furan-3-ylcarbamoyl)-phenyl, 4'-(tetrahydro-pyran-4-ylcarbamoyl)-phenyl, 4'-[(pyridin-3-ylmethyl)-carbamoyl]-phenyl, 4'-[(pyridin-4-ylmethyl)-carbamoyl]-phenyl, 4'-[(tetrahydro-furan-2-ylmethyl)-carbamoyl]-phenyl, 4'-[(tetrahydro-pyran-4-ylmethyl)-carbamoyl]-phenyl, 4'-[(thiophen-2-ylmethyl)-carbamoyl]-phenyl, 4'-Acetyl-phenyl, 4'-Benzylcarbamoyl-phenyl, 4'-Carbamoyl-2'-methyl-phenyl, 4'-Carboxy-2'-methyl-phenyl, 4'-Chloro-3'-cyano-phenyl, 4'-Chloro-phenyl, 4'-Cyano-phenyl, 4'-fluoro-2'-trifluoromethyl-phenyl, 4'-fluoro-phenyl, 4'-methoxy-2'-nitro-phenyl, 4'-methoxy-2'-trifluoromethyl-phenyl, 4'-nitro-phenyl, 4'-phenethylcarbamoyl-phenyl, 5'-Acetyl-2'-chloro-phenyl, 5'-Carbamoyl-2'-chloro-phenyl, 5'-Chloro-2'-cyano-phenyl, 6'-chloro-2'-fluoro-3'-methyl-phenyl, 6'-chloro-2'-fluoro-phenyl, 6'-fluoro-3'-methyl-phenyl or phenyl.

In another aspect, the invention is directed to compounds of Formula I, which is selected from the group consisting of
4-[4-(4-Fluoro-phenyl)-thiazol-2-yl]-2'-nitro-biphenyl-2-carboxylic acid,
2'-Nitro-4-[4-(4-trifluoromethoxy-phenyl)-thiazol-2-yl]-biphenyl-2-carboxylic acid,
4-[4-(4-Difluoromethoxy-phenyl)-thiazol-2-yl]-2'-nitro-biphenyl-2-carboxylic acid,
2'-Nitro-4-[4-(2-trifluoromethyl-phenyl)-thiazol-2-yl]-biphenyl-2-carboxylic acid,
2'-Nitro-4-[4-(3-trifluoromethyl-phenyl)-thiazol-2-yl]-biphenyl-2-carboxylic acid,
2'-Nitro-4-[4-(4-trifluoromethyl-phenyl)-thiazol-2-yl]-biphenyl-2-carboxylic acid,
4-[4-(4-Chloro-3-methyl-phenyl)-thiazol-2-yl]-2'-nitro-biphenyl-2-carboxylic acid,
4-[4-(2-Chloro-phenyl)-thiazol-2-yl]-2'-nitro-biphenyl-2-carboxylic acid,
4-[4-(4-Chloro-phenyl)-thiazol-2-yl]-2'-nitro-biphenyl-2-carboxylic acid,
4-[4-(3-Chloro-phenyl)-thiazol-2-yl]-2'-nitro-biphenyl-2-carboxylic acid,
4-[4-(3-Chloro-4-fluoro-phenyl)-thiazol-2-yl]-2'-nitro-biphenyl-2-carboxylic acid,
4-[4-(2-Fluoro-phenyl)-thiazol-2-yl]-2'-nitro-biphenyl-2-carboxylic acid,
4-[4-(3-Fluoro-phenyl)-thiazol-2-yl]-2'-nitro-biphenyl-2-carboxylic acid,
4-[4-(5-Bromo-thiophen-2-yl)-thiazol-2-yl]-2'-nitro-biphenyl-2-carboxylic acid,
4-[4-(3-Bromo-phenyl)-thiazol-2-yl]-2'-nitro-biphenyl-2-carboxylic acid,
4-[4-(4-Bromo-phenyl)-thiazol-2-yl]-2'-nitro-biphenyl-2-carboxylic acid,
4-[4-(2-Fluoro-4-methoxy-phenyl)-thiazol-2-yl]-2'-nitro-biphenyl-2-carboxylic acid,
4-[4-(2-Methoxy-phenyl)-thiazol-2-yl]-2'-nitro-biphenyl-2-carboxylic acid,
4-[4-(3-Methoxy-phenyl)-thiazol-2-yl]-2'-nitro-biphenyl-2-carboxylic acid,
4-[4-(4-Methoxy-phenyl)-thiazol-2-yl]-2'-nitro-biphenyl-2-carboxylic acid,
4-[4-(4-Methanesulfonyl-phenyl)-thiazol-2-yl]-2'-nitro-biphenyl-2-carboxylic acid,
4-[4-(3-Cyano-phenyl)-thiazol-2-yl]-2'-nitro-biphenyl-2-carboxylic acid,
4-[4-(4-Cyano-phenyl)-thiazol-2-yl]-2'-nitro-biphenyl-2-carboxylic acid,
2'-Nitro-4-(4-pyridin-2-yl-thiazol-2-yl)-biphenyl-2-carboxylic acid,
2'-Nitro-4-(4-pyridin-3-yl-thiazol-2-yl)-biphenyl-2-carboxylic acid,
2'-Nitro-4-(4-pyridin-4-yl-thiazol-2-yl)-biphenyl-2-carboxylic acid,
2'-Nitro-4-(4-p-tolyl-thiazol-2-yl)-biphenyl-2-carboxylic acid,
2'-Nitro-4-(4-thiophen-3-yl-thiazol-2-yl)-biphenyl-2-carboxylic acid,
2'-Nitro-4-(4-phenyl-thiazol-2-yl)-biphenyl-2-carboxylic acid,
2'-Nitro-4-(4-thiophen-2-yl-thiazol-2-yl)-biphenyl-2-carboxylic acid,
4-[4-(3,4-Dichloro-phenyl)-thiazol-2-yl]-2'-methyl-biphenyl-2,4'-dicarboxylic acid,
4-[4-(3,4-Dichloro-phenyl)-thiazol-2-yl]-2'-fluoro-biphenyl-2,4'-dicarboxylic acid,
4-[4-(2,3-Dihydro-benzo[1,4]dioxin-6-yl)-thiazol-2-yl]-2'-nitro-biphenyl-2-carboxylic acid,
4-[4-(2,4-Dichloro-phenyl)-thiazol-2-yl]-2'-nitro-biphenyl-2-carboxylic acid,
4-[4-(2,4-Difluoro-phenyl)-thiazol-2-yl]-2'-nitro-biphenyl-2-carboxylic acid,
4-[4-(2,4-Dimethyl-phenyl)-thiazol-2-yl]-2'-nitro-biphenyl-2-carboxylic acid,
4-[4-(2,5-Dichloro-phenyl)-thiazol-2-yl]-2'-nitro-biphenyl-2-carboxylic acid,
4-[4-(2,6-Difluoro-phenyl)-thiazol-2-yl]-2'-nitro-biphenyl-2-carboxylic acid,
4-[4-(3,4-Dichloro-phenyl)-thiazol-2-yl]-2'-nitro-5'-trifluoromethyl-biphenyl-2-carboxylic acid,
5'-Chloro-4-[4-(3,4-dichloro-phenyl)-thiazol-2-yl]-2'-nitro-biphenyl-2-carboxylic acid,
4-[4-(3,4-Dichloro-phenyl)-thiazol-2-yl]-2'-nitro-biphenyl-2-carboxylic acid,
4-[4-(3,4-Difluoro-phenyl)-thiazol-2-yl]-2'-nitro-biphenyl-2-carboxylic acid,
4-[4-(3,4-Dichloro-phenyl)-thiazol-2-yl]-4'-methoxy-2'-nitro-biphenyl-2-carboxylic acid,
4-[4-(3,4-Dichloro-phenyl)-thiazol-2-yl]-4'-nitro-biphenyl-2-carboxylic acid, 4-[4-(3,4-Dichloro-phenyl)-thiazol-2-yl]-3'-nitro-biphenyl-2-carboxylic acid,
4-[4-(3,4-Dichloro-phenyl)-thiazol-2-yl]-4'-(3-diethylamino-propylcarbamoyl)-biphenyl-2-carboxylic acid,
4-[4-(3,4-Dichloro-phenyl)-thiazol-2-yl]-4'-(3-dimethylamino-propylcarbamoyl)-biphenyl-2-carboxylic acid,
4-[4-(3,4-Dichloro-phenyl)-thiazol-2-yl]-4'-(2-dimethylamino-ethylcarbamoyl)-biphenyl-2-carboxylic acid,
4-[4-(3,4-Dichloro-phenyl)-thiazol-2-yl]-4'-[(2-methyl-2H-pyrazol-3-ylmethyl)-carbamoyl]-biphenyl-2-carboxylic acid,
4-[4-(3,4-Dichloro-phenyl)-thiazol-2-yl]-4'(1-methyl-piperidin-4-ylcarbamoyl)-biphenyl-2-carboxylic acid,
4'-(1-Acetyl-piperidin-4-ylcarbamoyl)-4-[4-(3,4-dichloro-phenyl)-thiazol-2-yl]-biphenyl-2-carboxylic acid,
4-[4-(3,4-Dichloro-phenyl)-thiazol-2-yl]-4'-(4-methyl-piperazine-1-carbonyl)-biphenyl-2-carboxylic acid,
4'-(4-Acetyl-piperazine-1-carbonyl)-4-[4-(3,4-dichloro-phenyl)-thiazol-2-yl]-biphenyl-2-carboxylic acid,
4-[4-(3,4-Dichloro-phenyl)-thiazol-2-yl]-4'-(4-hydroxy-piperidine-1-carbonyl)-biphenyl-2-carboxylic acid,
4-[4-(3,4-Dichloro-phenyl)-thiazol-2-yl]-4'-(morpholine-4-carbonyl)-biphenyl-2-carboxylic acid,
4-[4-(3,4-Dichloro-phenyl)-thiazol-2-yl]-4'-(pyrrolidine-1-carbonyl)-biphenyl-2-carboxylic acid,
4-[4-(3,4-Dichloro-phenyl)-thiazol-2-yl]-4'-(3-morpholin-4-yl-propylcarbamoyl)-biphenyl-2-carboxylic acid,
4-[4-(3,4-Dichloro-phenyl)-thiazol-2-yl]-4'-(2-morpholin-4-yl-ethylcarbamoyl)-biphenyl-2-carboxylic acid,
4-[4-(3,4-Dichloro-phenyl)-thiazol-2-yl]-4'-[(tetrahydro-pyran-4-ylmethyl)-carbamoyl]-biphenyl-2-carboxylic acid,
4-[4-(3,4-Dichloro-phenyl)-thiazol-2-yl]-4'-[(tetrahydro-furan-2-ylmethyl)-carbamoyl]-biphenyl-2-carboxylic acid,
4-[4-(3,4-Dichloro-phenyl)-thiazol-2-yl]-4'-(tetrahydro-furan-3-ylcarbamoyl)-biphenyl-2-carboxylic acid,
4-[4-(3,4-Dichloro-phenyl)-thiazol-2-yl]-4'-(tetrahydro-pyran-4-ylcarbamoyl)-biphenyl-2-carboxylic acid,
4-[4-(3,4-Dichloro-phenyl)-thiazol-2-yl]-4'-(4-methoxy-benzylcarbamoyl)-biphenyl-2-carboxylic acid,
4-[4-(3,4-Dichloro-phenyl)-thiazol-2-yl]-4'-(3-methoxy-benzylcarbamoyl)-biphenyl-2-carboxylic acid,
4-[4-(3,4-Dichloro-phenyl)-thiazol-2-yl]-4'-(2-pyridin-3-yl-ethylcarbamoyl)-biphenyl-2-carboxylic acid,
4-[4-(3,4-Dichloro-phenyl)-thiazol-2-yl]-4'-phenethylcarbamoyl-biphenyl-2-carboxylic acid,
4-[4-(3,4-Dichloro-phenyl)-thiazol-2-yl]-4'-[(pyridin-3-ylmethyl)-carbamoyl]-biphenyl-2-carboxylic acid,
4-[4-(3,4-Dichloro-phenyl)-thiazol-2-yl]-4'-[(pyridin-4-ylmethyl)-carbamoyl]-biphenyl-2-carboxylic acid,
4-[4-(3,4-Dichloro-phenyl)-thiazol-2-yl]-4'-(3-methyl-benzylcarbamoyl)-biphenyl-2-carboxylic acid,
4-[4-(3,4-Dichloro-phenyl)-thiazol-2-yl]-4'-(3-trifluoromethyl-benzylcarbamoyl)-biphenyl-2-carboxylic acid,
4-[4-(3,4-Dichloro-phenyl)-thiazol-2-yl]-4'-(4-fluoro-benzylcarbamoyl)-biphenyl-2-carboxylic acid,
4-[4-(3,4-Dichloro-phenyl)-thiazol-2-yl]-4'-(3-fluoro-benzylcarbamoyl)-biphenyl-2-carboxylic acid,
4-[4-(3,4-Dichloro-phenyl)-thiazol-2-yl]-4'-(2-fluoro-benzylcarbamoyl)-biphenyl-2-carboxylic acid,
4-[4-(3,4-Dichloro-phenyl)-thiazol-2-yl]-4'-[(thiophen-2-ylmethyl)-carbamoyl]-biphenyl-2-carboxylic acid,
4'-Benzylcarbamoyl-4-[4-(3,4-dichloro-phenyl)-thiazol-2-yl]-biphenyl-2-carboxylic acid,
2-(2-Carbamoyl-pyridin-3-yl)-5-[4-(3,4-dichloro-phenyl)-thiazol-2-yl]-benzoic acid,
4'-Carbamoyl-4-[4-(3,4-dichloro-phenyl)-thiazol-2-yl]-2'-methyl-biphenyl-2-carboxylic acid,
4-[4-(3,4-Dichloro-phenyl)-thiazol-2-yl]-4'-(1-phenyl-ethylcarbamoyl)-biphenyl-2-carboxylic acid,
2'-Carbamoyl-4-[4-(3,4-dichloro-phenyl)-thiazol-2-yl]-biphenyl-2-carboxylic acid,
5-[4-(3,4-Dichloro-phenyl)-thiazol-2-yl]-2-(2-ethoxy-pyrimidin-5-yl)-benzoic acid,
5-[4-(3,4-Dichloro-phenyl)-thiazol-2-yl]-2-(2-methoxy-pyrimidin-5-yl)-benzoic acid,
5-[4-(3,4-Dichloro-phenyl)-thiazol-2-yl]-2-(2-hydroxy-pyrimidin-5-yl)-benzoic acid,
5-[4-(3,4-Dichloro-phenyl)-thiazol-2-yl]-2-(6-methoxy-pyridin-2-yl)-benzoic acid,
5-[4-(3,4-Dichloro-phenyl)-thiazol-2-yl]-2-(2-methoxy-pyridin-3-yl)-benzoic acid,
4-[4-(3,4-Dichloro-phenyl)-thiazol-2-yl]-4'-methoxy-2'-trifluoromethyl-biphenyl-2-carboxylic acid,
2'-Chloro-4-[4-(3,4-dichloro-phenyl)-thiazol-2-yl]-5'-trifluoromethoxy-biphenyl-2-carboxylic acid,
2'-Chloro-4-[4-(3,4-dichloro-phenyl)-thiazol-2-yl]-4'-ethoxy-biphenyl-2-carboxylic acid,
6'-Chloro-4-[4-(3,4-dichloro-phenyl)-thiazol-2-yl]-2'-methoxy-biphenyl-2-carboxylic acid,
4-[4-(3,4-Dichloro-phenyl)-thiazol-2-yl]-3'-methoxy-biphenyl-2-carboxylic acid,
4-[4-(3,4-Dichloro-phenyl)-thiazol-2-yl]-2'-methoxy-biphenyl-2-carboxylic acid,
2'-Chloro-4-[4-(3,4-dichloro-phenyl)-thiazol-2-yl]-5'-methoxy-biphenyl-2-carboxylic acid,
2'-Chloro-4-[4-(3,4-dichloro-phenyl)-thiazol-2-yl]-4'-methoxy-biphenyl-2-carboxylic acid,
2'-Chloro-4-[4-(3,4-dichloro-phenyl)-thiazol-2-yl]-5'-hydroxy-biphenyl-2-carboxylic acid,
5-[4-(3,4-Dichloro-phenyl)-thiazol-2-yl]-2-(4-isopropyl-pyrimidin-5-yl)-benzoic acid,
5-[4-(3,4-Dichloro-phenyl)-thiazol-2-yl]-2-pyrimidin-5-yl-benzoic acid,
5-[4-(3,4-Dichloro-phenyl)-thiazol-2-yl]-2-(2-methyl-pyridin-3-yl)-benzoic acid,
5-[4-(3,4-Dichloro-phenyl)-thiazol-2-yl]-2-(3-methyl-pyridin-4-yl)-benzoic acid,
5-[4-(3,4-Dichloro-phenyl)-thiazol-2-yl]-2-(5-fluoro-pyridin-2-yl)-benzoic acid,
5-[4-(3,4-Dichloro-phenyl)-thiazol-2-yl]-2-pyridin-3-yl-benzoic acid,
2-(5-Chloro-pyridin-3-yl)-5-[4-(3,4-dichloro-phenyl)-thiazol-2-yl]-benzoic acid,
5-[4-(3,4-Dichloro-phenyl)-thiazol-2-yl]-2-pyridin-4-yl-benzoic acid,
2-(6-Cyano-pyridin-2-yl)-5-[4-(3,4-dichloro-phenyl)-thiazol-2-yl]-benzoic acid,
4'-Cyano-4-[4-(3,4-dichloro-phenyl)-thiazol-2-yl]-2'-methyl-biphenyl-2-carboxylic acid,
4'-Cyano-4-[4-(3,4-dichloro-phenyl)-thiazol-2-yl]-biphenyl-2-carboxylic acid,
3'-Cyano-4-[4-(3,4-dichloro-phenyl)-thiazol-2-yl]-biphenyl-2-carboxylic acid,
2'-Chloro-5'-cyano-4-[4-(3,4-dichloro-phenyl)-thiazol-2-yl]-biphenyl-2-carboxylic acid,
5'-Carbamoyl-2'-chloro-4-[4-(3,4-dichloro-phenyl)-thiazol-2-yl]-biphenyl-2-carboxylic acid,
5'-Chloro-2'-cyano-4-[4-(3,4-dichloro-phenyl)-thiazol-2-yl]-biphenyl-2-carboxylic acid,
2'-Cyano-4-[4-(3,4-dichloro-phenyl)-thiazol-2-yl]-biphenyl-2-carboxylic acid,
3'-Chloro-4'-cyano-4-[4-(3,4-dichloro-phenyl)-thiazol-2-yl]-biphenyl-2-carboxylic acid, 4'-Chloro-3'-cyano-4-[4-(3,4-dichloro-phenyl)-thiazol-2-yl]-biphenyl-2-carboxylic acid,
3'-Acetyl-4-[4-(3,4-dichloro-phenyl)-thiazol-2-yl]-biphenyl-2-carboxylic acid,
2'-Acetyl-4-[4-(3,4-dichloro-phenyl)-thiazol-2-yl]-biphenyl-2-carboxylic acid,
5'-Acetyl-2'-chloro-4-[4-(3,4-dichloro-phenyl)-thiazol-2-yl]-biphenyl-2-carboxylic acid,
2-(2-Acetyl-thiophen-3-yl)-5-[4-(3,4-dichloro-phenyl)-thiazol-2-yl]-benzoic acid,
4'-Acetyl-4-[4-(3,4-dichloro-phenyl)-thiazol-2-yl]-biphenyl-2-carboxylic acid,
4-[4-(3,4-Dichloro-phenyl)-thiazol-2-yl]-2'-formyl-5'-methyl-biphenyl-2-carboxylic acid,
4-[4-(3,4-Dichloro-phenyl)-thiazol-2-yl]-2'-formyl-biphenyl-2-carboxylic acid,
4-[4-(3,4-Dichloro-phenyl)-thiazol-2-yl]-4'-fluoro-2'-trifluoromethyl-biphenyl-2-carboxylic acid,
4-[4-(3,4-Dichloro-phenyl)-thiazol-2-yl]-2',4'-bis-trifluoromethyl-biphenyl-2-carboxylic acid,
2'-Chloro-4-[4-(3,4-dichloro-phenyl)-thiazol-2-yl]-3'-trifluoromethyl-biphenyl-2-carboxylic acid,
2'-Chloro-4-[4-(3,4-dichloro-phenyl)-thiazol-2-yl]-4'-trifluoromethyl-biphenyl-2-carboxylic acid,
2'-Chloro-4-[4-(3,4-dichloro-phenyl)-thiazol-2-yl]-5'-trifluoromethyl-biphenyl-2-carboxylic acid,
4-[4-(3,4-Dichloro-phenyl)-thiazol-2-yl]-4'-fluoro-biphenyl-2-carboxylic acid,
2'-Chloro-4-[4-(3,4-dichloro-phenyl)-thiazol-2-yl]-5'-fluoro-biphenyl-2-carboxylic acid,
4-[4-(3,4-Dichloro-phenyl)-thiazol-2-yl]-2',5'-difluoro-biphenyl-2-carboxylic acid,
4-[4-(3,4-Dichloro-phenyl)-thiazol-2-yl]-2',4'-difluoro-biphenyl-2-carboxylic acid,
4-[4-(3,4-Dichloro-phenyl)-thiazol-2-yl]-2',3',5'-trifluoro-biphenyl-2-carboxylic acid,
2'-Chloro-4-[4-(3,4-dichloro-phenyl)-thiazol-2-yl]-4'-fluoro-biphenyl-2-carboxylic acid,
4'-Chloro-4-[4-(3,4-dichloro-phenyl)-thiazol-2-yl]-2'-fluoro-biphenyl-2-carboxylic acid,
6'-Chloro-4-[4-(3,4-dichloro-phenyl)-thiazol-2-yl]-2'-fluoro-biphenyl-2-carboxylic acid,
4-[4-(3,4-Dichloro-phenyl)-thiazol-2-yl]-2'-fluoro-biphenyl-2-carboxylic acid,
4-[4-(3,4-Dichloro-phenyl)-thiazol-2-yl]-2',3'-difluoro-biphenyl-2-carboxylic acid,
2'-Chloro-4-[4-(3,4-dichloro-phenyl)-thiazol-2-yl]-6'-fluoro-3'-methyl-biphenyl-2-carboxylic acid,
6'-Chloro-4-[4-(3,4-dichloro-phenyl)-thiazol-2-yl]-2'-fluoro-3'-methyl-biphenyl-2-carboxylic acid,
4-[4-(3,4-Dichloro-phenyl)-thiazol-2-yl]-2'-methyl-biphenyl-2-carboxylic acid,
5-[4-(3,4-Dichloro-phenyl)-thiazol-2-yl]-2-(4-methyl-thiophen-3-yl)-benzoic acid,
2'-Chloro-4-[4-(3,4-dichloro-phenyl)-thiazol-2-yl]-4'-methyl-biphenyl-2-carboxylic acid,
2'-Chloro-4-[4-(3,4-dichloro-phenyl)-thiazol-2-yl]-5'-methyl-biphenyl-2-carboxylic acid,
2-(2-Chloro-thiophen-3-yl)-5-[4-(3,4-dichloro-phenyl)-thiazol-2-yl]-benzoic acid,
2-(3-Chloro-thiophen-2-yl)-5-[4-(3,4-dichloro-phenyl)-thiazol-2-yl]-benzoic acid,
4'-Chloro-4-[4-(3,4-dichloro-phenyl)-thiazol-2-yl]-biphenyl-2-carboxylic acid,
2',5'-Dichloro-4-[4-(3,4-dichloro-phenyl)-thiazol-2-yl]-biphenyl-2-carboxylic acid,
2',3',5'-Trichloro-4-[4-(3,4-dichloro-phenyl)-thiazol-2-yl]-biphenyl-2-carboxylic acid,
2',4'-Dichloro-4-[4-(3,4-dichloro-phenyl)-thiazol-2-yl]-biphenyl-2-carboxylic acid,
4-[4-(3,4-Dichloro-phenyl)-thiazol-2-yl]-biphenyl-2-carboxylic acid,
2',3'-Dichloro-4-[4-(3,4-dichloro-phenyl)-thiazol-2-yl]-biphenyl-2-carboxylic acid,
2'-Chloro-4-[4-(3,4-dichloro-phenyl)-thiazol-2-yl]-biphenyl-2-carboxylic acid,
4-[4-(3,5-Bis-trifluoromethyl-phenyl)-thiazol-2-yl]-2'-nitro-biphenyl-2-carboxylic acid, and
4-[4-(3,5-Difluoro-phenyl)-thiazol-2-yl]-2'-nitro-biphenyl-2-carboxylic acid, or pharmaceutically acceptable salts thereof.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

A bond drawn into a ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, triple, or aromatic bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth.

Certain compounds of Formula I may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomer usually produce a mixture whose chemical and physical properties are consistent with a mixture of compounds. The position of the equilibrium is dependent on chemical features within the molecule and the environment to which it is exposed e.g. solvent, temperature, pH, etc. For example, in many aliphatic aldehydes and ketones, such as acetaldehyde, the keto form predominates while, in phenols, the enol form predominates. Common prototropic tautomers include keto/enol (—C(=O)—CH2-↔—C(—OH)=CH—), amide/imidic acid (—C(=O)—NH—↔—C(—OH)=N—) and amidine (—C(=NR)—NH—↔—C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl and phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, hydroxymethyl, 3-hydroxypropyl, and so forth. Accordingly, as used herein, the term "hydroxyalkyl" is used to define a subset of heteroalkyl groups defined above. The term—(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term C$_{1-6}$ acyl refers to a group —C(=O)R where the R group contains up to 6 carbon atoms. The term "arylcarbonyl" as used herein means a group of formula C(=O)R wherein R is an aryl group; the term "benzoyl" as used herein denotes an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "C$_{1-10}$ alkyl" as used herein refers to an alkyl composed of 1 to 10 carbons. Examples of alkyl groups include, but are not limited to, lower alkyl groups including methyl, ethyl, propyl, i-propyl, n-butyl, i-butyl, t-butyl or pentyl, isopentyl, neopentyl, and hexyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., (CH$_2$)$_n$) or a branched saturated divalent hydrocarbon radical of 2 to 10 carbon atoms (e.g., —CHMe- or —CH$_2$CH(i-Pr)CH$_2$—), unless otherwise indicated. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above, such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "C$_{1-10}$ alkoxy" as used herein refers to an —O-alkyl wherein alkyl is C$_{1-10}$.

The term "aryl" denotes a monovalent aromatic carbocyclic mono- or bicyclic ring system comprising 6 to 10 carbon ring atoms. Examples of aryl moieties include phenyl and naphthyl.

The terms "haloalkoxy" or "halo-lower alkoxy" or "lower haloalkoxy" refers to a lower alkoxy group, wherein one or more carbon atoms are substituted with one or more halogen atoms. The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein.

The terms "alkylsulfonylamino" and "arylsulfonylamino" as used herein refers to a group of formula —NR'S(=O)$_2$R wherein R is alkyl or aryl respectively, R' is hydrogen or C$_{1-3}$ alkyl, and alkyl and aryl are as defined herein.

The term "cycloalkyl" as used herein refers to a saturated or unsaturated carbocyclic ring containing 3 to 8 carbon atoms, i.e. cyclopropyl, cyclobutyl, cyclopentyl, cyclohexyl, cycloheptyl or cyclooctyl. "C$_{3-7}$ cycloalkyl" or "lower cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms in which there is at least one aromatic ring containing at least one hetero-atom drawn from the list of N, O, or S heteroatoms. Thus, for the purposes of the invention, a heteroaryl group need only have some degree of aromatic character. Heteroaryl may be optionally substituted as defined directly below. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazolyl, isoxazolyl, thiazolyl, isothiazolyl, thiadiazolyl and which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazolyl, benzisoxazolyl, benzothiazolyl, naphthyridinyl, 5,6,7,8-tetrahydro-[1,6]naphthyridinyl, and benzisothiazolyl. Bicyclic moieties can be optionally substituted on either ring.

The term "heterocyclyl", "heterocycloalkyl" or "heterocycle" as used herein denotes a monovalent saturated or unsaturated cyclic radical, consisting of one or more rings, preferably one to two rings, including spirocyclic ring systems, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof.

Preparation of Compounds of the Invention

The compounds of the present invention can be prepared by any conventional means. Suitable processes for synthesizing these compounds are provided in the Examples. Generally, compounds of Formula 1 can be prepared according to the scheme described below.

Scheme 1

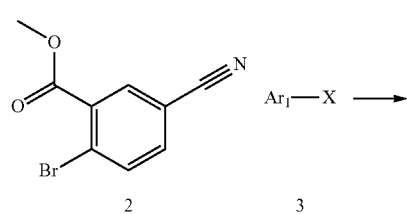

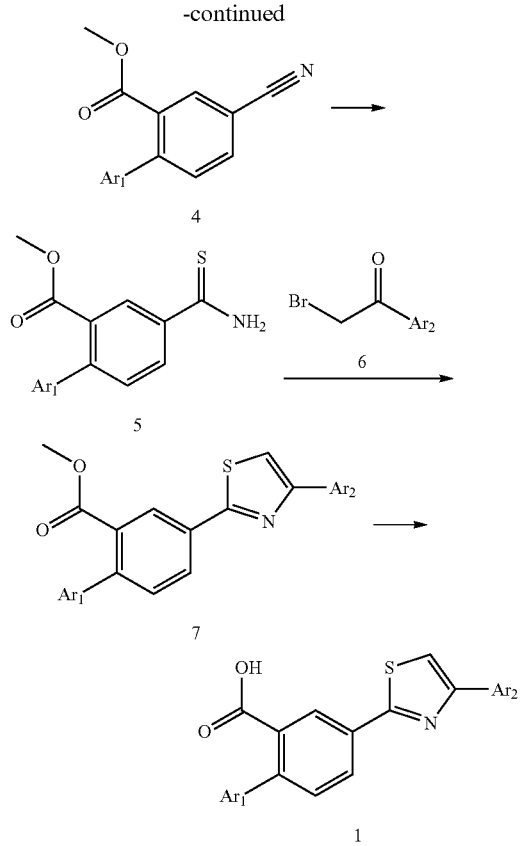

One general approach to the synthesis of compounds of the invention is shown in Scheme 1. That starting material for this scheme, methyl 2-bromo-5-cyanobenzoate, which has formula 2, is commercially available, for example from Ark Pharm, Inc., 1840 Industrial Drive, Suite 820, Libertyville, Ill. 60048, USA and from Apollo Scientific Ltd., Whitefield Road, Bredbury, Stockport, Cheshire SK6 2QR, United Kingdom. This compound can also be prepared as described below in the Examples.

According to the process outlined in Scheme 1, a compound of formula 2 undergoes a transition metal-catalyzed reaction with a compound of formula 3, in which X represents a group that can act as a leaving group in a noble metal-catalyzed coupling reaction such as a Suzuki reaction or a Stille reaction, to give a biaryl of formula 4. The nitrile of the compound of formula 4 is the converted to the thioamide, giving the compound of formula 5. The thioamide of formula 5 then undergoes the Hantzsch thiazole synthesis by reacting with a compound of formula 6 to give the compound of formula 7. The ester group of the compound of formula 7 is then cleaved to give the desired compound of formula 1.

The reaction of a compound of formula 2 with a compound of formula 3, where X represents boronic acid, boronate ester, potassium trifluoroborate, trimethyltin or tri-n-butyl-tin, to give a compound of formula 4 can be effected using Suzuki or Stille coupling conditions which are well known to one of average skill in the art. For example, the reaction can be conveniently carried out by reacting a compound of formula 2 with a compound of formula 3 where X represents $B(OH)_2$, in a convenient inert solvent such as a polar aprotic solvent (e.g., N,N-dimethylformamide) or an ether (e.g., dioxane) or water, or indeed in a mixture of such solvents, in the presence of a catalytic amount of a compound that can be reduced in situ to give palladium(0) (for example, palladium(II) acetate or bis(triphenylphosphine)palladium(II) chloride), in the optional additional presence of a catalytic amount of a phosphine ligand, for example tri-o-tolylphosphine or tri-tert-butylphosphine, or alternatively in the presence of a preformed complex of palladium(0) with a phosphine ligand such as bis(tri-cyclohexylphosphine)palladium, tetrakis(triphenylphosphine)-palladium(0) or [1,1-bis(diphenylphosphino)ferrocene]dichloropalladium(II)), and also in the presence of an inorganic base, for example, an alkali metal carbonate, bicarbonate or phosphate (e.g., potassium phosphate or sodium carbonate) at a temperature between about room temperature and about 100 degrees, and preferably between about room temperature and about 50 degrees. The Suzuki reaction is familiar to one of ordinary skill in the art of organic synthesis, and has been reviewed several times, notably in Miyaura, N.; Suzuki, A. *Chem. Rev.* 1995, 95, 2457-2483 and, more recently, in Alonso, F.; Beletskaya, I. P.; Yus, M. *Tetrahedron* 2008, 64, 3047-3101. Examples of specific conditions useful for Suzuki coupling may be found in many references in the literature including: Tiede, S. et al. *Angew. Chem. Intl. Edn.* 2010, 49, 3972-3975; Schmidt, A. and Rahimi, A. *Chem. Commun.* 2010, 46, 2995-2997; Lee, S. H. et al. US 20100063281; and Tobisu, M. et al. *J. Org. Chem.* 2010, 75, 4835-4840 (Supporting Information). Stille coupling is well known to one of average skill in the field of organic synthesis, and may be used as an alternative to the Suzuki coupling, examples of conditions for which have been provided above. Stille coupling has been reviewed, including in Farina, V. et al. *Org. Reactions* 1997, 50, 1-652. Examples of specific conditions that have been used for Stille coupling may be found in the literature, for example in Littke, A. F. et al. *J. Am. Chem. Soc.* 2002, 124, 5343-6348; in Alberati-Giani, D. et al. U.S. Pat. No. 7,462,617; and in Robl, J. A. U.S. Pat. No. 5,072,023.

The reaction of a nitrile of formula 4 to give a thioamide of formula 5 may be carried out using a variety of reactions that are well known in the field of organic chemistry. For example, this reaction may be carried out using sodium hydrogen sulfide in an inert solvent such as ethanol or water or dimethylformamide at a temperature between about room temperature and about 60° C. Exact conditions for such a reaction may be found in the literature, for example in Guo, X-Z. et al. *Bioorg. Med. Chem.* 2008, 16, 10301-10310; in Ali, A. et al. US 20090137548; in Kim, G. T. et al. WO 2005040127; and in Manaka, A. and Sato, M. *Synth. Commun.* 2005, 35, 761-764. Alternatively, the reaction may be carried out by treating the compound of formula 4 with ammonium sulfide in a solvent, such as a mixture of triethylamine and pyridine, or a mixture of water and methanol, at a temperature between about 50° C. and about 100° C., optionally under microwave irradiation. Exact conditions for such a reaction may be found in the literature, for example in Crane, L. J. et al. *Tetrahedron* 2004, 60, 5325-5330; or in Yao, W. et al. U.S. Pat. No. 7,776,874. Alternatively, the reaction may be carried out by adding hydrogen sulfide gas to a solution of the nitrile in triethylamine and in the optional additional presence of additional solvents and/or bases such as pyridine or dioxane, and allowing the reaction to proceed at a temperature between about room temperature and about 90° C. Exact conditions for such a reaction may be found in the literature, for example in Ash, M. L. et al. U.S. Pat. No. 6,329,528; in Jian, F. F. et al. *J. Fluorine Chem.* 2006, 127, 63-67; in Brunck, T. K. et al. U.S. Pat. No. 6,342,504; and in Hull, J. W. Jr. et al. *Org. Process Res. Devel.* 2009, 13, 1125-1129. The reaction may also be carried out using diethyl dithiophosphate, neat, in an inert solvent such as dichloromethane or hydrogen chloride in ethyl acetate at about room temperature, or in a mixture of tetrahydrofuran and water at about 80° C. Exact conditions for such a reaction may be found in the literature, for example in Choi, I. Y. et al. WO 2006137658; in Bouillot, A. M. J. et al. WO 2009071504; in Stump, B. et al. *Heterocycles* 2007, 72, 293-326; and in Soh, C. H. et al. *J. Comb. Chem.* 2006, 8, 464-468. The reaction may also be carried out by treating the nitrile of formula 4 with phosphorus pentasulfide in an inert solvent such as methanol or ethanol at a temperature between about room temperature and about 80° C. Exact conditions for such a reaction may be found in the literature, for example in Zhang, N. et al. US 20090270363; in Kaboudin, B. and Elhamifar, D. *Synthesis* 2006, 224-226; and in Cummings, C. G. et al. *Org. Lett.* 2009, 11, 25-28.

The reaction of a thioamide of formula 5 with a bromomethyl ketone of formula 6 may be carried out using any conventional means. For example, the reaction may be carried out by treating the thioamide of formula 5 with the bromomethyl ketone of formula 6 in an inert solvent such as an alcohol (e.g., ethanol) or an ether (e.g., tetrahydrofuran) at a temperature between about room temperature and about 100° C. Exact conditions for such a reaction may be found in the literature, for example in Oalmann, C. et al. WO 2009058348; in Saha, A. K. et al. U.S. Pat. No. 7,241,812; in Yu, D. T. et al. U.S. Pat. No. 6,156,776; in Dumaître, B. and Dodic, N. *J. Med. Chem.* 1996, 39, 1635-1644; and in Wright, S. W. et al. *J. Med. Chem.* 2002, 45, 3865-3877.

The hydrolysis of a compound of formula 7 to give the compound of the invention of formula 1 may be carried out using conditions that are well known in the field of organic synthesis, many of which are outlined in "Protective Groups in Organic Synthesis" [T. W. Greene and P. G. M. Wuts, $2^{nd}$ Edition, John Wiley & Sons, N.Y. 1991]. For example, the reaction can be conveniently effected by treating the compound of formula 7 with one or more equivalents of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 100° C. and about room temperature, preferably between about room temperature and about 60° C.

It will be apparent to one of average skill in the art of organic synthesis that any hydrolytically unstable groups, such as esters or nitriles or the like, in the $Ar_2$ group in the compound of formula 7 will also be subject to cleavage during the hydrolysis reaction mentioned above. This may be the desired outcome, such as where the desired compound contains a carboxylate or carboxamide group. As is well known in the art, cleavage of the methyl ester group to give desired acid of formula 1 without cleavage of other groups such as more hindered esters, amides, or nitriles by judicious choice of reaction conditions, such as the use of only one equivalent of base or by keeping the reaction temperature low (for example, around 0° C.).

Scheme 2

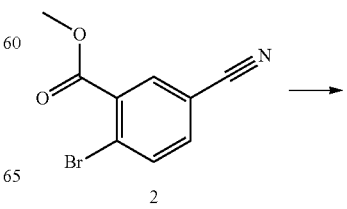

2

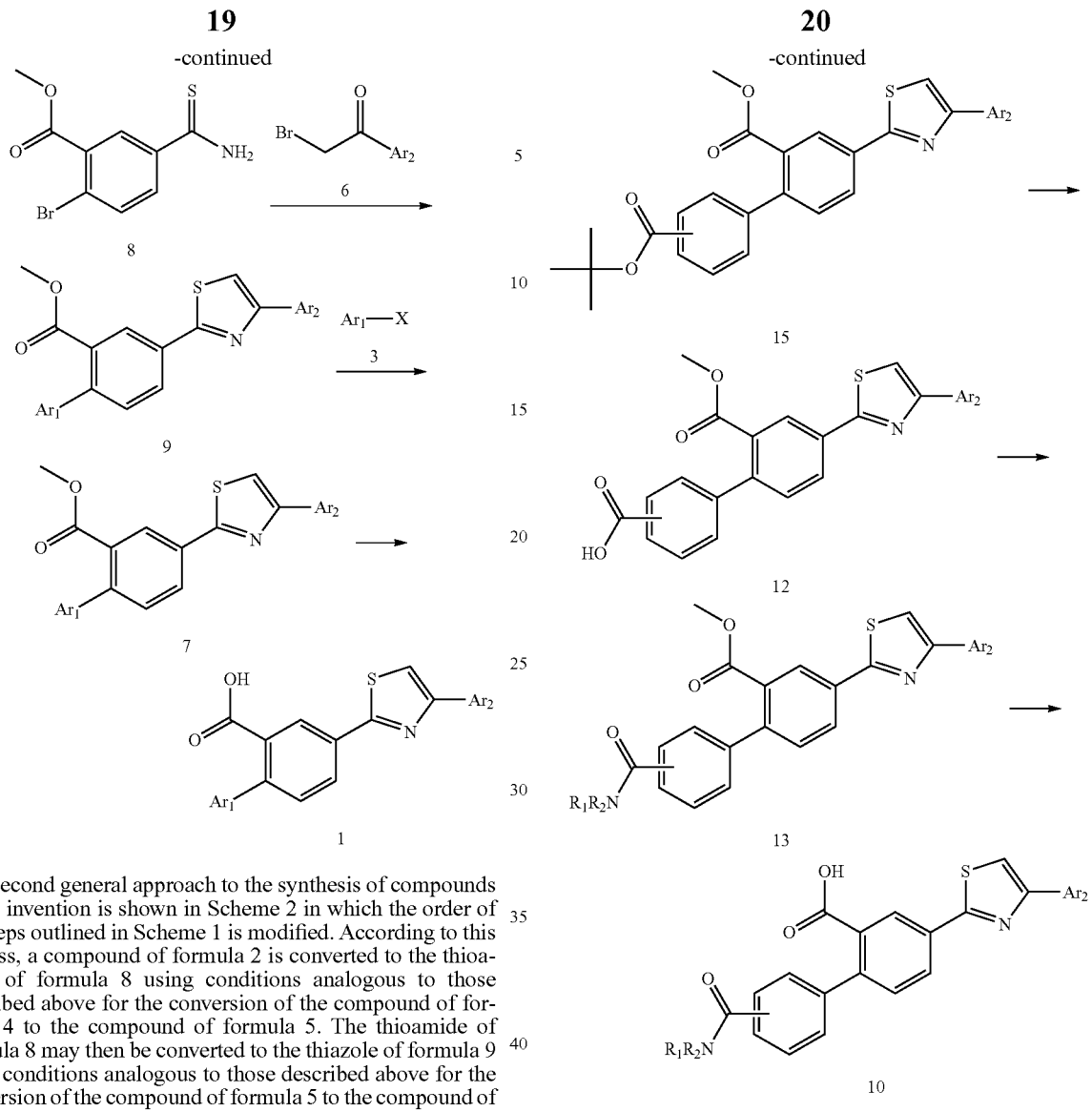

A second general approach to the synthesis of compounds of the invention is shown in Scheme 2 in which the order of the steps outlined in Scheme 1 is modified. According to this process, a compound of formula 2 is converted to the thioamide of formula 8 using conditions analogous to those described above for the conversion of the compound of formula 4 to the compound of formula 5. The thioamide of formula 8 may then be converted to the thiazole of formula 9 using conditions analogous to those described above for the conversion of the compound of formula 5 to the compound of formula 7. The aryl bromide of formula 9 then undergoes a transition metal-catalyzed reaction with a compound of formula 3, in which X represents a group that can act as a leaving group in a noble metal-catalyzed coupling reaction such as a Suzuki reaction or a Stille reaction, to give a biaryl of formula 7. Conditions for the noble metal-catalyzed coupling reaction are analogous to those described above for the conversion of the compound of formula 2 to the compound of formula 4. The ester group of the compound of formula 6 is then cleaved to give the desired compound of formula 1, for example using the conditions described above.

In one embodiment of the invention, the compound of the invention is a compound of formula 10. Such compounds may be made using the process outlined in Scheme 3.

Scheme 3

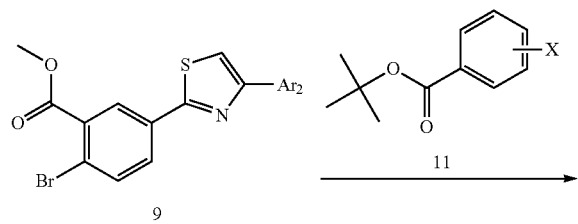

According to this process, a compound of formula 9, which may be prepared as described above, undergoes a transition metal-catalyzed reaction with a compound of formula 11, in which X represents boronic acid, boronate ester, potassium trifluoroborate, trimethyltin or tri-n-butyl-tin, to give a biaryl of formula 15. The tert-butyl ester is selectively cleaved to give the carboxylic acid of formula 12. The acid is then coupled with an amine of formula $HNR_1R_2$ to give the amide of formula 13 and then the methyl ester is cleaved to give the compound of the invention of formula 10.

The transition metal-catalyzed reaction of the aryl bromide of formula 9 with the compound of formula 11, where X represents boronic acid, boronate ester, potassium trifluoroborate, trimethyltin or tri-n-butyl-tin, to give a compound of formula 15 can be effected using any conventional means. For examples, this transformation may be carried out using conditions analogous to those described above for the conversion of the compound of formula 2 to the compound of formula 4.

The cleavage of the tert-butyl ester present in the compound of formula 7 to give the mono-ester of formula 8 may be carried out using conventional means. For example, the compound of formula 7 may be treated with a strong organic acid (preferably trifluoroacetic acid) in an inert solvent such as a halogenated hydrocarbon (preferably dichloromethane or chloroform) at a temperature about room temperature. Exact conditions for such a reaction may be found in the literature, for example in Bartel, S. et al. US 20100029772; in Thompson, T. and Willis, P. US 20080146612; in Ford, R. et al. US 20080153850; and in Hirashima, S. et al. *J. Med. Chem.* 2006, 49, 4721-4736.

The coupling of a carboxylic acid of formula 12 with an amine of structure $HNR_1R_2$ (availability and preparation thereof described hereinafter), according to Scheme 3, can be achieved using methods well known to one of ordinary skill in the art. For example, the transformation can be carried out by reaction of a carboxylic acid of formula 12 or of an appropriate derivative thereof such as an activated ester, with an amine of structure $HNR_1R_2$ or a corresponding acid addition salt (e.g., the hydrochloride salt) in the presence, if necessary, of a coupling agent (many examples are well known in peptide chemistry). The reaction is conveniently carried out by treating the carboxylic acid of formula 12 with the free base or hydrochloride of the amine of structure $HNR_1R_2$ in the presence of an appropriate base, such as diisopropylethylamine, a coupling agent such as O-(benzotriazol-1-yl)-1,1,3,3-tetramethyluronium hexafluorophosphate or TSTU or N-(3-dimethylaminopropyl)-N'-ethylcarbodiimide hydrochloride and in the optional addition presence of a catalyst such as 1-hydroxybenzotriazole or 1-hydroxy-7-azabenzotriazole, in an inert solvent, such as chlorinated hydrocarbon (e.g., dichloromethane) or N,N-dimethylformamide or N-methylpyrrolidinone, at a temperature between about 0° C. and about room temperature, preferably at room temperature.

Sources of Compounds of Formula 3

Many compounds of formula 3 where X represents $B(OH)_2$, are commercially available and examples are shown below.

From ASDI Incorporated, 601 Interchange Blvd., Newark, Del. 19711, USA: 2-acetylphenylboronic acid; phenylboronic acid.

From Aldrich Chemical Company, Inc., 1001 West Saint Paul Avenue, Milwaukee, Wis. 53233, USA.: 2-acetyl-3-thienylboronic acid; 2-methyl-4-cyanophenylboronic acid.

From Alfa Aesar, 26 Parkridge Road, Ward Hill, Mass. 01835, USA: 4-(methanesulfinyl)benzeneboronic acid.

From Chem-Impex International, Inc., 935 Dillon Drive, Wood Dale, Ill. 60191, USA: 4-methylpyridine-2-boronic acid.

From Combi-Blocks Inc., 7949 Silverton Avenue, Suite 915, San Diego, Calif. 92126, USA: 2,3,5-trifluorophenylboronic acid; 2,3-dichlorophenylboronic acid; 2,3-difluorophenylboronic acid; 2,4,6-trichlorophenylboronic acid; 2,4-dichlorophenylboronic acid; 2,5-dichlorophenylboronic acid; 2,5-difluorophenylboronic acid; 2-aminocarbonylphenylboronic acid; 2-chloro-4-fluorophenylboronic acid; 2-chloro-5-hydroxybenzeneboronic acid; 2-chloro-5-methoxyphenylboronic acid; 2-chloro-5-methylphenylboronic acid; 2-chlorophenylboronic acid; 2-chlorothiophene-3-boronic acid; 2-cyanophenylboronic acid; 2-ethoxypyrimidine-5-boronic acid; 2-fluorophenylboronic acid; 2-methoxypyridine-3-boronic acid hydrate; 2-methoxypyrimidine-5-boronic acid; 2-methylphenylboronic acid; 2-picoline-3-boronic acid hydrochloride salt; 3-acetylphenylboronic acid; 3-chloro-4-cyanophenylboronic acid; 3-chlorothiophene-2-boronic acid; 3-cyanophenylboronic acid; 3-methoxyphenylboronic acid; 3-picoline-4-boronic acid hcl, 4-acetylphenylboronic acid; 4-chloro-2-fluorophenylboronic acid; 4-chloro-3-cyanophenylboronic acid; 4-chlorophenylboronic acid; 4-cyano-2-fluorophenylboronic acid; 4-cyanophenylboronic acid; 4-isopropylpyrimidine-5-boronic acid; 4-methyl-3-thiopheneboronic acid; 4-nitrophenylboronic acid; 5-chloro-2-cyanophenylboronic acid; 5-chloropyridine-3-boronic acid; 5-fluoropyridine-2-boronic acid; 6-methoxypyridine-2-boronic acid; pyridine-3-boronic acid; pyridine-4-boronic acid; pyrimidine-5-boronic acid.

From CombiPhos Catalysts, Inc., P.O. Box 220, Princeton, N.J. 08542-0220, USA: 6-chloropyrazine-2-boronic acid; 6-cyanopyridine-2-boronic acid.

From Frontier Scientific, Inc., P.O. Box 31, Logan, Utah 84323-0031, USA: 2,4-difluorophenylboronic acid; 2-chloro-5-cyanophenylboronic acid; 2-formyl-5-methylphenylboronic acid; 2-formylphenylboronic acid; 2-methoxyphenylboronic acid; 3-nitrophenylboronic acid; 4-fluorophenylboronic acid.

From Matrix Scientific, P.O. Box 25067, Columbia, S.C. 29224-5067, USA: 2-cyanopyridine-3-boronic acid.

Several compounds of formula 3 where X represents trialkyltin, are commercially available and examples are shown below.

From Aldrich Chemical Company, Inc., 1001 West Saint Paul Avenue, Milwaukee, Wis. 53233, USA.: trimethyl(phenyl)tin; tributylphenylstannane; 5-(tributylstannyl)pyrimidine; 2-(tributylstannyl)pyrazine.

From Apollo Scientific Ltd., Whitefield Road, Bredbury, Stockport, Cheshire SK6 2QR, United Kingdom: 4-fluoro-(tributylstannyl)benzene; tributyl(5-fluoro-2-methoxyphenyl)stannane; 5-fluoro-2-methyl-(tributylstannyl)benzene; 3-methoxy(tri-n-butylstannyl)benzene; tributyl(2-methoxyphenyl)stannane; tributyl(3-(trifluoromethyl)phenyl)stannane.

From Matrix Scientific, P.O. Box 25067, Columbia, S.C. 29224-5067, USA: 4-(tributylstannyl)pyridine.

In addition to using commercially available compounds of formula 3 where X represents $B(OH)_2$ or trialkyltin, such compounds may be synthesized by procedures that are well known to one skilled in the art of organic synthesis. For example, a compound of this type can conveniently be synthesized according to Scheme 4 from a compound of formula 14, in which Y represents bromine or iodine, by treatment with an alkyllithium (e.g., n-butyllithium) or magnesium (to form the Grignard reagent) in a suitable inert solvent such as an ether (such as tetrahydrofuran or diethyl ether) at a temperature appropriate for the reaction (for example, at approximately −78° C. for reaction with an alkyllithium, or at approximately room temperature for reaction with magnesium), followed by treatment with a trialkyl borate or trialkyltin chloride to form the compound of formula 3 where X represents $B(OH)_2$ or trialkyltin, respectively. It will be obvious to one of average skill in the art of synthetic organic chemistry that this approach is disfavored for the preparation of compounds of formula 3 from compounds of formula 14 that contain functional groups that are not compatible with the alkyllithium or organomagnesium reagents used in the reaction. A convenient alternative approach is outlined below.

Scheme 4

Alternatively, the reaction may be carried out under noble metal catalysis. According to this route, the compound of formula 14 is conveniently reacted with a hexa-alkyl-distannane (such as hexamethyl-distannane or hexa-n-butyl-distannane) or 4,4,5,5-tetramethyl-[1,3,2]dioxaborolane or 4,4,5,5,4',4',5',5'-octamethyl-[2,2']bi[[1,3,2]dioxaborolanyl], in the presence of a noble metal catalyst (preferably a palladium catalyst such as tetrakis(triphenylphosphine)palladium(0) or palladium(II) chloride or palladium(II) acetate), and in the optional additional presence of a catalytic amount of a phosphine ligand, for example tri-o-tolylphosphine or tri-tert-butylphosphine. In the case of reaction with a hexa-alkyl-distannane, the reaction is optionally carried out in the presence of an organic base, for example, a tertiary amine (e.g., triethylamine), while in the case of reaction with a dioxaborolane, the reaction is carried out in the presence of an inorganic base (e.g., cesium fluoride, or potassium acetate, preferably potassium acetate). The reaction is conveniently carried out in an appropriate inert solvent such as a polar aprotic solvent (e.g., N,N-dimethylformamide, N,N-dimethylacetamide, dimethylsulfoxide, or acetonitrile) or an aromatic hydrocarbon (e.g., toluene) at a temperature between about room temperature and about 100 degrees, and preferably at between about room temperature and about 50° C. As additional examples, the specific reaction conditions utilized in the following publications may be followed: Baudoin, O. et al. *J. Org. Chem. Soc.* 2000, 65, 9268-9271; Ishiyama, T. et al. *Tetrahedron Lett.* 1997, 38, 3447-3450; Hylarides, M. D. *J. Organomet. Chem.* 1989, 367, 259-265; Read, M. W. et al. *Org. Lett.* 2000, 2, 3201-3204; Ishiyama, T. et al. *Tetrahedron* 1997, 57, 9813-9816; Fuerster, A. et al. *Org. Lett.* 2002, 4, 541-544.

Sources of Compounds of Formula 6

Many compounds of formula 6 are commercially available and examples are shown below.

From Aldrich Chemical Company, Inc., 1001 West Saint Paul Avenue, Milwaukee, Wis. 53233, USA.: 3-chlorophenacyl bromide; 4-(trifluoromethyl)phenacyl bromide; 4-(trifluoromethoxy)phenacyl bromide; 2-bromo-1-(3-fluorophenyl)ethan-1-one; 2-bromo-2',4'-difluoroacetophenone; 2-bromo-1-(2,4-dimethylphenyl)ethan-1-one; 2-bromo-4'-iodoacetophenone; 2-bromo-3'-chloro-4'-fluoroacetophenone; 2,3'-dibromo-4'-fluoroacetophenone; 2-bromo-1-(3,5-dichloro-2-fluorophenyl)ethanone; 3,4-dichlorophenacyl bromide; 2-bromo-2',4'-dichloroacetophenone; 2-bromo-2',5'-dimethoxyacetophenone; 2-bromo-4'-methoxyacetophenone; 2,4'-dibromoacetophenone; 2-bromo-4'-chloroacetophenone; 3'-methoxyphenacyl bromide; 2-bromo-4'-fluoroacetophenone; 4-cyanophenacyl bromide; 3-bromophenacyl bromide; 2-bromo-2'-chloroacetophenone; 2-bromoacetophenone; 2-bromo-2',4'-dimethoxyacetophenone; 2-bromo-4'-methylacetophenone; and 2-bromo-2'-methoxyacetophenone.

From Alfa Aesar, 26 Parkridge Road, Ward Hill, Mass. 01835, USA: 2-(2-bromoacetyl)thiophene; 3-(trifluoromethyl)phenacyl bromide and 1,4-benzodioxan-6-yl methyl ketone.

From Apollo Scientific Ltd., Whitefield Road, Bredbury, Stockport, Cheshire SK6 2QR, United Kingdom: 2-bromo-1-(3-thienyl)-1-ethanone; 3-(2-bromoacetyl)benzonitrile; 2-bromophenacyl bromide; 2-bromo-1-(4-chloro-3-methylphenyl)ethan-1-one; 2-bromo-1-(4-pentylphenyl)ethan-1-one; 3-ethylphenacyl bromide; 3,4-difluorophenacyl bromide; 3',5'-bis(trifluoromethyl)-2-bromoacetophenone; 4-(difluoromethoxy)phenacyl bromide; 2-(trifluoromethyl) phenacyl bromide; 2-bromo-2'-fluoroacetophenone; 4-fluoro-3-(trifluoromethyl)phenacyl bromide; 2-bromo-1-(4-chloro-2-fluoro-5-methylphenyl)-1-ethanone; 2,5-difluorophenacyl bromide; 3,5-difluorophenacyl bromide; 2-(trifluoromethoxy)phenacyl bromide; 2-fluoro-4-methoxyphenacyl bromide; 2-bromo-2',3'-difluoroacetophenone; 3-fluoro-4-methoxyphenacyl bromide; 2-(difluoromethoxy)phenacyl bromide; 3-(trifluoromethoxy)phenacyl bromide; 2-chloro-5-(trifluoromethyl)phenacyl bromide; 2,4-bis(trifluoromethyl)phenacyl bromide; 2-fluoro-6-(trifluoromethyl)phenacyl bromide; 2-fluoro-3-(trifluoromethyl)phenacyl bromide; 2-fluoro-4-(trifluoromethyl)phenacyl bromide; 2-fluoro-5-(trifluoromethyl)phenacyl bromide; 3-fluoro-5-(trifluoromethyl)phenacyl bromide; 4-fluoro-2-(trifluoromethyl)phenacyl bromide; 3-fluoro-4-(trifluoromethyl)phenacyl bromide; 4-methoxy-2-(trifluoromethyl)phenacyl bromide; 4-methoxy-3-(trifluoromethyl)phenacyl bromide; 2-bromo-4'-chloro-3'-(trifluoromethyl)acetophenone; 3,4,5-trifluorophenacyl bromide; 2,4,5-trifluorophenacyl bromide; 3-fluoro-4-methylphenacyl bromide; 2-chloro-4-fluorophenacyl bromide; 2-chloro-5-fluorophenacyl bromide; 2-bromo-3'-(difluoromethoxy)acetophenone; 2,3-difluoro-4-(trifluoromethyl)phenacyl bromide; 3,4-difluoro-5-(trifluoromethyl)phenacyl bromide; 2-bromo-1-(4-bromo-2-fluorophenyl)ethanone; 2-bromo-1-(2-bromo-4-fluorophenyl)ethanone; 2-bromo-1-(3,5-difluoro-4-methoxyphenyl)ethan-1-one; 2,4-difluoro-3-(trifluoromethyl)phenacyl bromide; and 2,3-difluoro-4-methylphenacyl bromide.

From Chontech, Inc., 9 Giovanni Drive, Waterford, Conn. 06385, USA: 2-bromo-1-(3,4-dimethoxyphenyl)ethanone; 2-bromo-1-(5-fluoro-2-methoxyphenyl)ethanone; 2-bromo-1-(2,5-dichlorophenyl)ethanone; 2-bromo-1-(5-chloro-2-methoxy-phenyl)-ethanone; 2-bromo-2',3'-dichloroacetophenone; 2-bromo-3'-chloro-4'-methoxyacetophenone; 2-bromo-1-(4-fluoro-2-methoxyphenyl)ethanone; 2-bromo-2'-chloro-4'-methoxyacetophenone; 2-bromo-5'-chloro-2'-fluoroacetophenone; and 2-bromo-4'-fluoro-3'-methoxyacetophenone.

From Matrix Scientific, P.O. Box 25067, Columbia, S.C. 29224-5067, USA: 2-bromo-1-(4-methoxy-2,5-dimethylphenyl)-ethanone; 2-bromo-1-(3-bromo-2-thienyl)-1-ethanone; 2-bromo-1-(3-chloro-2-thienyl)-1-ethanone; and 2-bromo-1-(5-chloro-thiophen-2-yl)-ethanone.

From Oakwood Products, Inc., 1741 Old Dunbar Road, West Columbia, S.C. 29172, USA: 2-bromo-1-(5-bromothiophen-2-yl)ethanone; 2-bromo-1-(5-chloro-2-methoxy-4-methylphenyl)ethanone; 2-bromo-1-(3-bromo-4-methoxyphenyl)ethanone; 2-bromo-1-(5-bromo-2-methoxyphenyl)ethanone; 2-bromo-1-(3,5-dichloro-2-methoxyphenyl)ethanone; and 2-bromo-1-(2,6-dimethoxyphenyl)ethanone.

From TimTec LLC, Harmony Business Park Bldg 301-A, Newark, Del. 19711, USA: 2-bromo-1-(2-methoxy-5-methyl-phenyl)-ethanone; 2-bromo-1-(2,4,6-trimethylphenyl) ethan-1-one; 2-bromo-1-(4-ethylphenyl)ethan-1-one; 2-bromo-1-(4-ethoxyphenyl)ethanone; 2-bromo-1-(3,4,5-trimethylphenyl)ethanone; and 2-bromo-1-(2,5-dimethylphenyl)ethan-1-one.

Scheme 5

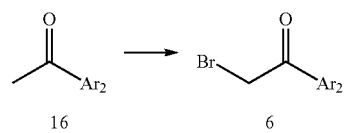

In addition to using commercially available compounds of formula 6, such compounds may be synthesized by procedures that are well known to one skilled in the art of organic synthesis. For example, a compound of this type can conveniently be synthesized according to Scheme 5 from a methyl ketone of formula 16, many of which are commercially available and which can be made using synthetic procedures that are well known to one of average skill in the art of organic synthesis (for example, by Friedel Crafts acetylation of an arene or by Stille coupling of a halo-arene with tributyl(1-ethoxyvinyl)tin followed by hydrolysis). According to this procedure, the reaction may be conveniently carried out by treating the compound of formula 16 with bromine in an inert solvent such as chloroform or 1,4-dioxane or acetic acid or diethyl ether or benzene at a temperature between about room temperature and about 40° C. Examples of specific conditions for such a reaction may be found in the literature, for example in Clive, D. L. J. et al. *J. Org. Chem.* 2003, 68, 9247-9254; in Kourounakis, A. P. et al. *Bioorg. Med. Chem.* 2010, 18, 7402-7412; in Laufer, S. A. et al. *Synthesis* 2008, 253-266; or in Perrone, R. et al. *J. Med. Chem.* 1992, 35, 3045-3049. As is well know in the field of organic chemistry, there are other brominating conditions that can be used instead of bromine to effect this reaction. Examples of such alternative conditions include tetra-n-butylammonium bromide in an inert solvent such as a mixture of methanol and dichloromethane at a temperature about room temperature; N-bromosuccinimide in carbon tetrachloride at a temperature between about room temperature and about 80° C.; and copper(II) bromide in chloroform at about 60° C. Examples of specific conditions for such reactions may be found in the literature, for example in Molino, B. F. et al. US 20060052378; in Kajigaeshi, S. et al. *Bull. Chem. Soc. Japan* 1987, 60, 1159-1160; in Tomoda, H. et al. *Bull. Chem. Soc. Japan* 1999, 72, 1327-1334; in Duan, J. et al. US 20050176716; or in Henry, R. A. et al. *J. Org. Chem.* 1990, 55, 1796-1801.

Scheme 6

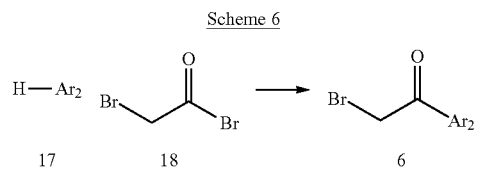

Certain compounds of formula 6 may also be made by means of a Friedel-Crafts reaction of an arene of formula 17 with bromoacetyl bromide, which has formula 18, in the presence of a Lewis acid catalyst such as aluminum chloride, in an inert solvent such as nitrobenzene or dichloromethane or DMF or carbon disulfide at a temperature of about 0° C. It is well known to one of average skill in the art of organic chemistry that the position of attachment of the bromoacetyl group in the product of this reaction of formula 6 depends on the electronics of the arene of formula 17, and so this reaction, although extremely useful for the preparation of certain compounds of formula 6, is not applicable for the synthesis of all compounds of formula 6. More information about this reaction and specifically with regard to the regiochemical outcome can be found in the literature, for example in March's Advanced Organic Chemistry: Reactions, Mechanisms, and Structure, 5th Edition (Smith, M. B.; March, J. (2001), New York: Wiley-Interscience; p 712 et seq.). Examples of specific conditions useful for this reaction can be found in the literature, for example in Yekini, I. et al. *Bioorg. Med. Chem.* 2009, 17, 7823-7830; in Calderwood, D. J. et al. US 20090270402; in Nitz, T. J. et al. US 20090215778; and in Perrone, M. G. et al. *Bioorg. Med. Chem.* 2008, 16, 2473-2488.

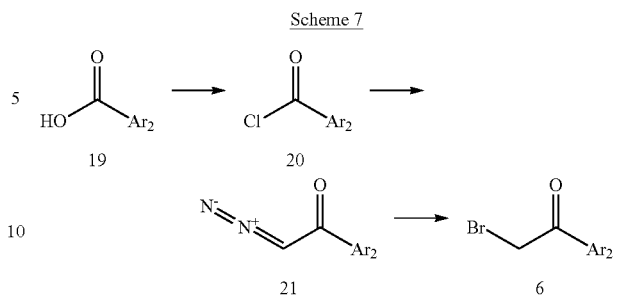

Another alternative synthesis of the compounds of formula 6 is shown in Scheme 7. This synthesis starts with the arene-carboxylic acid of formula 19, many examples of which are commercially available, or compounds that may be synthesized using known procedures. The compound of formula 19 may be treated with a chlorinating agent such as oxalyl chloride or thionyl chloride or phosphorus oxychloride either neat or in an inert solvent such as benzene or dichloromethane at a temperature between about room temperature and about the boiling point of the selected solvent, to give the acid chloride of formula 20. The acid chloride may then be treated with diazomethane or trimethylsilyldiazomethane in an inert solvent such as dichloromethane or diethyl ether or a mixture of tetrahydrofuran and acetonitrile at a temperature around 0° C. to give the diazoketone of formula 21. Without isolation, this compound may then be treated with 30% hydrogen bromide in acetic acid to give the bromomethylketone of formula 6. Examples of specific conditions useful for this reaction can be found in the literature, for example in Illig, C. R. et al. U.S. Pat. No. 6,291,514; in Wager, T. T. et al. WO 2008026046; in Dunn, J. P. et al. U.S. Pat. No. 7,166,738; in Melander, C. et al. US 20090270475; and in Huigens, R. W. III et al. *Bioorg, Med. Chem.* 2010, 18, 663-674.

Sources of Compounds of Formula HNR1R2

Many compounds of formula HNR1R2 are commercially available and examples are shown below.

From Acros Organics BVBA, Janssen Pharmaceuticalaan 3 A, 2440 Geel, Belgium: 2,5-dimethylpyrrolidine; piperidine; (tetrahydrofuran-3-yl)methanamine; 4-aminomethyltetrahydropyran; 4-fluorobenzylamine; 3-methylbenzylamine; 3,5-difluorobenzylamine; 3-methoxybenzylamine; 2,5-dimethylbenzylamine; 2-fluoro-5-methylbenzylamine; 3-fluoro-5-methylbenzylamine; 3-fluoro-2-methylbenzylamine; 2-fluoro-4-methylbenzylamine; 4-fluoro-2-methylbenzylamine; 2-bromophenethylamine; 3-bromophenethylamine; 2-(3-chlorophenyl)ethylamine; 2-methylphenethylamine; 4-methylphenethylamine; and 3-methylphenethylamine.

From Aldrich Chemical Company, Inc., 1001 West Saint Paul Avenue, Milwaukee, Wis. 53233, USA.: pyrrolidine; morpholine; 4-aminotetrahydropyran; tetrahydrofurfurylamine; 2-thiophenemethylamine; 4-chlorobenzylamine; benzylamine; 2-chloro-5-(trifluoromethyl)benzylamine; 4-(2-aminoethyl)pyridine; 4-methoxybenzylamine; 4-bromo-alpha-methylbenzylamine; 1-(4-fluorophenyl)ethylamine; (R)-(+)-1-phenylethylamine; (S)-(−)-1-phenylethylamine; (S)-(−)-1-(4-methoxyphenyl)ethylamine; 4-chloro-alpha-methylbenzylamine; (S)-1-(3-chlorophenyl)ethanamine; 4-isopropylphenethylamine hydrochloride; 2-(4-trifluoromethyl-phenyl)-ethylamine; 2,3-dimethoxyphenethylamine; 4-fluorophenethylamine hydrochloride; 3,4-difluoro-benzeneethanamine; and 2,4-difluorophenethylamine.

From Alfa Aesar, 26 Parkridge Road, Ward Hill, Mass. 01835, USA: 2-methylpyrrolidine; 1-acetyl-piperazine; (3-methyl-2-thienyl)methylamine; 2,4-difluorobenzylamine; 2,6-difluorobenzylamine; 3-chlorobenzylamine; 3-(trifluoromethyl)benzylamine; 3,5-bis(trifluoromethyl)benzylamine; and 2,3-difluorobenzylamine From Apollo Scientific Ltd., Whitefield Road, Bredbury, Stockport, Cheshire SK6 2QR, United Kingdom: 4-(2-aminethyl)tetrahydropyran; (4-methyl-2-thienyl)methylamine; 2-fluoro-5-(trifluoromethyl)benzylamine; 2-fluoro-5-(trifluoromethyl)benzylamine; 3-(trifluoromethyl)benzylamine; 4-(trifluoromethyl)benzylamine; 1-(2-trifluoromethylphenyl)ethylamine; and 1-(3-trifluoromethylphenyl)ethylamine.

From Matrix Scientific, P.O. Box 25067, Columbia, S.C. 29224-5067, USA: 1-acetylpiperidin-4-amine; tetrahydro-2H-pyran-3-methanamine; 1-(7-oxabicyclo[2.2.1]hept-2-yl)methanamine; 2-(tetrahydro-pyran-2-yl)-ethylamine; 2-tetrahydrofuran-2-ylethanamine; (5-chlorothiophen-2-yl)methanamine; 3,5-dimethylbenzylamine; 3-fluoro-4-methylbenzylamine; 4-cyanobenzylamine; 2,5-difluorobenzylamine; 3-fluorobenzylamine; 1-(4-methoxyphenyl)ethanamine; 1-(2-methoxy-phenyl)-ethylamine; 1-(3-methoxyphenyl)ethanamine; 1-(3,4-dichlorophenyl)ethanamine; 1-(3,4-dimethyl-phenyl)-ethylamine; 1-(4-tert-butylphenyl)ethanamine; and 1-(3-bromophenyl)ethanamine.

From Oakwood Products, Inc., 1741 Old Dunbar Road, West Columbia, S.C. 29172, USA: (tetrahydrofuran-3-yl)methanamine; tetrahydropyran-2-ylmethylamine; (1-methyl-1H-pyrazol-5-yl)methylamine; 1-(1-ethyl-1H-pyrazol-5-yl)methanamine; 5-fluoro-2-methylbenzylamine; 3,4-dimethylbenzylamine; 4-isopropylbenzylamine; 2,3-dimethylbenzylamine; 4-chloro-3-(trifluoromethyl)benzylamine; 1-pyridin-3-yl-ethylamine; 4-fluoro-3-methylbenzylamine; (2-[2-(trifluoromethoxy)phenyl]ethyl)amine; and 3-ethoxyphenethylamine.

From TimTec LLC, Harmony Business Park Bldg 301-A, Newark, Del. 19711, USA: 3-aminotetrahydrofuran; 2-(tetrahydro-2H-pyran-3-yl)ethanamine; 2-fluorobenzylamine; 2-methoxybenzylamine; 2,4-dimethylbenzylamine; 4-ethylbenzylamine; 2,4,6-trimethylbenzylamine; 2-(aminomethyl)benzonitrile; 4-propylbenzylamine; 2,6-dimethylbenzylamine; 1-pyridin-4-yl-ethylamine; 3-cyanobenzylamine; 1-(2',4'-difluorophenyl)ethylamine; and 1-[4-(difluoromethoxy)phenyl]ethylamine.

From TCI America, 9211 N. Harborgate Street, Portland, Oreg. 97203, USA: 4-hydroxypiperidine; 3,4-difluorobenzylamine; 2-chlorobenzylamine; 4-methylbenzylamine; 2-(aminomethyl)pyridine; 3-(aminomethyl)pyridine; 4-(aminomethyl)pyridine; 3-(2-aminoethyl)pyridine; 2-(2-aminoethyl)pyridine; DL-alpha-methylbenzylamine; 2-methylbenzylamine; 4-bromophenethylamine; 2,6-dichlorophenethylamine; 3,4-dichlorophenethylamine; 2,4-dichlorophenethylamine; 2-(3,4-dimethoxyphenyl)ethylamine; and 2-(2-chlorophenyl)ethylamine.

Many amines of formula HNR1R2 may be prepared using one of a variety of methods known to one of average skill in the art of organic synthesis. Many of these methods are enumerated in "The Chemistry of the Amino Group" [M. S. Gibson; S. Patai Ed.; John Wiley & Sons, Ltd. London 1968, 37-77], in "Advanced Organic Chemistry" [J. March, 3rd Edition, John Wiley & Sons, Inc. New York, 1985], on pages 1153-1154, and in "Comprehensive Organic Transformations: A Guide to Functional Group Preparations" [R. C. Larock, VCH Publishers, Inc. New York, 1989] on pages 1061-1063.

Amines of formula HNR1R2 where R1 is hydrogen and R2 is cycloalkyl or heterocycloalkyl may be made from a cyclic ketone by treating the ketone with hydrogen and ammonia in the presence of a noble metal catalyst such as palladium or ruthenium, either of which may optionally be supported on carbon, in the optional additional presence of ammonium chloride at a temperature of about 200° C. Exact conditions for such a reaction may be found in the literature, for example in T. Ikenaga et al. *Tetrahedron* 2005, 61, 2105-2109.

Amines of formula HNR1R2 which are substituted piperidine derivatives may be made by the catalytic hydrogenation of substituted pyridines. The reaction may be conveniently carried out by treating the pyridine derivative with hydrogen gas at a hydrogen pressure between about 1 atmosphere and about 30 atmospheres in the presence of a noble metal catalyst such as platinum on charcoal or platinum oxide or palladium on carbon in a mixture of ethanol and hydrochloric acid or in acetic acid or ethyl acetate or methanol at a temperature between about room temperature and about 50° C. Examples of precise conditions that may be used to carry out this reaction may be found in the literature, for example in Graf, C. D. et al. US 20110015400; in Boström, J. et al. US 20100261755; in Carpenter, A. J. et al. WO 2010014593; or in Motterle, R. et al. WO 2010100215.

Amines of formula HNR1R2 which are substituted morpholine derivatives may be made using a number of reactions sequences that are known in the art of organic synthesis. For example, substituted morpholine derivative may be made from a substituted allyloxy-alkyl azide by oxidizing the alkene by treating it with osmium tetroxide or potassium osmate, either stoichiometrically or using a stoichiometric oxidant such as N-methylmorpholine N-oxide, in a mixture of acetone and water at about room temperature, followed by treatment with sodium periodate in a mixture of acetone and water at about room temperature, followed by hydrogenation in the presence of a noble metal catalyst such as palladium-on carbon in methanol at about room temperature. Examples of precise conditions that may be used to carry out this reaction may be found in the literature, for example in Sawant, R. T. and Waghmode, S. B. *Tetrahedron* 2010, 66, 2010-2014.

Amines of formula HNR1R2 where R1 is hydrogen and R2 is cycloalkyl or heterocycloalkyl may be made from a cycloalkene by treating the cycloalkene with borane-tetrahydrofuran complex in an inert solvent such as tetrahydrofuran at about room temperature to form the corresponding organoborane, and then treating this material with chloramine in the presence of aqueous sodium hydroxide. Alternatively, the organoborane may be treated with hydroxylamine-O-sulfonic acid in diglyme at about 100° C. to give the amine of formula HNR1R2. Exact conditions for such a reaction may be found in the literature, for example in Brown, H. C. et al. *Tetrahedron* 1987, 43, 4071-4078.

Amines of formula HNR1R2 where R1 is hydrogen and R2 is cycloalkyl or heterocycloalkyl may be made from an alcohol of formula R2OH by conversion to the corresponding azide of formula $R2N_3$, and subsequent reduction of the azide. Displacement of the hydroxyl group of the alcohol of formula R2OH to give the corresponding azido analogue can be achieved by treating a mixture of the alcohol of formula R2OH and diphenylphosphoryl azide (DPPA) with 1,8-diazabicyclo[5.4.0]undec-7-ene (DBU) under anhydrous conditions at a temperature between about 0° C. and about 10° C. for approximately 18 hours in an inert solvent such as toluene or N,N-dimethylformamide. Exact conditions for carrying out such as reaction can be found in the literature, for example in Bremond, P. et al. *Synthesis* 2009, 290-296; in Wyrebek, P. et al. *Tetrahedron* 2009, 65, 1268-1275; in Ryu, H. et al. *J.*

Med. Chem. 2008, 51, 57-67; or in Izquierdo, I. et al. *Tetrahedron* 2006, 63, 1440-1447. Hydrogenation the above azido derivative to give the corresponding amine of formula HNR1R2 where R1 is hydrogen and R2 is cycloalkyl or heterocycloalkyl can be carried out in the presence of 5% palladium on carbon under a pressure of hydrogen between about atmospheric pressure and about 350 psi, at room temperature for 1.5 hour, in an organic solvent such as ethyl acetate, methanol, or ethanol. Exact conditions for carrying out such as reaction can be found in the literature, for example in Enomoto, M. and Kuwarahara, S. *Angew. Chem. Intl. Edn. Engl.* 2009, 48, 1144-1148; in Ooi, T. et al. US 2009131716; in Wang, X. et al. *Tetrahedron* 2007, 63, 6141-6145; or in Ciliberti, N. et al. *Bioorg. Med. Chem.* 2007, 15, 3065-3081. Alternatively, the reduction of the azide group to give the amine of formula HNR1R2 where R1 is hydrogen and R2 is cycloalkyl or heterocycloalkyl can be achieved by treating the azide with triphenylphosphine in an inert solvent such as tetrahydrofuran in the presence of water at a temperature between about room temperature and about 65° C. Exact conditions for carrying out such as reaction can be found in the literature, for example in Han, B. et al. WO 2008148689; in Liu, G. et al. *Org. Lett.* 2009, 11, 1143-1146; in Wang, X. et al. *Tetrahedron* 2007, 63, 6141-6145; or in Shimada, I. et al. *Bioorg. Med. Chem.* 2008, 16, 1966-1982.

Amines of formula HNR1R2 where R1 is hydrogen and R2 is optionally substituted benzyl may be conveniently prepared by catalytic hydrogenation of benzonitriles. According to this process, the nitrile of formula ArCN where the aryl group Ar represents the aromatic portion of the benzyl group R2, is treated with hydrogen in the presence of a noble metal catalyst such as palladium, nickel or cobalt, in an inert solvent such as ethanol at about room temperature. Exact conditions for carrying out such a reaction can be found in the literature, for example in Hegedus, L. et al. *Appl. Catal. A.* 2005, 296, 209-215; or in Gould, F. E. et al. *J. Org. Chem.* 1960, 25, 1658-1660. Alternatively, the reduction of the nitrile of formula ArCN where the aryl group Ar represents the aromatic portion of the benzyl group R2 may be carried out at elevated hydrogen pressure such as at about 50 bar in the presence of a homogeneous catalyst such as a mixture of bis(2-methylallyl)-1,5-cyclooctadieneruthenium(II), 1,1-bis(diphenylphosphino)ferrocene, and potassium tert-butoxide in toluene at about 80° C. using conditions similar to those disclosed in Enthaler, S. et al. *Chem. Eur. J.* 2008, 14, 9491-9494. As a further alternative, the reduction of the nitrile of formula ArCN where the aryl group Ar represents the aromatic portion of the benzyl group R2 may be carried out by treating the nitrile with diisopropylaminoborane in the presence of catalytic amounts of lithium borohydride in an inert solvent such as tetrahydrofuran at a temperature about room temperature, using conditions similar to those disclosed in Haddenham, D. et al. *J. Org. Chem.* 2009, 74, 1964-1970.

An example of a different method that can be used to prepare amines of formula HNR1R2 where R1 is hydrogen and R2 is optionally substituted benzyl is the conversion of a benzyl halide to a benzyl azide, followed by reduction of the azide to give the benzylamine. According to this process, the benzyl halide of formula R2X where X represents a leaving group such as a halide (for example, bromine, chlorine, iodine), alkyl or aryl sulfonate ester (for example, methane sulfonate or toluene sulfonate) is reacted with an alkali metal azide salt such as sodium azide in an inert solvent such as dimethylsulfoxide or ethanol at between about room temperature and about 80° C. Exact conditions for carrying out such as reaction can be found in the literature, for example in Zhao, Y. et al. *Bioorg. Med. Chem.* 2008, 16, 6333-6337 (supplementary material); in Compain-Batissou, M. et al. *Heterocycles* 2007, 71, 27-38; or in Tegtmeier, F. et al. US 20080044354. The resulting azide group can be reduced using conditions that are similar to those described above.

A further example of a method that can be used to prepare amines of formula HNR1R2 where R1 is hydrogen and R2 is optionally substituted benzyl involves reductive amination of a benzaldehyde derivative, where a benzaldehyde derivative is reacted with ammonia or an acid addition salt of ammonia such as ammonium chloride or ammonium acetate and the resulting imine is reduced to give the compound of formula HNR1R2. The reduction can be carried out using hydrogenation under noble metal catalysis, or it can be carried out by treating the imine with a reducing agent such as sodium borohydride or sodium cyanoborohydride or preferably sodium triacetoxyborohydride. The imine formation and reduction can be carried out as two separate steps, or they can be combined in a single step. The one-step approach is convenient and is well known to one of average skill in the art of organic synthesis. A review on this reaction with particular focus on the use of sodium triacetoxyborohydride as the reducing agent has recently been published (Abdel-Magid, A. F. and Mehrman, S. J. *Org. Process Res. Dev.* 2006, 10, 971-1031). The reaction is conveniently carried out by treating the benzaldehyde derivative with ammonium acetate in an inert solvent such as a halogenated hydrocarbon (for example dichloromethane or 1,2-dichloroethane) in the optional additional presence of an agent that absorbs water such as molecular sieves at about room temperature. A reducing agent such as sodium cyanoborohydride or preferably sodium triacetoxyborohydride is added either at the same time as the benzaldehyde derivative and ammonium acetate are combined, or after an interval, such as about one hour. Examples of conditions that can be used for this reaction can be found in the literature, for example in Sallem, W. et al. *Bioorg. Med. Chem.* 2006, 14, 7999-8013; in Brown, W. et al. WO 2006014133; in Bogatcheva, E. et al. *J. Med. Chem.* 2006, 49, 3045-3048; and in Boschelli, D. H. et al. *J. Med. Chem.* 2004, 47, 6666-6668.

Amines of formula HNR1R2 where R1 is hydrogen and R2 is optionally substituted 2-phenylethyl may be conveniently prepared by carrying out a Curtius rearrangement on a hydrocinnamic acid derivative, many examples of which are commercially available, or can be prepared easily for example by carrying out a Knoevenagel or related reaction of a benzaldehyde with a malonate derivative and then hydrogenating and decarboxylating the resulting intermediate. According to this procedure, the hydrocinnamic acid derivative is treated with diphenylphosphoryl azide and an organic base such as triethylamine or diisopropylethylamine in tert-butanol at a temperature about 80° C. to give a tert-butoxycarbonyl-protected 2-phenylethylamine derivative. Examples of precise conditions that can be used for this reaction can be found in the literature, for example in Matsumoto, T. et al. U.S. Pat. No. 6,911,468; in Yoshida, I. and Suzuki, S. U.S. Pat. No. 7,217,723; in Keil, S. et al. U.S. Pat. No. 7,655,679; and in Tsang, K. Y. et al. *J. Am. Chem. Soc.* 1994, 116, 3988-4005. The tert-butoxycarbonyl protective group may be conveniently removed by treatment of the compound of the intermediate carbamate with trifluoroacetic acid in dichloromethane at about room temperature, or it can be removed by treatment of the tert-butyl carbamate with hydrochloric acid in an alcoholic solvent (e.g., methanol or ethanol) or an ether (e.g., dioxane) or ethyl acetate, also at about room temperature. Exact conditions for such a reaction may be found in the literature, for example in Bartel, S. et al. US 20100029772; in Thompson, T. and Willis, P. US 20080146612; in Ford, R. et al. US 20080153850; and in Hirashima, S. et al. *J. Med. Chem.* 2006, 49, 4721-4736.

Abbreviations

The following abbreviations are used in the experimental section below:
br broad
$CDCl_3$ deuterated chloroform
$CH_2Cl_2$ dichloromethane
cm centimeters
Conc concentrated
DMF N,N-dimethylformamide
DMSO dimethylsulfoxide
DMSO-$d_6$ deuterated dimethyl sulfoxide
DTT dithiothreitol
EDTA ethylenediamine tetraacetic acid
EtOAc ethyl acetate
EtOH ethanol
g grams
h hours
$H_2O$ water
HCl hydrochloric acid
His histidine
HPLC high performance liquid chromatography
HPLC/MS high performance liquid chromatography/mass spectrometry
Hz Hertz
LCMS liquid chromatography/mass spectrometry
LiOH lithium hydroxide
LRMS low resolution mass spectrum
M molar
m/z Mass divided by charge
mBar millibar
MeOH methanol
mg milligrams
$MgSO_4$ magnesium sulfate
MHz megahertz
min minutes
mL milliliters
mM millimolar
mmol millimoles
mol moles
$N_2$ nitrogen
$Na_2CO_3$ sodium carbonate
$Na_2SO_4$ sodium sulfate
NaCl sodium chloride
$NaHCO_3$ sodium hydrogen carbonate
NaOH sodium hydroxide
nm nanometers
NMR nuclear magnetic resonance
Pd(dppf)$Cl_2$ 1,1'-bis(diphenylphosphino)ferrocene]dichloropalladium(II)
Pd(PPh$_3$)$_4$ tetrakis(triphenylphosphine)palladium(0)
ppm parts per million
q quartet
qd quartet of doublets
quin quintet
s singlet
sat saturated
spec spectrometry
t triplet
TFA trifluoroacetic acid
THF tetrahydrofuran
UV ultraviolet
μL microliters HPLC Purification Conditions A Compounds were purified using a mass-directed HPLC/MS system using Shimadzu LC-8A pumps and a Shimadzu 2020 mass spec (Shimadzu Scientific Instruments). The samples were applied on a Sunfire C-18 (3×10 cm) column (Waters Corporation), and elution was carried out using a linear gradient solvent system of (A) 0.05% TFA/$H_2O$ and (B) 0.05% TFA/Acetonitrile over 20 min. The collected fractions were pooled, evaporated, and lyophilized.

HPLC Purification Conditions B

Compounds were purified using a mass-directed HPLC/MS system using Shimadzu LC-8A pumps (Shimadzu Scientific Instruments) and a PE Sciex 150 EX mass spec (Perkin Elmer). The samples were applied on a Varian Pursuit C-18 (2×10 cm) column (Varian, Inc.), and elution was carried out using a linear gradient solvent system of (A) 0.05% TFA/$H_2O$ and (B) 0.05% TFA/Acetonitrile over 20 min. The collected fractions were pooled, evaporated, and lyophilized.

Pharmaceutical Compositions and Administration

Another embodiment of the invention provides pharmaceutical compositions or medicaments containing the compounds of the invention and a therapeutically inert carrier, diluent or excipient, as well as methods of using the compounds of the invention to prepare such compositions and medicaments. In one example, the compounds of the invention may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the invention is formulated in an acetate buffer, at pH 5. In another embodiment, the compounds of the invention are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 1 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An embodiment, therefore, includes a pharmaceutical composition comprising a compound of the invention as set forth above or a stereoisomer or pharmaceutically acceptable salt thereof. A further embodiment includes a pharmaceutical composition comprising a compound of the invention or a stereoisomer or pharmaceutically acceptable salt thereof, together with a pharmaceutically acceptable carrier or excipient.

Another embodiment includes a pharmaceutical composition comprising a compound of the invention for use in the treatment of a hyperproliferative disease. Another embodiment includes a pharmaceutical composition comprising a compound of the invention for use in the treatment of cancer.

The compounds of the inhibit binding of eIF4E to eIF4G. Accordingly, the compounds of the invention are useful for inhibition of cellular proliferation and induction of apoptosis in cancer cells. Thus, the compounds of the invention may be useful for the treatment of cancer in mammals, and in particular humans.

PREPARATION OF INTERMEDIATES

Intermediate 1

2-Amino-5-cyano-benzoic acid methyl ester

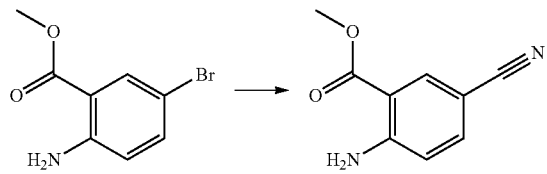

Copper(I) cyanide (available from Alfa Aesar; 10.71 g, 0.12 mol) was added to a stirred solution of methyl 2-amino-5-bromobenzoate (available from Aldrich Chemical Company, Inc.; 25.0 g, 0.11 mol) in N-methyl-2-pyrrolidone (50 mL) and the mixture was stirred at 180° C. for 4 h. The reaction mixture was cooled to room temperature, diluted with aqueous ethylenediamine (water:ethylenediamine=1:1; 250 mL), and filtered through pad of Celite. The filtrate was extracted with EtOAc (3×100 mL), and the combined organic layers were washed with water (100 mL) and brine (100 mL), dried over sodium sulfate, filtered, evaporated under reduced pressure, and purified by silica gel chromatography (100-200 mesh), using 5-10% ethyl acetate/hexanes as eluent, to give 2-amino-5-cyanobenzoic acid methyl ester (14.0 g, 73%) as a yellow powder. $^1$H NMR (400 MHz, DMSO-d$_6$) δ 8.05 (d, J=1.9 Hz, 1H), 7.57 (dd, J=1.9, 8.8 Hz, 1H), 7.44 (br s, 2H), 6.88 (d, J=8.8 Hz, 1H), 3.81 (s, 3H).

Intermediate 2

2-Bromo-5-cyano-benzoic acid methyl ester

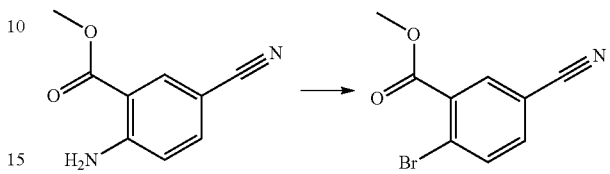

tert-Butyl nitrite (available from Aldrich Chemical Company, Inc.; 13.4 mL, 0.11 mol) was added dropwise to a suspension of copper(II) bromide (available from Aldrich Chemical Company, Inc.; 21.32 g, 0.10 mol) in acetonitrile (300 mL) at 0° C. and the mixture was stirred for 5 min. 2-Amino-5-cyano-benzoic acid methyl ester (which may be prepared as described for Intermediate 1; 14.0 g, 79.5 mmol) was added in portions and the mixture was stirred for 2 h at 0° C. and then at room temperature for 16 h. The reaction mixture was concentrated to half its volume, and then made acidic to pH 2 (approximately) by the addition of 1 M HCl. The mixture was extracted with ethyl acetate (3×100 mL) and the combined organic extracts were dried over sodium sulfate, filtered, and evaporated to give 2-bromo-5-cyano-benzoic acid methyl ester (18.0 g, 94%) as a yellow solid. $^1$H NMR (400 MHz, DMSO-d$_6$) δ 8.23 (d, J=1.9 Hz, 1H), 8.00 (d, J=8.3 Hz, 1H), 7.93 (dd, J=2.0, 8.3 Hz, 1H), 3.89 (s, 3H).

Intermediate 3

4-Cyano-2'-nitro-biphenyl-2-carboxylic acid methyl ester

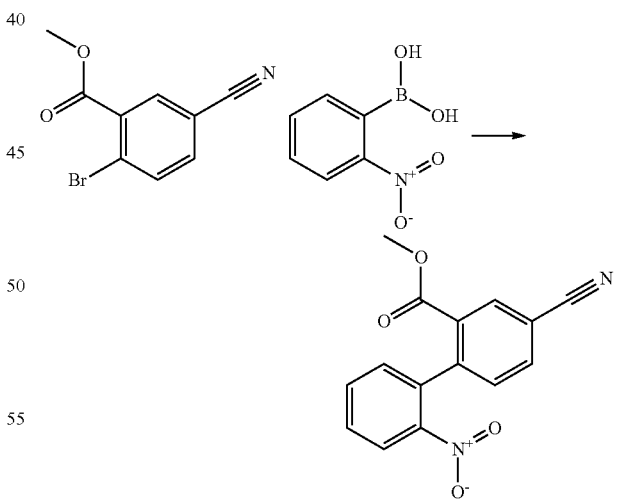

A mixture of 2-bromo-5-cyano-benzoic acid methyl ester (which may be prepared as described for Intermediate 2; 17.4 g, 72.6 mmol), 2-nitrophenylboronic acid (available from Aldrich Chemical Company, Inc.; 13.2 g, 79.9 mmol), Pd(dppf)Cl$_2$ (available from Aldrich Chemical Company, Inc.; 7 g, 8.7 mmol) and K$_2$CO$_3$ (29.9 g, 218 mmol) in a mixture of water (26.5 mL) and dioxane (530 mL) was heated at reflux for 3.5 h. The reaction mixture was cooled and evaporated to dryness. The residue was co-evaporated with toluene, and then purified by silica gel chromatography, using 20-33% ethyl acetate/petroleum ether as eluent, to give 4-cyano-2'-nitro-biphenyl-2-carboxylic acid methyl ester (10.4 g, 51%). $^1$H NMR (300 MHz, CDCl$_3$) δ 8.38 (d, J=1.7 Hz, 1H), 8.20 (d, J=8.0 Hz, 1H), 7.88-7.83 (m, 1H), 7.71-7.57 (m, 2H), 7.37 (d, J=7.9 Hz, 1H), 7.30-7.22 (m, 1H), 3.71 (s, 3H).

Intermediate 4

2'-Nitro-4-thiocarbamoyl-biphenyl-2-carboxylic acid methyl ester

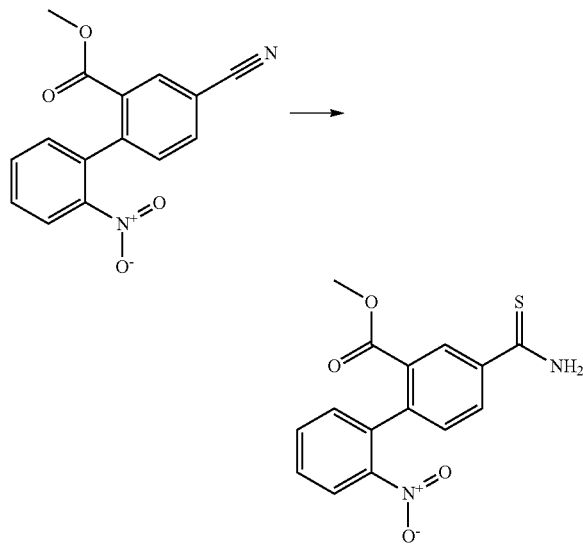

O,O'-Diethyl dithiophosphate (available from Aldrich Chemical Company, Inc.; 6.85 g, 36.8 mmol) was added to a solution of compound 4-cyano-2'-nitro-biphenyl-2-carboxylic acid methyl ester (which may be prepared as described for Intermediate 3; 8.62 g, 30.5 mmol) in a mixture of THF (96 mL) and water (24 mL). The resulting mixture was stirred at 80° C. for 45 h and then evaporated to a small volume. Ethyl acetate (500 mL) was added and the mixture was washed with water (250 mL) and sat. NaHCO$_3$ (250 mL), dried over anhydrous sodium sulfate, filtered, evaporated, and purified by silica gel chromatography, using 17-50% ethyl acetate/petroleum ether as eluent, to give 2'-nitro-4-thiocarbamoyl-biphenyl-2-carboxylic acid methyl ester (5.0 g, 52%). $^1$H NMR (300 MHz, CDCl$_3$) δ 8.50 (d, J=2.1 Hz, 1H), 8.18-8.15 (m, 2H), 7.70-7.54 (m, 3H), 7.32 (s, 1H), 7.30 (s, 1H), 7.24 (d, J=1.2 Hz, 1H), 3.69 (s, 3H).

Intermediate 5

2-bromo-5-thiocarbamoyl-benzoic acid methyl ester

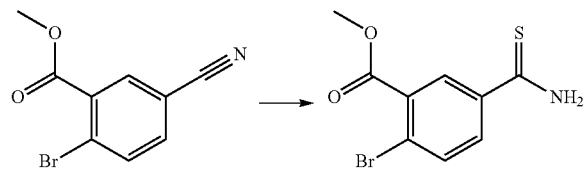

Phosphorus pentasulfide (available from Aldrich Chemical Company, Inc.; 3.33 g, 750 mmol) in EtOH (1000 mL) was stirred at room temperature for 30 min and then 2-bromo-5-cyanobenzoic acid methyl ester (which may be prepared as described for Intermediate 2; 36.0 g, 150 mmol) was added. The mixture was stirred at room temperature overnight. The solvent was evaporated and ethyl acetate was added. The mixture was washed with three times water, and the solvent was evaporated from the organic layer to give a mixture of a yellow liquid and a solid. The solid was filtered off to give 2-bromo-5-thiocarbamoyl-benzoic acid methyl ester (36.13 g, 83%) as a light yellow solid.

Intermediate 6

2-Bromo-5-[4-(3,4-dichloro-phenyl)-thiazol-2-yl]-benzoic acid methyl ester

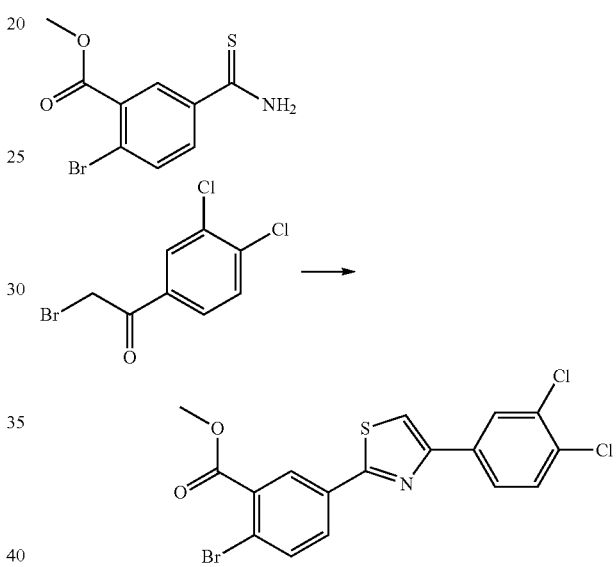

A mixture of 2-bromo-5-carbamothioylbenzoic acid methyl ester (which may be prepared as described for Intermediate 5; 13.7 g, 50 mmol) and 2-bromo-3',4'-dichloroacetophenone (available from Aldrich Chemical Company, Inc.; 13.5 g, 50.5 mmol) in EtOH (200 mL) was heated at 70° C. overnight. The solid was filtered off to give 2-bromo-5-[4-(3,4-dichloro-phenyl)-thiazol-2-yl]-benzoic acid methyl ester (18.14 g, 82%).

Intermediate 7

4-[4-(3,4-Dichloro-phenyl)-thiazol-2-yl]-biphenyl-2,4'-dicarboxylic acid 4'-tert-butyl ester 2-methyl ester

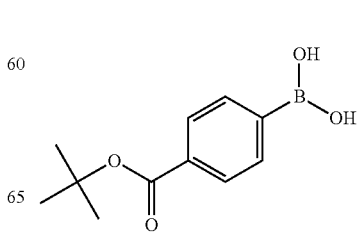

-continued

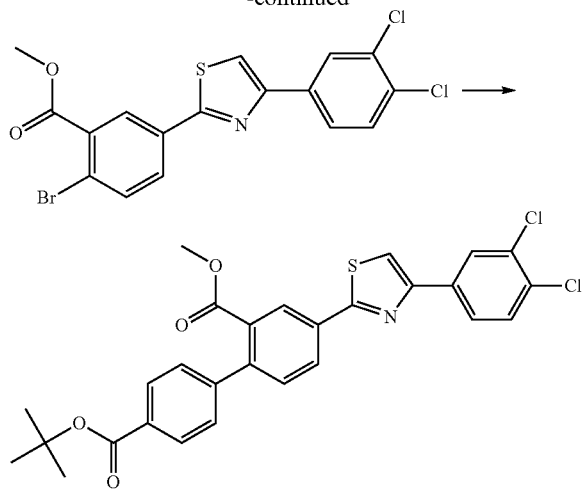

The reaction was carried out in two batches. The reaction mixtures were combined and then purified together.

First Batch:

Argon was bubbled through a mixture of 2-bromo-5-[4-(3,4-dichloro-phenyl)-thiazol-2-yl]-benzoic acid methyl ester (which may be prepared as described for Intermediate 6; 6.00 g, 13.5 mmol), 4-(tert-butoxycarbonyl)phenylboronic acid (available from Combi-Blocks Inc.; 5.1 g, 23 mmol), Pd(PPh$_3$)$_4$ (available from Aldrich Chemical Company, Inc.; 1.05 g, 0.91 mmol), and aqueous potassium carbonate (2 M; 31.3 mL, 62.6 mmol) in 1,4-dioxane (200 mL) for 25 min. The mixture was heated to 95-100° C. overnight. An additional portion of 4-(tert-butoxycarbonyl)phenylboronic acid (available from Combi-Blocks Inc.; 1.2 g, 5.4 mmol) was added and the mixture was heated for a further 4 h. The mixture was allowed to cool.

Second Batch:

Argon was bubbled through a mixture of 2-bromo-5-[4-(3,4-dichloro-phenyl)-thiazol-2-yl]-benzoic acid methyl ester (which may be prepared as described for Intermediate 6; 2.00 g, 4.5 mmol), 4-(tert-butoxycarbonyl)phenylboronic acid (available from Combi-Blocks Inc.; 2.00 g, 9.0 mmol), Pd(PPh$_3$)$_4$ (available from Aldrich Chemical Company, Inc.; 420 mg, 0.36 mmol), and aqueous potassium carbonate (2 M; 12.5 mL, 25 mmol) in 1,4-dioxane (62.7 mL) for 25 min. The mixture was heated to 95-100° C. overnight and then allowed to cool.

Workup and Purification:

The two reaction mixtures were combined and water was added. The mixture was extracted with ethyl acetate, and the organic extract was washed with water and brine, dried over anhydrous sodium sulfate, filtered, and evaporated to give a tan foam (17.1 g). This material was purified by flash chromatography (silica gel, 220 g column, 0-40% CH$_2$Cl$_2$/hexanes over 35 min). Fractions containing the product were evaporated to give 4-[4-(3,4-dichloro-phenyl)-thiazol-2-yl]-biphenyl-2,4'-dicarboxylic acid 4'-tert-butyl ester 2-methyl ester (7.6 g, 78%) as an off-white solid. $^1$H NMR (300 MHz, DMSO-d$_6$) δ ppm 8.51 (s, 1H), 8.44 (s, 1H), 8.36 (s, 1H), 8.32 (d, J=8.1 Hz, 1H), 8.11 (d, J=6.6 Hz, 1H), 8.00 (d, J=8.1 Hz, 2H), 7.80 (d, J=8.5 Hz, 1H), 7.66 (d, J=8.1 Hz, 1H), 7.51 (d, J=8.3 Hz, 2H), 3.71 (s, 3H), 1.60 (s, 9H).

Intermediate 8

4-[4-(3,4-Dichloro-phenyl)-thiazol-2-yl]-biphenyl-2,4'-dicarboxylic acid 2-methyl ester

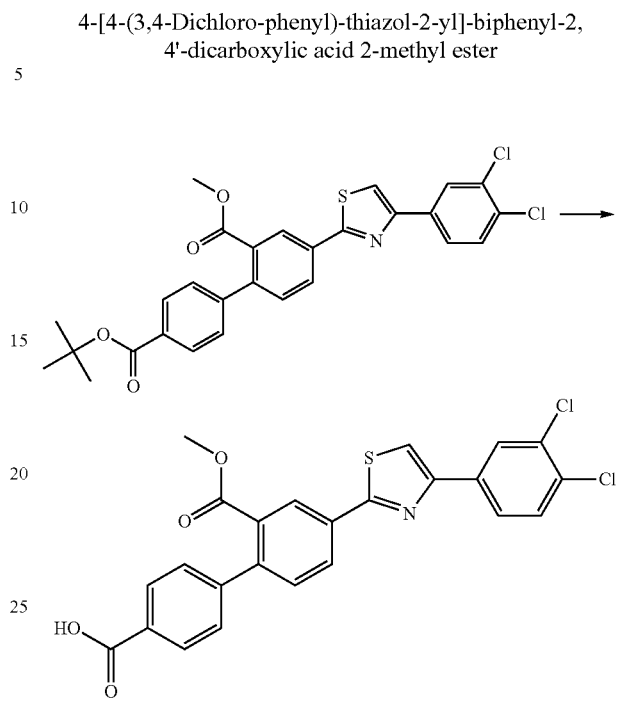

Trifluoroacetic acid (8.3 mL, 108 mmol) was added to a solution of 4-[4-(3,4-dichloro-phenyl)-thiazol-2-yl]-biphenyl-2,4'-dicarboxylic acid 4'-tert-butyl ester 2-methyl ester (which may be prepared as described for Intermediate 7; 5.8 g, 10.7 mmol) in CH$_2$Cl$_2$ (25 mL) at 0-5° C. The mixture was allowed to warm to room temperature and stir for 3 h. The resulting solution was concentrated under a stream of nitrogen and then dried under high vacuum to give 4-[4-(3,4-dichloro-phenyl)-thiazol-2-yl]-biphenyl-2,4'-dicarboxylic acid 2-methyl ester (5.1 g, 98%) as a tan solid. $^1$H NMR (400 MHz, DMSO-d$_6$) δ ppm 13.08 (br s, 1H), ppm 8.49 (s, 1H), 8.42 (s, 1H), 8.35 (s, 1H), 8.30 (d, J=8.0 Hz, 1H), 8.10 (d, J=8.3 Hz, 1H), 8.02 (d, J=8.0 Hz, 2H), 7.77 (d, J=8.5 Hz, 1H), 7.66 (d, J=8.0 Hz, 1H), 7.49 (d, J=8.3 Hz, 2H).

General Procedures

General Procedure A for Suzuki Coupling and Hydrolysis in Parallel Mode

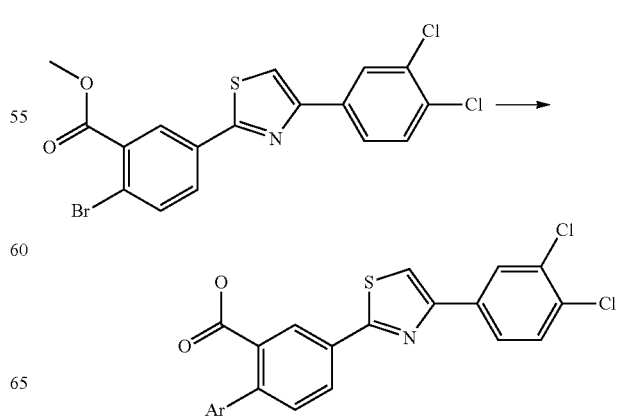

32 reactions were run at a time in parallel mode as follows: Each vial was charged with an arylboronic acid or the pinacol ester thereof (0.5 mmol), 2-bromo-5-[4-(3,4-dichloro-phenyl)-thiazol-2-yl]-benzoic acid methyl ester (which may be prepared as described for Intermediate 6; 111 mg, 0.25 mmol), palladium(II) acetate (3 mg, 12.5 µmol), copper(I) chloride (25 mg, 250 mmol), cesium carbonate (326 mg, 1.0 mmol), bis(diphenylphosphino)ferrocene (available from Aldrich Chemical Company, Inc.; 14 mg, 25 µmol) and DMF (2 mL). The vial was degassed under high vacuum and the vial was then filled with $N_2$ twice. The vial was heated in a shaker at 100° C. for 24 h. Using a 48-well filter and plates, the reaction mixtures were filtered through DMSO-wetted Celite and the Celite was washed with DMSO (4 mL) with each compound collected on two plates. The filtrates were concentrated using a HT-12 Series II System (Genevac Inc.) at 8 mBar at 40° C. overnight to concentrate to about half volume, combining the contents of wells from the same reaction, and then evaporating again overnight at full vacuum at 40° C. To each vial was added tetrahydrofuran (1 mL) and 1 M aqueous NaOH solution (2 mL, 2 mmol). The vials were then heated on a shaker at 60° C. for 24 h. To each vial was added concentrated HCl (200 µL) and DMSO (1 mL) and the contents were analyzed by LC-MS. The contents of each vial were evaporated overnight using a using a Genevac Series II HT-12 (Genevac Inc.) at full vacuum at 40° C., then purified by mass-directed preparative HPLC using a Shimadzu HPLC system (Shimadzu Scientific Instruments), a PE Sciex 150 EX mass spec (Perkin Elmer), a LEAP CTC injector (LEAP Technologies, Inc.) and a Gilson 215 collector (Gilson, Inc.). The column was a Varian Pursuit C-18 phase (2×10 cm) (Varian, Inc.), and elution was carried out using a linear gradient solvent system of (A) 0.05% TFA/$H_2O$ and (B) 0.035% TFA/Acetonitrile at 20 mL/min. The collected fractions were evaporated in a Genevac Series II HT-12 (Genevac Inc.) and lyophilized.

General Procedure B for Suzuki Coupling and Hydrolysis in Parallel Mode

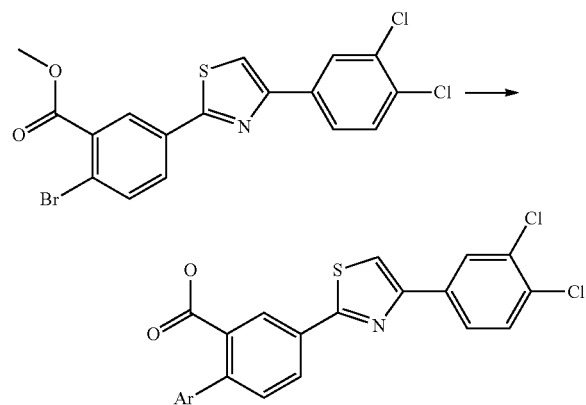

73 reactions were run at a time in parallel mode as follows: Each vial was charged with an arylboronic acid or the pinacol ester thereof (0.4 mmol), 2-bromo-5-[4-(3,4-dichloro-phenyl)-thiazol-2-yl]-benzoic acid methyl ester (which may be prepared as described for Intermediate 6; 89 mg, 0.2 mmol), tetrakis(triphenylphosphine)palladium(0) (available from Aldrich Chemical Company, Inc.; 19 mg, 16 µmol), 3 M aqueous potassium carbonate solution (133 µL, 0.4 mmol) and DMF (2 mL). The vial was heated on an orbital shaker at 100° C. for 20 h and then cooled to room temperature. To each vial was added tetrahydrofuran (1 mL) and 1M aqueous sodium hydroxide solution (1 mL, 1 mmol). The vials were then heated on a shaker at 60° C. for 24 h. Water (2 mL) and dichloromethane (2 mL) were added to each vial and the aqueous layer was separated. In several cases, there was solid that did not dissolve in either layer. For each reaction, 1M HCl solution (1.5 mL) was added to the aqueous layer, and 1 M HCl solution (1.5 mL) was added to the combination of organic layer and solid. The solid was filtered off. For each reaction, the three fractions (aqueous layer, organic layer, and solid) were evaporated separately, then dissolved in DMSO (1 mL) and combined. The DMSO solution was filtered through Celite and the Celite was washed with DMSO (1 mL). The samples were purified by mass-directed preparative HPLC using a Shimadzu HPLC system (Shimadzu Scientific Instruments), a PE Sciex 150 EX mass spec (Perkin Elmer), a LEAP CTC injector (LEAP Technologies, Inc.) and a Gilson 215 collector (Gilson, Inc.). The column was a Varian Pursuit C-18 phase (2×10 cm) (Varian, Inc.), and elution was carried out using a linear gradient solvent system of (A) 0.05% TFA/$H_2O$ and (B) 0.035% TFA/Acetonitrile at 20 mL/min. The collected fractions were evaporated in a Genevac Series II HT-12 (Genevac Inc.) and lyophilized.

General Procedure C for Suzuki Coupling and Hydrolysis in Parallel Mode

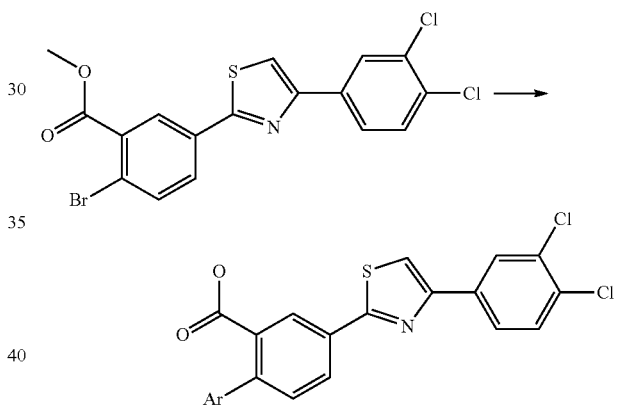

A mixture of 2-bromo-5-[4-(3,4-dichloro-phenyl)-thiazol-2-yl]-benzoic acid methyl ester (which may be prepared as described for Intermediate 6) and aqueous sodium carbonate solution was extracted with $CH_2Cl_2$, and the organic extract was dried, filtered and evaporated. 111 mg (0.25 mmol) of the resulting material was placed into each of a set of 31 vials. To each vial was added an arylboronic acid (0.5 mmol), palladium(II) acetate (available from Aldrich Chemical Company, Inc.; 2.8 mg, 0.0125 mmol), copper(I) chloride (25 mg, 0.025 mmol), cesium carbonate (326 mg, 1 mmol), bis(diphenylphosphino)ferrocene (available from Aldrich Chemical Company, Inc.; 14 mg, 25 µmol), and DMF (2 mL). The vial was evacuated and filled with nitrogen twice, and then heated at 100° C. overnight. The mixture was filtered through Celite, and washed with DMSO (4 mL). The extent of each reaction was checked by LC-MS, and the DMSO was evaporated. To each vial was added THF (1 mL) and 1 M NaOH (1 mL, 1 mmol). The mixtures were heated at 60° C. overnight and then cooled. Conc HCl (0.2 mL) was added to each vial and the contents were mixed. The mixtures were evaporated overnight using a Genevac Series II HT-12 (Genevac Inc.), and then DMSO (1 mL) was added. The mixtures were filtered and purified by mass-directed preparative HPLC using a Shimadzu HPLC system (Shimadzu Scientific Instruments).

General Procedure D for Amide Coupling in Parallel Mode

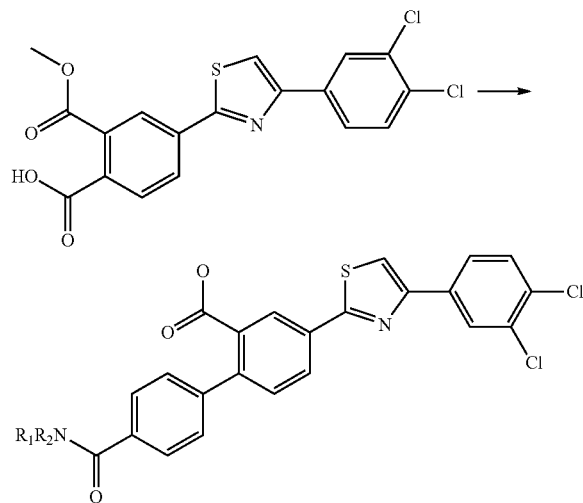

A mixture of 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol), an amine of formula HNR1R2 (0.21 mmol), triethylamine (42 mg, 0.41 mmol), N-(3-dimethylaminopropyl)-N'-ethylcarbodiimide hydrochloride (79 mg, 0.41 mmol) and 1-hydroxybenzotriazole hydrate (56 mg, 0.37 mmol) in DMF (3 mL) was stirred at room temperature overnight. The reaction mixture was concentrated and 0.1 M HCl (2 mL) was added. The mixture was centrifuged and the supernatant was decanted away from the solid amide product.

General Procedure E for Amide Coupling and Hydrolysis in Parallel Mode

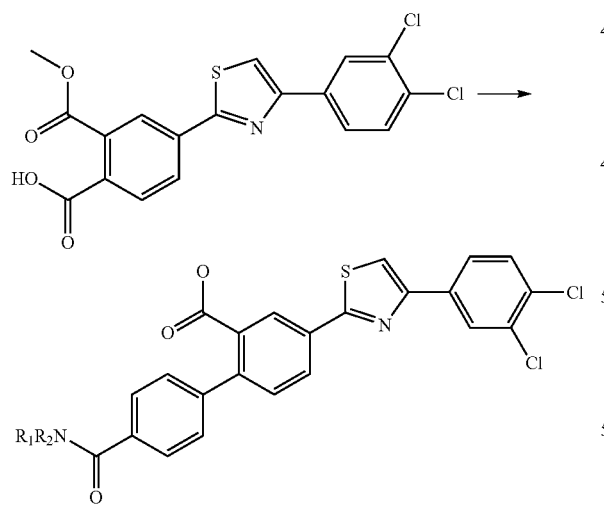

31 reactions were run at a time in parallel mode as follows: Approximately 0.62 mmol of each of 31 amines of formula HNR1R2 was placed in one of 31 15-mL vials (one amine per vial). A stock solution was prepared from by dissolving 1-hydroxybenzotriazole hydrate (available from Aldrich Chemical Company, Inc.; 2.6 g, 17.0 mmol) in DMF (31 mL) and adding triethylamine (2.2 mL, 15.8 mmol). 1.1 mL of this solution was added to each of the 31 vials. A stock solution was prepared by dissolving N-(3-dimethylaminopropyl)-N'-ethylcarbodiimide hydrochloride (available from Alfa Aesar; 3.7 g, 19.3 mmol) in DMF (62 mL). The mixture was heated to get the solid to dissolve. 2.1 mL of this solution was added to each of the 31 vials. A stock solution was prepared by dissolving 4-[4-(3,4-dichloro-phenyl)-thiazol-2-yl]-biphenyl-2,4'-dicarboxylic acid 2-methyl ester (which may be prepared as described for Intermediate 8; 4.7 g, 9.7 mmol) in DMF (62 mL). The mixture was heated to get the solid to dissolve. 2.1 mL of this solution was added to each of the 31 vials.

The reaction vials were placed on an orbital shaker and shaken at room temperature over the weekend. The solvent was evaporated using a Genevac Series II HT-12 and the residue was hydrolyzed without purification as follows. To each vial were added THF (2 mL), MeOH (1 mL), and aqueous LiOH (0.5 mL of a solution prepared by dissolving lithium hydroxide monohydrate (1.3 g, 31 mmol) in water (15.5 mL); 1 mmol). The vials were sealed, heated at 60° C. for 4 h and then stirred at room temperature for two days. To each solution was added a further portion of lithium hydroxide monohydrate (42 mg, 1 mmol) and THF if necessary to dissolve any solid in the vial. The mixture was heated at 60° C. for 5 h. The reaction mixtures were allowed to cool, stored in the freezer over the weekend, and then concentrated under vacuum using a Genevac Series II HT-12. Water (1 mL) was added to each vial, the contents were mixed, and then 1 M HCl (3 mL) was added. The contents of the vial were mixed again, concentrated under vacuum using a Genevac Series II HT-12 at 40° C., and purified using HPLC Purification Conditions B to give the product.

EXAMPLES

The invention will be more fully understood by reference to the following examples. They should not, however, be construed as limiting the scope of the invention.

Example 1

4-[4-(4-Fluoro-phenyl)-thiazol-2-yl]-2'-nitro-biphenyl-2-carboxylic acid

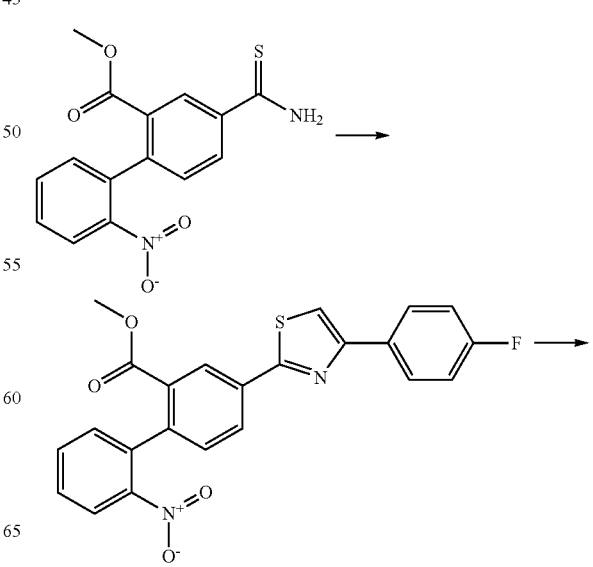

-continued

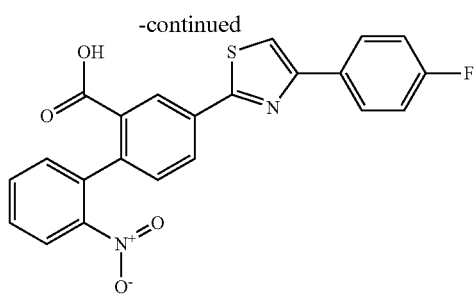

Step 1: 4-[4-(4-Fluoro-phenyl)-thiazol-2-yl]-2'-nitro-biphenyl-2-carboxylic acid methyl ester 4-Fluorophenacyl bromide (available from Alfa Aesar; 35 mg, 0.16 mmol) was added to a suspension of 2'-nitro-4-thiocarbamoyl-biphenyl-2-carboxylic acid methyl ester (which may be prepared as described for Intermediate 4; 50 mg, 0.16 mmol) in ethanol (2 mL) and the resulting mixture was stirred at 45° C. for 20 h. The reaction mixture was concentrated to a small volume and cooled. The precipitate was collected by filtration to give 4-[4-(4-fluoro-phenyl)-thiazol-2-yl]-2'-nitro-biphenyl-2-carboxylic acid methyl ester (40 mg) which was used directly in the next step without purification.

Step 2: 4-[4-(4-Fluoro-phenyl)-thiazol-2-yl]-2'-nitro-biphenyl-2-carboxylic acid Sodium hydroxide (40 mg, 1 mmol) was added to a suspension of 4-[4-(4-fluoro-phenyl)-thiazol-2-yl]-2'-nitro-biphenyl-2-carboxylic acid methyl ester (40 mg) in a mixture of water (1 mL) and dioxane (1 mL). The resulting mixture was heated at 50° C. for 4 h. The solvent was evaporated and water (5 mL) was added. The mixture was filtered and the filtrate was made acidic to pH 3 by the addition of concentrated HCl. The precipitate was collected by filtration and dried to give 4-[4-(4-fluoro-phenyl)-thiazol-2-yl]-2'-nitro-biphenyl-2-carboxylic acid (45 mg, 58% for two steps). $^1$H NMR (300 MHz, DMSO-$d_6$) δ 13.21 (br s, 1H), 8.65 (s, 1H), 8.17-8.33 (m, 5H), 7.86 (t, J=7.6 Hz, 1H), 7.73 (t, J=7.8 Hz, 1H), 7.52 (t, J=8.5 Hz, 2H), 7.40 (t, J=8.6 Hz, 2H).

Example 2

2'-Nitro-4-[4-(4-trifluoromethoxy-phenyl)-thiazol-2-yl]-biphenyl-2-carboxylic acid

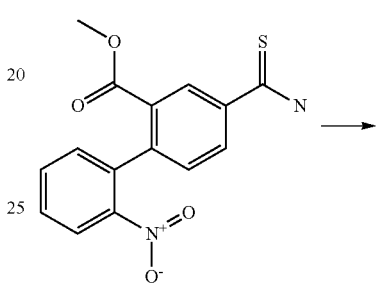

2'-Nitro-4-[4-(4-trifluoromethoxy-phenyl)-thiazol-2-yl]-biphenyl-2-carboxylic acid (190 mg, 62%) was prepared from 2'-nitro-4-thiocarbamoyl-biphenyl-2-carboxylic acid methyl ester (which may be prepared as described for Intermediate 4) and 4-(trifluoromethoxy)phenacyl bromide (available from Matrix Scientific) using the procedure described for the preparation of Example 1. $^1$H NMR (300 MHz, DMSO-$d_6$) δ 13.17 (s, 1H), 8.58 (d, J=2.0 Hz, 1H), 8.13-8.28 (m, 4H), 7.63-7.82 (m, 2H), 7.41-7.51 (m, 4H).

Example 3

4-[4-(4-Difluoromethoxy-phenyl)-thiazol-2-yl]-2'-nitro-biphenyl-2-carboxylic acid

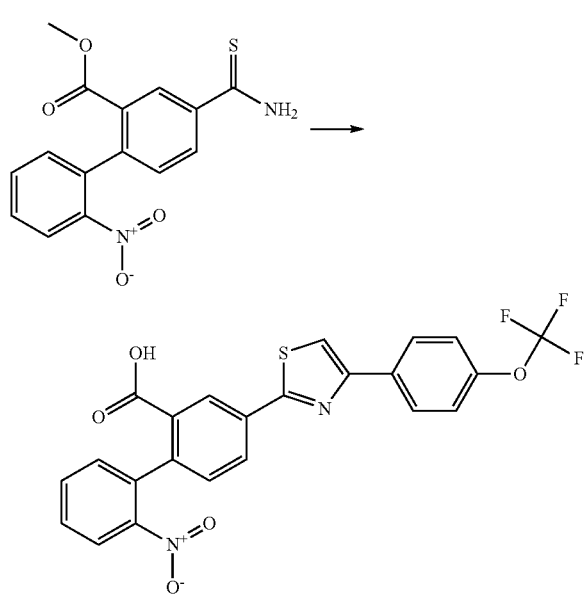

4-[4-(4-Difluoromethoxy-phenyl)-thiazol-2-yl]-2'-nitro-biphenyl-2-carboxylic acid (180 mg, 61%) was prepared from 2'-nitro-4-thiocarbamoyl-biphenyl-2-carboxylic acid methyl ester (which may be prepared as described for Intermediate 4) and 4-(difluoromethoxy)phenacyl bromide (available from Oakwood Products, Inc.) using the procedure described for the preparation of Example 1. $^1$H NMR (300 MHz, DMSO-$d_6$) δ 13.15 (s, 1H), 8.57 (d, J=1.9 Hz, 1H), 8.11-8.27 (m, 5H), 7.63-7.81 (m, 2H), 7.41-7.48 (m, 2H), 7.30 (d, J=9.2 Hz, 1H).

Example 4

4-[4-(3,4-Dichloro-phenyl)-thiazol-2-yl]-2'-nitro-5'-trifluoromethyl-biphenyl-2-carboxylic acid

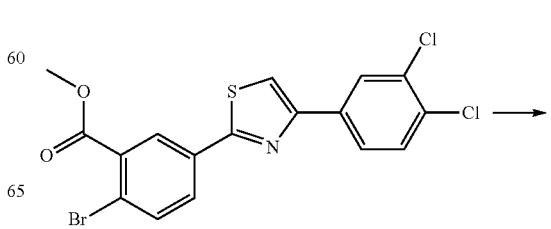

-continued

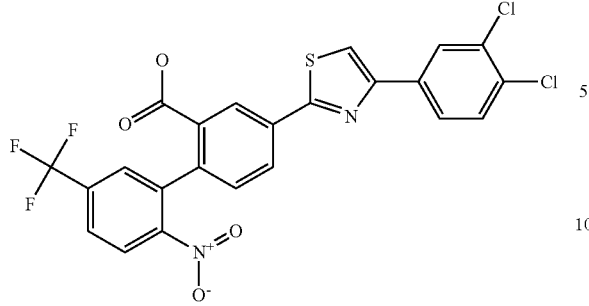

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-5-(trifluoromethyl)phenylboronic acid (2-nitro-5-trifluoromethylphenylboronic acid, pinacol ester (available from Combi-Blocks Inc.; 117 mg, 0.5 mmol). The resulting ester was hydrolyzed and the acid was purified to give 4-[4-(3,4-dichloro-phenyl)-thiazol-2-yl]-2'-nitro-5'-trifluoromethyl-biphenyl-2-carboxylic acid (31 mg, 23%). $^1$H NMR (300 MHz, DMSO-d$_6$) δ 13.48 (s, 1H), 8.55 (d, J=1.7 Hz, 1H), 8.51 (s, 1H), 8.29-8.37 (m, 2H), 8.24 (d, J=8.3 Hz, 1H), 8.10 (dd, J=8.4, 2.0 Hz, 1H), 8.03 (s, 1H), 7.97 (d, J=8.5 Hz, 1H), 7.77 (d, J=8.5 Hz, 1H), 7.67 (d, J=8.1 Hz, 1H).

Example 5

2'-Nitro-4-[4-(2-trifluoromethyl-phenyl)-thiazol-2-yl]-biphenyl-2-carboxylic acid

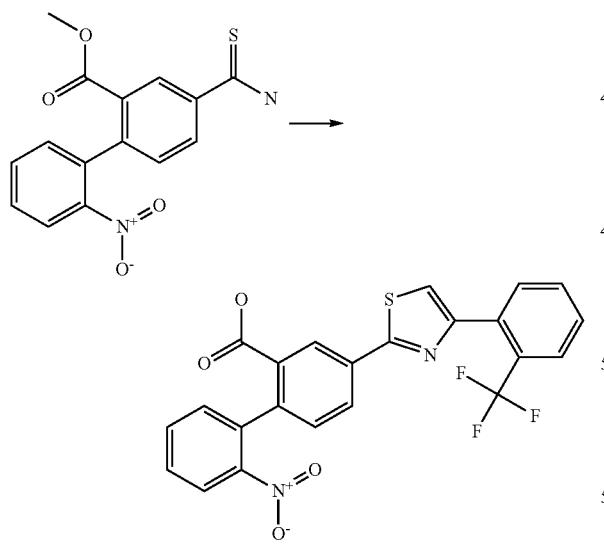

2'-Nitro-4-[4-(2-trifluoromethyl-phenyl)-thiazol-2-yl]-biphenyl-2-carboxylic acid (56 mg, 19%) was prepared from 2'-nitro-4-thiocarbamoyl-biphenyl-2-carboxylic acid methyl ester (which may be prepared as described for Intermediate 4) and 2-(trifluoromethyl)phenacyl bromide (available from Maybridge) using the procedure described for the preparation of Example 18 except that the entire 4 mL of water was added at the beginning of the hydrolysis step rather than being added in two portions. $^1$H NMR (300 MHz, DMSO-d$_6$) δ 13.06 (br s, 1H), 8.52 (d, J=1.6 Hz, 1H), 8.20 (dd, J=8.2, 1.7 Hz, 1H), 8.13 (d, J=8.0 Hz, 1H), 7.96 (s, 1H), 7.88 (d, J=7.6 Hz, 1H), 7.64-7.80 (m, 4H), 7.40-7.46 (m, 2H).

Example 6

2'-Nitro-4-[4-(3-trifluoromethyl-phenyl)-thiazol-2-yl]-biphenyl-2-carboxylic acid

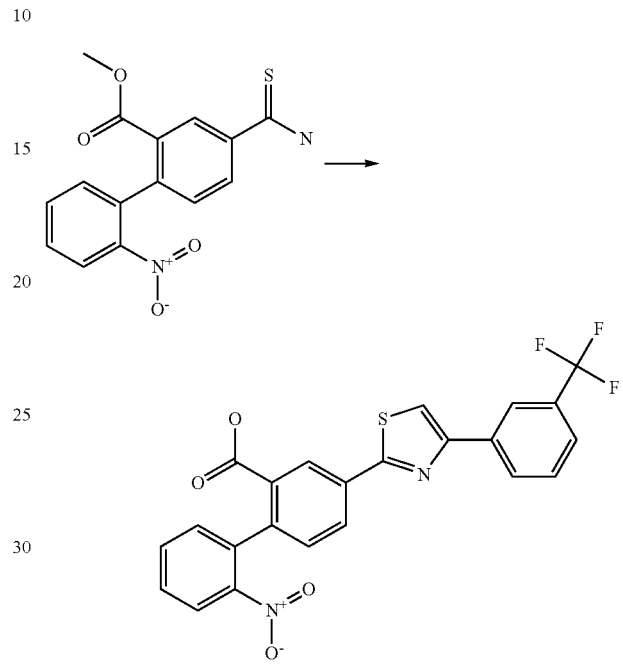

2'-Nitro-4-[4-(3-trifluoromethyl-phenyl)-thiazol-2-yl]-biphenyl-2-carboxylic acid (53 mg, 18%) was prepared from 2'-nitro-4-thiocarbamoyl-biphenyl-2-carboxylic acid methyl ester (which may be prepared as described for Intermediate 4) and 3-(trifluoromethyl)phenacyl bromide (available from Oakwood Products, Inc.) using the procedure described for the preparation of Example 18 except that the entire 4 mL of water was added at the beginning of the hydrolysis step rather than being added in two portions. $^1$H NMR (300 MHz, DMSO-d$_6$) δ 13.13 (br s, 1H), 8.53-8.58 (m, 2H), 8.38 (s, 2H), 8.27-8.31 (m, 1H), 8.13-8.18 (m, 1H), 7.63-7.82 (m, 4H), 7.41-7.49 (m, 2H).

Example 7

2'-Nitro-4-[4-(4-trifluoromethyl-phenyl)-thiazol-2-yl]-biphenyl-2-carboxylic acid

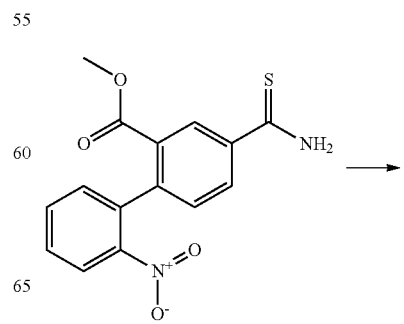

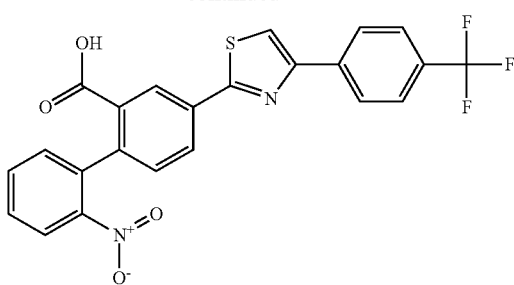

2'-Nitro-4-[4-(4-trifluoromethyl-phenyl)-thiazol-2-yl]-biphenyl-2-carboxylic acid (120 mg, 40%) was prepared from 2'-nitro-4-thiocarbamoyl-biphenyl-2-carboxylic acid methyl ester (which may be prepared as described for Intermediate 4) and 4-(trifluoromethyl)phenacyl bromide (available from Oakwood Products, Inc.) using the procedure described for the preparation of Example 1. $^1$H NMR (300 MHz, DMSO-$d_6$) δ 13.16 (s, 1H), 8.59 (s, 1H), 8.51 (s, 1H), 8.27-8.31 (m, 3H), 8.15 (d, J=8.1 Hz, 1H), 7.77-7.87 (m, 3H), 7.66 (t, J=8.0 Hz, 1H), 7.42-7.49 (m, 2H).

Example 8

4-[4-(3,5-Bis-trifluoromethyl-phenyl)-thiazol-2-yl]-2'-nitro-biphenyl-2-carboxylic acid

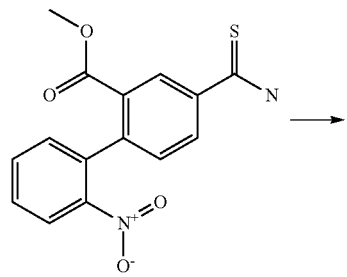

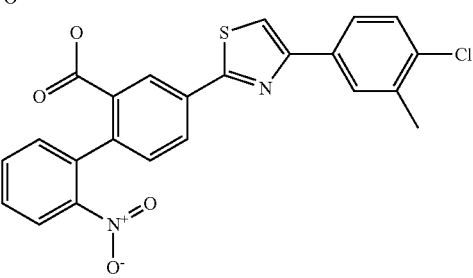

4-[4-(3,5-Bis-trifluoromethyl-phenyl)-thiazol-2-yl]-2'-nitro-biphenyl-2-carboxylic acid (110 mg, 32%) was prepared from 2'-nitro-4-thiocarbamoyl-biphenyl-2-carboxylic acid methyl ester (which may be prepared as described for Intermediate 4) and 3',5'-bis(trifluoromethyl)-2-bromoacetophenone (available from Oakwood Products, Inc.) using the procedure described for the preparation of Example 1. $^1$H NMR (300 MHz, DMSO-$d_6$) δ 13.20 (s, 1H), 8.79 (s, 1H), 8.72 (s, 2H), 8.55 (s, 1H), 8.32 (d, J=8.1 Hz, 1H), 8.12-8.17 (m, 2H), 7.79 (t, J=7.6 Hz, 1H), 7.66 (t, J=7.6 Hz, 1H), 7.41-7.50 (m, 2H).

Example 9

4-[4-(4-Chloro-3-methyl-phenyl)-thiazol-2-yl]-2'-nitro-biphenyl-2-carboxylic acid

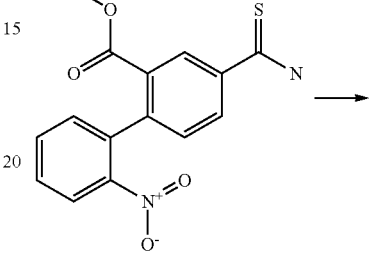

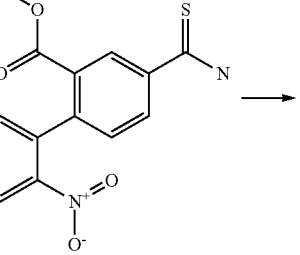

4-[4-(2-Fluoro-4-methoxy-phenyl)-thiazol-2-yl]-2'-nitro-biphenyl-2-carboxylic acid (180 mg, 63%) was prepared from 2'-nitro-4-thiocarbamoyl-biphenyl-2-carboxylic acid methyl ester (which may be prepared as described for Intermediate 4) and 2-bromo-1-(4-chloro-3-methylphenyl)ethan-1-one (available from Maybridge) using the procedure described for the preparation of Example 1. $^1$H NMR (300 MHz, DMSO-$d_6$) δ 8.55 (d, J=1.9 Hz, 1H), 8.23-8.28 (m, 2H), 8.13 (d, J=7.9 Hz, 1H), 8.05 (d, J=1.6 Hz, 1H), 7.91 (dd, J=10.1 Hz, 1H), 7.78 (t, J=7.5 Hz, 1H), 7.65 (t, J=7.5 Hz, 1H), 7.40-7.53 (m, 3H), 2.42 (s, 3H).

Example 10

4-[4-(2,4-Dichloro-phenyl)-thiazol-2-yl]-2'-nitro-biphenyl-2-carboxylic acid

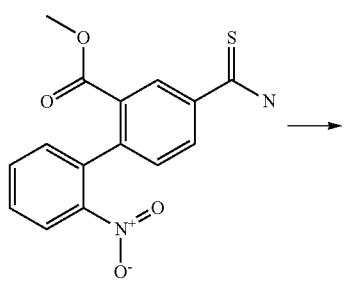

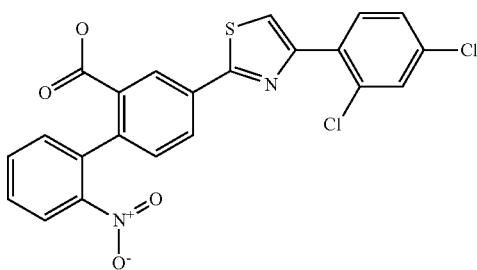

4-[4-(2,4-Dichloro-phenyl)-thiazol-2-yl]-2'-nitro-biphenyl-2-carboxylic acid (24 mg, 8%) was prepared from 2'-nitro-4-thiocarbamoyl-biphenyl-2-carboxylic acid methyl ester (which may be prepared as described for Intermediate 4) and 2-bromo-2',4'-dichloroacetophenone (available from Oakwood Products, Inc.) using the procedure described for the preparation of Example 1. $^1$H NMR (300 MHz, DMSO-$d_6$) δ 13.16 (s, 1H), 8.55 (d, J=1.4 Hz, 1H), 8.29 (s, 1H), 8.23 (d, J=8.0 Hz, 1H), 8.14 (d, J=7.9 Hz, 1H), 8.05 (d, J=8.4 Hz, 1H), 7.57-7.78 (m, 4H), 7.43 (t, J=8.3 Hz, 2H).

Example 11

4-[4-(2-Chloro-phenyl)-thiazol-2-yl]-2'-nitro-biphenyl-2-carboxylic acid

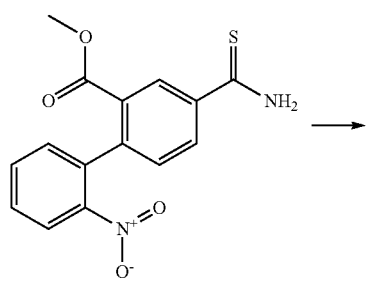

4-[4-(2-Chloro-phenyl)-thiazol-2-yl]-2'-nitro-biphenyl-2-carboxylic acid (116 mg, 44%) was from 2'-nitro-4-thiocarbamoyl-biphenyl-2-carboxylic acid methyl ester (which may be prepared as described for Intermediate 4) and 2-chlorophenacyl bromide (available from Oakwood Products, Inc.) using the procedure described for the preparation of Example 1. $^1$H NMR (300 MHz, DMSO-$d_6$) δ 8.55 (d, J=1.7 Hz, 1H), 8.21-8.27 (m, 2H), 8.14 (d, J=8.1 Hz, 1H), 7.99 (dd, J=7.4, 1.9 Hz, 1H), 7.78 (t, J=7.4 Hz, 1H), 7.60-7.67 (m, 2H), 7.41-7.52 (m, 4H).

Example 12

4-[4-(2,5-Dichloro-phenyl)-thiazol-2-yl]-2'-nitro-biphenyl-2-carboxylic acid

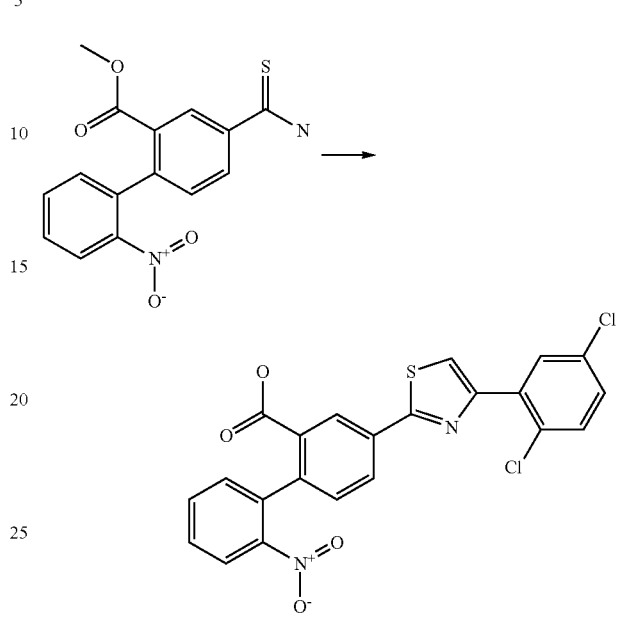

4-[4-(2,5-Dichloro-phenyl)-thiazol-2-yl]-2'-nitro-biphenyl-2-carboxylic acid (130 mg, 44%) was prepared from 2'-nitro-4-thiocarbamoyl-biphenyl-2-carboxylic acid methyl ester (which may be prepared as described for Intermediate 4) and 2-bromo-1-(2,5-dichlorophenyl)ethanone (available from Oakwood Products, Inc.) using the procedure described for the preparation of Example 1. $^1$H NMR (300 MHz, DMSO-$d_6$) δ 8.50 (d, J=1.5 Hz, 1H), 8.33 (s, 1H), 8.05-8.19 (m, 3H), 7.74 (t, J=7.6 Hz, 1H), 7.50-7.66 (m, 3H), 7.37 (d, J=7.8 Hz, 2H).

Example 13

4-[4-(4-Chloro-phenyl)-thiazol-2-yl]-2'-nitro-biphenyl-2-carboxylic acid

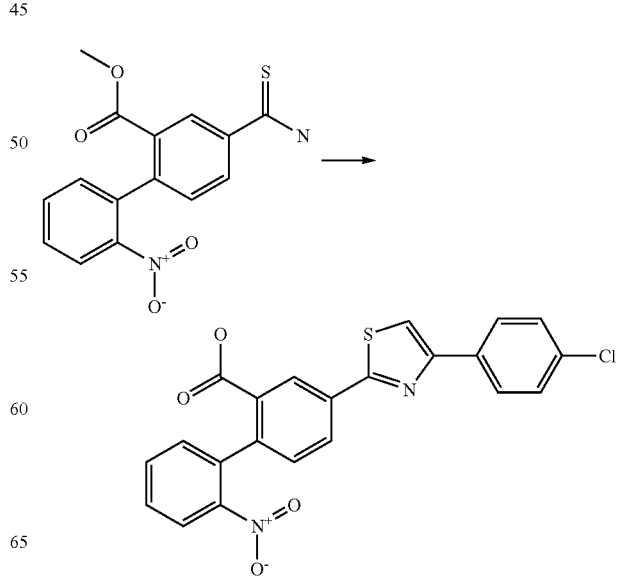

4-[4-(4-Chloro-phenyl)-thiazol-2-yl]-2'-nitro-biphenyl-2-carboxylic acid (59 mg, 21%) was prepared from 2'-nitro-4-thiocarbamoyl-biphenyl-2-carboxylic acid methyl ester (which may be prepared as described for Intermediate 4) and 2-bromo-4'-chloroacetophenone (available from Alfa Aesar) using the procedure described for the preparation of Example 18 except that the entire 4 mL of water was added at the beginning of the hydrolysis step rather than being added in two portions. $^1$H NMR (300 MHz, DMSO-d$_6$) δ 13.12 (br s, 1H), 8.57 (s, 1H), 8.33 (s, 1H), 8.26 (d, J=8.8 Hz, 1H), 8.09-8.16 (m, 3H), 7.41-7.79 (m, 6H).

Example 14

5'-Chloro-4-[4-(3,4-dichloro-phenyl)-thiazol-2-yl]-2'-nitro-biphenyl-2-carboxylic acid

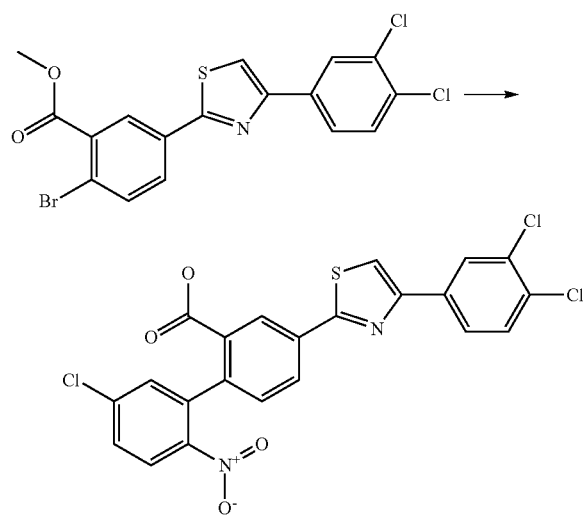

5'-Chloro-4-[4-(3,4-dichloro-phenyl)-thiazol-2-yl]-2'-nitro-biphenyl-2-carboxylic acid was prepared in 7% yield (for two steps) from 2-bromo-5-[4-(3,4-dichloro-phenyl)-thiazol-2-yl]-benzoic acid methyl ester (which may be prepared as described for Intermediate 6) and 5-chloro-2-nitrophenylboronic acid (available from Combi-Blocks Inc.) using General Procedure A for Suzuki Coupling and Hydrolysis in Parallel Mode. $^1$H NMR (300 MHz, DMSO-d$_6$) δ 13.29 (br s, 1H), 8.60 (d, J=1.9 Hz, 1H), 8.50 (s, 1H), 8.29-8.37 (m, 2H), 8.20 (d, J=8.9 Hz, 2H), 8.10 (dd, J=8.4, 2.0 Hz, 1H), 7.73-7.82 (m, 2H), 7.60 (d, J=2.3 Hz, 1H), 7.53 (d, J=7.9 Hz, 1H).

Example 15

4-[4-(3,4-Dichloro-phenyl)-thiazol-2-yl]-2'-nitro-biphenyl-2-carboxylic acid

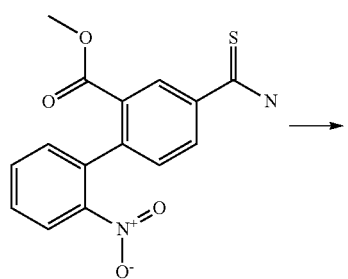

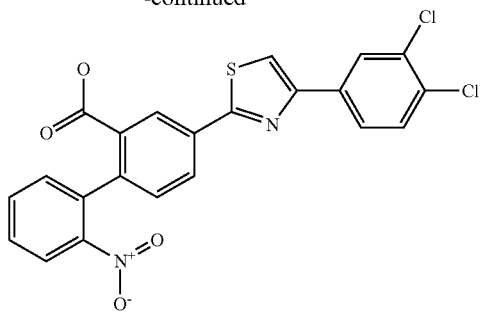

4-[4-(3,4-Dichloro-phenyl)-thiazol-2-yl]-2'-nitro-biphenyl-2-carboxylic acid (109 mg, 37%) was prepared from 2'-nitro-4-thiocarbamoyl-biphenyl-2-carboxylic acid methyl ester (which may be prepared as described for Intermediate 4) and 2-bromo-3',4'-dichloroacetophenone (available from Oakwood Products, Inc.) using the procedure described for the preparation of Example 1. The compound of Example 15 has the same formula as the compound of Example 16. $^1$H NMR (300 MHz, DMSO-d$_6$) δ 13.18 (s, 1H), 8.56 (s, 1H), 8.47 (s, 1H), 8.26-8.32 (m, 2H), 8.15 (d, J=8.2 Hz, 1H), 8.07 (d, J=8.4 Hz, 1H), 8.03 (d, J=8.6 Hz, 1H), 7.41-7.81 (m, 5H).

Example 16

4-[4-(3,4-Dichloro-phenyl)-thiazol-2-yl]-2'-nitro-biphenyl-2-carboxylic acid

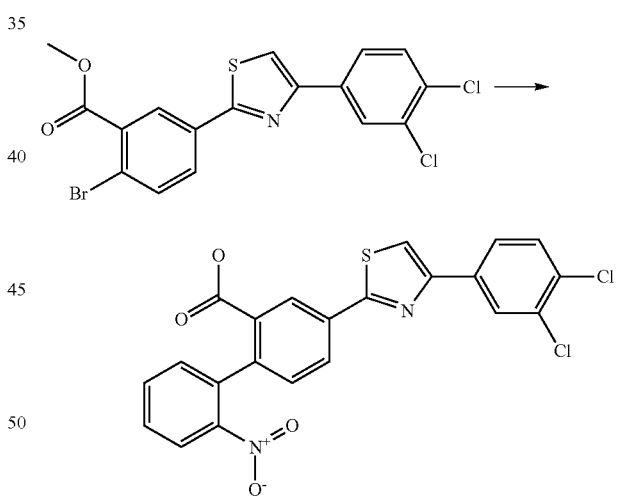

2-Bromo-5-[4-(3,4-dichloro-phenyl)-thiazol-2-yl]-benzoic acid methyl ester (which may be prepared as described for Intermediate 6; 608 mg, 1.4 mmol) was treated with a saturated aqueous solution of Na$_2$CO$_3$ and the mixture was extracted with CH$_2$Cl$_2$. The organic extract was dried, filtered, and evaporated. 2-Nitrophenylboronic acid (available from Aldrich Chemical Company, Inc.; 194 mg, 1.2 mmol), Pd(PPh$_3$)$_4$ (available from Aldrich Chemical Company, Inc.; 107 mg, 0.093 mmol) and 1 M aqueous K$_2$CO$_3$ (1 M; 3.0 mL, 3.0 mmol) and dioxane (4.6 mL) were added. The mixture was irradiated in a microwave at 150° C. for 30 min. The mixture was allowed to cool and the solvent was evaporated.

The reaction mixture was purified by silica gel chromatography on an 80 g column, using 0-15% EtOAc/hexanes as eluent to give a yellow solid (60 mg). Tetrahydrofuran (2.4 mL) and 1 M aqueous NaOH (2.4 mL, 2.4 mmol) were added. The mixture was heated at 60° C. overnight. 1 M HCl was added to bring the pH to ~3, and then the mixture was extracted three times with EtOAc. The organic layers were combined and evaporated. The crude product was purified first by silica gel chromatography (using 50-100% EtOAc/hexanes as eluent) and then by preparative HPLC to give 4-[4-(3,4-dichloro-phenyl)-thiazol-2-yl]-2'-nitro-biphenyl-2-carboxylic acid (18 mg, 3%) as a light yellow solid. The compound of Example 16 has the same formula as the compound of Example 15. $^1$H NMR (300 MHz, DMSO-d$_6$) δ 13.11 (br s, 1H), 8.51 (d, J=1.8 Hz, 1H), 8.43 (s, 1H), 8.28 (d, J=1.8 Hz, 1H), 8.24 (dd, J=8.0, 1.7 Hz, 1H), 8.10 (d, J=8.2 Hz, 1H), 8.03 (dd, J=8.5, 1.8 Hz, 1H), 7.68-7.77 (m, 2H), 7.56-7.65 (m, 1H), 7.42 (d, J=8.2 Hz, 1H), 7.37 (d, J=7.5 Hz, 1H).

Example 17

4-[4-(3-Chloro-phenyl)-thiazol-2-yl]-2'-nitro-biphenyl-2-carboxylic acid

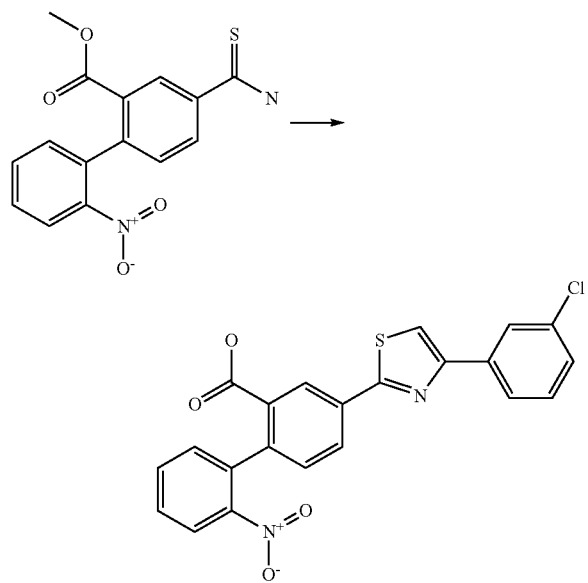

4-[4-(3-Chloro-phenyl)-thiazol-2-yl]-2'-nitro-biphenyl-2-carboxylic acid (82 mg, 30%) was prepared from 2'-nitro-4-thiocarbamoyl-biphenyl-2-carboxylic acid methyl ester (which may be prepared as described for Intermediate 4) and 3-chlorophenacyl bromide (available from Oakwood Products, Inc.) using the procedure described for the preparation of Example 18 except that the entire 4 mL of water was added at the beginning of the hydrolysis step rather than being added in two portions. $^1$H NMR (300 MHz, DMSO-d$_6$) δ 13.12 (br s, 1H), 8.56 (d, J=1.7 Hz, 1H), 8.42 (s, 1H), 8.28 (dd, J=8.0, 1.9 Hz, 1H), 8.12-8.16 (m, 2H), 8.03-8.07 (m, 1H), 7.76-7.81 (m, 1H), 7.62-7.68 (m, 1H), 7.41-7.55 (m, 4H).

Example 18

4-[4-(3-Chloro-4-fluoro-phenyl)-thiazol-2-yl]-2'-nitro-biphenyl-2-carboxylic acid

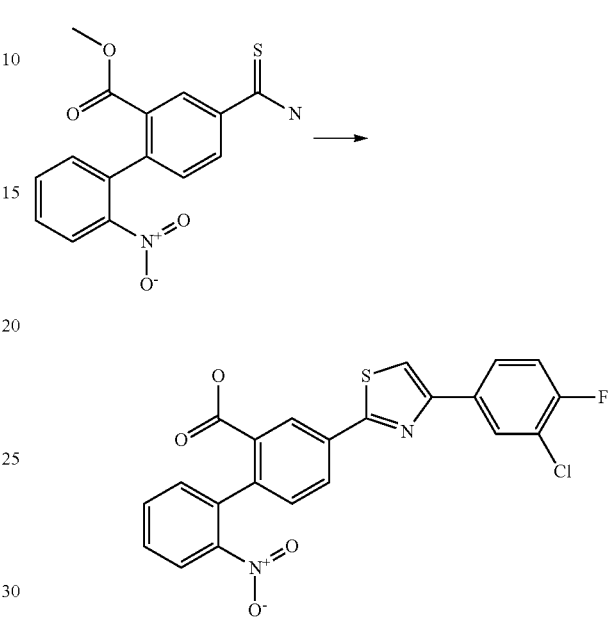

Step 1: 4-[4-(3-Chloro-4-fluoro-phenyl)-thiazol-2-yl]-2'-nitro-biphenyl-2-carboxylic acid methyl ester 2-Bromo-3'-chloro-4'-fluoroacetophenone (available from Aldrich Chemical Company, Inc.; 80.5 mg, 0.32 mmol) was added to a solution of 2'-nitro-4-thiocarbamoyl-biphenyl-2-carboxylic acid methyl ester (which may be prepared as described for Intermediate 4; 100 mg, 0.32 mmol) in THF (2 mL), and the resulting mixture was stirred at 40° C. for 20 h. The reaction mixture was evaporated to dryness and the residue was stirred with ethanol (5 mL). The precipitate was collected by filtration (100 mg) and used directly in the next step without purification.

Step 2: 4-[4-(3-Chloro-4-fluoro-phenyl)-thiazol-2-yl]-2'-nitro-biphenyl-2-carboxylic acid Sodium hydroxide (100 mg, 2.5 mmol) was added to a suspension of 4-[4-(3-chloro-4-fluoro-phenyl)-thiazol-2-yl]-2'-nitro-biphenyl-2-carboxylic acid methyl ester (100 mg) in a mixture of water (2 mL) and dioxane (4 mL). The reaction mixture was stirred at 50° C. for 2 h. An additional portion of water (2 mL) was added and the reaction mixture was stirred at 50° C. for a further 2 h. The reaction mixture was evaporated to dryness and water (5 mL) was added. The mixture was filtered and the filtrate was made acidic to pH 3-4 by the addition of concentrated HCl. The precipitate was collected by filtration and dried to give 4-[4-(3-chloro-4-fluoro-phenyl)-thiazol-2-yl]-2'-nitro-biphenyl-2-carboxylic acid (60 mg, 41% for two steps). $^1$H NMR (300 MHz, DMSO-d$_6$) δ 13.18 (br s, 1H), 8.56 (s, 1H), 8.39 (s, 1H), 8.27 (d, J=8.3 Hz, 1H), 8.08-8.16 (m, 2H), 7.79 (t, J=7.4 Hz, 1H), 7.66 (t, J=7.9 Hz, 1H), 7.41-7.58 (m, 3H).

Example 19

4-[4-(2,4-Difluoro-phenyl)-thiazol-2-yl]-2'-nitro-biphenyl-2-carboxylic acid

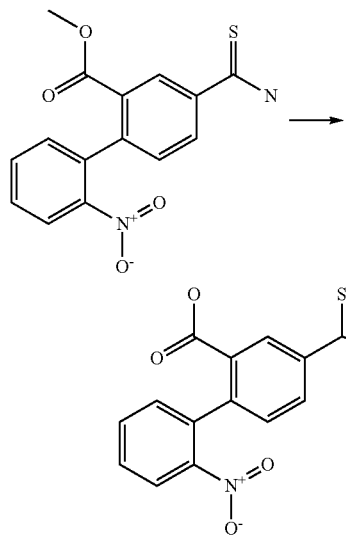

4-[4-(2,4-Difluoro-phenyl)-thiazol-2-yl]-2'-nitro-biphenyl-2-carboxylic acid (66 mg, 23%) was prepared from 2'-nitro-4-thiocarbamoyl-biphenyl-2-carboxylic acid methyl ester (which may be prepared as described for Intermediate 4) and 2-bromo-2',4'-difluoroacetophenone (available from Matrix Scientific) using the procedure described for the preparation of Example 18. $^1$H NMR (300 MHz, DMSO-$d_6$) δ 8.57 (d, J=1.4 Hz, 2H), 8.10-8.35 (m, 4H), 7.21-7.33 (m, 3H), 7.77 (t, J=7.5 Hz, 1H), 7.64 (t, J=7.7 Hz, 1H), 7.23-7.50 (m, 4H).

Example 20

4-[4-(2,6-Difluoro-phenyl)-thiazol-2-yl]-2'-nitro-biphenyl-2-carboxylic acid

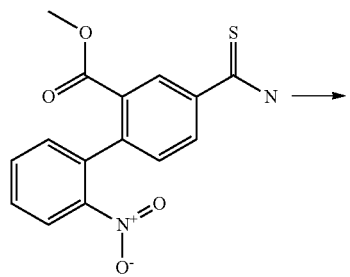

4-[4-(2,6-Difluoro-phenyl)-thiazol-2-yl]-2'-nitro-biphenyl-2-carboxylic acid (45 mg, 16%) was prepared from 2'-nitro-4-thiocarbamoyl-biphenyl-2-carboxylic acid methyl ester (which may be prepared as described for Intermediate 4) and 2-bromo-2',6'-difluoroacetophenone (available from SynQuest Laboratories, Inc.) using the procedure described for the preparation of Example 18 except that the entire 4 mL of water was added at the beginning of the hydrolysis step rather than being added in two portions. $^1$H NMR (300 MHz, DMSO-$d_6$) δ 8.45 (d, J=1.9 Hz, 1H), 7.94-8.04 (m, 3H), 7.50-7.70 (m, 3H), 7.19-7.32 (m, 4H).

Example 21

4-[4-(2-Fluoro-phenyl)-thiazol-2-yl]-2'-nitro-biphenyl-2-carboxylic acid

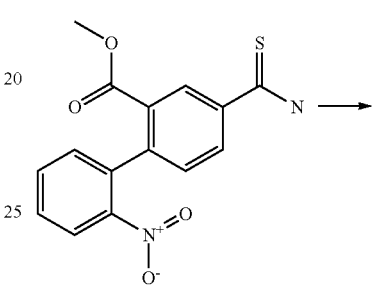

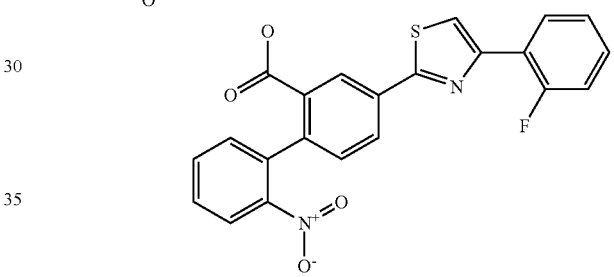

4-[4-(2-Fluoro-phenyl)-thiazol-2-yl]-2'-nitro-biphenyl-2-carboxylic acid (46 mg, 18%) was prepared from 2'-nitro-4-thiocarbamoyl-biphenyl-2-carboxylic acid methyl ester (which may be prepared as described for Intermediate 4) and 2-fluorophenacyl bromide (available from Matrix Scientific) using the procedure described for the preparation of Example 18 except that the entire 4 mL of water was added at the beginning of the hydrolysis step rather than being added in two portions. $^1$H NMR (300 MHz, DMSO-$d_6$) δ 8.57 (d, J=1.8 Hz, 1H), 8.12-8.30 (m, 4H), 7.61-7.80 (m, 2H), 7.34-7.50 (m, 5H).

Example 22

4-[4-(3,5-Difluoro-phenyl)-thiazol-2-yl]-2'-nitro-biphenyl-2-carboxylic acid

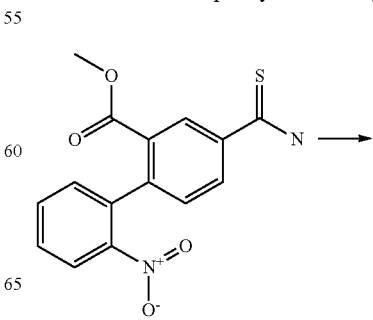

J=1.7 Hz, 1H), 8.36 (s, 1H), 8.10-8.24 (m, 3H), 7.95-7.99 (m, 1H), 7.75-7.80 (m, 1H), 7.53-7.67 (m, 2H), 7.40-7.43 (m, 2H).

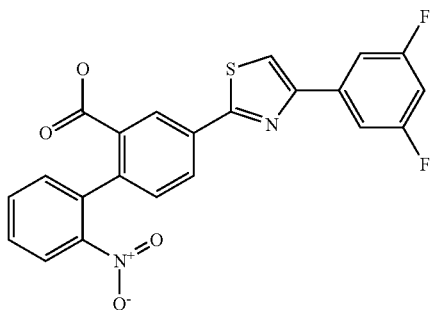

4-[4-(3,5-Difluoro-phenyl)-thiazol-2-yl]-2'-nitro-biphenyl-2-carboxylic acid (38 mg, 14%) was prepared from 2'-nitro-4-thiocarbamoyl-biphenyl-2-carboxylic acid methyl ester (which may be prepared as described for Intermediate 4) and 3,5-difluorophenacyl bromide (available from SynQuest Laboratories, Inc.) using the procedure described for the preparation of Example 18. $^1$H NMR (300 MHz, DMSO-$d_6$) δ 8.41-8.50 (m, 2H), 8.03 (d, J=8.1 Hz, 2H), 7.79 (d, J=7.2 Hz, 2H), 7.50-7.68 (m, 2H), 7.21-7.33 (m, 3H).

Example 23

4-[4-(3,4-Difluoro-phenyl)-thiazol-2-yl]-2'-nitro-biphenyl-2-carboxylic acid

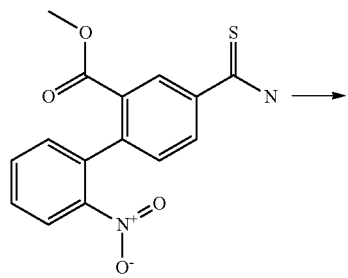

4-[4-(3,4-Difluoro-phenyl)-thiazol-2-yl]-2'-nitro-biphenyl-2-carboxylic acid (114 mg, 41%) was prepared from 2'-nitro-4-thiocarbamoyl-biphenyl-2-carboxylic acid methyl ester (which may be prepared as described for Intermediate 4) and 3,4-difluorophenacyl bromide (available from Matrix Scientific) using the procedure described for the preparation of Example 18. $^1$H NMR (300 MHz, DMSO-$d_6$) δ 8.56 (d,

Example 24

4-[4-(3-Fluoro-phenyl)-thiazol-2-yl]-2'-nitro-biphenyl-2-carboxylic acid

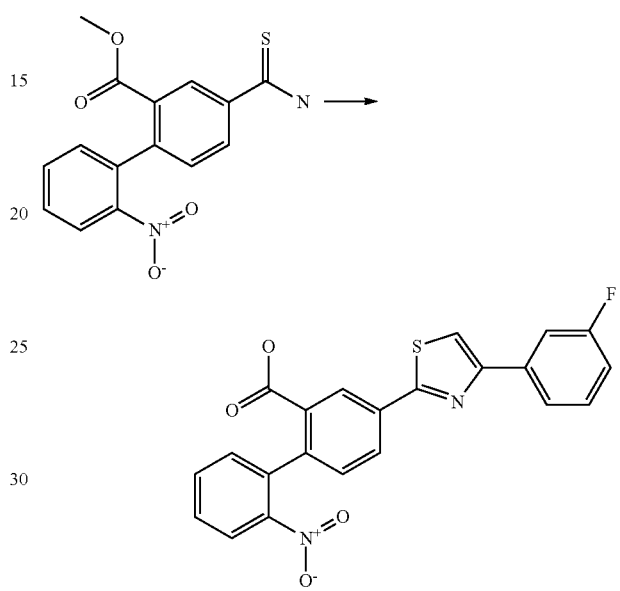

4-[4-(3-Fluoro-phenyl)-thiazol-2-yl]-2'-nitro-biphenyl-2-carboxylic acid (150 mg, 57%) was prepared from 2'-nitro-4-thiocarbamoyl-biphenyl-2-carboxylic acid methyl ester (which may be prepared as described for Intermediate 4) and 3-fluorophenacyl bromide (available from Aldrich Chemical Company, Inc.) using the procedure described for the preparation of Example 18 except that the entire 4 mL of water was added at the beginning of the hydrolysis step rather than being added in two portions. $^1$H NMR (300 MHz, DMSO-$d_6$) δ 13.14 (br s, 1H), 8.58 (d, J=1.8 Hz, 1H), 8.25-8.28 (m, 2H), 8.10-8.17 (m, 3H), 7.63-7.82 (m, 2H), 7.30-7.48 (m, 4H).

Example 25

4-[4-(5-Bromo-thiophen-2-yl)-thiazol-2-yl]-2'-nitro-biphenyl-2-carboxylic acid

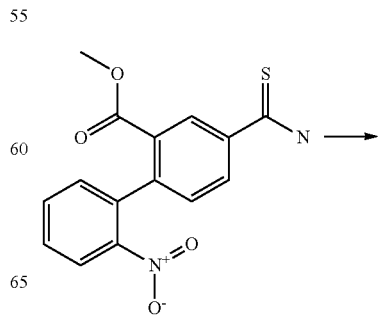

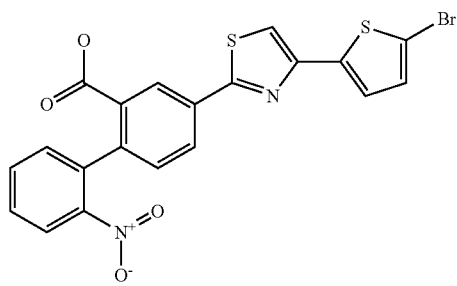

4-[4-(5-Bromo-thiophen-2-yl)-thiazol-2-yl]-2'-nitro-biphenyl-2-carboxylic acid (180 mg, 33%) was prepared from 2'-nitro-4-thiocarbamoyl-biphenyl-2-carboxylic acid methyl ester (which may be prepared as described for Intermediate 4) and 2-bromo-1-(5-bromothiophen-2-yl)ethanone (available from Oakwood Products, Inc.) using the procedure described for the preparation of Example 1. $^1$H NMR (300 MHz, DMSO-d$_6$) δ 13.16 (s, 1H), 8.50 (d, J=1.8 Hz, 1H), 8.13-8.22 (m, 3H), 7.52 (d, J=3.9 Hz, 1H), 7.40-7.48 (m, 2H), 7.28 (d, J=3.9 Hz, 1H).

Example 26

4-[4-(3-Bromo-phenyl)-thiazol-2-yl]-2'-nitro-biphenyl-2-carboxylic acid

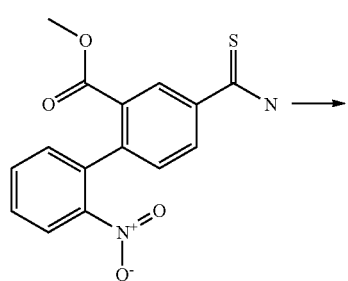

4-[4-(3-Bromo-phenyl)-thiazol-2-yl]-2'-nitro-biphenyl-2-carboxylic acid (106 mg, 34%) was prepared from 2'-nitro-4-thiocarbamoyl-biphenyl-2-carboxylic acid methyl ester (which may be prepared as described for Intermediate 4) and 3-bromophenacyl bromide (available from Aldrich Chemical Company, Inc.) using the procedure described for the preparation of Example 1. $^1$H NMR (300 MHz, DMSO-d$_6$) δ 13.17 (s, 1H), 8.56 (d, J=1.8 Hz, 1H), 8.43 (s, 1H), 8.08-8.29 (m, 4H), 7.41-7.82 (m, 6H).

Example 27

4-[4-(4-Bromo-phenyl)-thiazol-2-yl]-2'-nitro-biphenyl-2-carboxylic acid

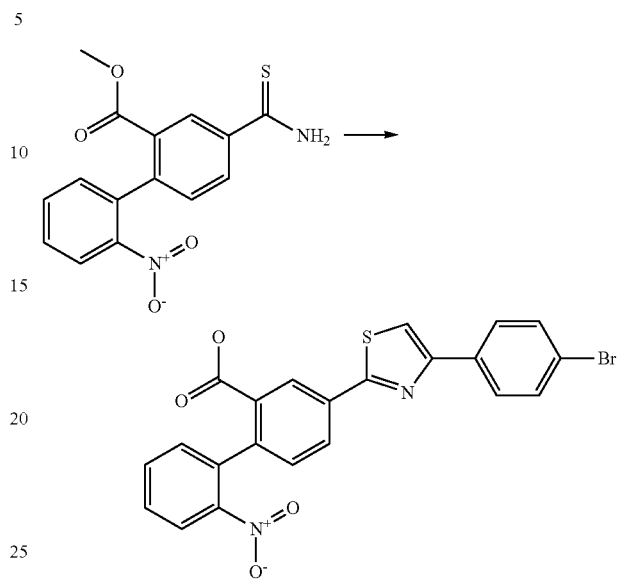

4-[4-(4-Bromo-phenyl)-thiazol-2-yl]-2'-nitro-biphenyl-2-carboxylic acid (205 mg, 68%) was prepared from 2'-nitro-4-thiocarbamoyl-biphenyl-2-carboxylic acid methyl ester (which may be prepared as described for Intermediate 4) and 2,4'-dibromoacetophenone (available from Alfa Aesar) using the procedure described for the preparation of Example 1. $^1$H NMR (300 MHz, DMSO-d$_6$) δ 13.15 (s, 1H), 8.57 (d, J=1.9 Hz, 1H), 8.34 (s, J=8.3, 1H), 8.25 (dd, J=8.0, 2.0 Hz, 1H), 8.14 (dd, J=8.1, 1.1 Hz, 1H), 8.03 (d, J=8.6 Hz, 1H), 7.62-7.81 (m, 4H), 7.40-7.47 (m, 2H).

Example 28

4-[4-(3,4-Dichloro-phenyl)-thiazol-2-yl]-4'-methoxy-2'-nitro-biphenyl-2-carboxylic acid

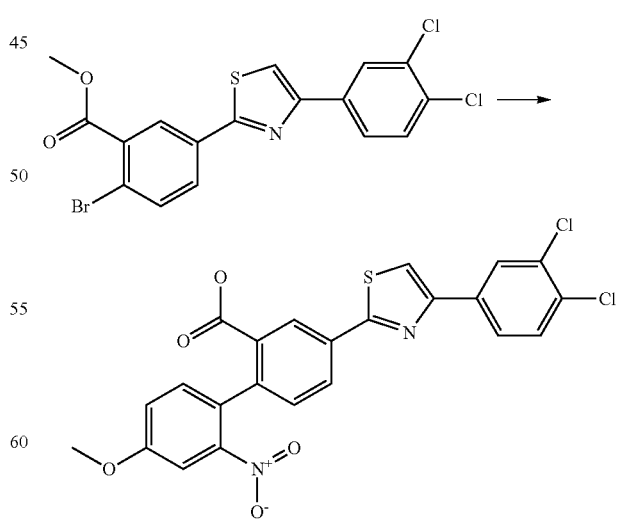

4-[4-(3,4-Dichloro-phenyl)-thiazol-2-yl]-4'-methoxy-2'-nitro-biphenyl-2-carboxylic acid was prepared in 1% yield (for two steps) from 2-bromo-5-[4-(3,4-dichloro-phenyl)- thiazol-2-yl]-benzoic acid methyl ester (which may be prepared as described for Intermediate 6) and 2-(4-methoxy-2-nitrophenyl)-4,4,5,5-tetramethyl-1,3,2-dioxaborolane (available from Combi-Blocks Inc.) using General Procedure A for Suzuki Coupling and Hydrolysis in Parallel Mode. $^1$H NMR (300 MHz, DMSO-$d_6$) δ 8.55 (s, 1H), 8.49 (s, 1H), 8.45 (s, 1H), 8.31-8.36 (m, 1H), 8.27 (d, J=7.9 Hz, 1H), 8.03-8.13 (m, 1H), 7.73-7.80 (m, 1H), 7.67 (s, 1H), 7.45 (d, J=8.1 Hz, 1H), 7.37 (d, J=4.5 Hz, 1H), 3.92 (s, 3H).

Example 29

4-[4-(2-Fluoro-4-methoxy-phenyl)-thiazol-2-yl]-2'-nitro-biphenyl-2-carboxylic acid

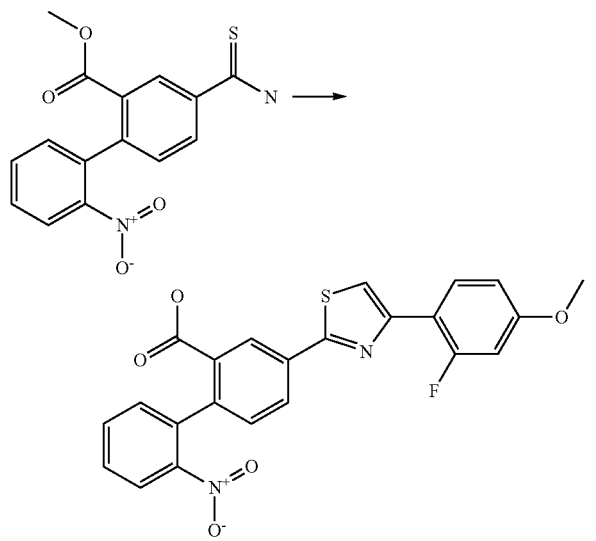

4-[4-(2-Fluoro-4-methoxy-phenyl)-thiazol-2-yl]-2'-nitro-biphenyl-2-carboxylic acid (253 mg, 89%) was prepared from 2'-nitro-4-thiocarbamoyl-biphenyl-2-carboxylic acid methyl ester (which may be prepared as described for Intermediate 4) and 2-fluoro-4-methoxyphenacyl bromide (available from ASDI Incorporated) using the procedure described for the preparation of Example 1. $^1$H NMR (300 MHz, DMSO-$d_6$) δ 8.54 (d, J=1.8 Hz, 1H), 8.10-8.21 (m, 3H), 7.94 (d, J=2.4 Hz, 1H), 7.59-7.78 (m, 2H), 7.39 (d, J=8.0 Hz, 2H), 6.93-7.02 (m, 2H), 3.83 (s, 3H).

Example 30

4-[4-(2-Methoxy-phenyl)-thiazol-2-yl]-2'-nitro-biphenyl-2-carboxylic acid

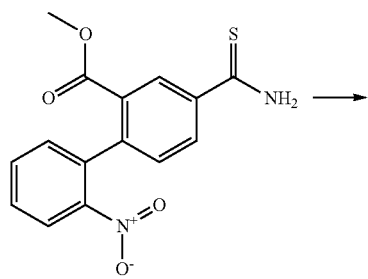

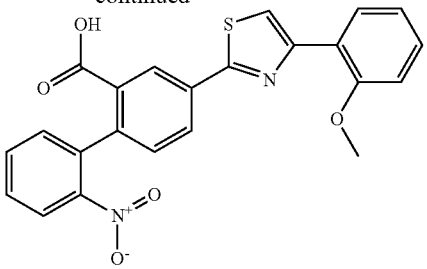

4-[4-(2-Methoxy-phenyl)-thiazol-2-yl]-2'-nitro-biphenyl-2-carboxylic acid (183 mg, 67%) was prepared from 2'-nitro-4-thiocarbamoyl-biphenyl-2-carboxylic acid methyl ester (which may be prepared as described for Intermediate 4) and 2-bromo-2'-methoxyacetophenone (available from ASDI Incorporated) using the procedure described for the preparation of Example 1. $^1$H NMR (300 MHz, DMSO-$d_6$) δ 13.13 (s, 1H), 8.57 (d, J=1.9 Hz, 1H), 8.13-8.31 (m, 4H), 7.63-7.81 (m, 2H), 7.35-7.47 (m, 3H), 7.18 (d, J=8.3 Hz, 1H), 7.10 (t, J=7.6 Hz, 1H).

Example 31

4-[4-(3-Methoxy-phenyl)-thiazol-2-yl]-2'-nitro-biphenyl-2-carboxylic acid

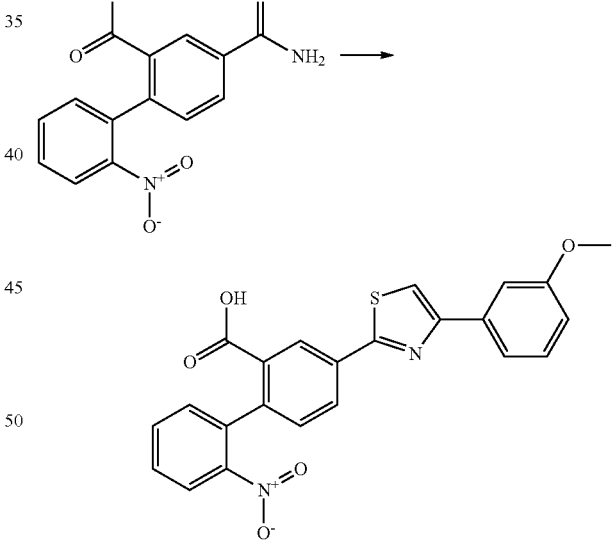

4-[4-(3-Methoxy-phenyl)-thiazol-2-yl]-2'-nitro-biphenyl-2-carboxylic acid (148 mg, 54%) was prepared from 2'-nitro-4-thiocarbamoyl-biphenyl-2-carboxylic acid methyl ester (which may be prepared as described for Intermediate 4) and 3'-methoxyphenacyl bromide (available from Aldrich Chemical Company, Inc.) using the procedure described for the preparation of Example 1. $^1$H NMR (300 MHz, DMSO-$d_6$) δ 8.56 (d, J=1.9 Hz, 1H), 8.30 (s, 1H), 8.27 (dd, J=6.0, 2.0 Hz, 1H), 8.15 (dd, J=8.1, 1.1 Hz, 1H), 7.76-7.82 (m, 1H), 7.61-7.69 (m, 3H), 7.38-7.48 (m, 3H), 6.97 (dd, J=8.2, 2.4 Hz, 1H).

Example 32

4-[4-(4-Methoxy-phenyl)-thiazol-2-yl]-2'-nitro-biphenyl-2-carboxylic acid

Example 33

4-[4-(4-Methanesulfonyl-phenyl)-thiazol-2-yl]-2'-nitro-biphenyl-2-carboxylic acid

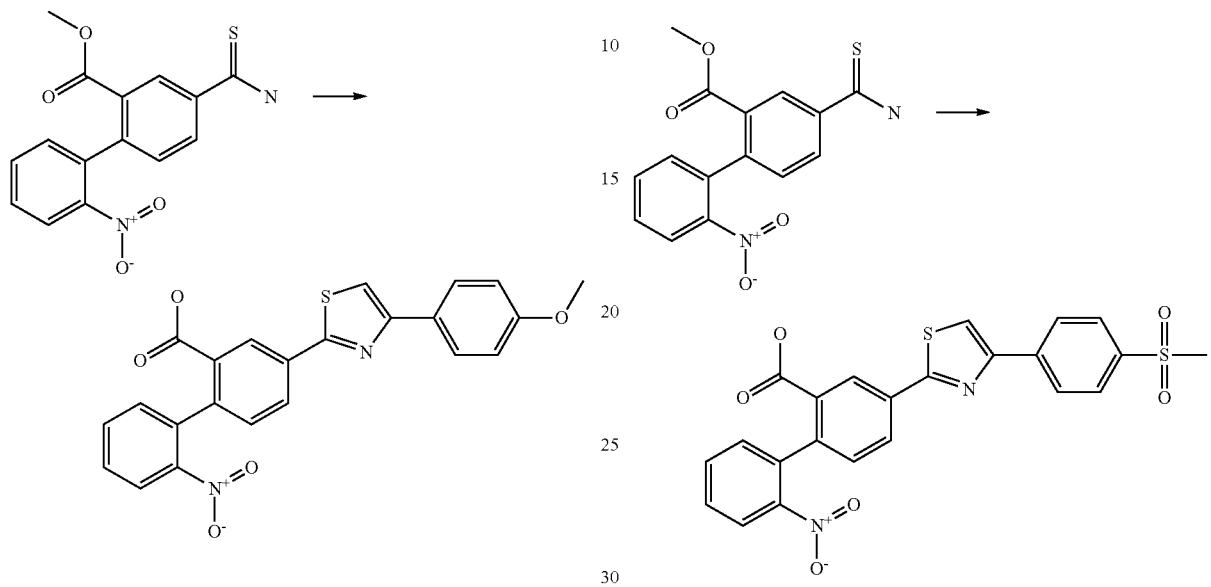

Step 1: 4-[4-(4-Methoxy-phenyl)-thiazol-2-yl]-2'-nitro-biphenyl-2-carboxylic acid methyl ester 2-Bromo-4'-methoxyacetophenone (available from Oakwood Products, Inc.; 144.3 mg, 0.63 mmol) was added to a suspension of 2'-nitro-4-thiocarbamoyl-biphenyl-2-carboxylic acid methyl ester (which may be prepared as described for Intermediate 4; 200 mg, 0.63 mmol) in dioxane (4 mL), and the resulting mixture was stirred at 40° C. for 16 h. The precipitate was collected by filtration (187 mg) and used directly in the next step without purification.

Step 2: 4-[4-(4-Methoxy-phenyl)-thiazol-2-yl]-2'-nitro-biphenyl-2-carboxylic acid Sodium hydroxide (200 mg, 5 mmol) was added to a suspension of 4-[4-(4-methoxy-phenyl)-thiazol-2-yl]-2'-nitro-biphenyl-2-carboxylic acid methyl ester (187 mg) in a mixture of water (8 mL) and dioxane (8 mL). The reaction mixture was stirred at 50° C. for 2 h. The reaction mixture was evaporated to dryness and water (15 mL) was added. The mixture was filtered and the filtrate was made acidic to pH 3-4 by the addition of concentrated HCl. The precipitate was collected by filtration and dried to give 4-[4-(4-methoxy-phenyl)-thiazol-2-yl]-2'-nitro-biphenyl-2-carboxylic acid (100 mg, 37% for two steps). $^1$H NMR (300 MHz, DMSO-$d_6$) δ 13.17 (br s, 1H), 8.56 (d, J=1.8 Hz, 1H), 8.24 (dd, J=8.0, 1.9 Hz, 1H), 8.11-8.16 (m, 2H), 8.01 (d, J=8.8 Hz, 2H), 7.76-7.81 (m, 1H), 7.63-7.68 (m, 1H), 7.41-7.47 (m, 2H), 7.05 (d, J=8.8 Hz, 2H), 3.82 (s, 3H).

4-[4-(4-Methanesulfonyl-phenyl)-thiazol-2-yl]-2'-nitro-biphenyl-2-carboxylic acid (33 mg, 11%) was prepared from 2'-nitro-4-thiocarbamoyl-biphenyl-2-carboxylic acid methyl ester (which may be prepared as described for Intermediate 4) and 2-bromo-1-[4-(methylsulfonyl)phenyl]-1-ethanone (available from TCI America) using the procedure described for the preparation of Example 1. $^1$H NMR (300 MHz, DMSO-$d_6$) δ 8.57 (d, J=8.3 Hz, 2H), 8.27-8.35 (m, 3H), 8.14 (d, J=7.8 Hz, 1H), 8.03 (d, J=8.1 Hz, 1H), 7.79 (t, J=8.4 Hz, 1H), 7.65 (t, J=7.6 Hz, 1H), 7.41-7.48 (m, 2H), 3.26 (s, 3H).

Example 34

4-[4-(2,3-Dihydro-benzo[1,4]dioxin-6-yl)-thiazol-2-yl]-2'-nitro-biphenyl-2-carboxylic acid

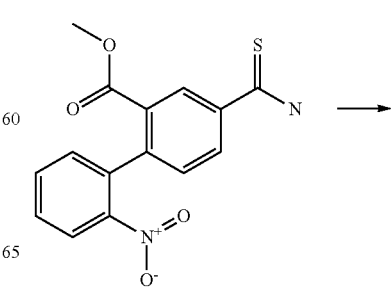

-continued

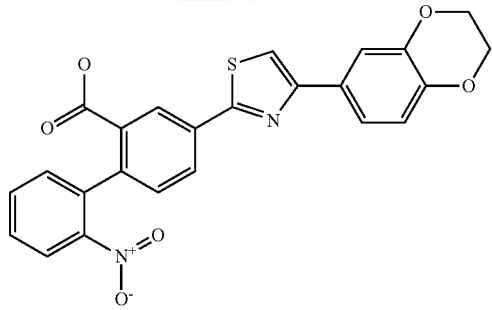

4-[4-(2,3-Dihydro-benzo[1,4]dioxin-6-yl)-thiazol-2-yl]-2'-nitro-biphenyl-2-carboxylic acid (205 mg, 71%) was prepared from 2'-nitro-4-thiocarbamoyl-biphenyl-2-carboxylic acid methyl ester (which may be prepared as described for Intermediate 4) and 2-bromo-1-(2,3-dihydro-1,4-benzodioxin-6-yl)ethan-1-one (available from Alfa Aesar) using the procedure described for the preparation of Example 1. $^1$H NMR (300 MHz, DMSO-d$_6$) δ 8.53 (d, J=1.8 Hz, 2H), 8.24 (dd, J=8.0, 1.9 Hz, 1H), 8.11-8.16 (m, 2H), 7.78 (t, J=7.8 Hz, 1H), 7.52-7.68 (m, 3H), 7.43 (t, J=8.0 Hz, 2H), 6.95 (d, J=9.0 Hz, 1H), 4.29 (s, 4H).

Example 35

4-[4-(3-Cyano-phenyl)-thiazol-2-yl]-2'-nitro-biphenyl-2-carboxylic acid

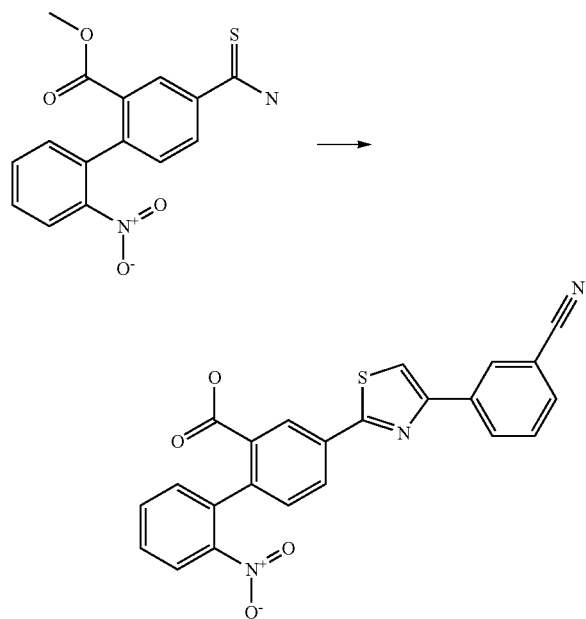

4-[4-(3-Cyano-phenyl)-thiazol-2-yl]-2'-nitro-biphenyl-2-carboxylic acid (150 mg, 56%) was prepared from 2'-nitro-4-thiocarbamoyl-biphenyl-2-carboxylic acid methyl ester (which may be prepared as described for Intermediate 4) and 3-(2-bromoacetyl)benzonitrile (available from Oakwood Products, Inc.) using the procedure described for the preparation of Example 1. $^1$H NMR (300 MHz, DMSO-d$_6$) δ 13.17 (s, 1H), 8.59 (d, J=1.6 Hz, 1H), 8.54 (s, 1H), 8.51 (s, 1H), 8.44 (d, J=7.7 Hz, 1H), 8.31 (dd, J=8.0, 1.6 Hz, 1H), 8.16 (d, J=7.5 Hz, 1H), 7.64-7.88 (m, 4H), 7.43-7.49 (m, 2H).

Example 36

4-[4-(4-Cyano-phenyl)-thiazol-2-yl]-2'-nitro-biphenyl-2-carboxylic acid

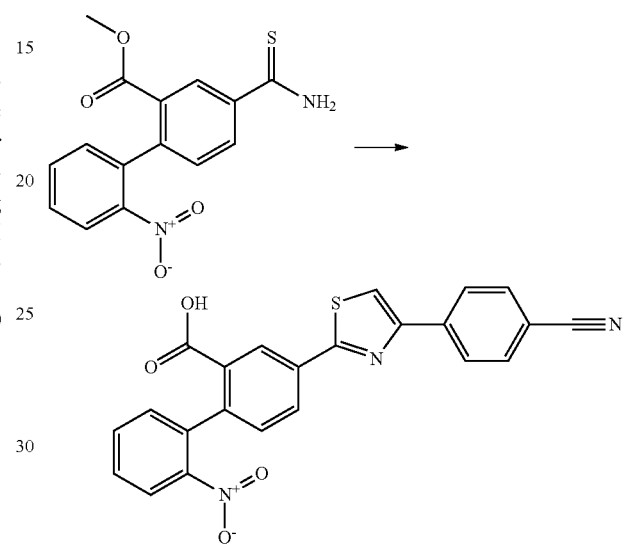

4-[4-(4-Cyano-phenyl)-thiazol-2-yl]-2'-nitro-biphenyl-2-carboxylic acid (100 mg, 37%) was prepared from 2'-nitro-4-thiocarbamoyl-biphenyl-2-carboxylic acid methyl ester (which may be prepared as described for Intermediate 4) and 4-cyanophenacyl bromide (available from Oakwood Products, Inc.) using the procedure described for the preparation of Example 1. $^1$H NMR (300 MHz, DMSO-d$_6$) δ 8.44-8.47 (m, 2H), 8.27 (d, J=8.5 Hz, 2H), 7.94-8.00 (m, 4H), 7.63-7.68 (m, 1H), 7.47-7.52 (m, 1H), 7.28 (dd, J=7.6, 1.4 Hz, 1H), 7.20 (d, J=7.9 Hz, 1H).

Example 37

2'-Nitro-4-(4-pyridin-2-yl-thiazol-2-yl)-biphenyl-2-carboxylic acid

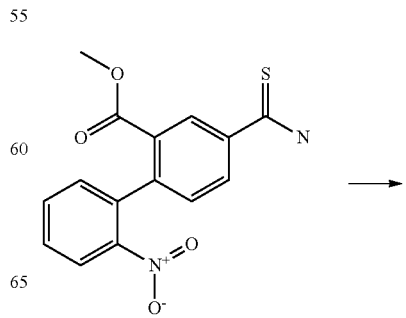

-continued

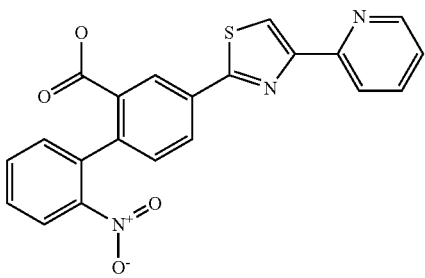

2'-Nitro-4-(4-pyridin-2-yl-thiazol-2-yl)-biphenyl-2-carboxylic acid (200 mg, 79%) was prepared from 2'-nitro-4-thiocarbamoyl-biphenyl-2-carboxylic acid methyl ester (which may be prepared as described for Intermediate 4) and 2-(bromoacetyl)pyridine hydrobromide (available from Oakwood Products, Inc.) using the procedure described for the preparation of Example 1. $^1$H NMR (300 MHz, DMSO-$d_6$) δ 8.67 (d, J=4.9 Hz, 1H), 8.60 (d, J=1.9 Hz, 1H), 8.50 (s, 1H), 8.26-8.30 (m, 2H), 8.15 (d, J=7.5 Hz, 2H), 8.00-8.05 (m, 1H), 7.76-7.81 (m, 1H), 7.62-7.68 (m, 1H), 7.41-7.49 (m, 3H).

Example 38

2'-Nitro-4-(4-pyridin-3-yl-thiazol-2-yl)-biphenyl-2-carboxylic acid

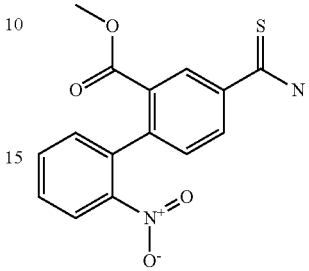

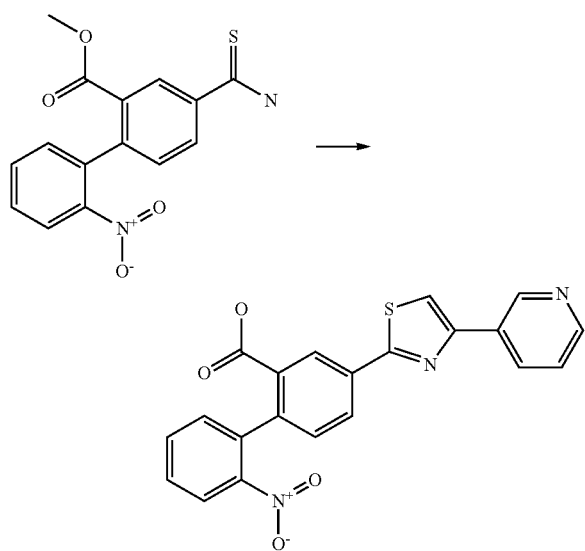

2'-Nitro-4-(4-pyridin-3-yl-thiazol-2-yl)-biphenyl-2-carboxylic acid (120 mg, 47%) was prepared from 2'-nitro-4-thiocarbamoyl-biphenyl-2-carboxylic acid methyl ester (which may be prepared as described for Intermediate 4) and 3-(bromoacetyl)pyridine hydrobromide (available from Oakwood Products, Inc.) using the procedure described for the preparation of Example 1. $^1$H NMR (300 MHz, DMSO-$d_6$) δ 9.32 (d, J=1.9 Hz, 1H), 8.64 (dd, J=4.8, 1.4 Hz, 1H), 8.55-8.58 (m, 2H), 8.50 (s, 1H), 8.29 (dd, J=8.0, 2.0 Hz, 1H), 8.14 (dd, J=8.0, 1.2 Hz, 1H), 7.76-7.81 (m, 1H), 7.62-7.68 (m, 2H), 7.41-7.49 (m, 1H).

Example 39

2'-Nitro-4-(4-pyridin-4-yl-thiazol-2-yl)-biphenyl-2-carboxylic acid

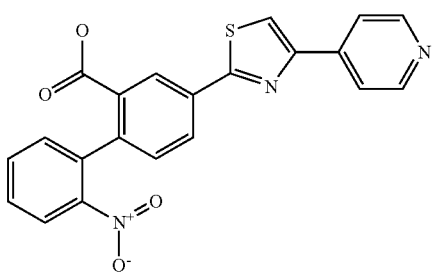

2'-Nitro-4-(4-pyridin-4-yl-thiazol-2-yl)-biphenyl-2-carboxylic acid (195 mg, 77%) was prepared from 2'-nitro-4-thiocarbamoyl-biphenyl-2-carboxylic acid methyl ester (which may be prepared as described for Intermediate 4) and 4-(bromoacetyl)pyridine hydrobromide (available from Oakwood Products, Inc.) using the procedure described for the preparation of Example 1. $^1$H NMR (300 MHz, DMSO-$d_6$) δ 13.14 (s, 1H), 8.68 (d, J=5.2 Hz, 2H), 8.61 (s, 1H), 8.58 (d, J=1.1 Hz, 1H), 8.28 (dd, J=7.9, 0.9 Hz, 1H), 8.14 (d, J=8.2 Hz, 1H), 8.02 (d, J=5.4 Hz, 2H), 7.78 (t, J=7.5 Hz, 1H), 7.65 (t, J=7.6 Hz, 1H), 7.41-7.49 (m, 2H).

Example 40

4-[4-(2,4-Dimethyl-phenyl)-thiazol-2-yl]-2'-nitro-biphenyl-2-carboxylic acid

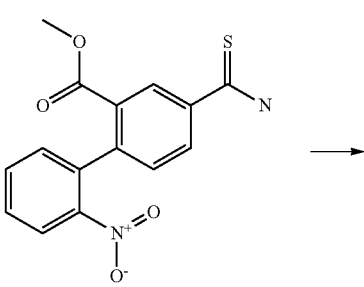

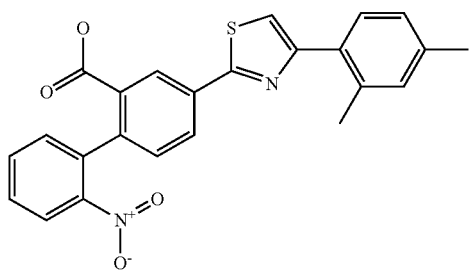

4-[4-(2,4-Dimethyl-phenyl)-thiazol-2-yl]-2'-nitro-biphenyl-2-carboxylic acid (126 mg, 47%) was prepared from 2'-nitro-4-thiocarbamoyl-biphenyl-2-carboxylic acid methyl ester (which may be prepared as described for Intermediate 4) and 2-bromo-1-(2,4-dimethylphenyl)ethan-1-one (available from ASDI Incorporated) using the procedure described for the preparation of Example 1. $^1$H NMR (300 MHz, DMSO-$d_6$) δ 8.52 (d, J=1.8 Hz, 1H), 8.10-8.18 (m, 2H), 7.85 (s, 1H), 7.76 (t, J=7.7 Hz, 1H), 7.11-7.40 (m, 4H), 2.48 (s, 3H), 2.34 (s, 3H).

Example 41

2'-Nitro-4-(4-p-tolyl-thiazol-2-yl)-biphenyl-2-carboxylic acid

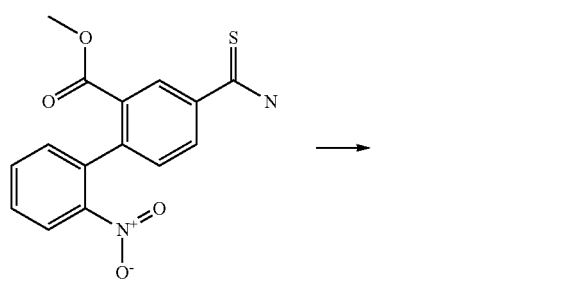

2'-Nitro-4-(4-p-tolyl-thiazol-2-yl)-biphenyl-2-carboxylic acid (85 mg, 32%) was prepared from 2'-nitro-4-thiocarbamoyl-biphenyl-2-carboxylic acid methyl ester (which may be prepared as described for Intermediate 4) and 2-bromo-4'-methylacetophenone (available from ASDI Incorporated) using the procedure described for the preparation of Example 39. $^1$H NMR (400 MHz, DMSO-$d_6$) δ 13.15 (br s, 1H), 8.57 (d, J=1.9 Hz, 2H), 8.26 (dd, J=8.0, 1.9 Hz, 1H), 8.20 (s, 1H), 8.15 (dd, J=8.1, 0.9 Hz, 1H), 7.97 (d, J=8.1 Hz, 2H), 7.77-7.82 (m, 1H), 7.63-7.69 (m, 1H), 7.42-7.48 (m, 2H), 7.30 (d, J=8.0 Hz, 2H), 2.36 (s, 3H).

Example 42

2'-Nitro-4-(4-thiophen-3-yl-thiazol-2-yl)-biphenyl-2-carboxylic acid

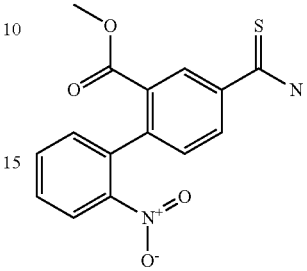

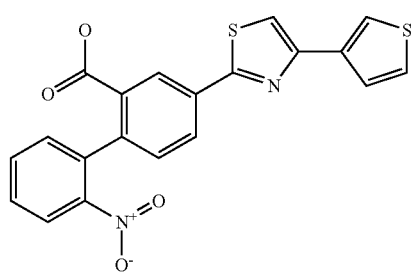

2'-Nitro-4-(4-thiophen-3-yl-thiazol-2-yl)-biphenyl-2-carboxylic acid (50 mg, 19%) was prepared from 2'-nitro-4-thiocarbamoyl-biphenyl-2-carboxylic acid methyl ester (which may be prepared as described for Intermediate 4) and 2-bromo-1-(3-thienyl)-1-ethanone (available from Maybridge) using the procedure described for the preparation of Example 1. $^1$H NMR (300 MHz, DMSO-$d_6$) δ 13.13 (s, 1H), 8.54 (d, J=1.7 Hz, 1H), 8.23 (dd, J=7.8, 1.8 Hz, 1H), 8.04-8.15 (m, 3H), 7.78 (t, J=6.8 Hz, 1H), 7.62-7.69 (m, 3H), 7.44 (t, J=8.1 Hz, 2H).

Example 43

2'-Nitro-4-(4-phenyl-thiazol-2-yl)-biphenyl-2-carboxylic acid

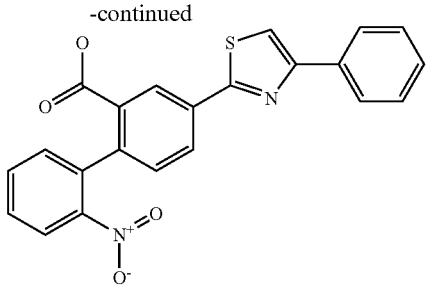

2'-Nitro-4-(4-phenyl-thiazol-2-yl)-biphenyl-2-carboxylic acid (100 mg, 39%) was prepared from 2'-nitro-4-thiocarbamoyl-biphenyl-2-carboxylic acid methyl ester (which may be prepared as described for Intermediate 4) and 2-bromoacetophenone (available from Chem-Impex International, Inc.) using the procedure described for the preparation of Example 18 except that the entire 4 mL of water was added at the beginning of the hydrolysis step rather than being added in two portions. $^1$H NMR (300 MHz, DMSO-$d_6$) δ 13.16 (br s, 1H), 8.58 (d, J=1.9 Hz, 1H), 8.06-8.28 (m, 5H), 7.36-7.82 (m, 7H).

Example 44

2'-Nitro-4-(4-thiophen-2-yl-thiazol-2-yl)-biphenyl-2-carboxylic acid

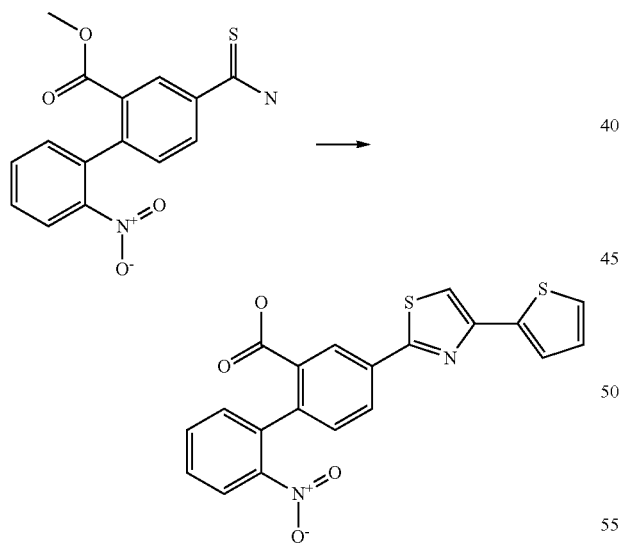

2'-Nitro-4-(4-thiophen-2-yl-thiazol-2-yl)-biphenyl-2-carboxylic acid (120 mg, 47%) was prepared from 2'-nitro-4-thiocarbamoyl-biphenyl-2-carboxylic acid methyl ester (which may be prepared as described for Intermediate 4) and 2-(2-bromoacetyl)thiophene (available from Maybridge) using the procedure described for the preparation of Example 1. $^1$H NMR (300 MHz, DMSO-$d_6$) δ 8.51 (d, J=1.7 Hz, 1H), 8.10-8.20 (m, 3H), 7.71 (t, J=8.1 Hz, 1H), 7.57-7.67 (m, 3H), 7.41 (t, J=8.3 Hz, 2H), 7.15 (t, J=4.6 Hz, 2H).

Example 45

4-[4-(3,4-Dichloro-phenyl)-thiazol-2-yl]-4'-nitro-biphenyl-2-carboxylic acid

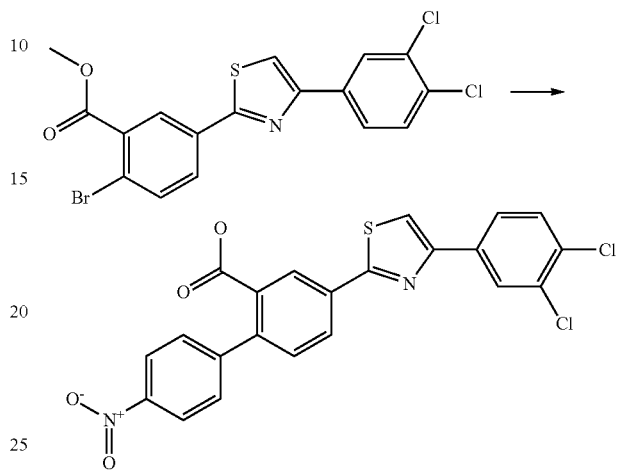

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 4-nitrophenylboronic acid (available from Combi-Blocks Inc.; 67 mg, 0.4 mmol). The resulting ester was hydrolyzed and the acid was purified to give 4-[4-(3,4-dichloro-phenyl)-thiazol-2-yl]-4'-nitro-biphenyl-2-carboxylic acid (17 mg, 18%). $^1$H NMR (400 MHz, DMSO-$d_6$) δ 13.35 (br s, 3H), 8.50 (s, 1H) 8.47 (s, 1H), 8.34 (s, 1H), 8.27-8.32 (m, 2H), 8.10 (d, J=8.5 Hz, 1H), 7.77 (d, J=6.8 Hz, 1H), 7.68 (d, J=7.0 Hz, 2H), 7.61 (d, J=6.5 Hz, 1H).

Example 46

4-[4-(3,4-Dichloro-phenyl)-thiazol-2-yl]-3'-nitro-biphenyl-2-carboxylic acid

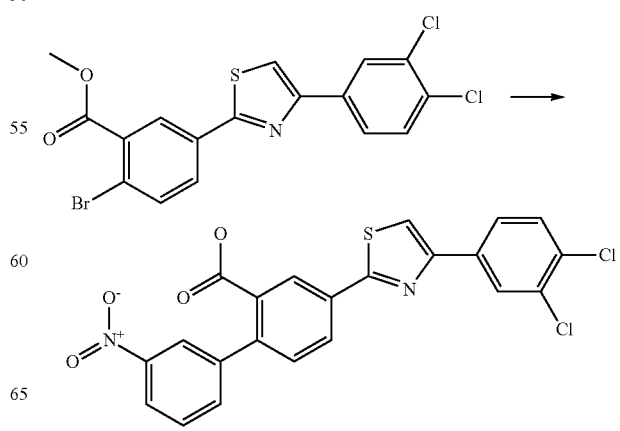

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 3-nitrophenylboronic acid (available from Aldrich Chemical Company, Inc.; 67 mg, 0.4 mmol). The resulting ester was hydrolyzed and the acid was purified to give 4-[4-(3,4-dichloro-phenyl)-thiazol-2-yl]-3'-nitro-biphenyl-2-carboxylic acid (36 mg, 38%). $^1$H NMR (400 MHz, DMSO-d$_6$) δ 8.46-8.51 (m, 2H), 8.18-8.39 (m, 4H), 8.06-8.15 (m, 1H), 7.87 (d, J=7.0 Hz, 1H), 7.73-7.79 (m, 2H), 7.63-7.68 (m, 1H).

Example 47

4-[4-(3,4-Dichloro-phenyl)-thiazol-2-yl]-4'-(3-diethylamino-propylcarbamoyl)-biphenyl-2-carboxylic acid

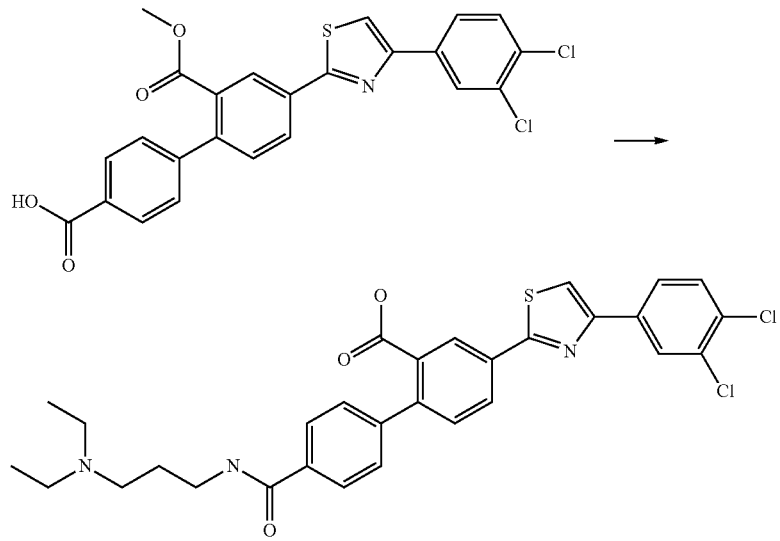

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with N,N-diethyl-1,3-propanediamine (available from Aldrich Chemical Company, Inc.; 81 mg, 0.62 mmol). The resulting ester was hydrolyzed and the acid was purified using HPLC Purification Conditions B to give 4-[4-(3,4-dichloro-phenyl)-thiazol-2-yl]-4'-(3-diethylamino-propylcarbamoyl)-biphenyl-2-carboxylic acid (104 mg, 87%). $^1$H NMR (400 MHz, DMSO-d$_6$) δ ppm 13.63 (br s, 1H), 9.48 (br s, 1H), $^1$H NMR (400 MHz, DMF), d ppm 9.14 (t, J=5.6 Hz, 1H), 8.92 (s, 1H), 8.83 (d, J=1.8 Hz, 1H), 8.77 (d, J=2.0 Hz, 1H), 8.68 (dd, J=8.0, 2.0 Hz, 1H), 8.52 (dd, J=8.3, 2.0 Hz, 1H), 8.34 (d, J=8.3 Hz, 2H), 8.20 (d, J=8.5 Hz, 1H), 8.01 (d, J=8.0 Hz, 1H), 7.93 (d, J=8.0 Hz, 2H), 3.77-3.84 (m, 2H), 3.51-3.63 (m, 6H), 2.28-2.38 (m, 2H), 1.62 (t, J=7.2 Hz, 6H).

Example 48

4-[4-(3,4-Dichloro-phenyl)-thiazol-2-yl]-4'-(3-dimethylamino-propylcarbamoyl)-biphenyl-2-carboxylic acid

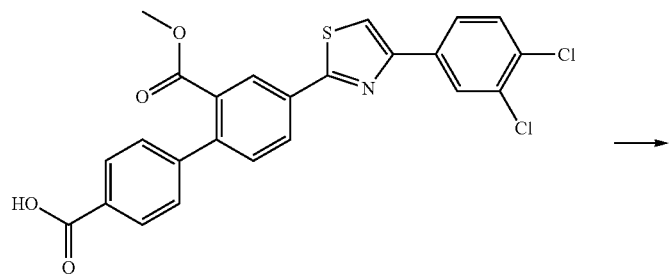

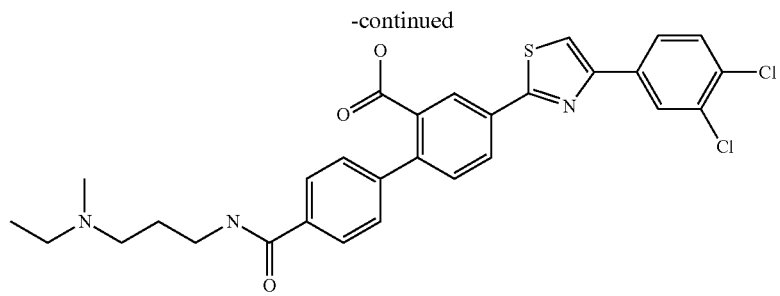

Using the conditions of General Procedure D for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with N,N-dimethyl-1,3-propanediamine (available from Aldrich Chemical Company, Inc.; 42 mg, 0.41 mmol) to give the crude amide product. The crude amide was hydrolyzed by adding THF (2 mL), water (0.05 mL), MeOH (1 mL), and lithium hydroxide monohydrate (12.3 mg, 0.29 mmol) and stirring the mixture overnight at room temperature. Lithium hydroxide monohydrate (22 mg, 0.52 mmol) was added. The reaction mixture was stirred overnight, and then another portion of lithium hydroxide monohydrate (22 mg, 0.52 mmol) was added. The reaction mixture was stirred overnight. The reaction mixture was concentrated to dryness under vacuum at 40° C. 1 M HCl (3 mL) was added, and the mixture was stirred, concentrated to dryness, and purified and purified using HPLC Purification Conditions A to give 4-[4-(3,4-dichloro-phenyl)-thiazol-2-yl]-4'-(3-dimethylamino-propylcarbamoyl)-biphenyl-2-carboxylic acid (102 mg, 89%) as a white solid. $^1$H NMR (400 MHz, DMSO-$d_6$) δ ppm 13.16 (br s, 1H), 8.68 (t, J=5.6 Hz, 1H), 8.48 (s, 1H), 8.40 (d, J=1.8 Hz, 1H), 8.34 (d, J=2.0 Hz, 1H), 8.25 (dd, J=8.0, 1.8 Hz, 1H), 8.09 (dd, J=8.5, 2.0 Hz, 1H), 7.92 (d, J=8.3 Hz, 2H), 7.77 (d, J=8.3 Hz, 1H), 7.58 (d, J=8.0 Hz, 1H), 7.50 (d, J=8.3 Hz, 2H), 3.34-3.40 (m, 2H), 3.08-3.16 (m, 2H), 2.79-2.82 (m, 6H), 1.86-1.95 (m, 2H).

Example 49

4-[4-(3,4-Dichloro-phenyl)-thiazol-2-yl]-4'-(2-dimethylamino-ethylcarbamoyl)-biphenyl-2-carboxylic acid

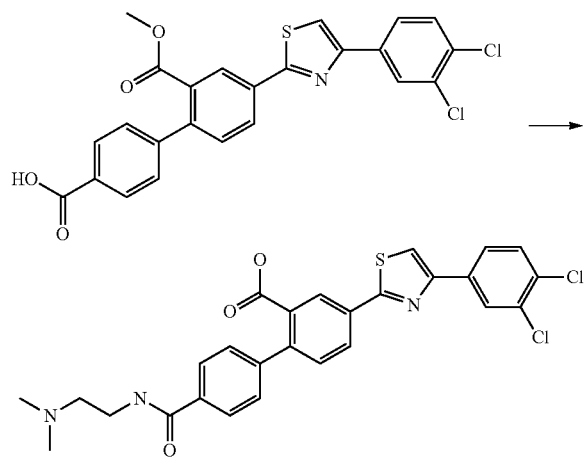

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with N,N-dimethylethylenediamine (available from Aldrich Chemical Company, Inc.; 55 mg, 0.62 mmol). The resulting ester was hydrolyzed and the acid was purified using HPLC Purification Conditions B to give 4-[4-(3,4-dichloro-phenyl)-thiazol-2-yl]-4'-(2-dimethylamino-ethylcarbamoyl)-biphenyl-2-carboxylic acid (81 mg, 73%). $^1$H NMR (400 MHz, DMSO-$d_6$) δ ppm 8.73 (t, J=5.4 Hz, 1H), 8.47 (s, 1H), 8.41 (d, J=2.0 Hz, 1H), 8.33 (d, J=2.0 Hz, 1H), 8.25 (dd, J=8.0, 1.8 Hz, 1H), 8.09 (dd, J=8.5, 2.0 Hz, 1H), 7.93 (d, J=8.3 Hz, 2H), 7.77 (d, J=8.5 Hz, 1H), 7.58 (d, J=8.0 Hz, 1H), 7.52 (d, J=8.3 Hz, 2H), 3.63 (q, J=5.8 Hz, 2H), 3.22-3.27 (m, 2H), 2.84 (s, 6H).

Example 50

4-[4-(3,4-Dichloro-phenyl)-thiazol-2-yl]-4'-[(2-methyl-2H-pyrazol-3-ylmethyl)-carbamoyl]-biphenyl-2-carboxylic acid

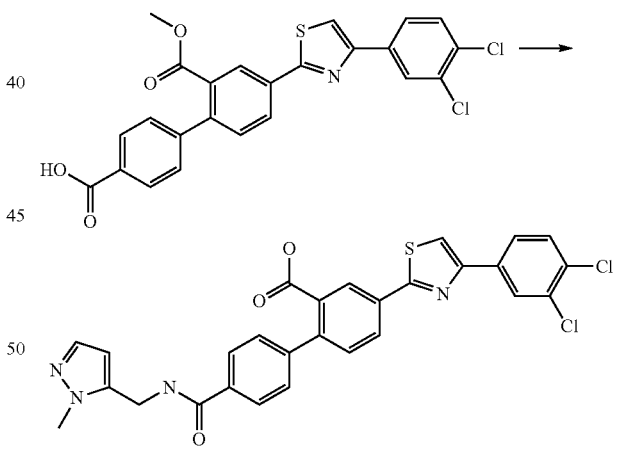

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with (1-methyl-1H-pyrazol-5-yl)methylamine (available from Aldrich Chemical Company, Inc.; 69 mg, 0.62 mmol). The resulting ester was hydrolyzed and the acid was purified using HPLC Purification Conditions B to give 4-[4-(3,4-dichloro-phenyl)-thiazol-2-yl]-4'-[(2-methyl-2H-pyrazol-3-ylmethyl)-carbamoyl]-biphenyl-2-carboxylic acid (100 mg, 86%). $^1$H NMR (400 MHz, DMSO-$d_6$) δ ppm 13.23 (br s, 1H), 9.07 (t, J=5.6 Hz, 1H), 8.48 (s, 1H), 8.38 (d, J=1.8 Hz, 1H), 8.34 (d, J=2.0 Hz, 1H), 8.24 (dd, J=8.0, 1.8 Hz, 1H), 8.10 (dd, J=8.4, 1.9 Hz, 1H), 7.94 (d, J=8.3 Hz, 2H), 7.77 (d, J=8.5 Hz, 1H), 7.59 (d, J=8.0 Hz, 1H), 7.50 (d, J=8.3 Hz, 2H), 7.32 (d, J=1.8 Hz, 1H), 6.19 (d, J=1.5 Hz, 1H), 4.55 (d, J=5.5 Hz, 2H), 3.84 (s, 3H).

Example 51

4-[4-(3,4-Dichloro-phenyl)-thiazol-2-yl]-4'-(1-methyl-piperidin-4-ylcarbamoyl)-biphenyl-2-carboxylic acid

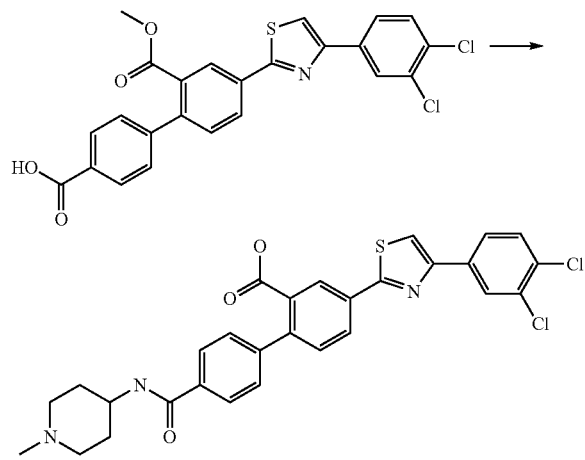

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-amino-1-methylpiperidine (available from Aldrich Chemical Company, Inc.; 71 mg, 0.62 mmol). The resulting ester was hydrolyzed and the acid was purified using HPLC Purification Conditions B to give 4-[4-(3,4-dichloro-phenyl)-thiazol-2-yl]-4'-(1-methyl-piperidin-4-ylcarbamoyl)-biphenyl-2-carboxylic acid (135 mg, 116%). $^1$H NMR (400 MHz, DMSO-$d_6$) δ ppm 13.20 (br s, 1H), 8.55 (d, J=7.5 Hz, 1H), 8.49 (s, 1H), 8.40 (d, J=1.8 Hz, 1H), 8.35 (d, J=2.0 Hz, 1H), 8.26 (dd, J=8.2, 1.9 Hz, 1H), 8.10 (dd, J=8.3, 2.0 Hz, 1H), 7.92 (d, J=8.3 Hz, 2H), 7.78 (d, J=8.3 Hz, 1H), 7.58 (d, J=8.0 Hz, 1H), 7.50 (d, J=8.3 Hz, 2H), 4.01-4.10 (m, 1H), 3.45-3.51 (m, 2H), 3.05-3.18 (m, 2H), 2.78-2.81 (m, 2H), 2.54 (s, 3H), 2.02-2.10 (m, 2H).

Example 52

4'-(1-Acetyl-piperidin-4-ylcarbamoyl)-4-[4-(3,4-dichloro-phenyl)-thiazol-2-yl]-biphenyl-2-carboxylic acid

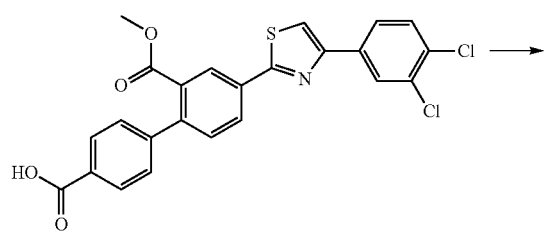

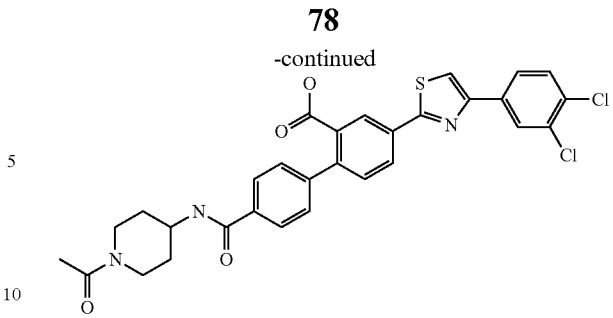

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 1-acetylpiperidin-4-amine (available from Aldrich Chemical Company, Inc.; 88 mg, 0.62 mmol). The resulting ester was hydrolyzed and the acid was purified using HPLC Purification Conditions B to give 4'-(1-acetyl-piperidin-4-ylcarbamoyl)-4-[4-(3,4-dichloro-phenyl)-thiazol-2-yl]-biphenyl-2-carboxylic acid (5 mg, 4%). $^1$H NMR (400 MHz, DMSO-$d_6$) δ ppm 13.19 (br s, 1H), 8.45 (s, 1H), 8.33 (s, 3H), 8.19 (d, J=7.8 Hz, 1H), 8.09 (d, J=8.5 Hz, 1H), 7.90 (d, J=8.0 Hz, 2H), 7.76 (d, J=8.3 Hz, 1H), 7.55 (d, J=8.0 Hz, 1H), 7.50 (d, J=8.0 Hz, 2H), 4.35 (d, J=12.3 Hz, 1H), 4.05 (br s, 1H), 3.85 (d, J=13.3 Hz, 1H), 3.16 (t, J=11.8 Hz, 1H), 2.69 (d, J=13.3 Hz, 1H), 2.02 (s, 3H), 1.78-1.93 (m, 1H), 1.18-1.58 (m, 4H).

Example 53

4-[4-(3,4-Dichloro-phenyl)-thiazol-2-yl]-4'-(4-methyl-piperazine-1-carbonyl)-biphenyl-2-carboxylic acid

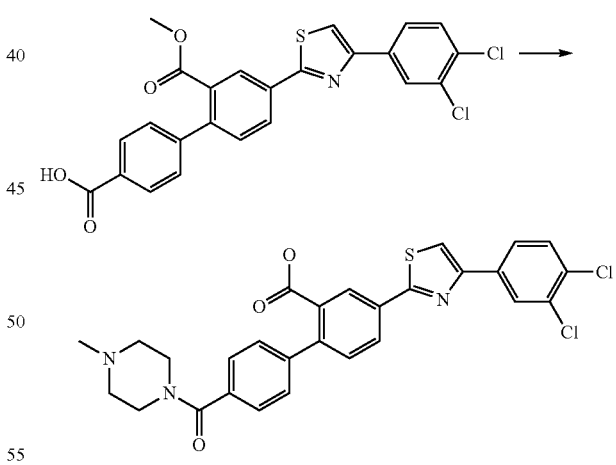

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 1-methylpiperazine (available from Aldrich Chemical Company, Inc.; 62 mg, 0.62 mmol). The resulting ester was hydrolyzed and the acid was purified using HPLC Purification Conditions B to give 4-[4-(3,4-dichloro-phenyl)-thiazol-2-yl]-4'-(4-methyl-piperazine-1-carbonyl)-biphenyl-2-carboxylic acid (86 mg, 75%). $^1$H NMR (400 MHz, DMSO-$d_6$) δ ppm 13.20 (br s, 1H), 9.97

(br s, 1H), 8.47 (s, 1H), 8.39 (s, 1H), 8.34 (s, 1H), 8.26 (d, J=8.3 Hz, 1H), 8.09 (d, J=8.3 Hz, 1H), 7.77 (d, J=8.5 Hz, 1H), 7.59 (d, J=8.0 Hz, 1H), 7.48-7.57 (m, 4H), 3.25-3.44 (m, 8H), 2.81 (br s, 3H).

Example 54

4'-(4-Acetyl-piperazine-1-carbonyl)-4-[4-(3,4-dichloro-phenyl)-thiazol-2-yl]-biphenyl-2-carboxylic acid

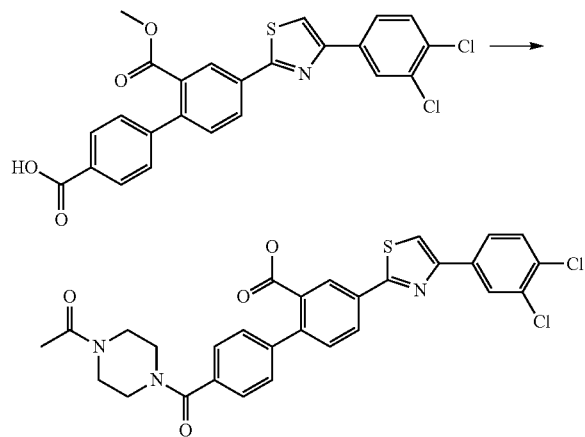

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 1-acetylpiperazine (available from Aldrich Chemical Company, Inc.; 79 mg, 0.62 mmol). The resulting ester was hydrolyzed and the acid was purified using HPLC Purification Conditions B to give 4'-(4-acetyl-piperazine-1-carbonyl)-4-[4-(3,4-dichloro-phenyl)-thiazol-2-yl]-biphenyl-2-carboxylic acid (81 mg, 68%). $^1$H NMR (400 MHz, DMSO-d$_6$) δ ppm 13.24 (br s, 1H), 8.48 (s, 1H), 8.37 (d, J=1.8 Hz, 1H), 8.34 (d, J=2.0 Hz, 1H), 8.24 (dd, J=8.0, 2.0 Hz, 1H), 8.10 (dd, J=8.3, 2.0 Hz, 1H), 7.77 (d, J=8.3 Hz, 1H), 7.60 (d, J=8.0 Hz, 1H), 7.45-7.53 (m, 4H), 3.46-3.59 (br s, 6H), 3.32-3.36 (s, 6H), 2.03 (s, 3H).

Example 55

4-[4-(3,4-Dichloro-phenyl)-thiazol-2-yl]-4'-(4-hydroxy-piperidine-1-carbonyl)-biphenyl-2-carboxylic acid

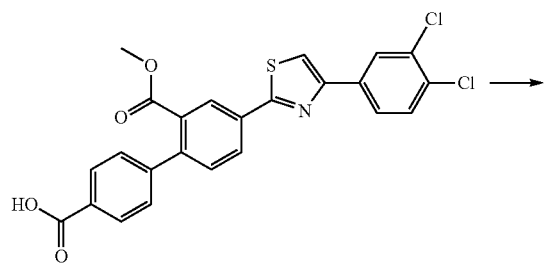

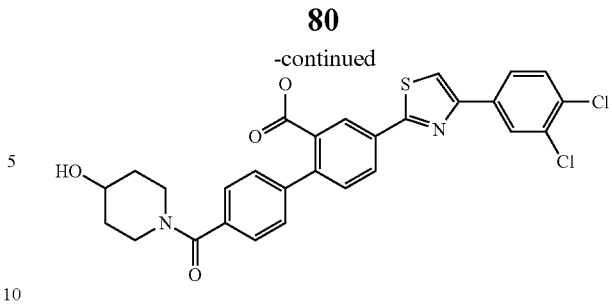

Using the conditions of General Procedure D for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-hydroxypiperidine (available from Aldrich Chemical Company, Inc.; 42 mg, 0.42 mmol) to give the crude amide product. The crude amide was hydrolyzed by adding THF (2 mL), water (0.05 mL), MeOH (1 mL), and lithium hydroxide monohydrate (12.3 mg, 0.29 mmol) and stirring the mixture overnight at room temperature. The reaction mixture was concentrated to dryness under vacuum at 40° C. 1 M HCl (3 mL) was added, and the mixture was stirred, concentrated to dryness, and purified using HPLC Purification Conditions A to give 4-[4-(3,4-dichloro-phenyl)-thiazol-2-yl]-4'-(4-hydroxy-piperidine-1-carbonyl)-biphenyl-2-carboxylic acid (48 mg, 52%) as a white solid. $^1$H NMR (400 MHz, DMSO-d$_6$) δ ppm 13.18 (br s, 1H), 8.47 (s, 1H), 8.37 (d, J=1.8 Hz, 1H), 8.34 (d, J=2.0 Hz, 1H), 8.24 (dd, J=8.0, 2.0 Hz, 1H), 8.09 (dd, J=8.3, 2.0 Hz, 1H), 7.76 (d, J=8.5 Hz, 1H), 7.60 (d, J=8.0 Hz, 1H), 7.42-7.49 (m, 4H), 3.73-3.79 (m, 1H), 3.36-3.52 (m, 2H+water peak), 3.15-3.27 (m, 2H), 1.70-1.82 (m, 2H), 1.32-1.47 (m, 2H).

Example 56

4-[4-(3,4-Dichloro-phenyl)-thiazol-2-yl]-4'-(morpholine-4-carbonyl)-biphenyl-2-carboxylic acid

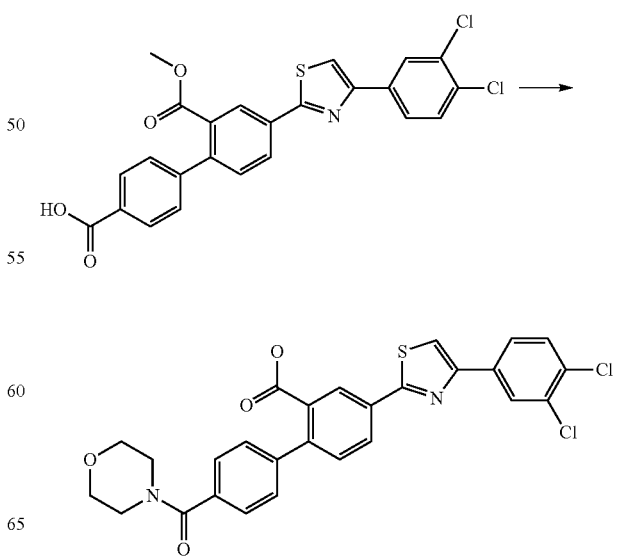

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with morpholine (available from Aldrich Chemical Company, Inc.; 54 mg, 0.62 mmol). The resulting ester was hydrolyzed and the acid was purified using HPLC Purification Conditions B to give 4-[4-(3,4-dichloro-phenyl)-thiazol-2-yl]-4'-(morpholine-4-carbonyl)-biphenyl-2-carboxylic acid (76 mg, 69%). ¹H NMR (400 MHz, DMSO-d₆) δ ppm 13.17 (br s, 1H), 8.46 (s, 1H), 8.37 (s, 1H), 8.33 (s, 1H), 8.24 (d, J=8.0 Hz, 1H), 8.09 (d, J=8.3 Hz, 1H), 7.76 (d, J=8.5 Hz, 1H), 7.59 (d, J=8.0 Hz, 1H), 7.44-7.51 (m, 4H), 3.60-3.67 (m, 4H), 3.26-3.30 (m, 4H).

Example 57

4-[4-(3,4-Dichloro-phenyl)-thiazol-2-yl]-4'-(pyrrolidine-1-carbonyl)-biphenyl-2-carboxylic acid

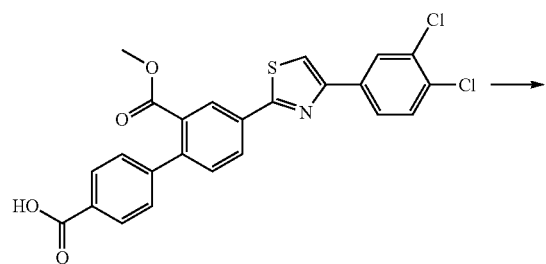

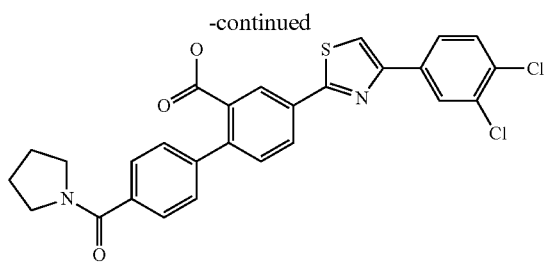

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with pyrrolidine (available from Aldrich Chemical Company, Inc.; 44 mg, 0.62 mmol). The resulting ester was hydrolyzed and the acid was purified using HPLC Purification Conditions B to give 4-[4-(3,4-dichloro-phenyl)-thiazol-2-yl]-4'-(pyrrolidine-1-carbonyl)-biphenyl-2-carboxylic acid (58 mg, 54%). ¹H NMR (400 MHz, DMSO-d₆) δ ppm 13.17 (br s, 1H), 8.46 (s, 1H), 8.35 (dd, J=11.7, 1.9 Hz, 2H), 8.23 (dd, J=8.2, 1.9 Hz, 1H), 8.09 (dd, J=8.5, 2.0 Hz, 1H), 7.76 (d, J=8.5 Hz, 1H), 7.59 (dd, J=8.3, 2.3 Hz, 3H), 7.46 (d, J=8.0 Hz, 2H), 3.40-3.54 (m, 4H), 1.73-2.01 (m, 4H).

Example 58

4-[4-(3,4-Dichloro-phenyl)-thiazol-2-yl]-4'-(3-morpholin-4-yl-propylcarbamoyl)-biphenyl-2-carboxylic acid

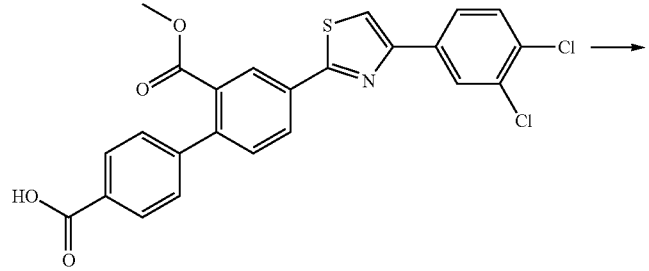

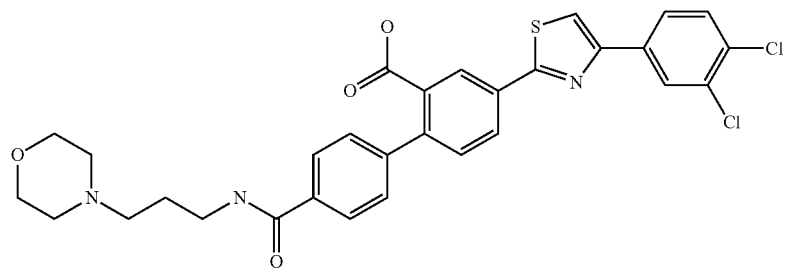

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with N-(3-aminopropyl)morpholine (available from Aldrich Chemical Company, Inc.; 89 mg, 0.62 mmol). The resulting ester was hydrolyzed and the acid was purified using HPLC Purification Conditions B to give 4-[4-(3,4-dichloro-phenyl)-thiazol-2-yl]-4'-(3-morpholin-4-yl-propylcarbamoyl)-biphenyl-2-carboxylic acid (80 mg, 65%). $^1$H NMR (400 MHz, DMSO-$d_6$) δ ppm 13.13 (br s, 1H), 9.60 (br s, 1H), 8.67 (br t, 1H), 8.47 (s, 1H), 8.40 (s, 1H), 8.34 (s, 1H), 8.25 (d, J=8.0 Hz, 1H), 8.09 (d, J=8.5 Hz, 1H), 7.92 (d, J=8.0 Hz, 2H), 7.77 (d, J=8.3 Hz, 1H), 7.58 (d, J=8.0 Hz, 1H), 7.50 (d, J=8.0 Hz, 6H), 3.60-4.00 (m, 4H), 3.34-3.42 (m, 3H), 2.93-3.21 (m, 4H), 1.87-1.97 (m, 2H).

Example 59

4-[4-(3,4-Dichloro-phenyl)-thiazol-2-yl]-4'-(2-morpholin-4-yl-ethylcarbamoyl)-biphenyl-2-carboxylic acid

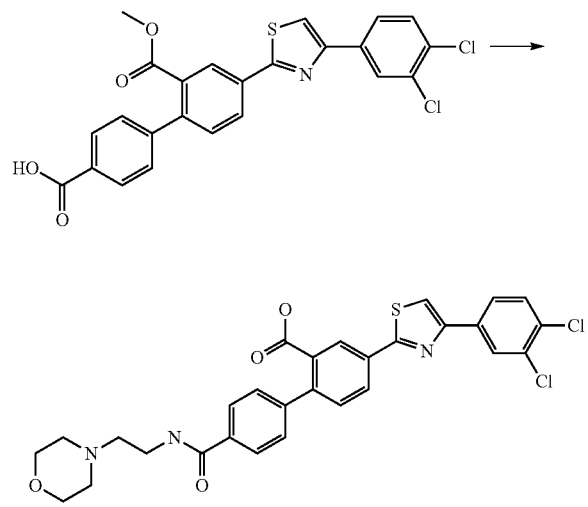

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-(2-aminoethyl)morpholine (available from Aldrich Chemical Company, Inc.; 81 mg, 0.62 mmol). The resulting ester was hydrolyzed and the acid was purified using HPLC Purification Conditions B to give 4-[4-(3,4-dichloro-phenyl)-thiazol-2-yl]-4'-(2-morpholin-4-yl-ethylcarbamoyl)-biphenyl-2-carboxylic acid (82 mg, 68%). $^1$H NMR (400 MHz, DMSO-$d_6$) δ ppm 13.16 (br s, 1H), 8.47 (s, 1H), 8.41 (d, J=1.8 Hz, 1H), 8.34 (d, J=2.0 Hz, 1H), 8.25 (dd, J=8.0, 1.8 Hz, 1H), 8.09 (dd, J=8.3, 2.0 Hz, 1H), 7.94 (d, J=8.3 Hz, 2H), 7.77 (d, J=8.5 Hz, 1H), 7.59 (d, J=8.0 Hz, 1H), 7.53 (d, J=8.0 Hz, 2H), 3.90-4.10 (m, 2H), 3.50-3.72 (m, 4H), 3.27-3.44 (m, 4H), 3.08-3.23 (m, 2H).

Example 60

4-[4-(3,4-Dichloro-phenyl)-thiazol-2-yl]-4'-[(tetrahydro-pyran-4-ylmethyl)-carbamoyl]-biphenyl-2-carboxylic acid

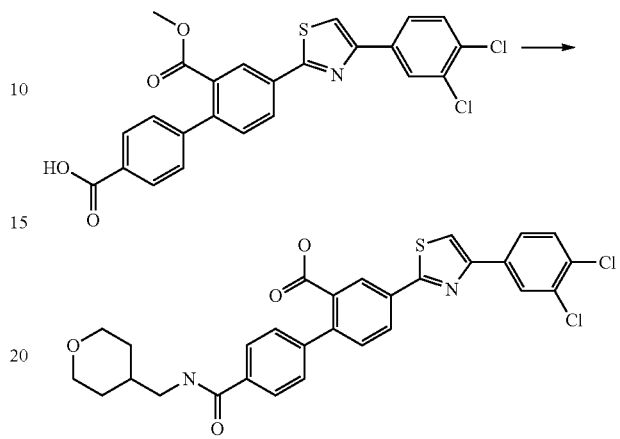

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-aminomethyltetrahydropyran (available from Aldrich Chemical Company, Inc.; 71 mg, 0.62 mmol). The resulting ester was hydrolyzed and the acid was purified using HPLC Purification Conditions B to give 4-[4-(3,4-dichloro-phenyl)-thiazol-2-yl]-4'-[(tetrahydro-pyran-4-ylmethyl)-carbamoyl]-biphenyl-2-carboxylic acid (81 mg, 69%). $^1$H NMR (400 MHz, DMSO-$d_6$) δ ppm 13.22 (br s, 1H), 8.58 (t, J=5.8 Hz, 1H), 8.48 (s, 1H), 8.38 (d, J=1.8 Hz, 1H), 8.34 (d, J=2.0 Hz, 1H), 8.24 (dd, J=8.0, 1.8 Hz, 1H), 8.10 (dd, J=8.5, 2.0 Hz, 1H), 7.91 (d, J=8.3 Hz, 2H), 7.77 (d, J=8.3 Hz, 1H), 7.58 (d, J=8.0 Hz, 1H), 7.48 (d, J=8.3 Hz, 2H), 3.86 (dd, J=11.2, 2.6 Hz, 2H), 3.27 (t, J=10.9 Hz, 2H), 3.19 (t, J=6.4 Hz, 2H), 1.77-1.87 (m, 1H), 1.61 (d, J=11.3 Hz, 2H), 1.15-1.27 (m, 2H).

Example 61

4-[4-(3,4-Dichloro-phenyl)-thiazol-2-yl]-4'-[(tetrahydro-furan-2-ylmethyl)-carbamoyl]-biphenyl-2-carboxylic acid

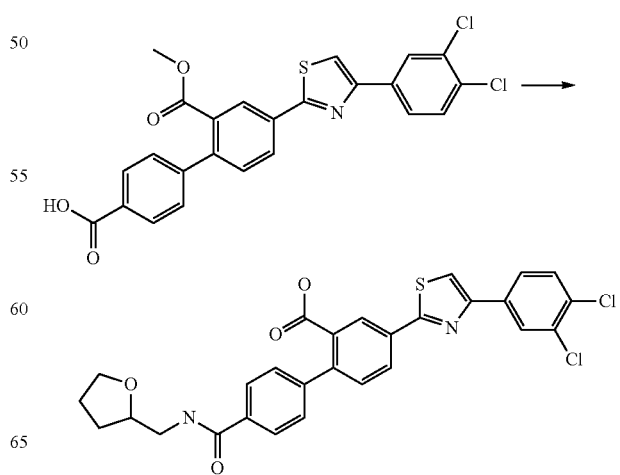

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-aminomethyltetrahydrofuran (available from Acros Organics BVBA; 63 mg, 0.62 mmol). The resulting ester was hydrolyzed and the acid was purified using HPLC Purification Conditions B to give 4-[4-(3,4-dichloro-phenyl)-thiazol-2-yl]-4'-[(tetrahydro-furan-2-ylmethyl)-carbamoyl]-biphenyl-2-carboxylic acid (43 mg, 38%). $^1$H NMR (400 MHz, DMSO-$d_6$) δ ppm 8.58 (br. t., 1H), 8.46 (s, 1H), 8.35 (d, J=15.6 Hz, 2H), 8.23 (d, J=8.0 Hz, 1H), 8.09 (d, J=8.3 Hz, 1H), 7.92 (d, J=7.8 Hz, 2H), 7.76 (d, J=8.3 Hz, 1H), 7.58 (d, J=7.8 Hz, 1H), 7.48 (d, J=7.8 Hz, 2H), 4.01 (t, J=5.9 Hz, 1H), 3.64 (q, J=7.1 Hz, 1H), 3.35 (d, J=5.5 Hz, 2H), 1.77-1.99 (m, 3H), 1.63 (d, J=10.0 Hz, 1H).

Example 62

4-[4-(3,4-Dichloro-phenyl)-thiazol-2-yl]-4'-(tetrahydro-furan-3-ylcarbamoyl)-biphenyl-2-carboxylic acid

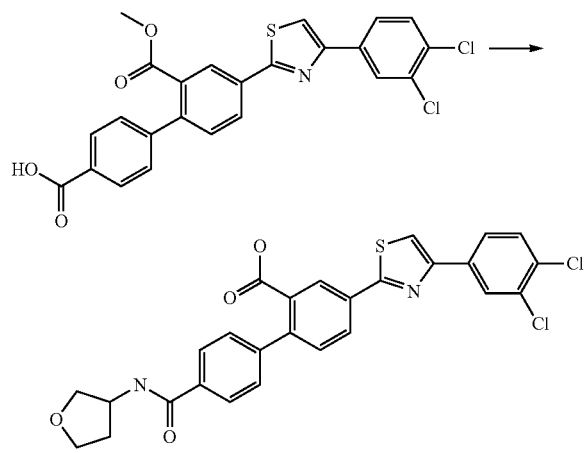

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-aminotetrahydrofuran (available from Aldrich Chemical Company, Inc.; 54 mg, 0.62 mmol). The resulting ester was hydrolyzed and the acid was purified using HPLC Purification Conditions B to give 4-[4-(3,4-dichloro-phenyl)-thiazol-2-yl]-4'-(tetrahydro-furan-3-ylcarbamoyl)-biphenyl-2-carboxylic acid (135 mg, 121%). $^1$H NMR (400 MHz, DMSO-$d_6$) δ ppm 13.20 (br s, 1H), 8.62 (d, J=6.5 Hz, 1H), 8.48 (s, 1H), 8.39 (d, J=2.0 Hz, 1H), 8.34 (d, J=2.0 Hz, 1H), 8.25 (dd, J=8.0, 2.0 Hz, 1H), 8.10 (dd, J=8.5, 2.0 Hz, 1H), 7.93 (d, J=8.3 Hz, 2H), 7.77 (d, J=8.5 Hz, 1H), 7.59 (d, J=8.0 Hz, 1H), 7.48 (d, J=8.3 Hz, 2H), 4.43-4.54 (m, 1H), 3.84-3.92 (m, 2H), 3.69-3.77 (m, 1H), 3.61 (dd, J=8.9, 4.4 Hz, 1H), 2.12-2.22 (m, 1H), 1.90-2.00 (m, 1H).

Example 63

4-[4-(3,4-Dichloro-phenyl)-thiazol-2-yl]-4'-(tetrahydro-pyran-4-ylcarbamoyl)-biphenyl-2-carboxylic acid

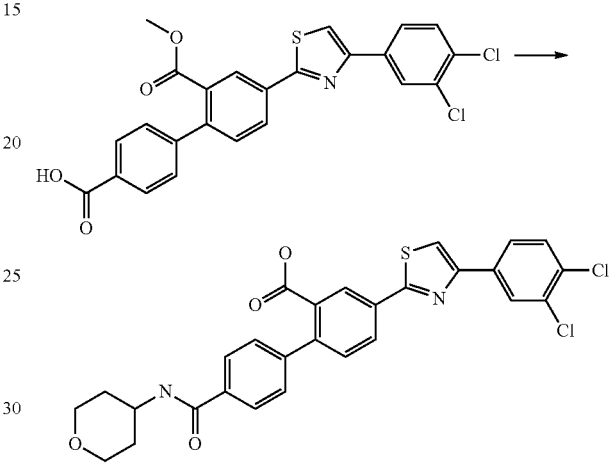

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-aminotetrahydropyran (available from Aldrich Chemical Company, Inc.; 63 mg, 0.62 mmol). The resulting ester was hydrolyzed and the acid was purified using HPLC Purification Conditions B to give 4-[4-(3,4-dichloro-phenyl)-thiazol-2-yl]-4'-(tetrahydro-pyran-4-ylcarbamoyl)-biphenyl-2-carboxylic acid (32 mg, 28%). $^1$H NMR (400 MHz, DMSO-$d_6$) δ ppm 13.08 (br s, 1H), 8.39 (s, 1H), 8.25-8.33 (m, 3H), 8.17 (dd, J=8.0, 1.8 Hz, 1H), 8.02 (dd, J=8.3, 2.0 Hz, 1H), 7.85 (d, J=8.3 Hz, 2H), 7.69 (d, J=8.5 Hz, 1H), 7.51 (d, J=8.0 Hz, 1H), 7.41 (d, J=8.3 Hz, 2H), 3.91-4.03 (m, 1H), 3.83 (d, J=9.8 Hz, 2H), 3.30-3.38 (m, 2H), 1.68-1.76 (m, 2H), 1.54 (qd, J=11.9, 4.3 Hz, 2H).

Example 64

4-[4-(3,4-Dichloro-phenyl)-thiazol-2-yl]-4'-(4-methoxy-benzylcarbamoyl)-biphenyl-2-carboxylic acid

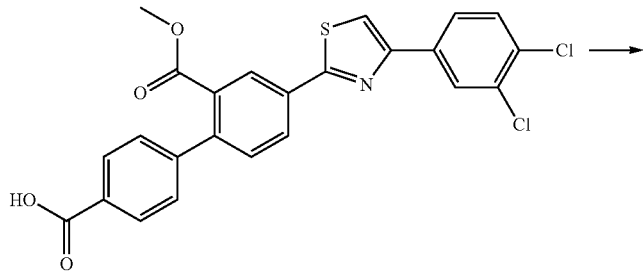

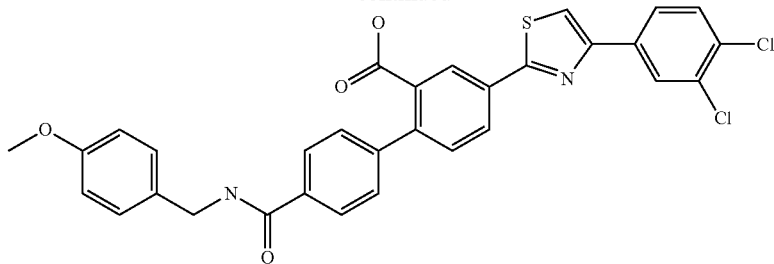

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-methoxybenzylamine (available from Aldrich Chemical Company, Inc.; 85 mg, 0.62 mmol). The resulting ester was hydrolyzed and the acid was purified using HPLC Purification Conditions B to give 4-[4-(3,4-dichloro-phenyl)-thiazol-2-yl]-4'-(4-methoxy-benzylcarbamoyl)-biphenyl-2-carboxylic acid (85 mg, 70%). $^1$H NMR (400 MHz, DMSO-d$_6$) δ ppm 13.20 (br s, 1H), 9.08 (t, J=5.9 Hz, 1H), 8.48 (s, 1H), 8.38 (d, J=1.8 Hz, 1H), 8.34 (d, J=2.0 Hz, 1H), 8.24 (dd, J=8.0, 1.8 Hz, 1H), 8.10 (dd, J=8.5, 2.0 Hz, 1H), 7.95 (d, J=8.3 Hz, 2H), 7.77 (d, J=8.3 Hz, 1H), 7.59 (d, J=8.0 Hz, 1H), 7.49 (d, J=8.3 Hz, 2H), 7.27 (d, J=8.5 Hz, 2H), 6.90 (d, J=8.5 Hz, 2H), 4.44 (d, J=6.0 Hz, 2H), 3.73 (s, 11H).

Example 65

4-[4-(3,4-Dichloro-phenyl)-thiazol-2-yl]-4'-(3-methoxy-benzylcarbamoyl)-biphenyl-2-carboxylic acid

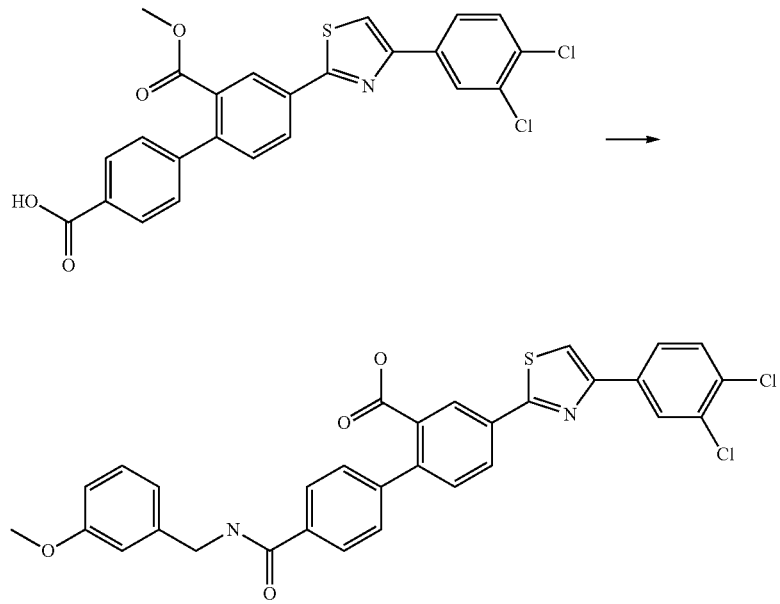 [SMILES: COC(=O)c1cc(-c2nc(-c3ccc(Cl)c(Cl)c3)cs2)ccc1-c1ccc(C(=O)O)cc1 ; CCN(C)CCCNC(=O)c1ccc(-c2ccc(-c3nc(-c4ccc(Cl)c(Cl)c4)cs3)cc2C(=O)O)cc1]

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-methoxybenzylamine (available from Aldrich Chemical Company, Inc.; 85 mg, 0.62 mmol). The resulting ester was hydrolyzed and the acid was purified using HPLC Purification Conditions B to give 4-[4-(3,4-dichloro-phenyl)-thiazol-2-yl]-4'-(3-methoxy-benzylcarbamoyl)-biphenyl-2-carboxylic acid (94 mg, 77%). $^1$H NMR (400 MHz, DMSO-d$_6$) δ ppm 13.18 (br s, 1H), 9.08 (t, J=5.6 Hz, 1H), 8.46 (s, 1H), 8.38 (s, 1H), 8.33 (s, 1H), 8.24 (d, J=8.0 Hz, 1H), 8.09 (d, J=8.5 Hz, 1H), 7.96 (d, J=7.8 Hz, 2H), 7.76 (d, J=8.3 Hz, 1H), 7.59 (d, J=8.0 Hz, 1H), 7.50 (d, J=7.8 Hz, 2H), 7.26 (t, J=7.9 Hz, 1H), 6.89-6.94 (m, 2H), 6.83 (d, J=8.3 Hz, 1H), 4.49 (d, J=5.8 Hz, 2H), 3.75 (s, 3H).

Example 66

4-[4-(3,4-Dichloro-phenyl)-thiazol-2-yl]-4'-(2-pyridin-3-yl-ethylcarbamoyl)-biphenyl-2-carboxylic acid

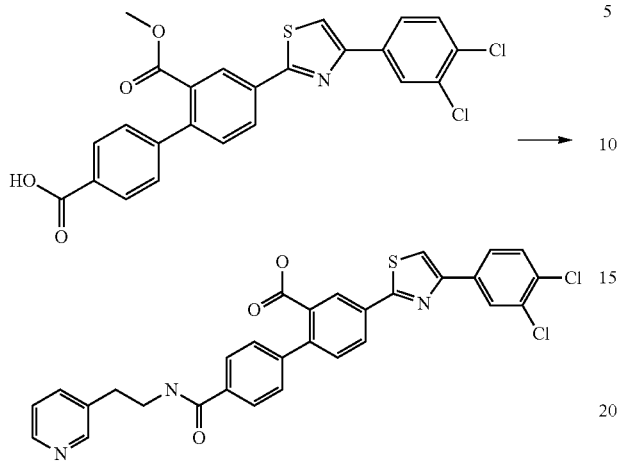

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-(2-aminoethyl)pyridine (available from Aldrich Chemical Company, Inc.; 76 mg, 0.62 mmol). The resulting ester was hydrolyzed and the acid was purified using HPLC Purification Conditions B to give 4-[4-(3,4-dichloro-phenyl)-thiazol-2-yl]-4'-(2-pyridin-3-yl-ethylcarbamoyl)-biphenyl-2-carboxylic acid (129 mg, 109%). $^1$H NMR (400 MHz, DMSO-d$_6$) δ ppm 13.14 (br s, 1H), 8.63 (t, J=5.5 Hz, 1H), 8.57 (s, 1H), 8.51 (d, J=4.3 Hz, 1H), 8.47 (s, 1H), 8.39 (d, J=1.8 Hz, 1H), 8.33 (d, J=2.0 Hz, 1H), 8.24 (d, J=8.0, 2.0 Hz, 1H), 8.09 (dd, J=8.4, 1.9 Hz, 1H), 7.83-7.90 (m, 3H), 7.76 (d, J=8.3 Hz, 1H), 7.58 (d, J=8.3 Hz, 1H), 7.45-7.52 (m, 3H), 3.58 (q, J=6.6 Hz, 2H), 2.95 (t, J=6.9 Hz, 7H).

Example 67

4-[4-(3,4-Dichloro-phenyl)-thiazol-2-yl]-4'-phenethylcarbamoyl-biphenyl-2-carboxylic acid

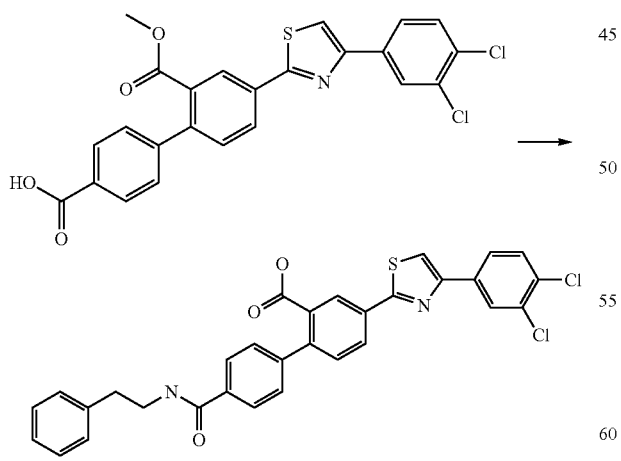

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 2-phenylethylamine (available from Aldrich Chemical Company, Inc.; 75 mg, 0.62 mmol). The resulting ester was hydrolyzed and the acid was purified using HPLC Purification Conditions B to give 4-[4-(3,4-dichloro-phenyl)-thiazol-2-yl]-4'-phenethylcarbamoyl-biphenyl-2-carboxylic acid (74 mg, 62%). $^1$H NMR (400 MHz, DMSO-d$_6$) δ ppm 13.17 (br s, 1H), 8.62 (t, J=5.4 Hz, 1H), 8.46 (s, 1H), 8.38 (s, 1H), 8.33 (s, 1H), 8.24 (d, J=7.8 Hz, 1H), 8.09 (d, J=8.5 Hz, 1H), 7.88 (d, J=8.0 Hz, 2H), 7.76 (d, J=8.3 Hz, 1H), 7.59 (d, J=8.0 Hz, 1H), 7.48 (d, J=8.0 Hz, 2H), 7.18-7.35 (m, 5H), 3.52 (q, J=6.7 Hz, 2H), 2.88 (t, J=7.4 Hz, 8H).

Example 68

4-[4-(3,4-Dichloro-phenyl)-thiazol-2-yl]-4'-[(pyridin-3-ylmethyl)-carbamoyl]-biphenyl-2-carboxylic acid

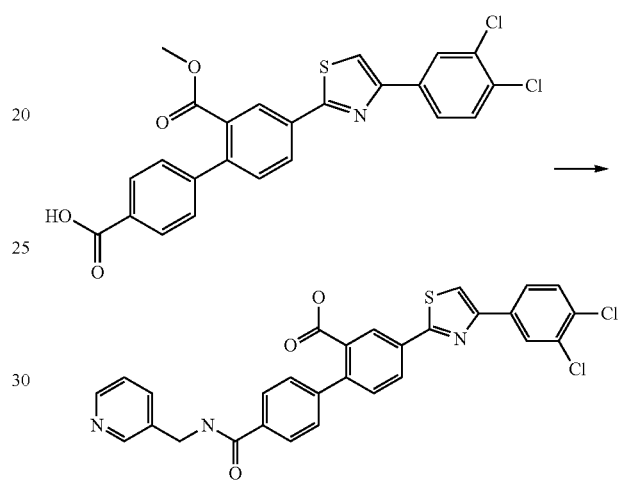

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-(aminomethyl)pyridine (available from Aldrich Chemical Company, Inc.; 67 mg, 0.62 mmol). The resulting ester was hydrolyzed and the acid was purified using HPLC Purification Conditions B to give 4-[4-(3,4-dichloro-phenyl)-thiazol-2-yl]-4'-[(pyridin-3-ylmethyl)-carbamoyl]-biphenyl-2-carboxylic acid (85 mg, 73%). $^1$H NMR (400 MHz, DMSO-d$_6$) δ ppm 13.16 (br s, 1H), 9.19 (t, J=5.9 Hz, 1H), 8.66 (s, 1H), 8.55 (d, J=3.5 Hz, 1H), 8.47 (s, 1H), 8.40 (d, J=1.8 Hz, 1H), 8.33 (d, J=2.0 Hz, 1H), 8.25 (dd, J=8.0, 2.0 Hz, 1H), 8.09 (dd, J=8.5, 2.0 Hz, 1H), 7.90-8.01 (m, 3H), 7.76 (d, J=8.3 Hz, 1H), 7.59 (d, J=8.0 Hz, 1H), 7.45-7.55 (m, 3H), 4.57 (d, J=5.8 Hz, 2H).

Example 69

4-[4-(3,4-Dichloro-phenyl)-thiazol-2-yl]-4'-[(pyridin-4-ylmethyl)-carbamoyl]-biphenyl-2-carboxylic acid

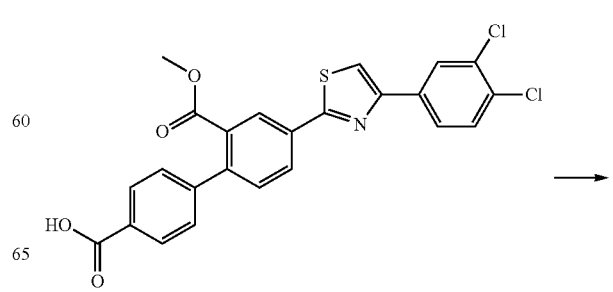

91

-continued

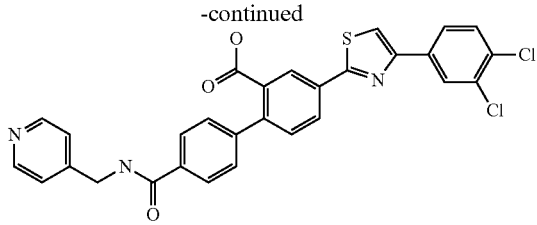

92

-continued

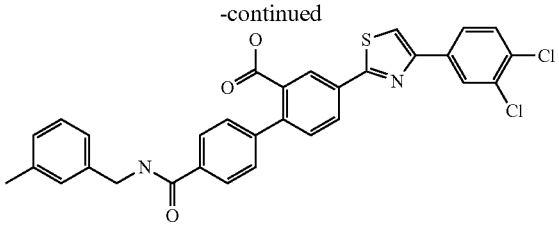

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-(aminomethyl)pyridine (available from Aldrich Chemical Company, Inc.; 67 mg, 0.62 mmol). The resulting ester was hydrolyzed and the acid was purified using HPLC Purification Conditions B to give 4-[4-(3,4-dichloro-phenyl)-thiazol-2-yl]-4'-[(pyridin-4-ylmethyl)-carbamoyl]-biphenyl-2-carboxylic acid (78 mg, 68%). $^1$H NMR (400 MHz, DMSO-d$_6$) δ ppm 13.16 (br s, 1H), 9.25 (t, J=5.8 Hz, 1H), 8.60 (d, J=6.0 Hz, 2H), 8.47 (s, 1H), 8.40 (d, J=1.8 Hz, 1H), 8.34 (d, J=2.0 Hz, 1H), 8.25 (dd, J=8.0, 2.0 Hz, 1H), 8.09 (dd, J=8.3, 2.0 Hz, 1H), 7.99 (d, J=8.3 Hz, 2H), 7.77 (d, J=8.3 Hz, 1H), 7.60 (d, J=8.0 Hz, 1H), 7.46-7.55 (m, 4H), 4.60 (d, J=5.8 Hz, 7H).

Example 70

4-[4-(3,4-Dichloro-phenyl)-thiazol-2-yl]-4'-(3-methyl-benzylcarbamoyl)-biphenyl-2-carboxylic acid

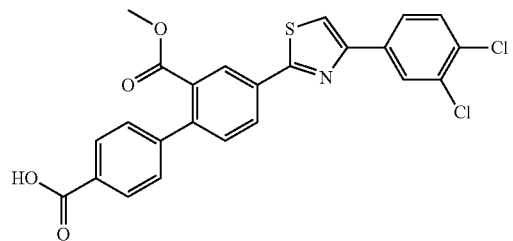

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-methylbenzylamine (available from Aldrich Chemical Company, Inc.; 75 mg, 0.62 mmol). The resulting ester was hydrolyzed and the acid was purified using HPLC Purification Conditions B to give 4-[4-(3,4-dichloro-phenyl)-thiazol-2-yl]-4'-(3-methyl-benzylcarbamoyl)-biphenyl-2-carboxylic acid (46 mg, 39%). $^1$H NMR (400 MHz, DMSO-d$_6$) δ ppm 13.18 (br s, 1H), 9.07 (t, J=5.9 Hz, 1H), 8.46 (s, 1H), 8.38 (d, J=1.8 Hz, 1H), 8.33 (d, J=2.0 Hz, 1H), 8.24 (dd, J=8.0, 2.0 Hz, 1H), 8.09 (dd, J=8.5, 2.0 Hz, 1H), 7.97 (d, J=8.3 Hz, 2H), 7.76 (d, J=8.5 Hz, 1H), 7.59 (d, J=8.0 Hz, 1H), 7.50 (d, J=8.3 Hz, 2H), 7.19-7.26 (m, 1H), 7.11-7.18 (m, 2H), 7.07 (d, J=7.3 Hz, 1H), 4.48 (d, J=5.8 Hz, 2H), 2.30 (s, 3H).

Example 71

4-[4-(3,4-Dichloro-phenyl)-thiazol-2-yl]-4'-(3-trifluoromethyl-benzylcarbamoyl)-biphenyl-2-carboxylic acid

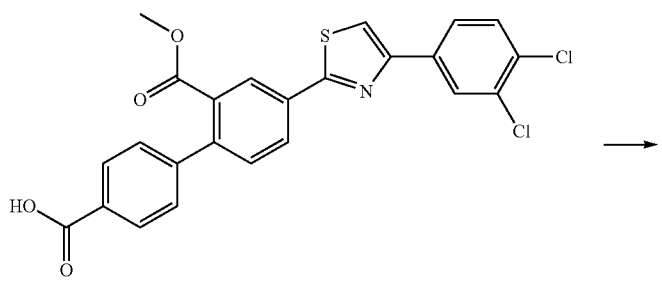

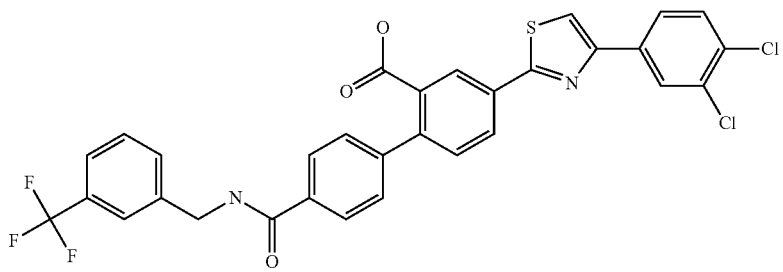

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-(trifluoromethyl)benzylamine (available from Aldrich Chemical Company, Inc.; 108 mg, 0.62 mmol). The resulting ester was hydrolyzed and the acid was purified using HPLC Purification Conditions B to give 4-[4-(3,4-dichloro-phenyl)-thiazol-2-yl]-4'-(3-trifluoromethyl-benzylcarbamoyl)-biphenyl-2-carboxylic acid (53 mg, 41%). $^1$H NMR (400 MHz, DMSO-$d_6$) δ ppm 13.17 (br s, 1H), 9.20 (t, J=6.0 Hz, 1H), 8.46 (s, 1H), 8.39 (d, J=1.8 Hz, 1H), 8.33 (d, J=2.0 Hz, 1H), 8.24 (dd, J=8.2, 1.9 Hz, 1H), 8.09 (dd, J=8.3, 2.0 Hz, 1H), 7.97 (d, J=8.3 Hz, 2H), 7.76 (d, J=8.5 Hz, 1H), 7.56-7.72 (m, 5H), 7.51 (d, J=8.3 Hz, 2H), 4.60 (d, J=5.8 Hz, 2H).

Example 72

4-[4-(3,4-Dichloro-phenyl)-thiazol-2-yl]-4'-(4-fluoro-benzylcarbamoyl)-biphenyl-2-carboxylic acid

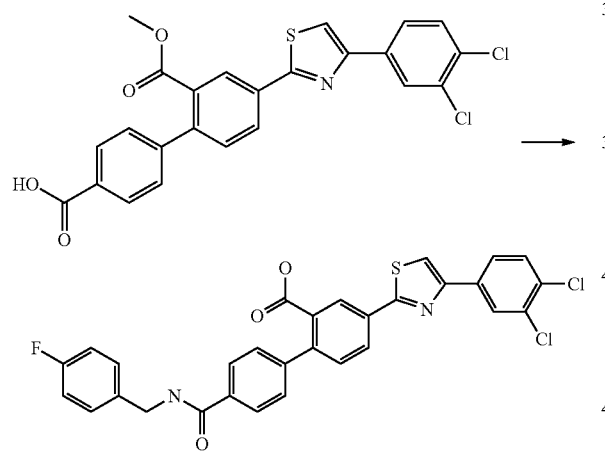

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 4-fluorobenzylamine (available from Aldrich Chemical Company, Inc.; 78 mg, 0.62 mmol). The resulting ester was hydrolyzed and the acid was purified using HPLC Purification Conditions B to give 4-[4-(3,4-dichloro-phenyl)-thiazol-2-yl]-4'-(4-fluoro-benzylcarbamoyl)-biphenyl-2-carboxylic acid (88 mg, 84%). $^1$H NMR (400 MHz, DMSO-$d_6$) δ ppm 13.17 (br s, 1H), 9.11 (t, J=5.8 Hz, 1H), 8.46 (s, 1H), 8.38 (s, 1H), 8.33 (s, 1H), 8.24 (d, J=7.8 Hz, 1H), 8.09 (d, J=8.3 Hz, 1H), 7.96 (d, J=8.0 Hz, 2H), 7.76 (d, J=8.5 Hz, 1H), 7.59 (d, J=8.0 Hz, 1H), 7.50 (d, J=8.0 Hz, 2H), 7.35-7.41 (m, 2H), 7.16 (t, J=8.7 Hz, 2H), 4.50 (d, J=5.8 Hz, 8H).

Example 73

4-[4-(3,4-Dichloro-phenyl)-thiazol-2-yl]-4'-(3-fluoro-benzylcarbamoyl)-biphenyl-2-carboxylic acid

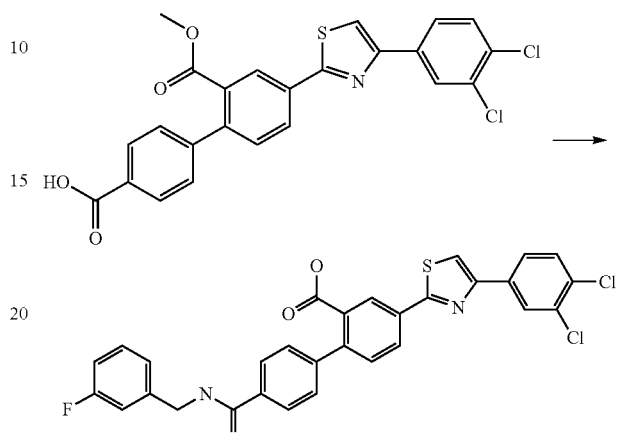

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 3-fluorobenzylamine (available from Aldrich Chemical Company, Inc.; 78 mg, 0.62 mmol). The resulting ester was hydrolyzed and the acid was purified using HPLC Purification Conditions B to give 4-[4-(3,4-dichloro-phenyl)-thiazol-2-yl]-4'-(3-fluoro-benzylcarbamoyl)-biphenyl-2-carboxylic acid (89 mg, 74%). $^1$H NMR (400 MHz, DMSO-$d_6$) δ ppm 13.17 (br s, 1H), 9.14 (t, J=6.0 Hz, 1H), 8.46 (s, 1H), 8.39 (d, J=1.8 Hz, 1H), 8.33 (d, J=2.0 Hz, 1H), 8.24 (dd, J=8.0, 1.8 Hz, 1H), 8.09 (dd, J=8.5, 2.0 Hz, 1H), 7.97 (d, J=8.3 Hz, 2H), 7.76 (d, J=8.3 Hz, 1H), 7.59 (d, J=8.0 Hz, 1H), 7.51 (d, J=8.3 Hz, 2H), 7.35-7.43 (m, 1H), 7.13-7.23 (m, 2H), 7.04-7.11 (m, 1H), 4.53 (d, J=6.0 Hz, 8H).

Example 74

4-[4-(3,4-Dichloro-phenyl)-thiazol-2-yl]-4'-(2-fluoro-benzylcarbamoyl)-biphenyl-2-carboxylic acid

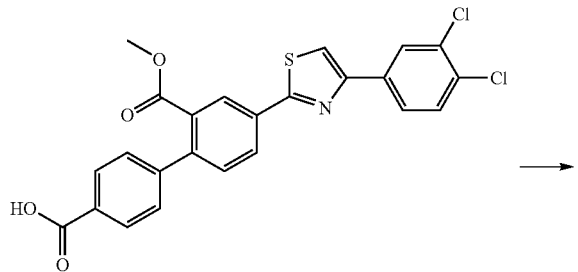

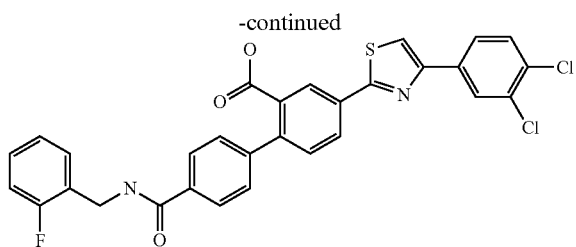

Using the conditions of General Procedure D for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 2-fluorobenzylamine (available from Aldrich Chemical Company, Inc.; 52 mg, 0.42 mmol) to give the crude amide product. The crude amide was hydrolyzed by adding THF (2 mL), water (0.05 mL), MeOH (1 mL), and lithium hydroxide monohydrate (12.3 mg, 0.29 mmol) and stirring the mixture overnight at room temperature. Tetrahydrofuran (2 mL) was added to dissolve the solid, and lithium hydroxide monohydrate (22 mg, 0.52 mmol) was added. The reaction mixture was stirred overnight, and then another portion of lithium hydroxide monohydrate (22 mg, 0.52 mmol) was added. The reaction mixture was stirred overnight. The reaction mixture was concentrated to dryness under vacuum at 40° C. 1 M HCl (3 mL) was added, and the mixture was stirred, concentrated to dryness, and purified and purified using HPLC Purification Conditions A to give 4-[4-(3,4-dichloro-phenyl)-thiazol-2-yl]-4'-(2-fluoro-benzylcarbamoyl)-biphenyl-2-carboxylic acid (75 mg, 63%) as a white solid. $^1$H NMR (400 MHz, DMSO-$d_6$) δ ppm 13.18 (br s, 1H), 9.10 (t, J=5.8 Hz, 1H), 8.47 (s, 1H), 8.39 (d, J=1.8 Hz, 1H), 8.33 (d, J=2.0 Hz, 1H), 8.24 (dd, J=8.0, 1.8 Hz, 1H), 8.09 (dd, J=8.5, 2.0 Hz, 1H), 7.97 (d, J=8.3 Hz, 2H), 7.76 (d, J=8.5 Hz, 1H), 7.59 (d, J=8.0 Hz, 1H), 7.50 (d, J=8.3 Hz, 2H), 7.40 (t, J=7.7 Hz, 1H), 7.29-7.36 (m, 1H), 7.16-7.23 (m, 2H), 4.56 (d, J=5.8 Hz, 2H).

Example 75

4-[4-(3,4-Dichloro-phenyl)-thiazol-2-yl]-4'-[(thiophen-2-ylmethyl)-carbamoyl]-biphenyl-2-carboxylic acid

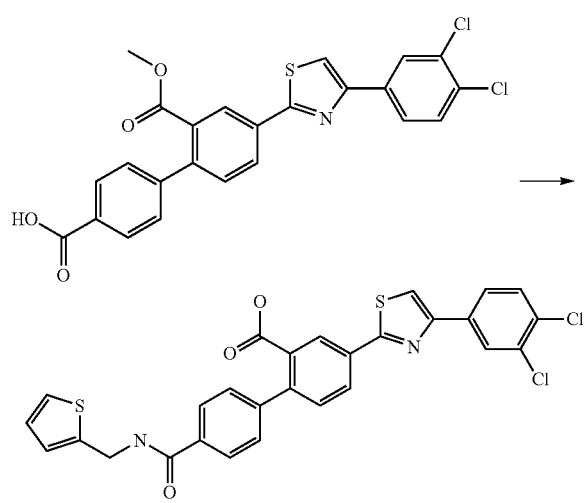

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with 2-thiophenemethylamine (available from Aldrich Chemical Company, Inc.; 70 mg, 0.62 mmol). The resulting ester was hydrolyzed and the acid was purified using HPLC Purification Conditions B to give 4-[4-(3,4-dichloro-phenyl)-thiazol-2-yl]-4'-[(thiophen-2-ylmethyl)-carbamoyl]-biphenyl-2-carboxylic acid (47 mg, 40%). $^1$H NMR (400 MHz, DMSO-$d_6$) δ ppm 13.24 (br s, 1H), 9.24 (t, J=5.9 Hz, 1H), 8.48 (s, 1H), 8.36 (dd, J=16.8, 2.0 Hz, 2H), 8.24 (dd, J=8.0, 2.0 Hz, 1H), 8.10 (dd, J=8.4, 2.1 Hz, 1H), 7.94 (d, J=8.3 Hz, 2H), 7.77 (d, J=8.5 Hz, 1H), 7.59 (d, J=8.3 Hz, 1H), 7.50 (d, J=8.3 Hz, 2H), 7.40 (dd, J=5.1, 1.1 Hz, 1H), 7.04 (d, J=2.5 Hz, 1H), 6.98 (dd, J=5.0, 3.5 Hz, 1H), 4.67 (d, J=5.8 Hz, 2H).

Example 76

4'-Benzylcarbamoyl-4-[4-(3,4-dichloro-phenyl)-thiazol-2-yl]-biphenyl-2-carboxylic acid

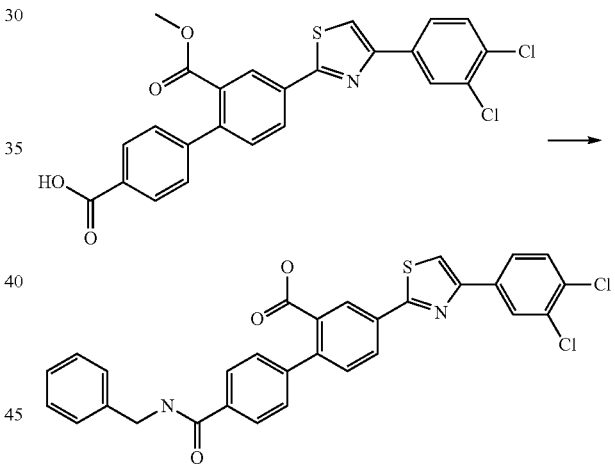

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with benzylamine (available from Aldrich Chemical Company, Inc.; 66 mg, 0.62 mmol). The resulting ester was hydrolyzed and the acid was purified using HPLC Purification Conditions B to give 4'-benzylcarbamoyl-4-[4-(3,4-dichloro-phenyl)-thiazol-2-yl]-biphenyl-2-carboxylic acid (73 mg, 64%). $^1$H NMR (400 MHz, DMSO-$d_6$) δ ppm 13.23 (br s, 1H), 9.15 (t, J=6.0 Hz, 1H), 8.48 (s, 1H), 8.39 (d, J=1.8 Hz, 1H), 8.34 (d, J=2.0 Hz, 1H), 8.24 (dd, J=8.0, 1.8 Hz, 1H), 8.10 (dd, J=8.5, 2.0 Hz, 1H), 7.97 (d, J=8.3 Hz, 2H), 7.77 (d, J=8.5 Hz, 1H), 7.59 (d, J=8.0 Hz, 1H), 7.50 (d, J=8.3 Hz, 2H), 7.34 (d, J=4.3 Hz, 4H), 7.21-7.29 (m, 1H), 4.52 (d, J=6.0 Hz, 2H).

Example 77

2-(2-Carbamoyl-pyridin-3-yl)-5-[4-(3,4-dichloro-phenyl)-thiazol-2-yl]-benzoic acid

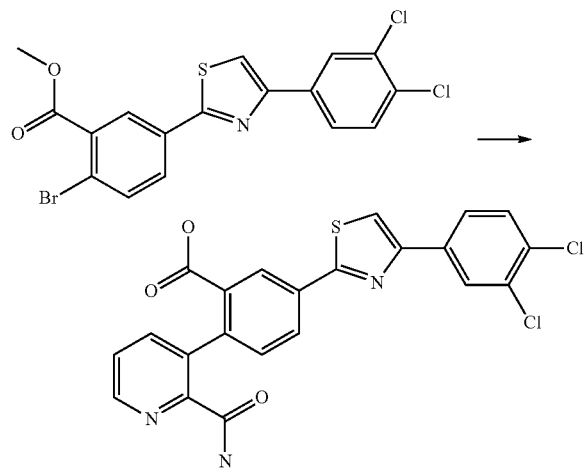

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-cyanopyridine-3-boronic acid (available from Matrix Scientific; 74 mg, 0.5 mmol). The resulting ester was hydrolyzed and the acid was purified to give 2-(2-carbamoyl-pyridin-3-yl)-5-[4-(3,4-dichloro-phenyl)-thiazol-2-yl]-benzoic acid (7 mg, 6%). $^1$H NMR (400 MHz, DMSO-d$_6$) δ 13.32 (br s, 1H), 9.02 (d, J=8.8 Hz, 1H), 8.77 (d, J=4.0 Hz, 1H), 8.66 (br s, 1H), 8.40 (s, 1H), 8.28-8.35 (m, 2H), 8.23 (d, J=7.8 Hz, 1H), 8.04-8.14 (m, 2H), 7.69-7.79 (m, 2H), 6.53 (s, 1H).

Examples 78 and 79

4'-Carbamoyl-4-[4-(3,4-dichloro-phenyl)-thiazol-2-yl]-2'-methyl-biphenyl-2-carboxylic acid and 4-[4-(3,4-Dichloro-phenyl)-thiazol-2-yl]-2'-methyl-biphenyl-2,4'-dicarboxylic acid

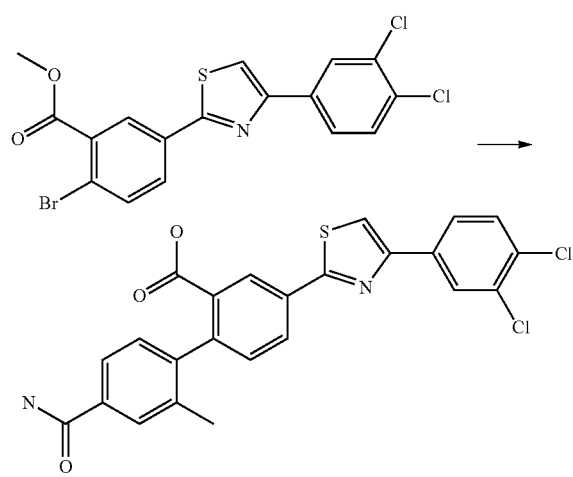

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-methyl-4-cyanophenyl-boronic acid (available from Combi-Blocks Inc.; 69 mg, 0.5 mmol). The resulting ester was hydrolyzed and the products were separated by preparative HPLC to give 4'-carbamoyl-4-[4-(3,4-dichloro-phenyl)-thiazol-2-yl]-2'-methyl-biphenyl-2-carboxylic acid (Example 78; 24 mg, 20%) {$^1$H NMR (400 MHz, DMSO-d$_6$) δ 12.99 (br s, 1H) 8.50 (d, J=1.8 Hz, 1H) 8.48 (s, 1H) 8.34 (d, J=2.0 Hz, 1H) 8.25 (dd, J=8.0, 2.0 Hz, 1H) 8.09 (dd, J=8.5, 2.0 Hz, 1H) 7.98 (br s, 1H) 7.75-7.81 (m, 2H) 7.72 (d, J=7.8 Hz, 1H) 7.41 (d, J=7.8 Hz, 1H) 7.35 (br s, 1H) 7.17 (d, J=7.8 Hz, 1H) 2.10 (s, 3H)} and 4-[4-(3,4-dichloro-phenyl)-thiazol-2-yl]-2'-methyl-biphenyl-2,4'-dicarboxylic acid (Example 79; 55, 46%) {$^1$H NMR (400 MHz, DMSO-d$_6$) δ 8.52 (s, 1H), 8.48 (s, 1H), 8.34 (s, 1H), 8.27 (d, J=8.0 Hz, 1H), 8.10 (d, J=8.3 Hz, 1H), 7.85 (s, 1H), 7.75-7.83 (m, 2H), 7.42 (d, J=8.0 Hz, 1H), 7.23 (d, J=7.8 Hz, 1H), 2.11 (s, 3H)}.

Example 80

4-[4-(3,4-Dichloro-phenyl)-thiazol-2-yl]-4'-(1-phenyl-ethylcarbamoyl)-biphenyl-2-carboxylic acid

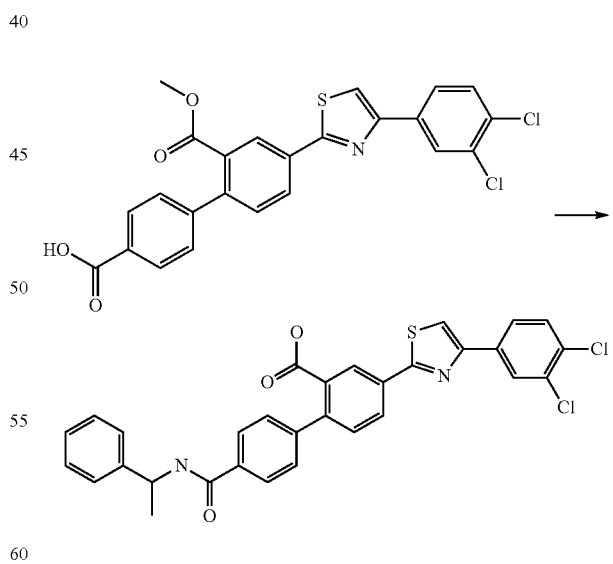

Using the conditions of General Procedure E for Amide Coupling in Parallel Mode, 4-[4-(3,4-dichloro-phenyl)-thiazol-2-yl]-biphenyl-2,4'-dicarboxylic acid 2-methyl ester (which may be prepared as described for Intermediate 8; 100 mg, 0.21 mmol) was reacted with DL-alpha-methylbenzylamine (available from Aldrich Chemical Company, Inc.; 75 mg, 0.62 mmol). The resulting ester was hydrolyzed and the acid was purified using HPLC Purification Conditions B to give 4-[4-(3,4-dichloro-phenyl)-thiazol-2-yl]-4'-(1-phenyl-ethylcarbamoyl)-biphenyl-2-carboxylic acid (69 mg, 59%). $^1$H NMR (400 MHz, DMSO-$d_6$) δ ppm 13.22 (br s, 1H), 8.90 (d, J=8.0 Hz, 1H), 8.48 (s, 1H), 8.38 (d, J=1.8 Hz, 1H), 8.34 (d, J=2.0 Hz, 1H), 8.24 (dd, J=8.0, 1.8 Hz, 1H), 8.10 (dd, J=8.5, 2.0 Hz, 1H), 7.96 (d, J=8.3 Hz, 2H), 7.77 (d, J=8.3 Hz, 1H), 7.59 (d, J=8.0 Hz, 1H), 7.49 (d, J=8.3 Hz, 2H), 7.39-7.45 (m, 2H), 7.34 (t, J=7.7 Hz, 2H), 7.18-7.28 (m, 1H), 5.20 (quin, J=7.3 Hz, 1H), 1.50 (d, J=7.0 Hz, 3H).

Example 81

2'-Carbamoyl-4-[4-(3,4-dichloro-phenyl)-thiazol-2-yl]-biphenyl-2-carboxylic acid

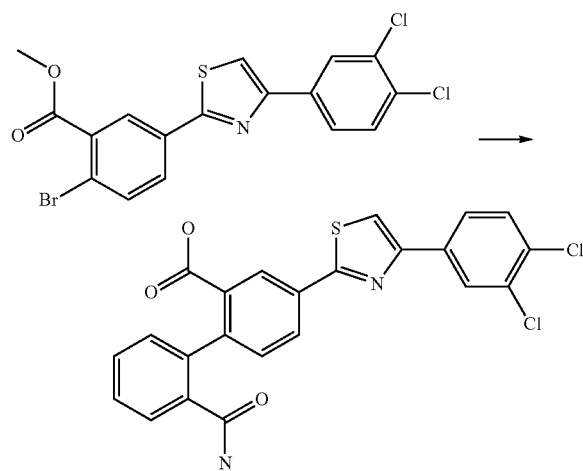

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-aminocarbonylphenylboronic acid (available from Combi-Blocks Inc.; 66 mg, 0.4 mmol). The resulting ester was hydrolyzed and the acid was purified to give 2'-carbamoyl-4-[4-(3,4-dichloro-phenyl)-thiazol-2-yl]-biphenyl-2-carboxylic acid (15 mg, 8%). $^1$H NMR (300 MHz, DMSO-$d_6$) δ 13.07 (br s, 1H), 8.46 (s, 1H), 8.36 (d, J=14.1 Hz, 2H), 8.04-8.18 (m, 2H), 7.77 (d, J=8.5 Hz, 1H), 7.58 (d, J=7.2 Hz, 2H), 7.42-7.51 (m, 2H), 7.12-7.34 (m, 3H). The compound of Example 81 has the same formula as the compound of Example 113.

Example 82

5-[4-(3,4-Dichloro-phenyl)-thiazol-2-yl]-2-(2-ethoxy-pyrimidin-5-yl)-benzoic acid

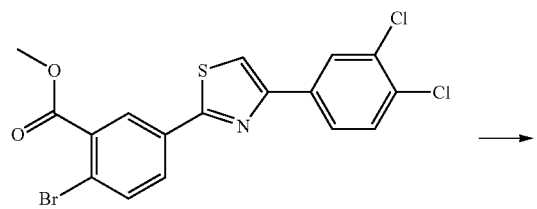

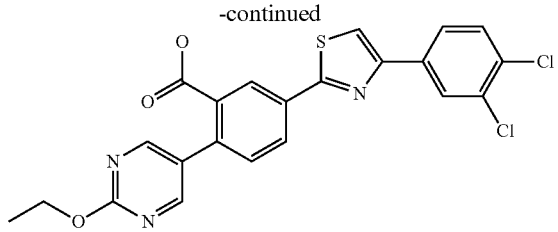

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-ethoxypyrimidine-5-boronic acid (available from Combi-Blocks Inc.; 84 mg, 0.5 mmol). The resulting ester was hydrolyzed and the acid was purified to give 5-[4-(3,4-dichloro-phenyl)-thiazol-2-yl]-2-(2-ethoxy-pyrimidin-5-yl)-benzoic acid (3 mg, 3%). LCMS analysis indicated that the material was ~69% pure, as measured by UV at 214 nm. LRMS m/z 471.8 (M+H$^+$).

Example 83

5-[4-(3,4-Dichloro-phenyl)-thiazol-2-yl]-2-(2-methoxy-pyrimidin-5-yl)-benzoic acid

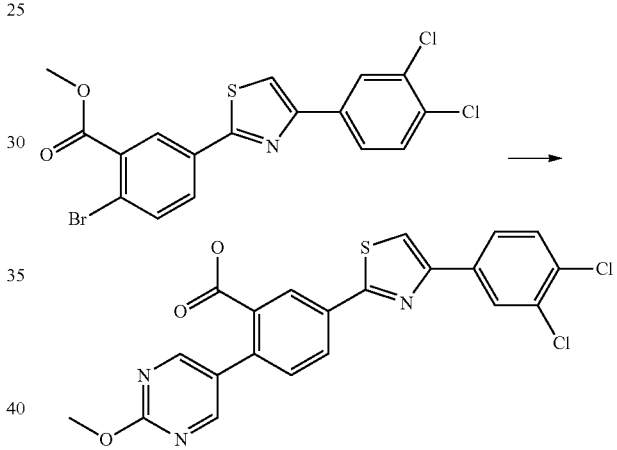

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-methoxypyrimidine-5-boronic acid (available from Combi-Blocks Inc.; 62 mg, 0.4 mmol). The resulting ester was hydrolyzed and the acid was purified to give 5-[4-(3,4-Dichloro-phenyl)-thiazol-2-yl]-2-(2-methoxy-pyrimidin-5-yl)-benzoic acid (0.9 mg, 1%). LCMS analysis indicated that the material was ~100% pure, as measured by UV at 214 nm. LRMS m/z 457.8 and 459.8 (M+H$^+$).

Example 84

5-[4-(3,4-Dichloro-phenyl)-thiazol-2-yl]-2-(2-hydroxy-pyrimidin-5-yl)-benzoic acid

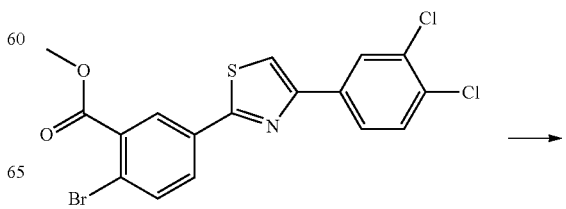

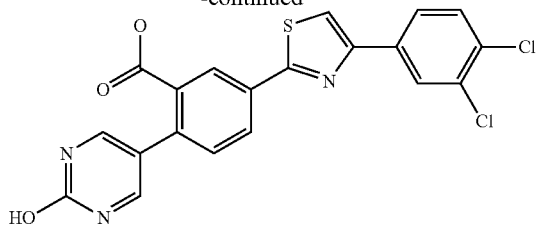

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-methoxypyrimidine-5-boronic acid (available from Combi-Blocks Inc.; 77 mg, 0.5 mmol). The resulting ester was hydrolyzed and the acid was purified to give 5-[4-(3,4-dichloro-phenyl)-thiazol-2-yl]-2-(2-hydroxy-pyrimidin-5-yl)-benzoic acid (85 mg, 76%). $^1$H NMR (400 MHz, DMSO-$d_6$) δ 13.40 (br s, 1H), 8.42-8.62 (m, 2H), 8.20-8.38 (m, 2H), 8.04-8.14 (m, 1H), 7.76 (d, J=8.3 Hz, 2H), 7.61 (d, J=7.5 Hz, 1H).

Example 85

5-[4-(3,4-Dichloro-phenyl)-thiazol-2-yl]-2-(6-methoxy-pyridin-2-yl)-benzoic acid

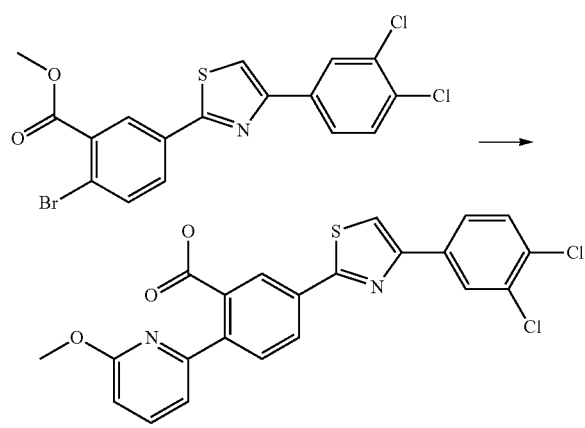

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 6-methoxypyridine-2-boronic acid (available from Combi-Blocks Inc.; 61 mg, 0.4 mmol). The resulting ester was hydrolyzed and the acid was purified to give 5-[4-(3,4-dichloro-phenyl)-thiazol-2-yl]-2-(6-methoxy-pyridin-2-yl)-benzoic acid (23 mg, 25%). $^1$H NMR (400 MHz, DMSO-$d_6$) δ 12.95 (br s, 3H), 8.48 (s, 1H), 8.34 (d, J=2.0 Hz, 1H), 8.21 (dd, J=4.3, 2.3 Hz, 2H), 8.10 (dd, J=8.3, 2.0 Hz, 1H), 7.73-7.94 (m, 3H), 7.39 (d, J=7.3 Hz, 1H), 6.83 (d, J=8.0 Hz, 1H), 3.88 (s, 3H), 2.54 (s, 9H).

Example 86

5-[4-(3,4-Dichloro-phenyl)-thiazol-2-yl]-2-(2-methoxy-pyridin-3-yl)-benzoic acid

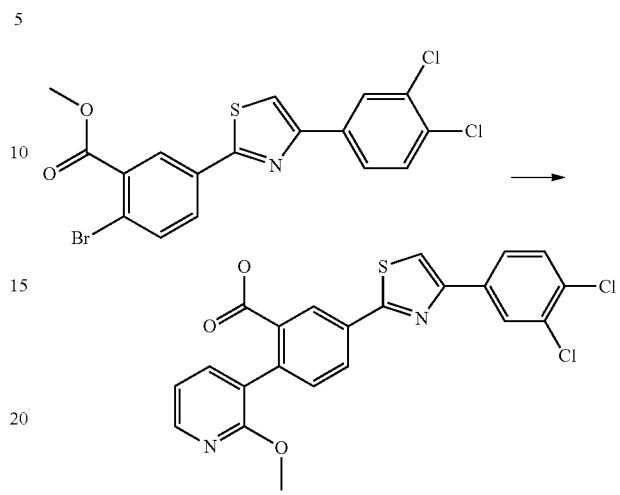

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-methoxypyridine-3-boronic acid hydrate (available from Combi-Blocks Inc.; 68 mg, 0.4 mmol). The resulting ester was hydrolyzed and the acid was purified to give 5-[4-(3,4-dichloro-phenyl)-thiazol-2-yl]-2-(2-methoxy-pyridin-3-yl)-benzoic acid (11 mg, 12%). $^1$H NMR (300 MHz, DMSO-$d_6$) δ 12.94 (br s, 1H), 8.47 (s, 1H), 8.41 (d, J=1.9 Hz, 1H), 8.33 (d, J=2.1 Hz, 1H), 8.25 (dd, J=8.0, 2.0 Hz, 1H), 8.18 (dd, J=5.0, 1.8 Hz, 1H), 8.09 (dd, J=8.5, 2.1 Hz, 1H), 7.77 (d, J=8.3 Hz, 1H), 7.70 (dd, J=7.3, 1.8 Hz, 1H), 7.52 (d, J=7.9 Hz, 1H), 7.10 (dd, J=7.2, 5.1 Hz, 1H), 3.78 (s, 3H).

Example 87

4-[4-(3,4-Dichloro-phenyl)-thiazol-2-yl]-4'-methoxy-2'-trifluoromethyl-biphenyl-2-carboxylic acid

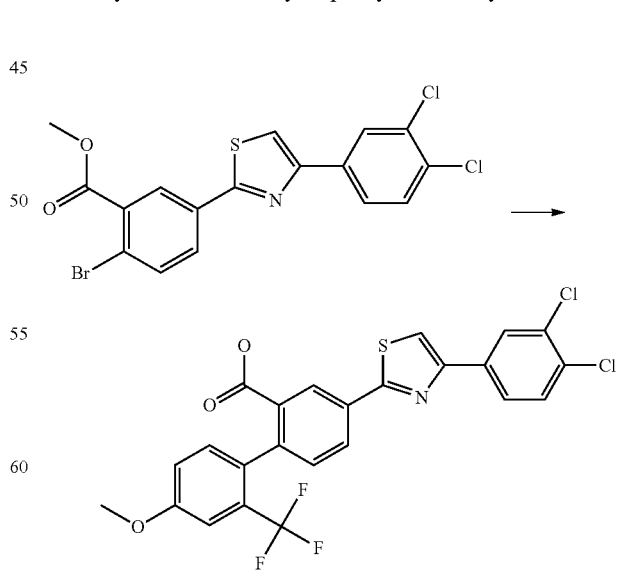

Using the conditions of General Procedure A for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 111 mg, 0.25 mmol) was reacted with 4-methoxy-2-(trifluoromethyl)phenylboronic acid (available from Combi-Blocks Inc.; 110 mg, 0.5 mmol). The resulting ester was hydrolyzed and the acid was purified to give 4-[4-(3,4-dichloro-phenyl)-thiazol-2-yl]-4'-methoxy-2'-trifluoromethyl-biphenyl-2-carboxylic acid (8 mg, 6%). $^1$H NMR (300 MHz, DMSO-d$_6$) δ 12.97 (br s, 1H), 8.54 (s, 1H), 8.48 (s, 1H), 8.34 (s, 1H), 8.23 (d, J=7.5 Hz, 1H), 8.09 (d, J=8.7 Hz, 1H), 7.77 (d, J=8.5 Hz, 1H), 7.41 (d, J=7.9 Hz, 1H), 7.26 (s, 3H), 3.88 (s, 3H).

Example 88

2'-Chloro-4-[4-(3,4-dichloro-phenyl)-thiazol-2-yl]-5'-trifluoromethoxy-biphenyl-2-carboxylic acid

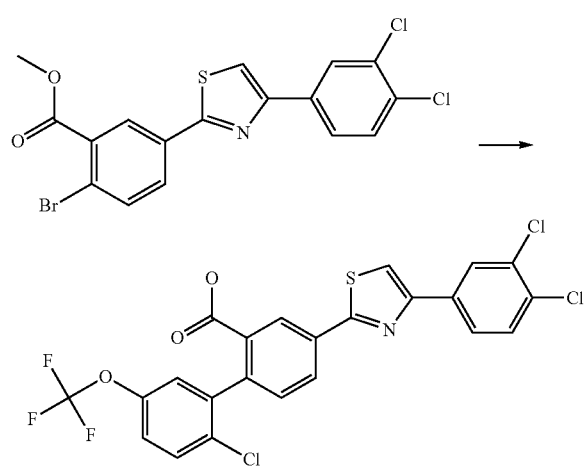

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted 2-chloro-5-(trifluoromethoxy)phenylboronic acid (available from Frontier Scientific, Inc.; 120 mg, 0.5 mmol). The resulting ester was hydrolyzed and the acid was purified to give 2'-chloro-4-[4-(3,4-dichloro-phenyl)-thiazol-2-yl]-5'-trifluoromethoxy-biphenyl-2-carboxylic acid (1.3 mg, 1%). LCMS analysis indicated that the material was ~100% pure, as measured by UV at 214 nm.

Example 89

2'-Chloro-4-[4-(3,4-dichloro-phenyl)-thiazol-2-yl]-4'-ethoxy-biphenyl-2-carboxylic acid

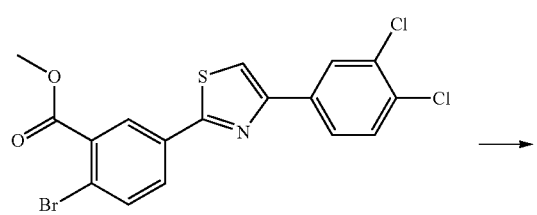

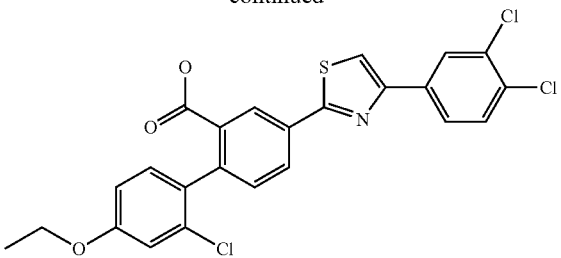

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-4-ethoxyphenylboronic acid (available from Combi-Blocks Inc.; 100 mg, 0.5 mmol). The resulting ester was hydrolyzed and the acid was purified to give 2'-chloro-4-[4-(3,4-dichloro-phenyl)-thiazol-2-yl]-4'-ethoxy-biphenyl-2-carboxylic acid (3 mg, 2%). $^1$H NMR (300 MHz, DMSO-d$_6$) δ 13.02 (br s, 1H), 8.48 (s, 2H), 8.33 (d, J=1.9 Hz, 1H), 8.24 (d, J=7.9 Hz, 1H), 8.09 (dd, J=8.4, 2.0 Hz, 1H), 7.77 (d, J=8.5 Hz, 1H), 7.43 (d, J=7.9 Hz, 1H), 7.25 (d, J=8.5 Hz, 1H), 7.08 (d, J=2.4 Hz, 1H), 6.90-7.02 (m, 2H), 4.10 (q, J=7.0 Hz, 2H), 1.36 (t, J=6.9 Hz, 3H).

Example 90

2'-Chloro-4-[4-(3,4-dichloro-phenyl)-thiazol-2-yl]-6'-methoxy-biphenyl-2-carboxylic acid

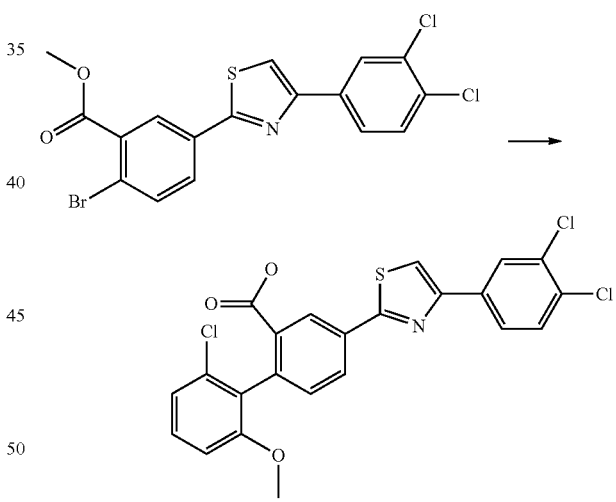

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted 2-chloro-6-methoxyphenylboronic acid (available from Aldrich Chemical Company, Inc.; 93 mg, 0.5 mmol). The resulting ester was hydrolyzed and the acid was purified to give 2'-chloro-4-[4-(3,4-dichloro-phenyl)-thiazol-2-yl]-6'-methoxy-biphenyl-2-carboxylic acid (5 mg, 4%). $^1$H NMR (300 MHz, DMSO-d$_6$), δ 12.87 (br s, 1H), 8.53 (d, J=1.7 Hz, 1H), 8.48 (s, 1H), 8.34 (d, J=1.9 Hz, 1H), 8.25 (d, J=8.0, 2.0 Hz, 1H), 8.09 (dd, J=8.4, 2.0 Hz, 1H), 7.77 (d, J=8.5 Hz, 1H), 7.32-7.41 (m, 2H), 7.10 (dd, J=18.2, 8.0 Hz, 2H), 3.67 (s, 3H).

Example 91

4-[4-(3,4-Dichloro-phenyl)-thiazol-2-yl]-3'-methoxy-biphenyl-2-carboxylic acid

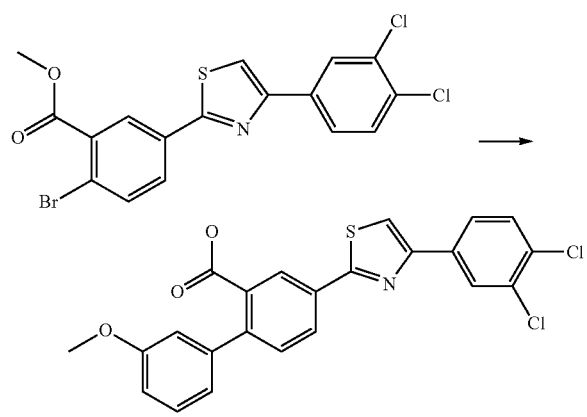

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 3-methoxyphenylboronic acid (available from Combi-Blocks Inc.; 61 mg, 0.4 mmol). The resulting ester was hydrolyzed and the acid was purified to give 4-[4-(3,4-dichloro-phenyl)-thiazol-2-yl]-3'-methoxy-biphenyl-2-carboxylic acid (65 mg, 71%). $^1$H NMR (400 MHz, DMSO-d$_6$) δ 13.15 (br s, 1H), 8.46 (s, 1H), 8.28-8.39 (m, 2H), 8.20 (d, J=7.8 Hz, 1H), 8.09 (dd, J=8.5, 1.8 Hz, 1H), 7.76 (d, J=8.5 Hz, 1H), 7.59 (d, J=8.0 Hz, 1H), 7.36 (t, J=7.8 Hz, 1H), 6.86-7.06 (m, 3H), 3.80 (s, 3H).

Example 92

4-[4-(3,4-Dichloro-phenyl)-thiazol-2-yl]-2'-methoxy-biphenyl-2-carboxylic acid

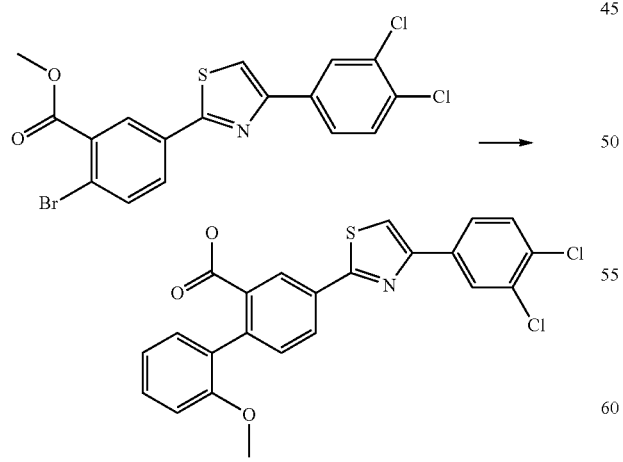

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-methoxyphenylboronic acid (available from Frontier Scientific, Inc.; 61 mg, 0.4 mmol). The resulting ester was hydrolyzed and the acid was purified to give 4-[4-(3,4-dichloro-phenyl)-thiazol-2-yl]-2'-methoxy-biphenyl-2-carboxylic acid (36 mg, 39%). $^1$H NMR (400 MHz, DMSO-d$_6$) δ 12.75 (br s, 1H), 8.45 (s, 1H), 8.31-8.37 (m, 2H), 8.21 (d, J=8.0 Hz, 1H), 8.09 (d, J=8.3 Hz, 1H), 7.77 (d, J=8.5 Hz, 1H), 7.46 (d, J=8.0 Hz, 1H), 7.36 (t, J=7.8 Hz, 1H), 7.27 (d, J=7.5 Hz, 1H), 7.04 (d, J=7.3 Hz, 2H), 3.69 (s, 3H).

Example 93

2'-Chloro-4-[4-(3,4-dichloro-phenyl)-thiazol-2-yl]-5'-methoxy-biphenyl-2-carboxylic acid

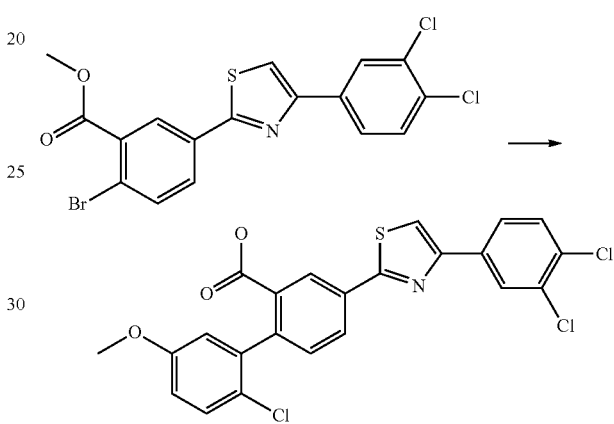

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-chloro-5-methoxyphenylboronic acid (available from Combi-Blocks Inc.; 75 mg, 0.4 mmol). The resulting ester was hydrolyzed and the acid was purified to give 2'-chloro-4-[4-(3,4-dichloro-phenyl)-thiazol-2-yl]-5'-methoxy-biphenyl-2-carboxylic acid (29 mg, 29%). $^1$H NMR (400 MHz, DMSO-d$_6$) δ 13.04 (br s, 1H), 8.45-8.58 (m, 2H), 8.34 (d, J=2.0 Hz, 1H), 8.26 (dd, J=7.9, 1.9 Hz, 1H), 8.09 (dd, J=8.4, 1.9 Hz, 1H), 7.77 (d, J=8.5 Hz, 1H), 7.46 (d, J=8.0 Hz, 1H), 7.40 (d, J=8.8 Hz, 1H), 6.98 (dd, J=8.8, 3.0 Hz, 1H), 6.92 (d, J=3.0 Hz, 1H), 3.79 (m, 3H).

Example 94

2'-Chloro-4-[4-(3,4-dichloro-phenyl)-thiazol-2-yl]-4'-methoxy-biphenyl-2-carboxylic acid

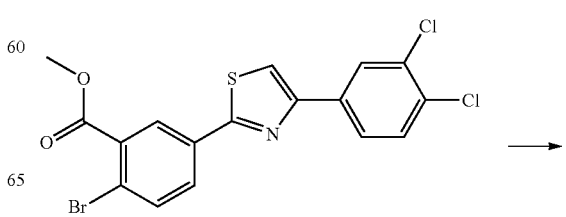

-continued

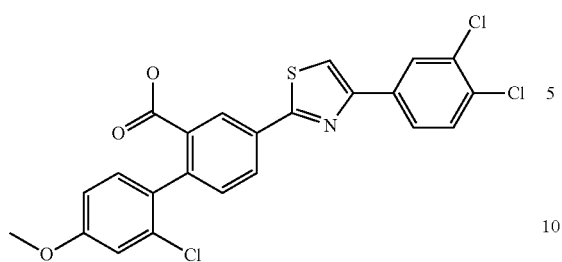

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-4-methoxyphenylboronic acid (available from Combi-Blocks Inc.; 93 mg, 0.5 mmol). The resulting ester was hydrolyzed and the acid was purified to give 2'-chloro-4-[4-(3,4-dichloro-phenyl)-thiazol-2-yl]-4'-methoxy-biphenyl-2-carboxylic acid (6 mg, 5%). $^1$H NMR (300 MHz, DMSO-$d_6$) δ 13.00 (br s, 1H), 8.46-8.51 (m, 2H), 8.33 (d, J=2.1 Hz, 1H), 8.24 (dd, J=8.1, 1.9 Hz, 1H), 8.09 (dd, J=8.5, 2.1 Hz, 1H), 7.77 (d, J=8.5 Hz, 1H), 7.43 (d, J=8.1 Hz, 1H), 7.27 (d, J=8.5 Hz, 1H), 7.10 (d, J=2.4 Hz, 1H), 6.99 (dd, J=8.5, 2.6 Hz, 1H), 3.83 (s, 3H).

Example 95

2'-Chloro-4-[4-(3,4-dichloro-phenyl)-thiazol-2-yl]-5'-hydroxy-biphenyl-2-carboxylic acid

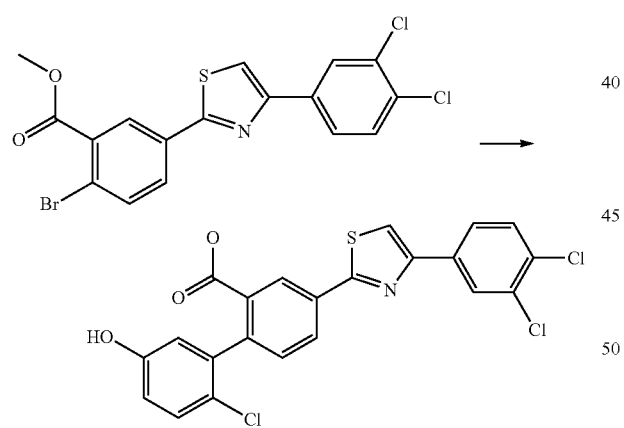

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-chloro-5-hydroxybenzeneboronic acid (available from Combi-Blocks Inc.; 69 mg, 0.4 mmol). The resulting ester was hydrolyzed and the acid was purified to give 2'-chloro-4-[4-(3,4-dichloro-phenyl)-thiazol-2-yl]-5'-hydroxy-biphenyl-2-carboxylic acid (71 mg, 74%). $^1$H NMR (400 MHz, DMSO-$d_6$) δ 13.01 (br s, 1H), 9.76 (s, 1H), 8.48 (s, 2H), 8.34 (d, J=2.0 Hz, 1H), 8.25 (dd, J=8.0, 1.8 Hz, 1H), 8.09 (dd, J=8.3, 2.0 Hz, 1H), 7.77 (d, J=8.5 Hz, 1H), 7.43 (d, J=8.0 Hz, 1H), 7.27 (d, J=8.5 Hz, 1H), 6.78 (dd, J=8.7, 2.9 Hz, 1H), 6.71 (d, J=2.8 Hz, 1H).

Example 96

5-[4-(3,4-Dichloro-phenyl)-thiazol-2-yl]-2-(4-isopropyl-pyrimidin-5-yl)-benzoic acid

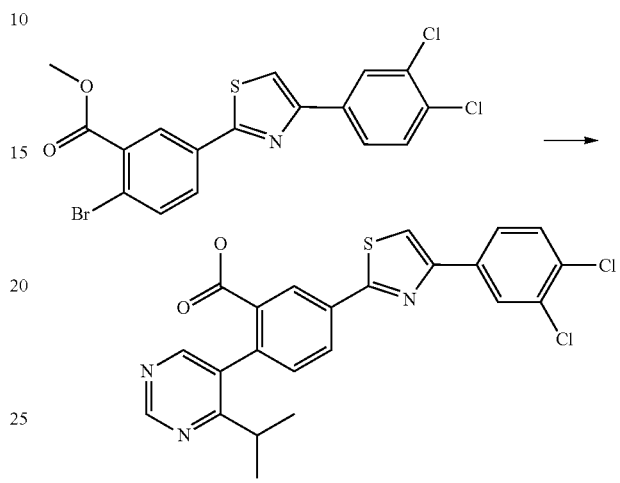

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 4-isopropylpyrimidine-5-boronic acid (available from Combi-Blocks Inc.; 66 mg, 0.4 mmol). The resulting ester was hydrolyzed and the acid was purified to give 5-[4-(3,4-dichloro-phenyl)-thiazol-2-yl]-2-(4-isopropyl-pyrimidin-5-yl)-benzoic acid (14 mg, 14%). $^1$H NMR (300 MHz, DMSO-$d_6$) δ 13.30 (br s, 1H), 9.14 (s, 1H), 8.62 (d, J=1.7 Hz, 1H), 8.50 (d, J=2.4 Hz, 2H), 8.29-8.36 (m, 2H), 8.10 (dd, J=8.4, 2.0 Hz, 1H), 7.78 (d, J=8.5 Hz, 1H), 7.55 (d, J=8.1 Hz, 5H), 2.75-2.85 (m, 1H), 1.03-1.19 (m, 6H).

Example 97

5-[4-(3,4-Dichloro-phenyl)-thiazol-2-yl]-2-pyrimidin-5-yl-benzoic acid

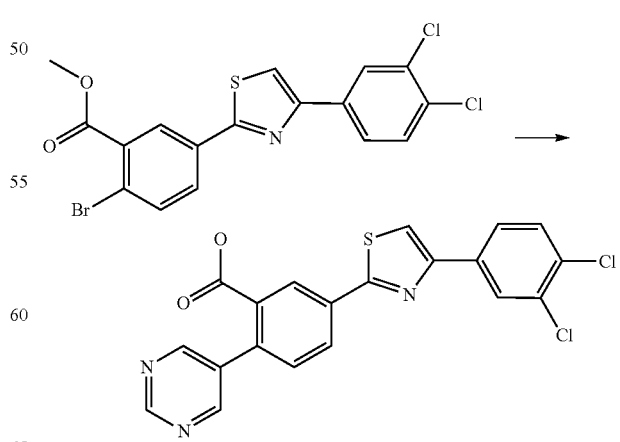

Using the conditions of General Procedure B for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 89 mg, 0.2 mmol) was reacted with and pyrimidine-5-boronic acid (available from Combi-Blocks Inc.; 50 mg, 0.4 mmol). The resulting ester was hydrolyzed and the acid was purified to give 5-[4-(3,4-dichloro-phenyl)-thiazol-2-yl]-2-pyrimidin-5-yl-benzoic acid (13 mg, 16%). $^1$H NMR (300 MHz, DMSO-d$_6$) δ 13.42 (br s, 1H), 9.21 (s, 1H), 8.86 (s, 2H), 8.58 (s, 1H), 8.50 (s, 1H), 8.29-8.37 (m, 2H), 8.10 (d, J=8.5 Hz, 1H), 7.77 (d, J=8.5 Hz, 1H), 7.67 (d, J=7.9 Hz, 1H).

Example 98

5-[4-(3,4-Dichloro-phenyl)-thiazol-2-yl]-2-(2-methyl-pyridin-3-yl)-benzoic acid

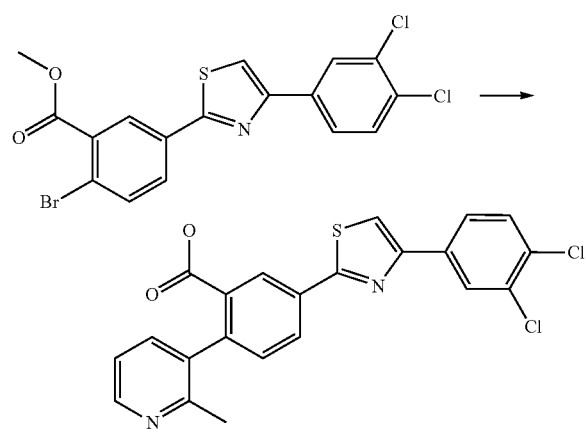

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-picoline-3-boronic acid hydrochloride salt (available from Combi-Blocks Inc.; 87 mg, 0.5 mmol). The resulting ester was hydrolyzed and the acid was purified to give 5-[4-(3,4-dichloro-phenyl)-thiazol-2-yl]-2-(2-methyl-pyridin-3-yl)-benzoic acid (65 mg, 59%). $^1$H NMR (400 MHz, DMSO-d$_6$) δ 8.56 (d, J=1.8 Hz, 1H), 8.49 (s, 1H), 8.34 (d, J=2.0 Hz, 1H), 8.30 (dd, J=7.9, 1.9 Hz, 1H), 8.09 (dd, J=8.5, 2.0 Hz, 1H), 7.77 (d, J=8.3 Hz, 1H), 7.43 (d, J=8.0 Hz, 1H), 7.21-7.30 (m, 1H), 2.08 (s, 3H).

Example 99

5-[4-(3,4-Dichloro-phenyl)-thiazol-2-yl]-2-(3-methyl-pyridin-4-yl)-benzoic acid

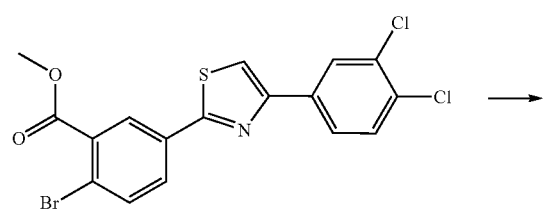

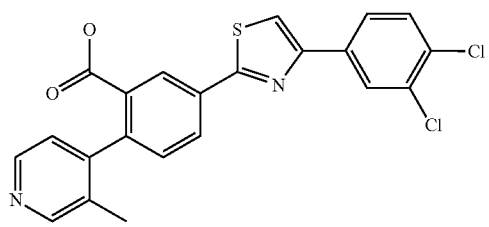

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 3-picoline-4-boronic acid hydrochloride salt (available from Combi-Blocks Inc.; 87 mg, 0.5 mmol). The resulting ester was hydrolyzed and the acid was purified to give 5-[4-(3,4-dichloro-phenyl)-thiazol-2-yl]-2-(3-methyl-pyridin-4-yl)-benzoic acid (46 mg, 42%). $^1$H NMR (300 MHz, DMSO-d$_6$) δ 13.30 (br s, 1H), 8.59-8.66 (m, 2H), 8.50 (s, 1H), 8.30-8.38 (m, 2H), 8.10 (dd, J=8.5, 1.9 Hz, 1H), 7.88-7.94 (m, 1H), 7.78 (d, J=8.5 Hz, 1H), 7.56-7.63 (m, 1H), 7.52 (d, J=8.1 Hz, 1H), 2.34 (s, 3H).

Example 100

5-[4-(3,4-Dichloro-phenyl)-thiazol-2-yl]-2-(5-fluoropyridin-2-yl)-benzoic acid

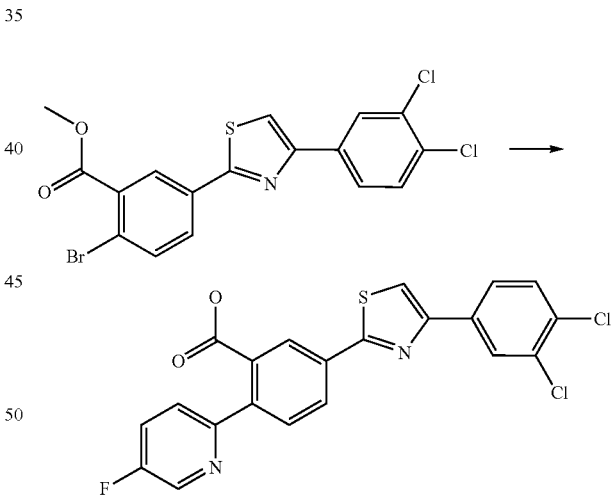

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 5-fluoropyridine-2-boronic acid (available from Combi-Blocks Inc.; 71 mg, 0.5 mmol). The resulting ester was hydrolyzed and the acid was purified to give 5-[4-(3,4-dichloro-phenyl)-thiazol-2-yl]-2-(5-fluoropyridin-2-yl)-benzoic acid (4 mg, 4%). LCMS analysis indicated that the material was ~100% pure, as measured by UV at 214 nm. LRMS m/z 444.8 (M+H$^+$).

Example 101

5-[4-(3,4-Dichloro-phenyl)-thiazol-2-yl]-2-pyridin-3-yl-benzoic acid

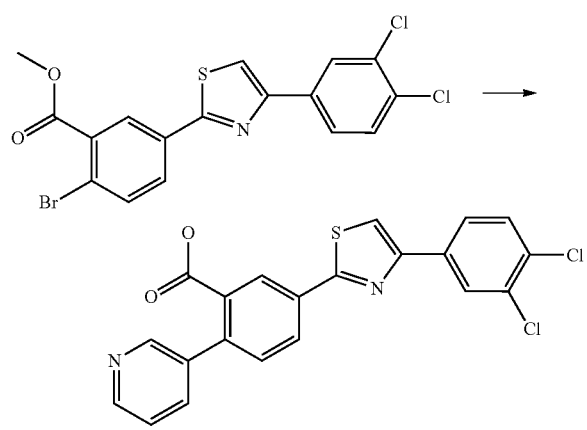

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with pyridine-3-boronic acid (available from Combi-Blocks Inc.; 49 mg, 0.4 mmol). The resulting ester was hydrolyzed and the acid was purified to give 5-[4-(3,4-dichloro-phenyl)-thiazol-2-yl]-2-pyridin-3-yl-benzoic acid (12 mg, 14%). $^1$H NMR (300 MHz, DMSO-$d_6$), δ 13.27 (br s, 1H), 8.56-8.63 (m, 2H), 8.45-8.51 (m, 2H), 8.34 (d, J=1.9 Hz, 1H), 8.28 (dd, J=7.9, 1.9 Hz, 1H), 8.10 (dd, J=8.5, 2.1 Hz, 1H), 7.83 (d, J=8.1 Hz, 1H), 7.77 (d, J=8.5 Hz, 1H), 7.61 (d, J=8.1 Hz, 1H), 7.48 (dd, J=7.7, 5.1 Hz, 1H).

Example 102

2-(5-Chloro-pyridin-3-yl)-5-[4-(3,4-dichloro-phenyl)-thiazol-2-yl]-benzoic acid

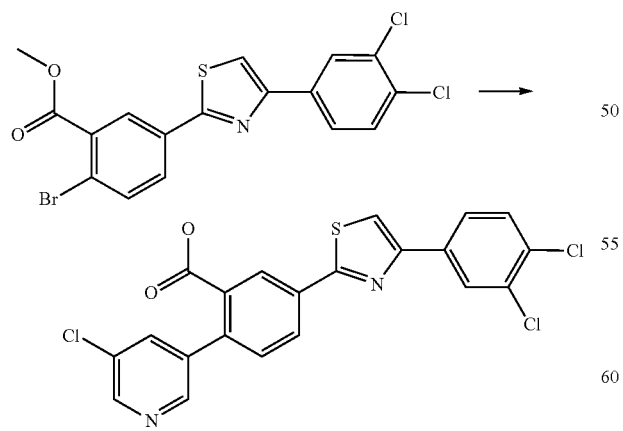

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 5-chloropyridine-3-boronic acid (available from Combi-Blocks Inc.; 63 mg, 0.4 mmol). The resulting ester was hydrolyzed and the acid was purified to give 2-(5-chloro-pyridin-3-yl)-5-[4-(3,4-dichloro-phenyl)-thiazol-2-yl]-benzoic acid (8 mg, 8%). $^1$H NMR (400 MHz, DMSO-$d_6$) δ 13.38 (br s, 1H), 8.66 (d, J=2.3 Hz, 1H), 8.47-8.55 (m, 3H), 8.34 (d, J=2.0 Hz, 1H), 8.29 (dd, J=8.0, 1.8 Hz, 1H), 8.10 (dd, J=8.5, 2.0 Hz, 1H), 8.02 (t, J=2.0 Hz, 1H), 7.77 (d, J=8.5 Hz, 1H), 7.64 (d, J=7.8 Hz, 1H).

Example 103

5-[4-(3,4-Dichloro-phenyl)-thiazol-2-yl]-2-pyridin-4-yl-benzoic acid

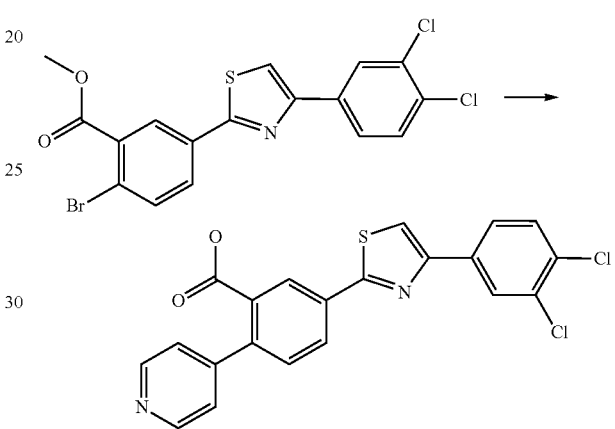

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with pyridine-4-boronic acid (available from Combi-Blocks Inc.; 49 mg, 0.4 mmol). The resulting ester was hydrolyzed and the acid was purified to give 5-[4-(3,4-dichloro-phenyl)-thiazol-2-yl]-2-pyridin-4-yl-benzoic acid (7 mg, 8%). $^1$H NMR (300 MHz, DMSO-$d_6$), δ 13.35 (br s, 1H), 8.69 (d, J=6.0 Hz, 2H), 8.50 (s, 1H), 8.48 (d, J=1.7 Hz, 1H), 8.34 (d, J=1.9 Hz, 1H), 8.30 (dd, J=7.9, 1.9 Hz, 1H), 8.10 (dd, J=8.5, 2.1 Hz, 1H), 7.77 (d, J=8.5 Hz, 1H), 7.61 (d, J=8.1 Hz, 1H), 7.54 (d, J=5.8 Hz, 2H).

Example 104

2-(6-Cyano-pyridin-2-yl)-5-[4-(3,4-dichloro-phenyl)-thiazol-2-yl]-benzoic acid

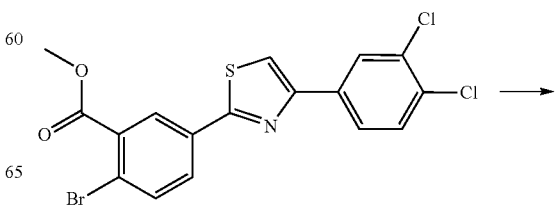

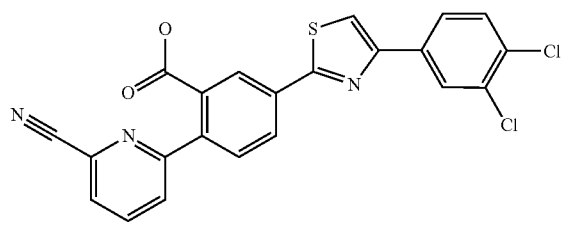

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 6-cyanopyridine-2-boronic acid (available from CombiPhos Catalysts, Inc.; 59 mg, 0.4 mmol). The resulting ester was hydrolyzed and the acid was purified to give 2-(6-cyano-pyridin-2-yl)-5-[4-(3,4-dichloro-phenyl)-thiazol-2-yl]-benzoic acid (14 mg, 16%). $^1$H NMR (300 MHz, DMSO-$d_6$) δ 13.14 (br s, 1H), 8.50 (s, 1H), 8.40 (s, 1H), 8.35 (s, 1H), 8.24-8.32 (m, 1H), 8.00-8.16 (m, 3H), 7.73-7.88 (m, 3H).

Example 105

4'-Cyano-4-[4-(3,4-dichloro-phenyl)-thiazol-2-yl]-2'-methyl-biphenyl-2-carboxylic acid

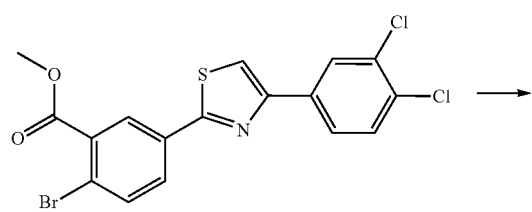

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-methyl-4-cyanophenylboronic acid (available from Aldrich Chemical Company, Inc.; 64 mg, 0.4 mmol). The resulting ester was hydrolyzed and the acid was purified to give 4'-cyano-4-[4-(3,4-dichloro-phenyl)-thiazol-2-yl]-2'-methyl-biphenyl-2-carboxylic acid (13 mg, 14%). $^1$H NMR (400 MHz, DMSO-$d_6$) δ 13.14 (br s, 1H), 8.54 (d, J=2.0 Hz, 1H), 8.49 (s, 1H), 8.34 (d, J=2.0 Hz, 1H), 8.28 (dd, J=8.0, 2.0 Hz, 1H), 8.09 (dd, J=8.5, 2.0 Hz, 1H), 7.75-7.83 (m, 2H), 7.71 (d, J=7.8 Hz, 1H), 7.41 (d, J=8.0 Hz, 1H), 7.31 (d, J=8.0 Hz, 1H).

Example 106

4'-Cyano-4-[4-(3,4-dichloro-phenyl)-thiazol-2-yl]-biphenyl-2-carboxylic acid

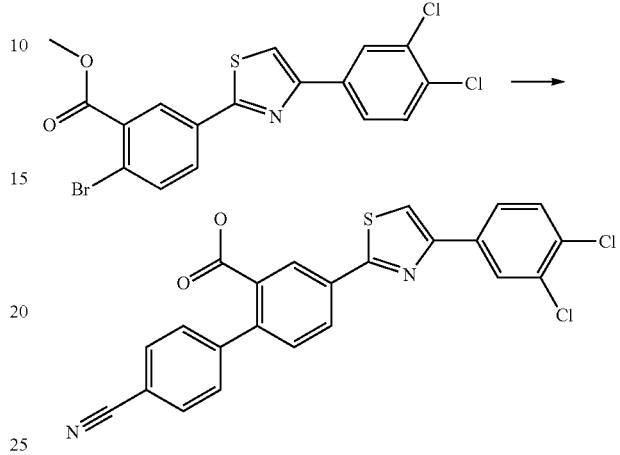

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 4-cyanophenylboronic acid (available from Combi-Blocks Inc.; 59 mg, 0.4 mmol). The resulting ester was hydrolyzed and the acid was purified to give 4'-cyano-4-[4-(3,4-dichloro-phenyl)-thiazol-2-yl]-biphenyl-2-carboxylic acid (20 mg, 22%). $^1$H NMR (400 MHz, DMSO-$d_6$) δ 13.31 (br s, 1H), 8.49 (s, 1H), 8.43 (d, J=1.8 Hz, 1H), 8.34 (d, J=2.0 Hz, 1H), 8.26 (dd, J=8.0, 2.0 Hz, 1H), 8.09 (dd, J=8.4, 2.1 Hz, 1H), 7.92 (d, J=8.3 Hz, 2H), 7.77 (d, J=8.5 Hz, 1H), 7.56-7.64 (m, 3H).

Example 107

3'-Cyano-4-[4-(3,4-dichloro-phenyl)-thiazol-2-yl]-biphenyl-2-carboxylic acid

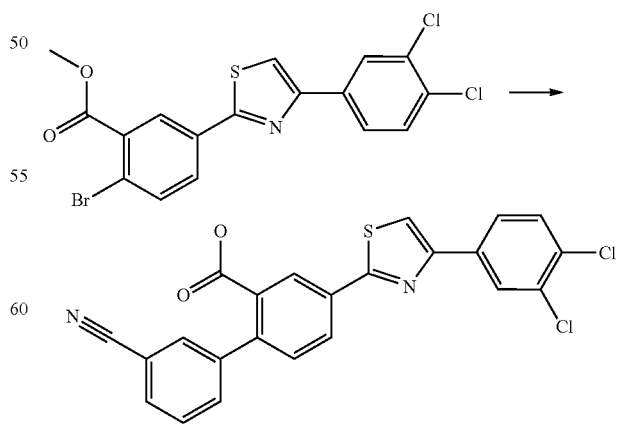

Using the conditions of General Procedure B for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 89 mg, 0.2 mmol) was reacted with 3-cyanophenylboronic acid (available from Combi-Blocks Inc.; 59 mg, 0.4 mmol). The resulting ester was hydrolyzed and the acid was purified to give 3'-cyano-4-[4-(3,4-dichloro-phenyl)-thiazol-2-yl]-biphenyl-2-carboxylic acid (19 mg, 21%). $^1$H NMR (400 MHz, DMSO-$d_6$) δ 13.30 (br s, 1H), 8.48 (s, 1H), 8.45 (d, J=1.8 Hz, 1H), 8.34 (d, J=2.0 Hz, 1H), 8.26 (dd, J=8.0, 1.8 Hz, 1H), 8.10 (dd, J=8.3, 2.0 Hz, 1H), 7.85-7.92 (m, 2H), 7.71-7.81 (m, 2H), 7.57-7.69 (m, 2H).

Examples 108 and 109

2'-Chloro-5'-cyano-4-[4-(3,4-dichloro-phenyl)-thiazol-2-yl]-biphenyl-2-carboxylic acid and 5'-Carbamoyl-2'-chloro-4-[4-(3,4-dichloro-phenyl)-thiazol-2-yl]-biphenyl-2-carboxylic acid

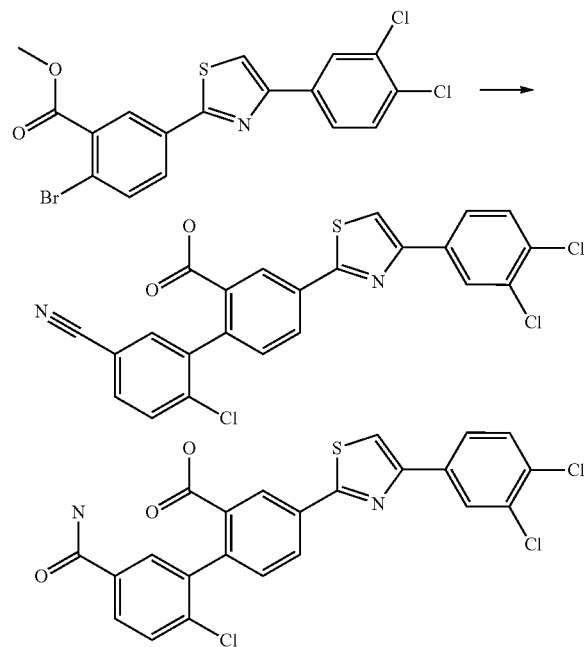

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-chloro-5-cyanophenylboronic acid (available from Frontier Scientific, Inc.; 73 mg, 0.4 mmol). The resulting ester was hydrolyzed and the acid was purified to give 2'-chloro-5'-cyano-4-[4-(3,4-dichloro-phenyl)-thiazol-2-yl]-biphenyl-2-carboxylic acid (Example 108; 27 mg, 28%) {$^1$H NMR (400 MHz, DMSO-$d_6$) δ 13.12 (br s, 1H), 8.57 (d, J=1.8 Hz, 1H), 8.50 (s, 1H), 8.26-8.39 (m, 2H), 8.04-8.15 (m, 2H), 7.85-7.96 (m, 2H), 7.78 (d, J=8.5 Hz, 1H), 7.61 (d, J=8.3 Hz, 1H), 7.50 (d, J=8.3 Hz, 2H)} and 5'-carbamoyl-2'-chloro-4-[4-(3,4-dichloro-phenyl)-thiazol-2-yl]-biphenyl-2-carboxylic acid (Example 109; 14 mg, 14%) {$^1$H NMR (400 MHz, DMSO-$d_6$) δ 8.57 (d, J=2.0 Hz, 1H), 8.50 (s, 1H), 8.34 (d, J=2.0 Hz, 1H), 8.32 (s, 1H), 8.30 (d, J=2.0 Hz, 1H), 8.10 (dd, J=8.3, 2.0 Hz, 1H), 8.06 (br s, 1H), 7.95 (dd, J=8.3, 2.0 Hz, 1H), 7.83 (d, J=2.3 Hz, 1H), 7.78 (d, J=8.2 Hz, 1H), 7.67 (d, J=8.5 Hz, 1H), 7.51 (d, J=7.7 Hz, 1H).

Example 110

5'-Chloro-2'-cyano-4-[4-(3,4-dichloro-phenyl)-thiazol-2-yl]-biphenyl-2-carboxylic acid

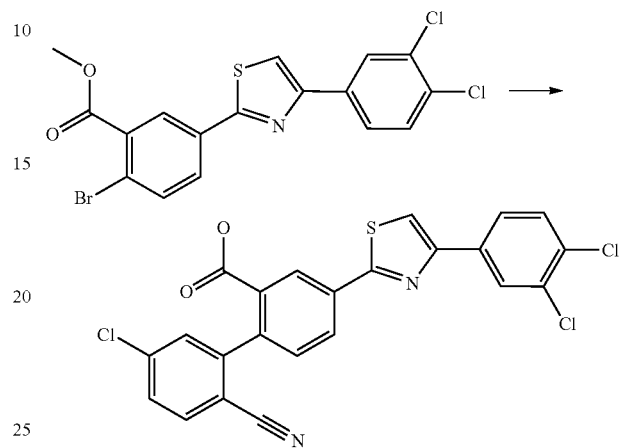

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 5-chloro-2-cyanophenylboronic acid (available from Combi-Blocks Inc.; 73 mg, 0.4 mmol). The resulting ester was hydrolyzed and the acid was purified to give 5'-chloro-2'-cyano-4-[4-(3,4-dichloro-phenyl)-thiazol-2-yl]-biphenyl-2-carboxylic acid (12 mg, 12%). $^1$H NMR (400 MHz, DMSO-$d_6$) δ 13.38 (br s, 1H), 8.63 (d, J=2.0 Hz, 1H), 8.52 (s, 1H), 8.31-8.37 (m, 2H), 8.10 (dd, J=8.5, 2.0 Hz, 1H), 7.97 (d, J=8.3 Hz, 1H), 7.78 (d, J=8.5 Hz, 1H), 7.65-7.73 (m, 2H), 7.59 (d, J=8.0 Hz, 1H).

Example 111

2'-Cyano-4-[4-(3,4-dichloro-phenyl)-thiazol-2-yl]-biphenyl-2-carboxylic acid

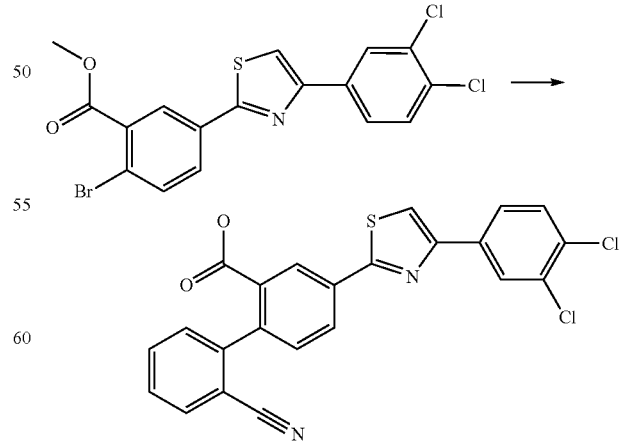

Using the conditions of General Procedure B for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 89 mg, 0.2 mmol) was reacted with 2-cyanophenylboronic acid (available from Aldrich Chemical Company, Inc.; 59 mg, 0.4 mmol). The resulting ester was hydrolyzed and the acid was purified to give 2'-cyano-4-[4-(3,4-dichloro-phenyl)-thiazol-2-yl]-biphenyl-2-carboxylic acid (2 mg, 1%). The compound of Example 111 has the same formula as the compound of Example 112. LCMS analysis indicated that the material was ~94% pure, as measured by UV at 214 nm. LRMS m/z 450.8 $(M+H^+)$.

Examples 112 and 113

2'-Cyano-4-[4-(3,4-dichloro-phenyl)-thiazol-2-yl]-biphenyl-2-carboxylic acid and 2'-Carbamoyl-4-[4-(3,4-dichloro-phenyl)-thiazol-2-yl]-biphenyl-2-carboxylic acid

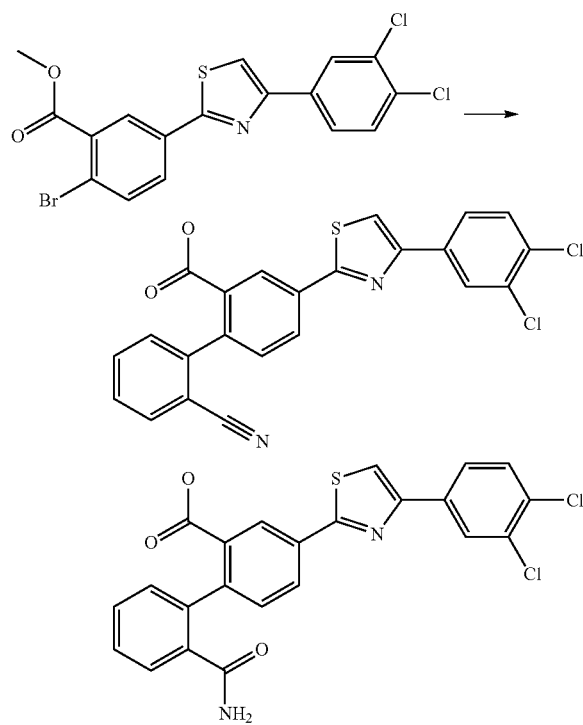

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-cyanophenylboronic acid (available from Aldrich Chemical Company, Inc.; 74 mg, 0.5 mmol). The resulting ester was hydrolyzed and the hydrolysis products were separated by preparative HPLC to give 2'-cyano-4-[4-(3,4-dichloro-phenyl)-thiazol-2-yl]-biphenyl-2-carboxylic acid (Example 112; 48 mg, 43%) {$^1$H NMR (300 MHz, DMSO-$d_6$) δ 13.25 (br s, 1H), 8.60 (d, J=1.7 Hz, 1H), 8.51 (s, 1H), 8.30-8.37 (m, 2H), 8.10 (dd, J=8.4, 2.0 Hz, 1H), 7.91 (d, J=7.5 Hz, 1H), 7.73-7.81 (m, 2H), 7.47-7.63 (m, 3H)} and 2'-carbamoyl-4-[4-(3,4-dichloro-phenyl)-thiazol-2-yl]-biphenyl-2-carboxylic acid (Example 113; 16 mg, 14%) {$^1$H NMR (300 MHz, DMSO-$d_6$) δ 13.10 (br s, 1H), 8.46 (s, 1H), 8.39 (s, 1H), 8.33 (s, 1H), 8.13-8.19 (m, 1H), 8.09 (d, J=8.3 Hz, 1H), 7.77 (d, J=8.5 Hz, 1H), 7.53-7.62 (m, 2H), 7.46 (t, J=5.7 Hz, 2H), 7.26-7.35 (m, 2H), 7.19 (d, J=6.2 Hz, 1H)}. The compound of Example 112 has the same formula as the compound of Example 111. The compound of Example 113 has the same formula as the compound of Example 81.

Example 114

3'-Chloro-4'-cyano-4-[4-(3,4-dichloro-phenyl)-thiazol-2-yl]-biphenyl-2-carboxylic acid

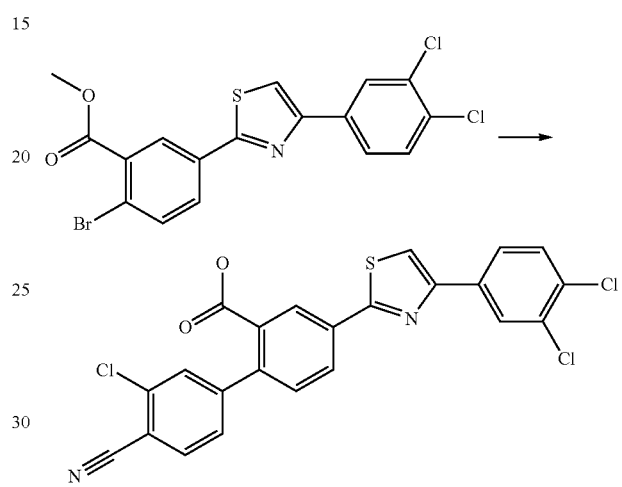

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 3-chloro-4-cyanophenylboronic acid (available from Combi-Blocks Inc.; 73 mg, 0.4 mmol). The resulting ester was hydrolyzed and the acid was purified to give 3'-chloro-4'-cyano-4-[4-(3,4-dichloro-phenyl)-thiazol-2-yl]-biphenyl-2-carboxylic acid (42 mg, 43%). $^1$H NMR (400 MHz, DMSO-$d_6$) δ 13.40 (br s, 1H) 8.44-8.55 (m, 2H), 8.34 (d, J=1.8 Hz, 1H), 8.28 (dd, J=8.0, 2.0 Hz, 1H), 8.07-8.13 (m, 1H), 8.05 (d, J=8.0 Hz, 1H), 7.81 (d, J=1.3 Hz, 1H), 7.77 (d, J=8.1 Hz, 1H), 7.61 (d, J=8.0 Hz, 1H), 7.56 (dd, J=8.0, 1.5 Hz, 1H).

Example 115

4'-Chloro-3'-cyano-4-[4-(3,4-dichloro-phenyl)-thiazol-2-yl]-biphenyl-2-carboxylic acid

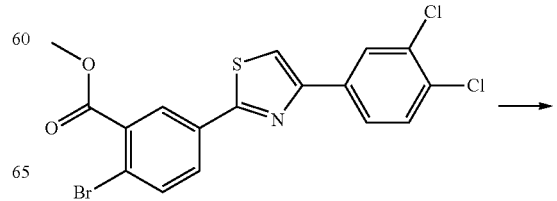

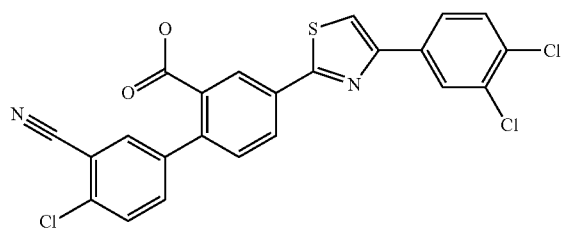

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 4-chloro-3-cyanophenylboronic acid (available from Combi-Blocks Inc.; 73 mg, 0.4 mmol). The resulting ester was hydrolyzed and the acid was purified to give 4'-chloro-3'-cyano-4-[4-(3,4-dichloro-phenyl)-thiazol-2-yl]-biphenyl-2-carboxylic acid (18 mg, 19%). $^1$H NMR (400 MHz, DMSO-$d_6$) δ 13.35 (br s, 1H), 8.44-8.51 (m, 2H), 8.34 (d, J=2.0 Hz, 1H), 8.28 (dd, J=8.0, 1.8 Hz, 1H), 8.09 (dd, J=8.5, 2.0 Hz, 1H), 8.06 (d, J=2.3 Hz, 1H), 7.82 (d, J=8.5 Hz, 1H), 7.77 (d, J=8.5 Hz, 1H), 7.74 (dd, J=8.5, 2.3 Hz, 1H), 7.61 (d, J=8.0 Hz, 1H).

Example 116

3'-Acetyl-4-[4-(3,4-dichloro-phenyl)-thiazol-2-yl]-biphenyl-2-carboxylic acid

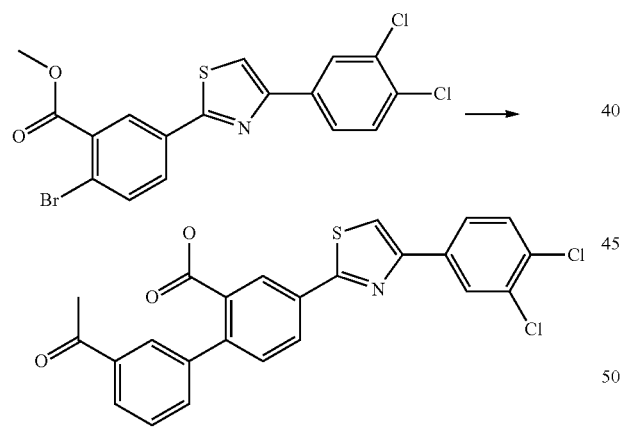

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 3-acetylphenylboronic acid (available from Combi-Blocks Inc.; 66 mg, 0.4 mmol). The resulting ester was hydrolyzed and the acid was purified to give 3'-acetyl-4-[4-(3,4-dichloro-phenyl)-thiazol-2-yl]-biphenyl-2-carboxylic acid (21 mg, 23%). $^1$H NMR (400 MHz, DMSO-$d_6$) δ 8.48 (s, 1H), 8.40 (d, J=1.8 Hz, 1H), 8.34 (d, J=2.0 Hz, 1H), 8.25 (dd, J=8.0, 2.0 Hz, 1H), 8.10 (dd, J=8.5, 2.0 Hz, 1H), 8.00 (d, J=7.8 Hz, 1H), 7.96 (s, 1H), 7.77 (d, J=8.5 Hz, 1H), 7.55-7.71 (m, 3H), 2.63 (s, 3H).

Example 117

2'-Acetyl-4-[4-(3,4-dichloro-phenyl)-thiazol-2-yl]-biphenyl-2-carboxylic acid

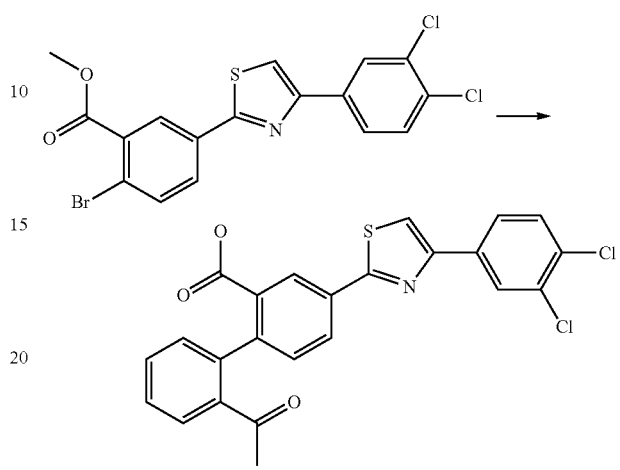

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-acetylphenylboronic acid (available from ASDI Incorporated; 66 mg, 0.4 mmol). The resulting ester was hydrolyzed and the acid was purified to give 2'-acetyl-4-[4-(3,4-dichloro-phenyl)-thiazol-2-yl]-biphenyl-2-carboxylic acid (14 mg, 15%). $^1$H NMR (400 MHz, DMSO-$d_6$) δ 12.97 (br s, 1H), 8.44-8.50 (m, 2H), 8.34 (d, J=1.8 Hz, 1H), 8.20 (dd, J=7.9, 1.9 Hz, 1H), 8.09 (dd, J=8.3, 2.0 Hz, 1H), 7.81-7.88 (m, 1H), 7.77 (d, J=8.5 Hz, 1H), 7.55-7.64 (m, 1H), 7.45-7.54 (m, 1H), 7.34 (d, J=8.0 Hz, 1H), 7.19-7.28 (m, 1H), 6.52 (s, 1H), 2.32 (s, 3H).

Example 118

5'-Acetyl-2'-chloro-4-[4-(3,4-dichloro-phenyl)-thiazol-2-yl]-biphenyl-2-carboxylic acid

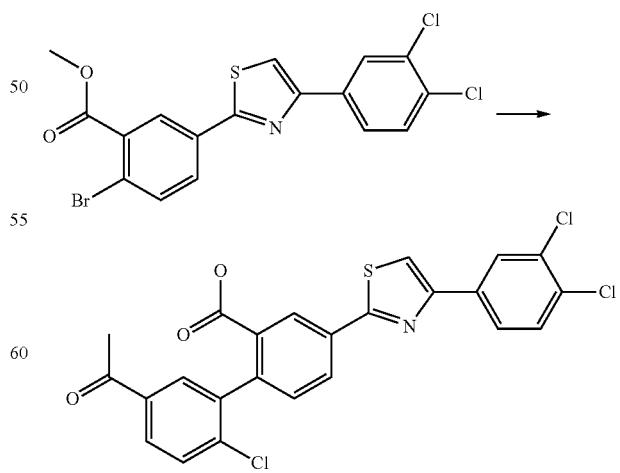

5'-Acetyl-2'-chloro-4-[4-(3,4-dichloro-phenyl)-thiazol-2-yl]-biphenyl-2-carboxylic acid was prepared in 7% yield (for two steps) from 2-bromo-5-[4-(3,4-dichloro-phenyl)-thiazol-2-yl]-benzoic acid methyl ester (which may be prepared as described for Intermediate 6) and 5-acetyl-2-chlorophenylboronic acid (available from Combi-Blocks Inc.) using General Procedure A for Suzuki Coupling and Hydrolysis in Parallel Mode. ¹H NMR (300 MHz, DMSO-d₆) δ 13.14 (s, 1H), 8.58 (d, J=1.9 Hz, 1H), 8.50 (s, 1H), 8.30-8.38 (m, 2H), 8.10 (dd, J=8.4, 2.0 Hz, 1H), 7.98 (dd, J=8.3, 2.1 Hz, 1H), 7.90 (d, J=2.1 Hz, 1H), 7.78 (d, J=8.5 Hz, 1H), 7.69 (d, J=8.5 Hz, 1H), 7.51 (d, J=8.1 Hz, 1H), 2.62 (s, 3H).

Example 119

2-(2-Acetyl-thiophen-3-yl)-5-[4-(3,4-dichloro-phenyl)-thiazol-2-yl]-benzoic acid

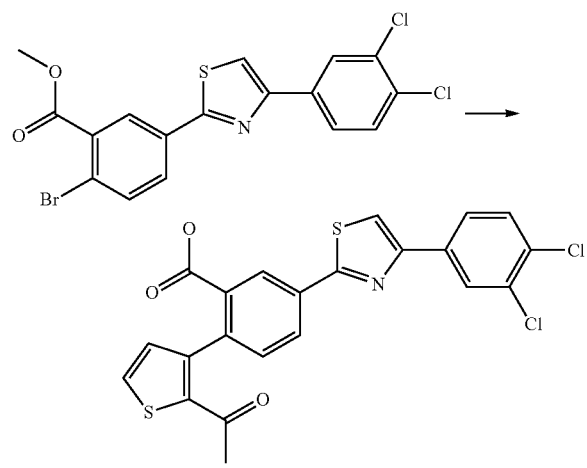

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-acetyl-3-thienylboronic acid (available from Aldrich Chemical Company, Inc.; 68 mg, 0.4 mmol). The resulting ester was hydrolyzed and the acid was purified to give 2-(2-acetyl-thiophen-3-yl)-5-[4-(3,4-dichloro-phenyl)-thiazol-2-yl]-benzoic acid (19 mg, 20%). ¹H NMR (400 MHz, DMSO-d₆) δ 13.12 (br s, 1H), 8.52 (d, J=1.8 Hz, 1H), 8.49 (s, 1H), 8.34 (d, J=2.0 Hz, 1H), 8.25 (dd, J=8.0, 2.0 Hz, 1H), 8.09 (dd, J=8.5, 2.0 Hz, 1H), 7.94 (d, J=5.0 Hz, 1H), 7.77 (d, J=8.3 Hz, 1H), 7.52 (d, J=8.0 Hz, 1H), 7.10 (d, J=5.0 Hz, 1H), 2.08 (s, 3H).

Example 120

4'-Acetyl-4-[4-(3,4-dichloro-phenyl)-thiazol-2-yl]-biphenyl-2-carboxylic acid

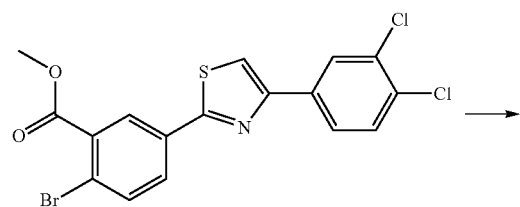

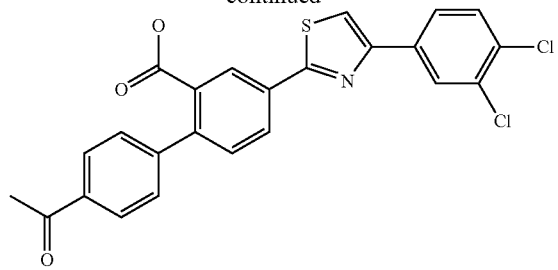

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 4-acetylphenylboronic acid (available from Combi-Blocks Inc.; 66 mg, 0.4 mmol). The resulting ester was hydrolyzed and the acid was purified to give 4'-acetyl-4-[4-(3,4-dichloro-phenyl)-thiazol-2-yl]-biphenyl-2-carboxylic acid (28 mg, 30%). ¹H NMR (400 MHz, DMSO-d₆) δ ppm 13.23 (br s, 1H), 8.48 (s, 1H), 8.40 (d, J=1.5 Hz, 1H), 8.34 (d, J=2.0 Hz, 1H), 8.25 (dd, J=8.0, 2.0 Hz, 1H), 8.10 (dd, J=8.3, 2.0 Hz, 1H), 8.03 (d, J=8.3 Hz, 2H), 7.77 (d, J=8.5 Hz, 1H), 7.60 (d, J=8.0 Hz, 1H), 7.55 (d, J=8.3 Hz, 2H), 2.63 (s, 3H).

Example 121

4-[4-(3,4-Dichloro-phenyl)-thiazol-2-yl]-2'-fluoro-biphenyl-2,4'-dicarboxylic acid

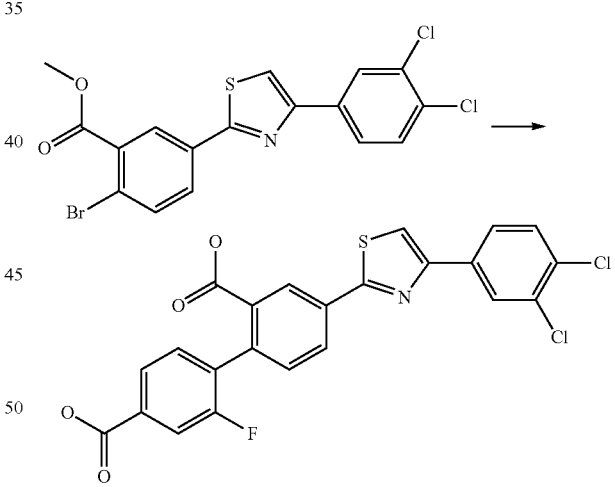

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 4-cyano-2-fluorophenylboronic acid (available from Combi-Blocks Inc.; 83 mg, 0.5 mmol). The resulting ester was hydrolyzed and the acid was purified to give 4-[4-(3,4-dichloro-phenyl)-thiazol-2-yl]-2'-fluoro-biphenyl-2,4'-dicarboxylic acid (49 mg, 40%). ¹H NMR (400 MHz, DMSO-d₆) δ 13.27 (br s, 1H), 8.53 (d, J=1.8 Hz, 1H), 8.50 (s, 1H), 8.30-8.36 (m, 2H), 8.10 (dd, J=8.3, 2.0 Hz, 1H), 7.87 (dd, J=7.9, 1.4 Hz, 1H), 7.77 (d, J=8.5 Hz, 1H), 7.69 (dd, J=10.4, 1.4 Hz, 1H), 7.55-7.62 (m, 2H).

Example 122

4-[4-(3,4-Dichloro-phenyl)-thiazol-2-yl]-2'-formyl-5'-methyl-biphenyl-2-carboxylic acid

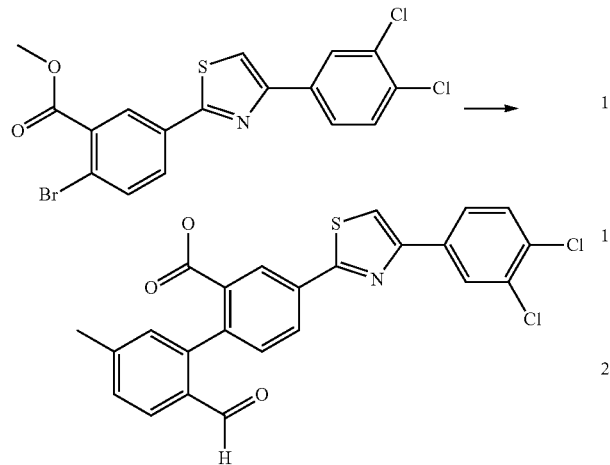

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-formyl-5-methylphenylboronic acid (available from Frontier Scientific, Inc.; 66 mg, 0.4 mmol). The resulting ester was hydrolyzed and the acid was purified to give 4-[4-(3,4-dichloro-phenyl)-thiazol-2-yl]-2'-formyl-5'-methyl-biphenyl-2-carboxylic acid (18 mg, 19%). $^1$H NMR (400 MHz, DMSO-d$_6$) δ 13.10 (br s, 1H), 9.72 (s, 1H), 8.52 (d, J=1.8 Hz, 1H), 8.49 (s, 1H), 8.34 (d, J=2.0 Hz, 1H), 8.26 (dd, J=8.0, 2.0 Hz, 1H), 8.10 (dd, J=8.5, 2.0 Hz, 1H), 7.83 (d, J=8.0 Hz, 1H), 7.77 (d, J=8.5 Hz, 1H), 7.49 (d, J=8.0 Hz, 1H), 7.41 (d, J=8.0 Hz, 1H), 7.17 (s, 1H), 2.43 (s, 3H).

Example 123

4-[4-(3,4-Dichloro-phenyl)-thiazol-2-yl]-2'-formyl-biphenyl-2-carboxylic acid

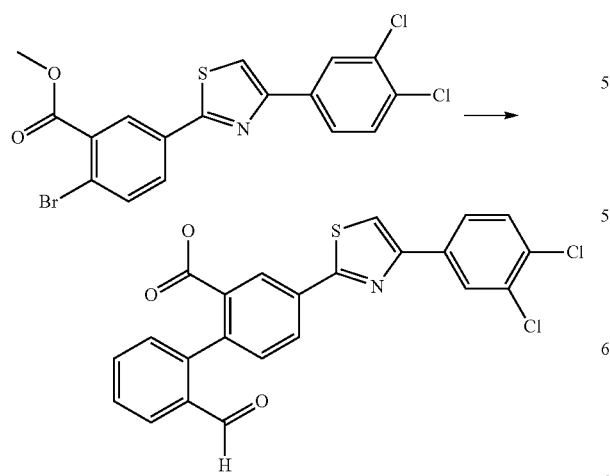

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-formylphenylboronic acid (available from Frontier Scientific, Inc.; 60 mg, 0.4 mmol). The resulting ester was hydrolyzed and the acid was purified to give 4-[4-(3,4-dichloro-phenyl)-thiazol-2-yl]-2'-formyl-biphenyl-2-carboxylic acid (45 mg, 49%). $^1$H NMR (400 MHz, DMSO-d$_6$) δ 13.11 (br s, 1H), 9.80 (br s, 1H), 8.54 (s, 1H), 8.49 (s, 1H), 8.34 (s, 1H), 8.27 (d, J=7.8 Hz, 1H), 8.10 (d, J=8.5 Hz, 1H), 7.93 (d, J=7.5 Hz, 1H), 7.78 (d, J=8.5 Hz, 1H), 7.73 (t, J=7.2 Hz, 1H), 7.61 (t, J=7.3 Hz, 1H), 7.51 (d, J=7.8 Hz, 1H), 7.36 (d, J=7.5 Hz, 1H).

Example 124

4-[4-(3,4-Dichloro-phenyl)-thiazol-2-yl]-4'-fluoro-2'-trifluoromethyl-biphenyl-2-carboxylic acid

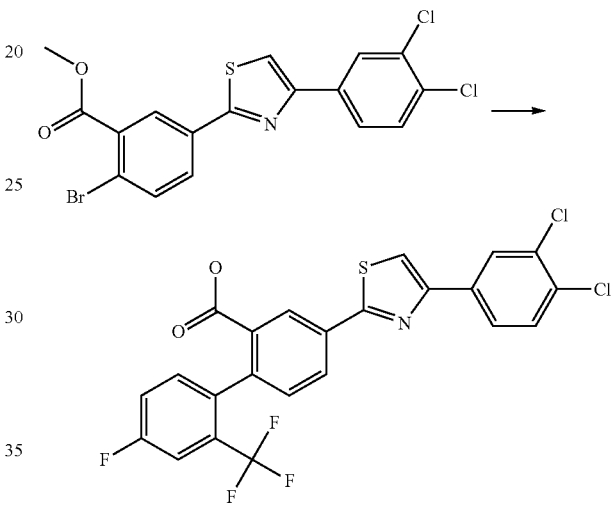

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 4-fluoro-2-(trifluoromethyl)benzeneboronic acid (available from Frontier Scientific, Inc.; 87 mg, 0.5 mmol). The resulting ester was hydrolyzed and the acid was purified to give 4-[4-(3,4-dichlorophenyl)-thiazol-2-yl]-4'-fluoro-2'-trifluoromethyl-biphenyl-2-carboxylic acid (4 mg, 3%). $^1$H NMR (300 MHz, DMSO-d$_6$) δ 13.14 (br s, 1H), 8.58 (s, 1H), 8.49 (s, 1H), 8.34 (d, J=1.9 Hz, 1H), 8.26 (d, J=6.6 Hz, 1H), 8.10 (d, J=8.3 Hz, 1H), 7.77 (d, J=8.5 Hz, 1H), 7.71 (d, J=9.4 Hz, 1H), 7.57 (d, J=8.1 Hz, 2H), 7.44 (d, J=8.3 Hz, 1H).

Example 125

4-[4-(3,4-Dichloro-phenyl)-thiazol-2-yl]-2',4'-bis-trifluoromethyl-biphenyl-2-carboxylic acid

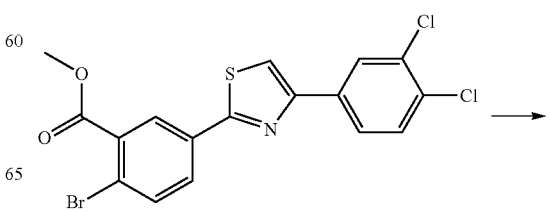

-continued

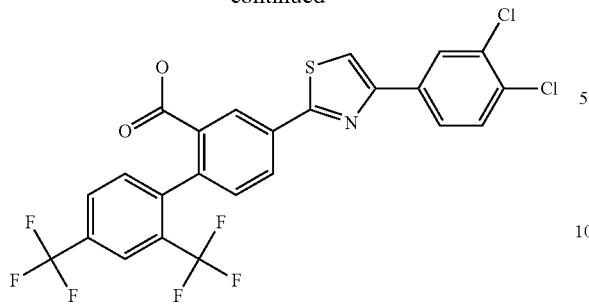

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2,4-bis(trifluoromethyl)phenylboronic acid (available from Combi-Blocks Inc.; 129 mg, 0.5 mmol). The resulting ester was hydrolyzed and the acid was purified to give 4-[4-(3,4-dichloro-phenyl)-thiazol-2-yl]-2',4'-bis-trifluoromethyl-biphenyl-2-carboxylic acid (7 mg, 5%). $^1$H NMR (300 MHz, DMSO-$d_6$) δ 13.17 (br s, 1H), 8.62 (s, 1H), 8.50 (s, 1H), 8.27-8.37 (m, 2H), 8.05-8.15 (m, 3H), 7.77 (d, J=8.3 Hz, 1H), 7.64 (d, J=7.9 Hz, 1H), 7.48 (d, J=8.1 Hz, 1H).

Example 126

2'-Chloro-4-[4-(3,4-dichloro-phenyl)-thiazol-2-yl]-3'-trifluoromethyl-biphenyl-2-carboxylic acid

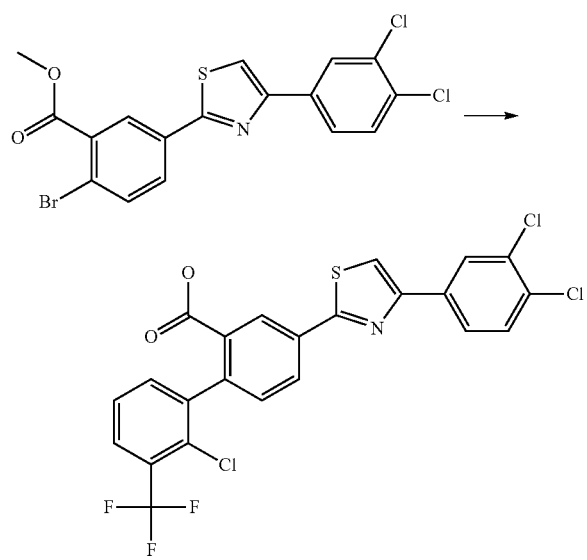

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-3-(trifluoromethyl)phenylboronic acid (available from Combi-Blocks Inc.; 112 mg, 0.5 mmol). The resulting ester was hydrolyzed and the acid was purified to give 2'-chloro-4-[4-(3,4-dichloro-phenyl)-thiazol-2-yl]-3'-trifluoromethyl-biphenyl-2-carboxylic acid (3 mg, 2%). $^1$H NMR (300 MHz, DMSO-$d_6$) δ 13.22 (br s, 1H), 8.58 (br. s., 1H), 8.50 (s, 1H), 8.27-8.36 (m, 2H), 8.10 (d, J=7.3 Hz, 1H), 7.87-7.93 (m, 1H), 7.78 (d, J=8.5 Hz, 1H), 7.61-7.70 (m, 2H), 7.47-7.53 (m, 1H).

Example 127

2'-Chloro-4-[4-(3,4-dichloro-phenyl)-thiazol-2-yl]-4'-trifluoromethyl-biphenyl-2-carboxylic acid

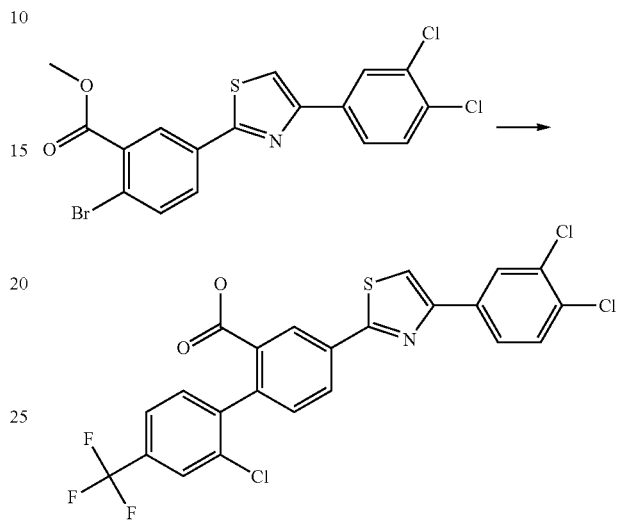

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-4-(trifluoromethyl)phenylboronic acid (available from Combi-Blocks Inc.; 100 mg, 0.5 mmol). The resulting ester was hydrolyzed and the acid was purified to give 2'-chloro-4-[4-(3,4-dichloro-phenyl)-thiazol-2-yl]-4'-trifluoromethyl-biphenyl-2-carboxylic acid (2 mg, 2%). LCMS analysis indicated that the material was ~100% pure, as measured by UV at 214 nm.

Example 128

2'-Chloro-4-[4-(3,4-dichloro-phenyl)-thiazol-2-yl]-5'-trifluoromethyl-biphenyl-2-carboxylic acid

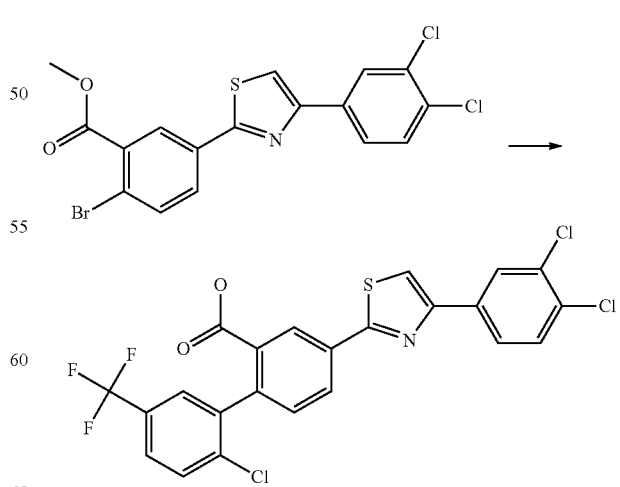

Using the conditions of General Procedure A for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 111 mg, 0.25 mmol) was reacted with 2-chloro-5-(trifluoromethyl)phenylboronic acid (available from Combi-Blocks Inc.; 112 mg, 0.5 mmol). The resulting ester was hydrolyzed and the acid was purified to give 2'-chloro-4-[4-(3,4-dichlorophenyl)-thiazol-2-yl]-5'-trifluoromethyl-biphenyl-2-carboxylic acid (5 mg, 4%). $^1$H NMR (300 MHz, DMSO-$d_6$) δ 13.19 (br s, 1H), 8.59 (s, 1H), 8.50 (s, 1H), 8.28-8.36 (m, 2H), 8.10 (d, J=8.5 Hz, 1H), 7.71-7.82 (m, 4H), 7.52 (d, J=8.1 Hz, 1H).

Example 129

4-[4-(3,4-Dichloro-phenyl)-thiazol-2-yl]-4'-fluoro-biphenyl-2-carboxylic acid

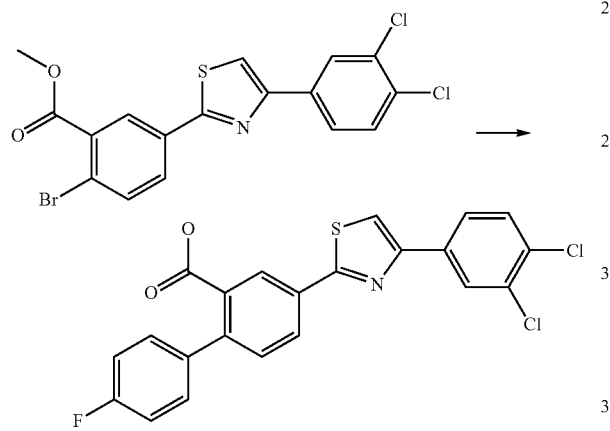

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 4-fluorophenylboronic acid (available from Frontier Scientific, Inc.; 56 mg, 0.4 mmol). The resulting ester was hydrolyzed and the acid was purified to give 4-[4-(3,4-dichloro-phenyl)-thiazol-2-yl]-4'-fluoro-biphenyl-2-carboxylic acid (63 mg, 71%). $^1$H NMR (400 MHz, DMSO-$d_6$) δ 13.18 (br s, 1H), 8.46 (s, 1H), 8.35 (d, J=8.5 Hz, 2H), 8.22 (d, J=8.0 Hz, 1H), 8.09 (d, J=8.3 Hz, 1H), 7.73-7.81 (m, 1H), 7.56 (d, J=8.0 Hz, 1H), 7.40-7.48 (m, 2H), 7.24-7.34 (m, 2H).

Example 130

2'-Chloro-4-[4-(3,4-dichloro-phenyl)-thiazol-2-yl]-5'-fluoro-biphenyl-2-carboxylic acid

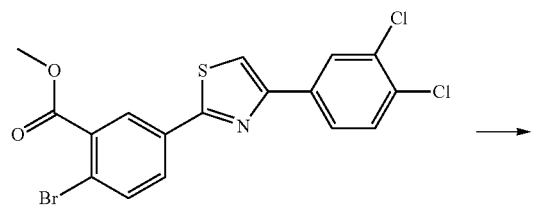

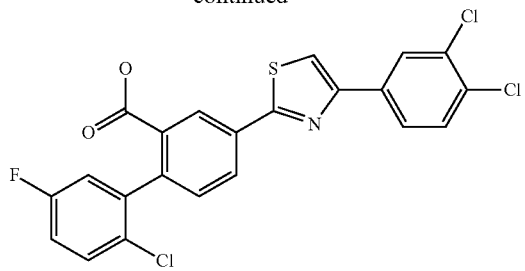

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-5-fluorophenylboronic acid (available from Combi-Blocks Inc.; 87 mg, 0.5 mmol). The resulting ester was hydrolyzed and the acid was purified to give 2'-chloro-4-[4-(3,4-dichloro-phenyl)-thiazol-2-yl]-5'-fluoro-biphenyl-2-carboxylic acid (12 mg, 10%). $^1$H NMR (300 MHz, DMSO-$d_6$) δ 13.14 (br s, 1H), 8.55 (d, J=1.7 Hz, 1H), 8.49 (s, 1H), 8.34 (d, J=1.9 Hz, 1H), 8.29 (dd, J=8.1, 1.9 Hz, 1H), 8.09 (dd, J=8.5, 2.1 Hz, 1H), 7.77 (d, J=8.5 Hz, 1H), 7.56 (dd, J=8.6, 5.7 Hz, 1H), 7.48 (d, J=8.1 Hz, 1H), 7.30 (d, J=8.7 Hz, 2H).

Example 131

4-[4-(3,4-Dichloro-phenyl)-thiazol-2-yl]-2',5'-difluoro-biphenyl-2-carboxylic acid

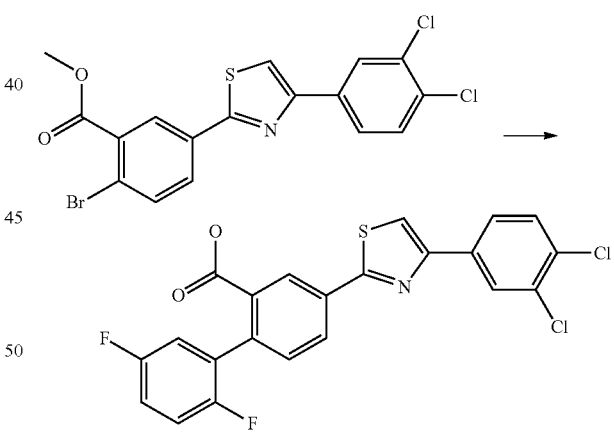

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2,5-difluorophenylboronic acid (available from Combi-Blocks Inc.; 63 mg, 0.4 mmol). The resulting ester was hydrolyzed and the acid was purified to give 4-[4-(3,4-dichloro-phenyl)-thiazol-2-yl]-2',5'-difluoro-biphenyl-2-carboxylic acid (71 mg, 77%). $^1$H NMR (400 MHz, DMSO-$d_6$) δ 13.22 (br s, 1H), 8.48-8.52 (m, 2H), 8.34 (s, 1H), 8.29 (d, J=8.0 Hz, 1H), 8.09 (d, J=8.3 Hz, 1H), 7.75-7.79 (m, 1H), 7.59 (d, J=6.8 Hz, 1H), 7.27-7.37 (m, 3H).

Example 132

4-[4-(3,4-Dichloro-phenyl)-thiazol-2-yl]-2',4'-difluoro-biphenyl-2-carboxylic acid

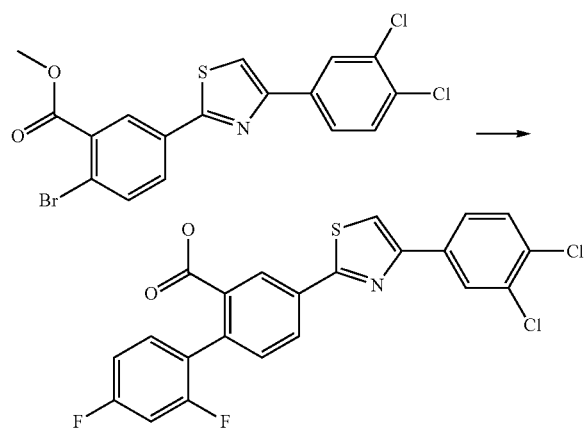

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2,4-difluorophenylboronic acid (available from Frontier Scientific, Inc.; 79 mg, 0.5 mmol). The resulting ester was hydrolyzed and the acid was purified to give 4-[4-(3,4-dichloro-phenyl)-thiazol-2-yl]-2',4'-difluoro-biphenyl-2-carboxylic acid (19 mg, 17%). $^1$H NMR (400 MHz, DMSO-$d_6$) δ 13.17 (br s, 1H), 8.46-8.52 (m, 2H), 8.33 (d, J=2.0 Hz, 1H), 8.26-8.31 (m, 1H), 8.09 (dd, J=8.5, 2.0 Hz, 1H), 7.77 (d, J=8.5 Hz, 1H), 7.55 (d, J=8.0 Hz, 1H), 7.44-7.52 (m, 1H), 7.27-7.36 (m, 1H), 7.15-7.24 (m, 1H).

Example 133

4-[4-(3,4-Dichloro-phenyl)-thiazol-2-yl]-2',3',5'-trifluoro-biphenyl-2-carboxylic acid

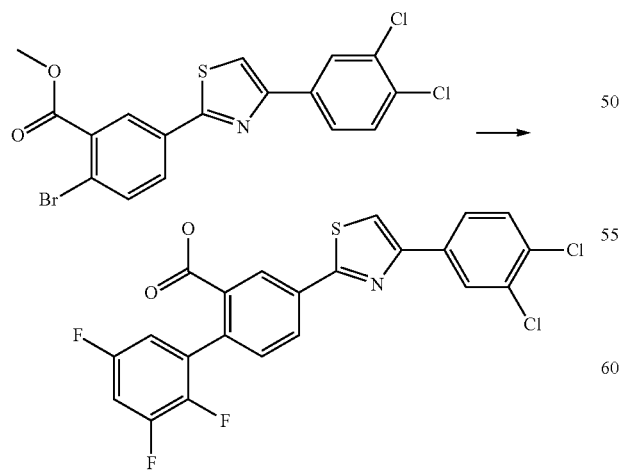

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2,3,5-trifluorophenylboronic acid (available from Combi-Blocks Inc.; 70 mg, 0.4 mmol). The resulting ester was hydrolyzed and the acid was purified to give 4-[4-(3,4-dichloro-phenyl)-thiazol-2-yl]-2',3',5'-trifluoro-biphenyl-2-carboxylic acid (23 mg, 24%). $^1$H NMR (400 MHz, DMSO-$d_6$) δ 13.36 (br s, 1H), 8.55 (s, 1H), 8.50 (s, 1H), 8.28-8.39 (m, 2H), 8.10 (d, J=8.3 Hz, 1H), 7.77 (dd, J=8.4, 1.6 Hz, 1H), 7.54-7.66 (m, 2H), 7.22-7.28 (m, 1H).

Example 134

2'-Chloro-4-[4-(3,4-dichloro-phenyl)-thiazol-2-yl]-4'-fluoro-biphenyl-2-carboxylic acid

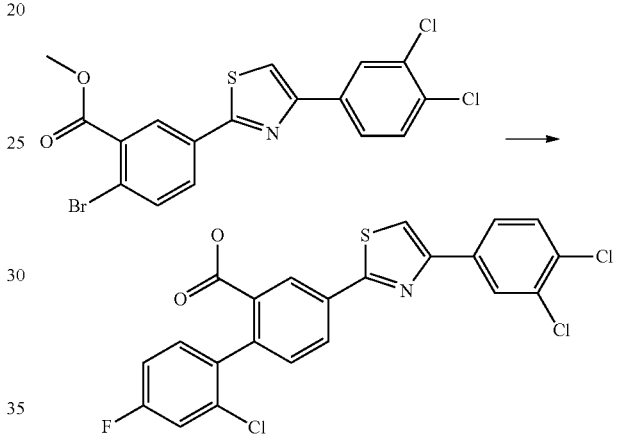

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-chloro-4-fluorophenylboronic acid (available from Combi-Blocks Inc.; 70 mg, 0.4 mmol). The resulting ester was hydrolyzed and the acid was purified to give 2'-chloro-4-[4-(3,4-dichloro-phenyl)-thiazol-2-yl]-4'-fluoro-biphenyl-2-carboxylic acid (8 mg, 8%). LCMS analysis indicated that the material was 93% pure, as measured by UV at 214 nm. LRMS m/z 479.7 (M+H$^+$).

Example 135

4'-Chloro-4-[4-(3,4-dichloro-phenyl)-thiazol-2-yl]-2'-fluoro-biphenyl-2-carboxylic acid

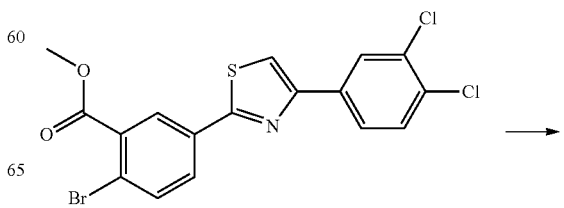

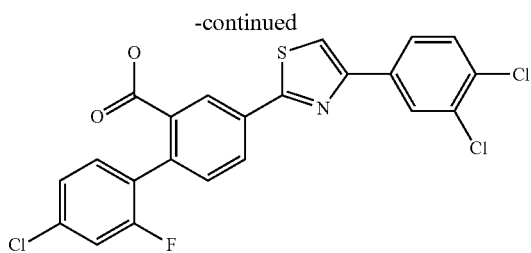

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 4-chloro-2-fluorophenylboronic acid (available from Combi-Blocks Inc.; 70 mg, 0.4 mmol). The resulting ester was hydrolyzed and the acid was purified to give 4'-chloro-4-[4-(3,4-dichloro-phenyl)-thiazol-2-yl]-2'-fluoro-biphenyl-2-carboxylic acid (0.6 mg, 0.3%). The same compound was also prepared using the conditions of General Procedure C for Suzuki Coupling and Hydrolysis in Parallel Mode when 2-bromo-5-[4-(3,4-dichloro-phenyl)-thiazol-2-yl]-benzoic acid methyl ester (which may be prepared as described for Intermediate 6; 111 mg, 0.25 mmol) was reacted with 4-chloro-2-fluorophenylboronic acid (available from Combi-Blocks Inc.; 87 mg, 0.5 mmol). The resulting ester was hydrolyzed and the acid was purified to give 4'-chloro-4-[4-(3,4-dichloro-phenyl)-thiazol-2-yl]-2'-fluoro-biphenyl-2-carboxylic acid (63.6 mg, 53%). The second sample was characterized by $^1$H NMR: (300 MHz, DMSO-$d_6$) δ 13.22 (br s, 1H), 8.50 (d, J=4.9 Hz, 2H), 8.26-8.37 (m, 2H), 8.09 (d, J=8.3 Hz, 1H), 7.77 (d, J=8.5 Hz, 1H), 7.37-7.60 (m, 4H).

Example 136

2'-Chloro-4-[4-(3,4-dichloro-phenyl)-thiazol-2-yl]-6'-fluoro-biphenyl-2-carboxylic acid

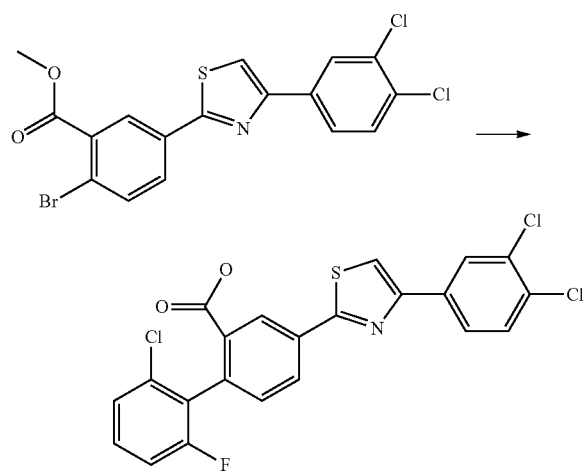

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted 2-chloro-6-fluorophenylboronic acid (available from Combi-Blocks Inc.; 87 mg, 0.5 mmol). The resulting ester was hydrolyzed and the acid was purified to give 2'-chloro-4-[4-(3,4-dichloro-phenyl)-thiazol-2-yl]-6'-fluoro-biphenyl-2-carboxylic acid (3 mg, 3%). $^1$H NMR (300 MHz, DMSO-$d_6$) δ 13.18 (br s, 1H), 8.61 (d, J=1.9 Hz, 1H), 8.50 (s, 1H), 8.28-8.38 (m, 2H), 8.10 (dd, J=8.4, 2.0 Hz, 1H), 7.78 (d, J=8.5 Hz, 1H), 7.39-7.57 (m, 3H), 7.33 (d, J=9.2 Hz, 1H).

Example 137

4-[4-(3,4-Dichloro-phenyl)-thiazol-2-yl]-2'-fluoro-biphenyl-2-carboxylic acid

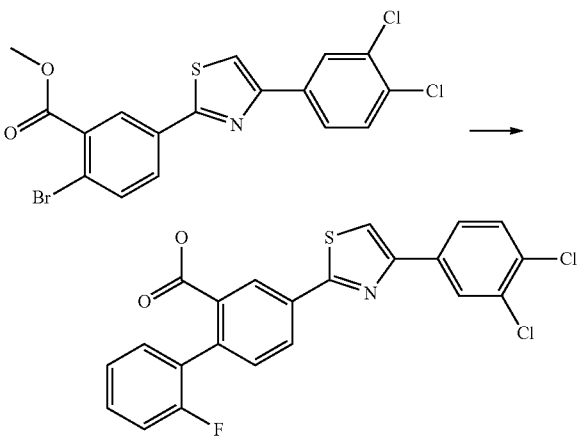

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-fluorophenylboronic acid (available from Combi-Blocks Inc.; 56 mg, 0.4 mmol). The resulting ester was hydrolyzed and the acid was purified to give 4-[4-(3,4-dichloro-phenyl)-thiazol-2-yl]-2'-fluoro-biphenyl-2-carboxylic acid (30 mg, 34%). $^1$H NMR (400 MHz, DMSO-$d_6$) δ 13.11 (br s, 1H), 8.48 (s, 2H), 8.34 (s, 1H), 8.28 (d, J=7.8 Hz, 1H), 8.09 (d, J=8.3 Hz, 1H), 7.77 (d, J=6.5 Hz, 1H), 7.56 (d, J=6.5 Hz, 1H), 7.39-7.48 (m, 2H), 7.20-7.35 (m, 2H).

Example 138

4-[4-(3,4-Dichloro-phenyl)-thiazol-2-yl]-2',3'-difluoro-biphenyl-2-carboxylic acid

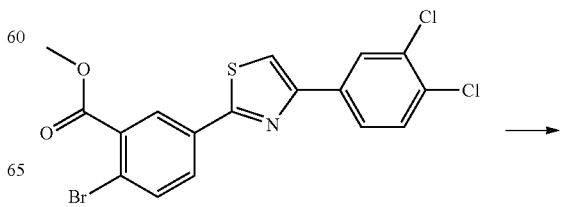

-continued

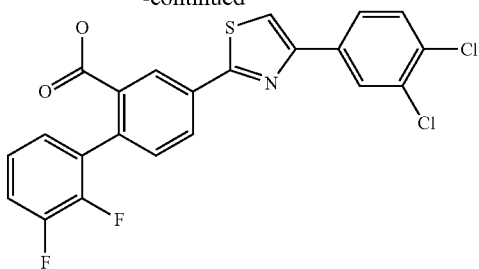

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2,3-difluorophenylboronic acid (available from Combi-Blocks Inc.; 63 mg, 0.4 mmol). The resulting ester was hydrolyzed and the acid was purified to give 4-[4-(3,4-dichloro-phenyl)-thiazol-2-yl]-2',3'-difluoro-biphenyl-2-carboxylic acid (64 mg, 69%). $^1$H NMR (400 MHz, DMSO-$d_6$) δ 13.26 (br s, 1H), 8.52 (s, 1H), 8.50 (d, J=1.5 Hz, 1H), 8.34 (s, 1H), 8.31 (d, J=8.0 Hz, 1H), 8.10 (d, J=8.5 Hz, 1H), 7.74-7.81 (m, 1H), 7.59 (d, J=8.0 Hz, 1H), 7.42-7.53 (m, 1H), 7.19-7.36 (m, 2H).

Example 139

2'-Chloro-4-[4-(3,4-dichloro-phenyl)-thiazol-2-yl]-6'-fluoro-3'-methyl-biphenyl-2-carboxylic acid

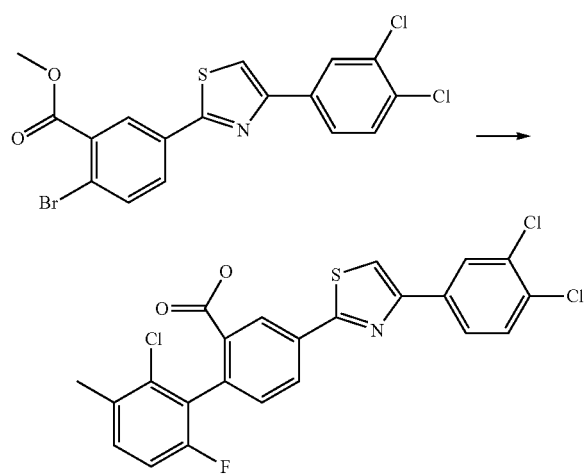

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-4-methylphenylboronic acid (available from Combi-Blocks Inc.; 94 mg, 0.5 mmol). The resulting ester was hydrolyzed and the acid was purified to give 2'-chloro-4-[4-(3,4-dichloro-phenyl)-thiazol-2-yl]-6'-fluoro-3'-methyl-biphenyl-2-carboxylic acid (4 mg, 3%). $^1$H NMR (300 MHz, DMSO-$d_6$) δ 13.14 (br s, 1H), 8.60 (s, 1H), 8.50 (s, 1H), 8.28-8.36 (m, 2H), 8.10 (d, J=8.1 Hz, 1H), 7.77 (d, J=8.3 Hz, 1H), 7.37-7.53 (m, 2H), 7.16-7.27 (m, 1H), 2.36 (s, 3H).

Example 140

2'-Chloro-4-[4-(3,4-dichloro-phenyl)-thiazol-2-yl]-6'-fluoro-5'-methyl-biphenyl-2-carboxylic acid

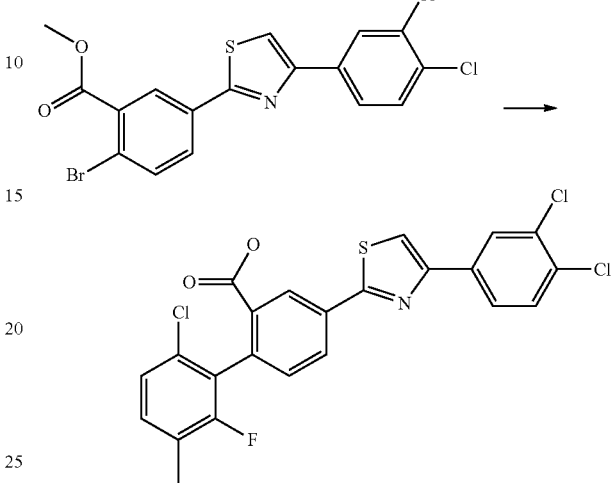

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-6-fluoro-5-methylphenylboronic acid (available from Combi-Blocks Inc.; 94 mg, 0.5 mmol). The resulting ester was hydrolyzed and the acid was purified to give 2'-chloro-4-[4-(3,4-dichloro-phenyl)-thiazol-2-yl]-6'-fluoro-5'-methyl-biphenyl-2-carboxylic acid (3 mg, 2%). $^1$H NMR (400 MHz, DMSO-$d_6$) δ 13.18 (br s, 1H), 8.60 (d, J=2.0 Hz, 1H), 8.48-8.56 (m, 1H), 8.26-8.37 (m, 2H), 8.10 (dd, J=8.5, 2.0 Hz, 1H), 7.78 (d, J=8.5 Hz, 1H), 7.49 (d, J=7.8 Hz, 1H), 7.27-7.39 (m, 2H), 2.54 (s, 8H).

Example 141

4-[4-(3,4-Dichloro-phenyl)-thiazol-2-yl]-2'-methyl-biphenyl-2-carboxylic acid

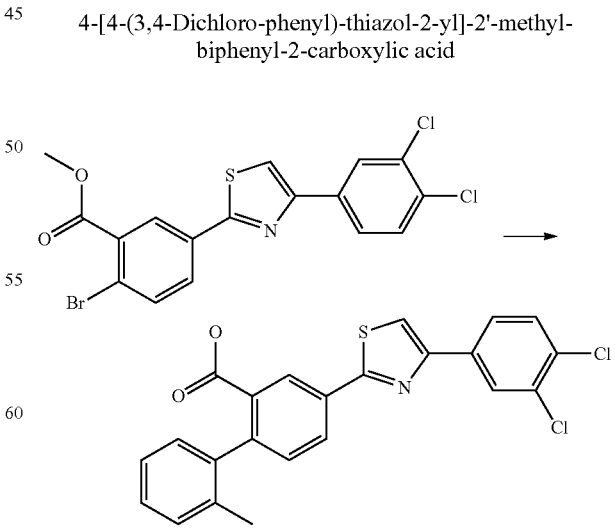

Using the conditions of General Procedure B for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 89 mg, 0.2 mmol) was reacted with 2-methylphenylboronic acid (available from Combi-Blocks Inc.; 54 mg, 0.4 mmol). The resulting ester was hydrolyzed and the acid was purified to give 4-[4-(3,4-dichloro-phenyl)-thiazol-2-yl]-2'-methyl-biphenyl-2-carboxylic acid (63 mg, 72%). $^1$H NMR (400 MHz, DMSO-d$_6$) δ 12.92 (br s, 1H), 8.46 (d, J=4.8 Hz, 2H), 8.34 (s, 1H), 8.22 (d, J=8.0 Hz, 1H), 8.09 (d, J=8.5 Hz, 1H), 7.77 (d, J=8.3 Hz, 1H), 7.39 (d, J=8.0 Hz, 1H), 7.17-7.32 (m, 3H), 7.09 (d, J=7.0 Hz, 1H), 2.08 (s, 3H).

Example 142

5-[4-(3,4-Dichloro-phenyl)-thiazol-2-yl]-2-(4-methyl-thiophen-3-yl)-benzoic acid

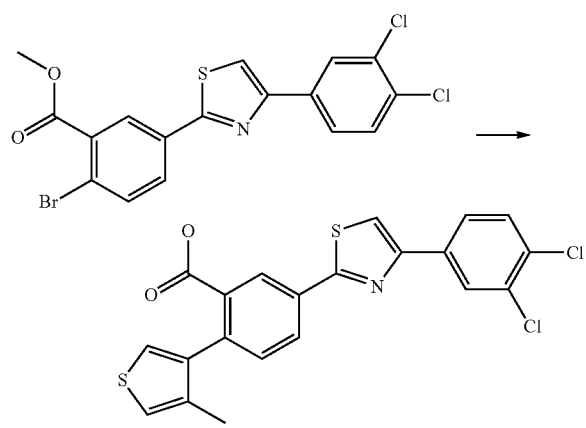

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 4-methyl-3-thiopheneboronic acid (available from Combi-Blocks Inc.; 57 mg, 0.4 mmol). The resulting ester was hydrolyzed and the acid was purified to give 5-[4-(3,4-dichloro-phenyl)-thiazol-2-yl]-2-(4-methyl-thiophen-3-yl)-benzoic acid (49 mg, 55%). $^1$H NMR (400 MHz, DMSO-d$_6$) δ 13.04 (br s, 1H), 8.47 (s, 1H), 8.41 (d, J=1.8 Hz, 1H), 8.33 (d, J=2.0 Hz, 1H), 8.20 (dd, J=8.0, 2.0 Hz, 1H), 8.09 (dd, J=8.3, 2.0 Hz, 1H), 7.77 (d, J=8.5 Hz, 1H), 7.45 (d, J=8.0 Hz, 1H), 7.35 (d, J=3.3 Hz, 1H), 7.13-7.26 (m, 1H), 2.54 (s, 3H).

Example 143

2'-Chloro-4-[4-(3,4-dichloro-phenyl)-thiazol-2-yl]-4'-methyl-biphenyl-2-carboxylic acid

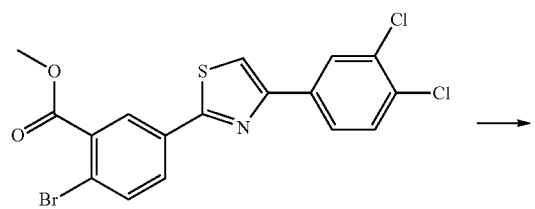

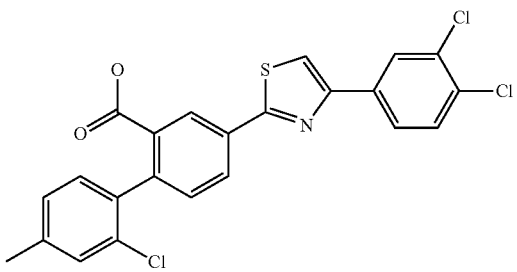

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-4-methylphenylboronic acid (available from Combi-Blocks Inc.; 85 mg, 0.5 mmol). The resulting ester was hydrolyzed and the acid was purified to give 2'-chloro-4-[4-(3,4-dichloro-phenyl)-thiazol-2-yl]-4'-methoxy-biphenyl-2-carboxylic acid (6 mg, 5%). $^1$H NMR (300 MHz, DMSO-d$_6$) δ 12.99 (br s, 1H), 8.49 (d, J=7.7 Hz, 2H), 8.33 (s, 1H), 8.26 (d, J=8.3 Hz, 1H), 8.09 (d, J=8.5 Hz, 1H), 7.77 (d, J=8.3 Hz, 1H), 7.42 (d, J=8.1 Hz, 1H), 7.35 (s, 1H), 7.23 (s, 2H), 2.37 (s, 3H).

Example 144

2'-Chloro-4-[4-(3,4-dichloro-phenyl)-thiazol-2-yl]-5'-methyl-biphenyl-2-carboxylic acid

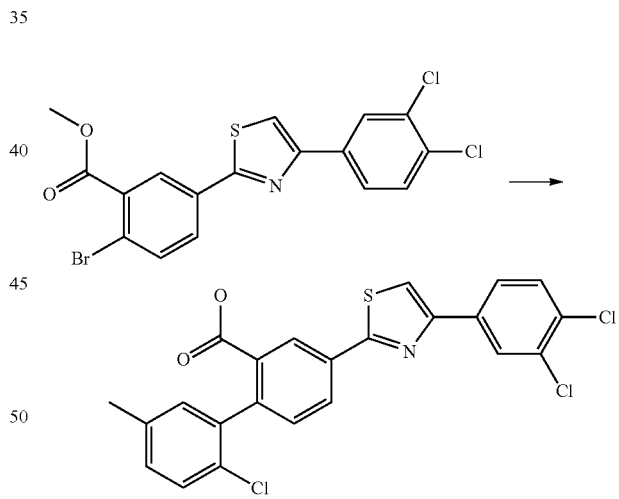

Using the conditions of General Procedure C for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2-chloro-5-methylphenylboronic acid (available from Combi-Blocks Inc.; 85 mg, 0.5 mmol). The resulting ester was hydrolyzed and the acid was purified to give 2'-chloro-4-[4-(3,4-dichloro-phenyl)-thiazol-2-yl]-5'-methyl-biphenyl-2-carboxylic acid (59 mg, 50%). $^1$H NMR (400 MHz, DMSO-d$_6$) δ 13.00 (br s, 3H), 8.51 (d, J=2.0 Hz, 1H), 8.48 (s, 1H), 8.34 (d, J=2.0 Hz, 1H), 8.27 (dd, J=8.0, 2.0 Hz, 1H), 8.09 (dd, J=8.5, 2.0 Hz, 1H), 7.77 (d, J=8.1 Hz, 1H), 7.44 (d, J=8.0 Hz, 1H), 7.38 (d, J=8.0 Hz, 1H), 7.19-7.24 (m, 1H), 7.18 (s, 1H), 2.34 (s, 3H).

Example 145

2-(2-Chloro-thiophen-3-yl)-5-[4-(3,4-dichloro-phenyl)-thiazol-2-yl]-benzoic acid

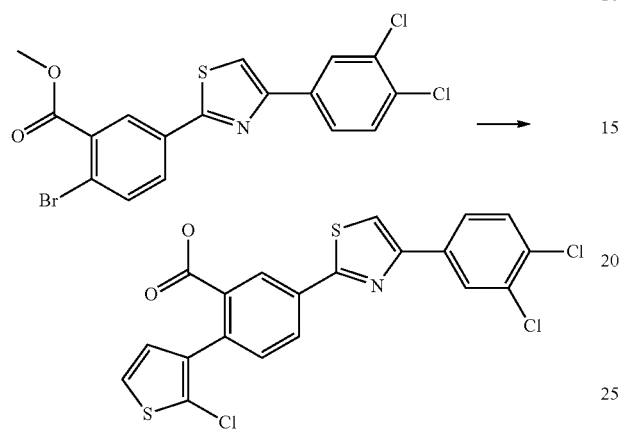

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with and 2-chlorothiophene-3-boronic acid (available from Combi-Blocks Inc.; 65 mg, 0.4 mmol). The resulting ester was hydrolyzed and the acid was purified to give 2-(2-chloro-thiophen-3-yl)-5-[4-(3,4-dichloro-phenyl)-thiazol-2-yl]-benzoic acid (42 mg, 45%). $^1$H NMR (400 MHz, DMSO-d$_6$) δ 13.18 (br s, 1H), 8.44-8.56 (m, 2H), 8.33 (d, J=2.0 Hz, 1H), 8.26 (dd, J=8.0, 2.0 Hz, 1H), 8.09 (dd, J=8.3, 2.0 Hz, 1H), 7.77 (d, J=8.5 Hz, 1H), 7.45-7.61 (m, 2H), 7.08 (d, J=5.5 Hz, 1H)

Example 146

2-(3-Chloro-thiophen-2-yl)-5-[4-(3,4-dichloro-phenyl)-thiazol-2-yl]-benzoic acid

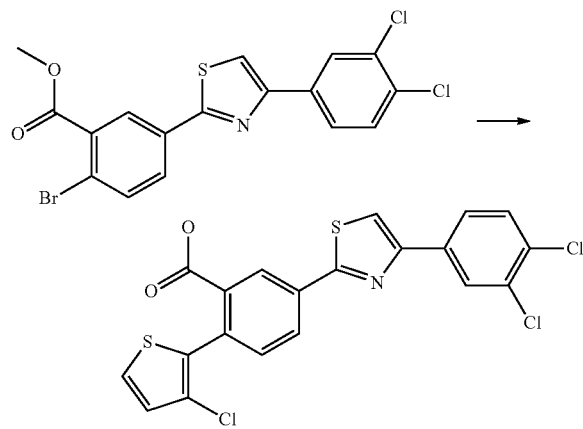

Using the conditions of General Procedure C for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 111 mg, 0.25 mmol) was reacted with 3-chlorothiophene-2-boronic acid (available from Combi-Blocks Inc.; 81 mg, 0.5 mmol). The resulting ester was hydrolyzed and the acid was purified to give 2-(3-Chloro-thiophen-2-yl)-5-[4-(3,4-dichloro-phenyl)-thiazol-2-yl]-benzoic acid (14 mg, 12%). $^1$H NMR (400 MHz, DMSO-d$_6$) δ 13.23 (br s, 1H), 8.50 (s, 1H), 8.47 (d, J=2.0 Hz, 1H), 8.33 (d, J=2.0 Hz, 1H), 8.27 (dd, J=8.0, 2.0 Hz, 1H), 8.09 (dd, J=8.5, 2.0 Hz, 1H), 7.74-7.81 (m, 2H), 7.60 (d, J=8.0 Hz, 1H), 7.15 (d, J=5.3 Hz, 1H), 7.15 (d, J=5.3 Hz, 3H).

Example 147

4'-Chloro-4-[4-(3,4-dichloro-phenyl)-thiazol-2-yl]-biphenyl-2-carboxylic acid

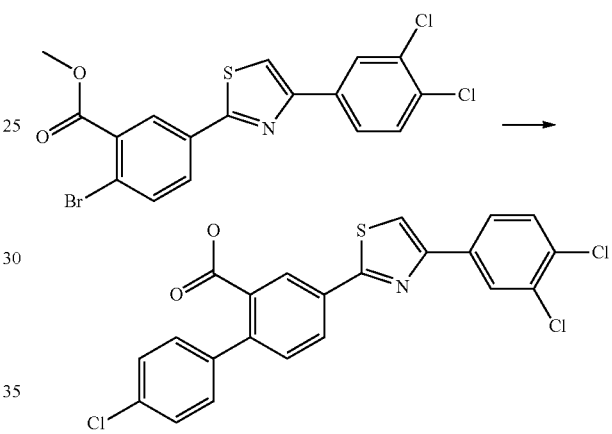

Using the conditions of General Procedure B for Suzuki Coupling and Hydrolysis in Parallel Mode, 2-bromo-5-[4-(3, 4-dichloro-phenyl)-thiazol-2-yl]-benzoic acid methyl ester (which may be prepared as described for Intermediate 6; 63 mg, 0.2 mmol) was reacted with 4-chlorophenylboronic acid (available from Combi-Blocks Inc.; 56 mg, 0.4 mmol). The resulting ester was hydrolyzed and the acid was purified to give 4'-chloro-4-[4-(3,4-dichloro-phenyl)-thiazol-2-yl]-biphenyl-2-carboxylic acid (27 mg, 29%). $^1$H NMR (400 MHz, DMSO-d$_6$) δ 8.47 (s, 1H), 8.37 (s, 1H), 8.33 (s, 1H), 8.22 (d, J=8.0 Hz, 1H), 8.09 (d, J=8.5 Hz, 1H), 7.76 (d, J=8.5 Hz, 1H), 7.56 (d, J=8.0 Hz, 1H), 7.51 (d, J=6.8 Hz, 2H), 7.42 (d, J=6.8 Hz, 2H).

Example 148

2',5'-Dichloro-4-[4-(3,4-dichloro-phenyl)-thiazol-2-yl]-biphenyl-2-carboxylic acid

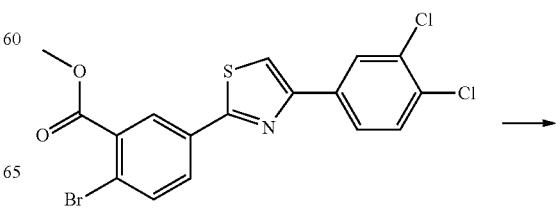

-continued

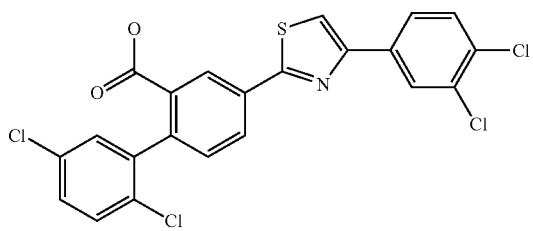

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2,5-dichlorophenylboronic acid (available from Combi-Blocks Inc.; 76 mg, 0.4 mmol). The resulting ester was hydrolyzed and the acid was purified to give 2',5'-dichloro-4-[4-(3,4-dichloro-phenyl)-thiazol-2-yl]-biphenyl-2-carboxylic acid (32 mg, 32%). $^1$H NMR (400 MHz, DMSO-$d_6$) δ 13.18 (br s, 1H), 8.56 (s, 1H), 8.50 (s, 1H), 8.34 (s, 1H), 8.29 (d, J=8.0 Hz, 1H), 8.10 (d, J=8.5 Hz, 1H), 7.77 (d, J=7.3 Hz, 1H), 7.54-7.57 (m, 1H), 7.49 (s, 1H), 7.47 (s, 2H).

Example 149

2',3',5'-Trichloro-4-[4-(3,4-dichloro-phenyl)-thiazol-2-yl]-biphenyl-2-carboxylic acid

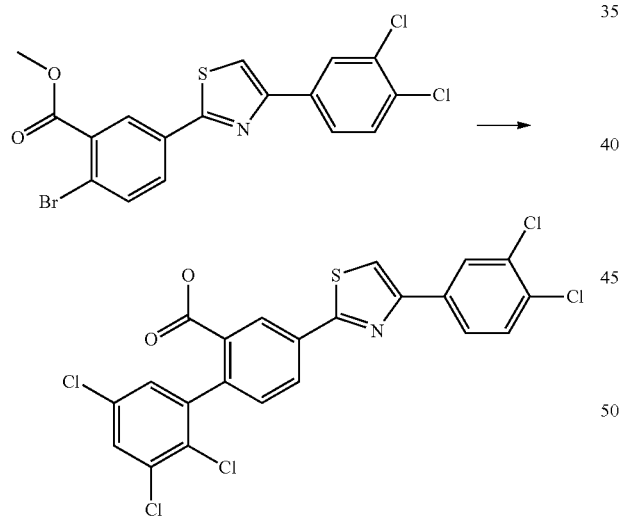

Using the conditions of General Procedure A for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 111 mg, 0.25 mmol) was reacted with 2,3,5-trichlorophenylboronic acid (available from Alfa Aesar; 113 mg, 0.5 mmol). The resulting ester was hydrolyzed and the acid was purified to give 2',3',5'-trichloro-4-[4-(3,4-dichloro-phenyl)-thiazol-2-yl]-biphenyl-2-carboxylic acid (2.5 mg, 2%). $^1$H NMR (300 MHz, DMSO-$d_6$) δ 13.27 (br s, 1H), 8.58 (d, J=1.9 Hz, 1H), 8.50 (s, 1H), 8.34 (d, J=2.1 Hz, 1H), 8.30 (d, J=7.9 Hz, 1H), 8.10 (dd, J=8.4, 2.0 Hz, 1H), 8.00 (d, J=2.4 Hz, 1H), 7.88 (d, J=2.4 Hz, 1H), 7.77 (d, J=8.5 Hz, 1H), 7.64 (d, J=2.4 Hz, 1H), 7.47-7.53 (m, 1H).

Example 150

2',4'-Dichloro-4-[4-(3,4-dichloro-phenyl)-thiazol-2-yl]-biphenyl-2-carboxylic acid

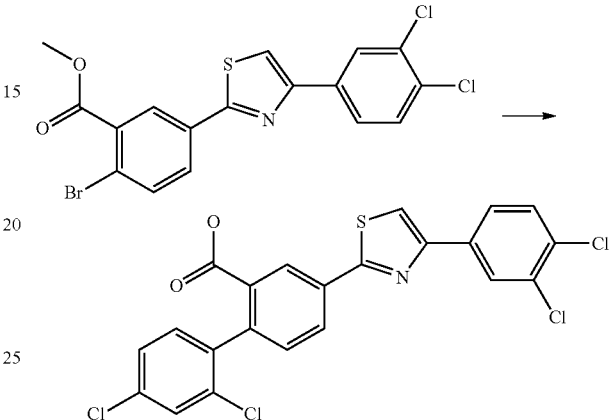

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2,4-dichlorophenylboronic acid (available from Combi-Blocks Inc.; 76 mg, 0.4 mmol). The resulting ester was hydrolyzed and the acid was purified to give 2',4'-dichloro-4-[4-(3,4-dichloro-phenyl)-thiazol-2-yl]-biphenyl-2-carboxylic acid (65 mg, 65%). $^1$H NMR (400 MHz, DMSO-$d_6$) δ 13.15 (br s, 1H), 8.55 (s, 1H), 8.49 (s, 1H), 8.34 (s, 1H), 8.29 (d, J=7.8 Hz, 1H), 8.09 (d, J=8.5 Hz, 1H), 7.78 (d, J=8.3 Hz, 1H), 7.70 (s, 1H), 7.51 (d, J=8.0 Hz, 1H), 7.46 (d, J=8.0 Hz, 1H), 7.36-7.43 (m, 1H).

Example 151

4-[4-(3,4-Dichloro-phenyl)-thiazol-2-yl]-biphenyl-2-carboxylic acid

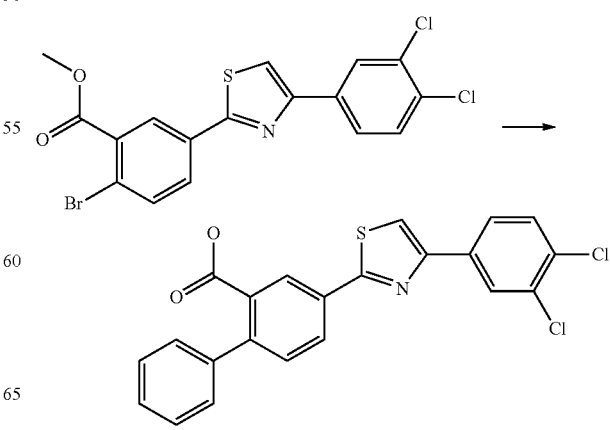

Methyl 2-bromo-5-(4-(3,4-dichlorophenyl)thiazol-2-yl)benzoate (177 mg, 0.4 mmol) was taken up in CH$_2$Cl$_2$ and washed with aqueous Na$_2$CO$_3$. The organic layer was dried (MgSO$_4$), filtered, and evaporated. Dioxane (2 mL) was added, along with tetrakis(triphenylphosphine)palladium(0) (37 mg, 0.032 mmol), 3 M aqueous K$_2$CO$_3$ (267 μL, 0.8 mmol) and phenylboronic acid (available from ASDI Incorporated; 97.5 mg, 0.8 mmol). The vial was evacuated and filled with nitrogen, and then the mixture was heated at 100° C. for 20 h. The mixture was purified on an ISCO Combiflash system, using 0-15% ethyl acetate/hexanes as eluent. Fractions homogeneous for the product were evaporated, and the resulting material was dissolved in THF (2 mL). 1 M aqueous NaOH (2 mL) was added and the mixture was heated at 60° C. overnight. 1 M aqueous HCl was added to bring the pH to approximately 2, and the mixture was extracted 4 times with EtOAc. The combined organic layers were washed with brine, dried (Na$_2$SO$_4$), filtered, evaporated, and purified by preparative HPLC, using the conditions outlined in General Procedure A for Suzuki Coupling and Hydrolysis in Parallel Mode, to give 4-[4-(3,4-dichloro-phenyl)-thiazol-2-yl]-biphenyl-2-carboxylic acid (33 mg, 20%) as a yellow solid. $^1$H NMR (400 MHz, DMSO-d$_6$) δ ppm 8.45 (s, 1H), 8.32 (d, J=1.6 Hz, 2H), 8.20 (dd, J=8.2, 2.0 Hz, 1H), 8.07 (dd, J=8.2, 2.0 Hz, 1H), 7.74 (d, J=8.6 Hz, 1H), 7.55 (d, J=8.2 Hz, 1H), 7.35-7.48 (m, 5H).

Example 152

2',3'-Dichloro-4-[4-(3,4-dichloro-phenyl)-thiazol-2-yl]-biphenyl-2-carboxylic acid

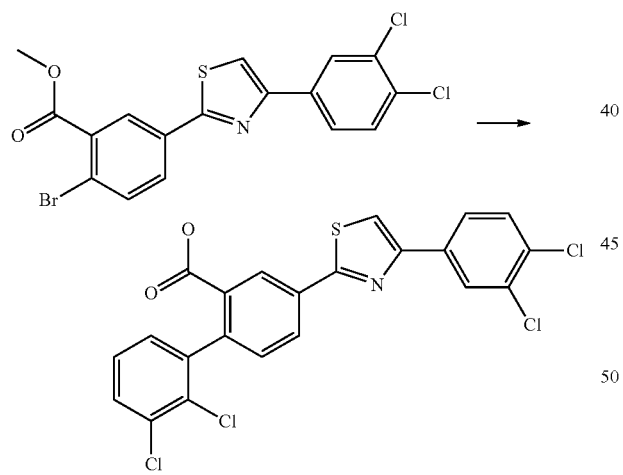

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2,3-dichlorophenylboronic acid (available from Combi-Blocks Inc.; 76 mg, 0.4 mmol). The resulting ester was hydrolyzed and the acid was purified to give 2',3'-dichloro-4-[4-(3,4-dichloro-phenyl)-thiazol-2-yl]-biphenyl-2-carboxylic acid (19 mg, 19%). $^1$H NMR (400 MHz, DMSO-d$_6$) δ 13.13 (br s, 1H), 8.56 (d, J=1.8 Hz, 1H), 8.49 (s, 1H), 8.34 (d, J=2.0 Hz, 1H), 8.29 (dd, J=7.9, 1.9 Hz, 1H), 8.09 (dd, J=8.3, 2.0 Hz, 1H), 7.77 (d, J=8.5 Hz, 1H), 7.66 (dd, J=8.0, 1.5 Hz, 1H), 7.47 (d, J=8.0 Hz, 1H), 7.43 (t, J=7.8 Hz, 1H), 7.33 (dd, J=7.7, 1.4 Hz, 1H).

Example 153

2'-Chloro-4-[4-(3,4-dichloro-phenyl)-thiazol-2-yl]-biphenyl-2-carboxylic acid

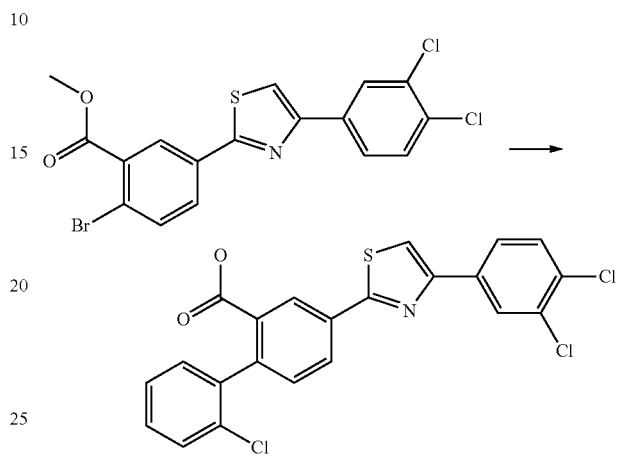

Using the conditions of General Procedure B for Suzuki Coupling and Hydrolysis in Parallel Mode, 2-bromo-5-[4-(3,4-dichloro-phenyl)-thiazol-2-yl]-benzoic acid methyl ester (which may be prepared as described for Intermediate 6; 89 mg, 0.2 mmol) was reacted with 2-chlorophenylboronic acid (available from Combi-Blocks Inc.; 63 mg, 0.4 mmol). The resulting ester was hydrolyzed and the acid was purified to give 2'-chloro-4-[4-(3,4-dichloro-phenyl)-thiazol-2-yl]-biphenyl-2-carboxylic acid (23 mg, 25%). $^1$H NMR (400 MHz, DMSO-d$_6$) δ 13.04 (br s, 1H), 8.53 (s, 1H), 8.49 (s, 1H), 8.34 (s, 1H), 8.28 (d, J=8.0 Hz, 1H), 8.09 (d, J=8.5 Hz, 1H), 7.78 (d, J=8.5 Hz, 1H), 7.33-7.56 (m, 5H).

Example 154

Testing of Compounds of the Invention In Vitro: Human eIF4E/4G Binding Assay

Human eIF4E (aa 28-217) with a C-terminal His tag (HH-eIF4E) was expressed in *E. coli* in inclusion bodies. The protein was solubilized with 8 M urea and purified under denaturing conditions using nickel-charged HisTrap HP columns (GE Healthcare). The protein was refolded by diluting to approximately 0.25 mg/mL with 6 M urea, 20 mM Hepes pH 7.0, 500 mM NaCl, 1 mM DTT, 1 mM EDTA, and 0.5 M arginine.HCl, and then dialyzing overnight into the same buffer without the urea. The protein was further dialyzed into 20 mM Hepes pH 6.5, 50 mM NaCl, 1 mM EDTA, and 1 mM DTT, filtered, and then concentrated using Hitrap SP sepharose FF columns (GE Healthcare). The protein was dialyzed into 20 mM Hepes pH 7.0, 500 mM NaCl, 5 mM DTT, and 10% glycerol and stored at −80° C. until use. Test compounds (1.6 mM stock in DMSO) were diluted 3 fold in series in DMSO. Compound solutions were diluted 4 fold in Assay Buffer (50 mM sodium phosphate, pH 6.5, 50 mM KCl, 1 mM DTT and 0.5 mg/mL gammaglobulin). Six microliters per well of compound solutions and 12 microliters per well of 187.5 nM HH-eIF4E in Assay Buffer were added to 384-well polypropylene microplates (Matrix Technologies Corp.). Twelve microliters per well of 187.5 nM biotin-labeled 4G2 peptide (Ac-Lys-Gln-Tyr-Asp-Arg-Glu-Phe-Leu-Leu-Asp-Phe-Gln-Phe-Met-Pro-Lys(Aha-Bio)-NH2 1:2 TFA) in Assay Buffer was added. The samples were incubated at room temperature for 20 minutes. Six microliters per well of 4.8 nM Eu-streptavidin (Columbia Biosciences) and 48 nM Allophycocyanin-anti His antibody (Columbia Biosciences) in Assay Buffer (without DTT) were then added and the samples were incubated at room temperature for 30 min. Assay signals were monitored by reading emission fluorescence at 665 nm on an EnVision Reader (PerkinElmer Life and Analytical Sciences). IC50 values were calculated using Condoseo software (Genedata AG).

The results of in vitro testing of the activity of compounds of the present invention as eIF4E antagonists are shown in the following Table:

| Example | Name | $IC_{50}$ (uM) |
|---|---|---|
| 1 | 4-[4-(4-Fluoro-phenyl)-thiazol-2-yl]-2'-nitro-biphenyl-2-carboxylic acid | 19 |
| 2 | 2'-Nitro-4-[4-(4-trifluoromethoxy-phenyl)-thiazol-2-yl]-biphenyl-2-carboxylic acid | 2.6 |
| 3 | 4-[4-(4-Difluoromethoxy-phenyl)-thiazol-2-yl]-2'-nitro-biphenyl-2-carboxylic acid | 9.9 |
| 4 | 4-[4-(3,4-Dichloro-phenyl)-thiazol-2-yl]-2'-nitro-5'-trifluoromethyl-biphenyl-2-carboxylic acid | 2 |
| 5 | 2'-Nitro-4-[4-(2-trifluoromethyl-phenyl)-thiazol-2-yl]-biphenyl-2-carboxylic acid | 23 |
| 6 | 2'-Nitro-4-[4-(3-trifluoromethyl-phenyl)-thiazol-2-yl]-biphenyl-2-carboxylic acid | 8.3 |
| 7 | 2'-Nitro-4-[4-(4-trifluoromethyl-phenyl)-thiazol-2-yl]-biphenyl-2-carboxylic acid | 2.4 |
| 8 | 4-[4-(3,5-Bis-trifluoromethyl-phenyl)-thiazol-2-yl]-2'-nitro-biphenyl-2-carboxylic acid | 2.5 |
| 9 | 4-[4-(4-Chloro-3-methyl-phenyl)-thiazol-2-yl]-2'-nitro-biphenyl-2-carboxylic acid | 5.9 |
| 10 | 4-[4-(2,4-Dichloro-phenyl)-thiazol-2-yl]-2'-nitro-biphenyl-2-carboxylic acid | 3.5 |
| 11 | 4-[4-(2-Chloro-phenyl)-thiazol-2-yl]-2'-nitro-biphenyl-2-carboxylic acid | 12 |
| 12 | 4-[4-(2,5-Dichloro-phenyl)-thiazol-2-yl]-2'-nitro-biphenyl-2-carboxylic acid | 2.9 |
| 13 | 4-[4-(4-Chloro-phenyl)-thiazol-2-yl]-2'-nitro-biphenyl-2-carboxylic acid | 5.2 |
| 14 | 5'-Chloro-4-[4-(3,4-dichloro-phenyl)-thiazol-2-yl]-2'-nitro-biphenyl-2-carboxylic acid | 1.3 |
| 15 | 4-[4-(3,4-Dichloro-phenyl)-thiazol-2-yl]-2'-nitro-biphenyl-2-carboxylic acid | 2.8 |
| 16 | 4-[4-(3,4-Dichloro-phenyl)-thiazol-2-yl]-2'-nitro-biphenyl-2-carboxylic acid | 0.5 |
| 17 | 4-[4-(3-Chloro-phenyl)-thiazol-2-yl]-2'-nitro-biphenyl-2-carboxylic acid | 3.1 |
| 18 | 4-[4-(3-Chloro-4-fluoro-phenyl)-thiazol-2-yl]-2'-nitro-biphenyl-2-carboxylic acid | 5 |
| 19 | 4-[4-(2,4-Difluoro-phenyl)-thiazol-2-yl]-2'-nitro-biphenyl-2-carboxylic acid | 13 |
| 20 | 4-[4-(2,6-Difluoro-phenyl)-thiazol-2-yl]-2'-nitro-biphenyl-2-carboxylic acid | >80 |
| 21 | 4-[4-(2-Fluoro-phenyl)-thiazol-2-yl]-2'-nitro-biphenyl-2-carboxylic acid | 14 |
| 22 | 4-[4-(3,5-Difluoro-phenyl)-thiazol-2-yl]-2'-nitro-biphenyl-2-carboxylic acid | 11 |
| 23 | 4-[4-(3,4-Difluoro-phenyl)-thiazol-2-yl]-2'-nitro-biphenyl-2-carboxylic acid | 20 |
| 24 | 4-[4-(3-Fluoro-phenyl)-thiazol-2-yl]-2'-nitro-biphenyl-2-carboxylic acid | 2.6 |
| 25 | 4-[4-(5-Bromo-thiophen-2-yl)-thiazol-2-yl]-2'-nitro-biphenyl-2-carboxylic acid | 4.4 |
| 26 | 4-[4-(3-Bromo-phenyl)-thiazol-2-yl]-2'-nitro-biphenyl-2-carboxylic acid | 3 |
| 27 | 4-[4-(4-Bromo-phenyl)-thiazol-2-yl]-2'-nitro-biphenyl-2-carboxylic acid | 4 |
| 28 | 4-[4-(3,4-Dichloro-phenyl)-thiazol-2-yl]-4'-methoxy-2'-nitro-biphenyl-2-carboxylic acid | 3.2 |
| 29 | 4-[4-(2-Fluoro-4-methoxy-phenyl)-thiazol-2-yl]-2'-nitro-biphenyl-2-carboxylic acid | 19 |
| 30 | 4-[4-(2-Methoxy-phenyl)-thiazol-2-yl]-2'-nitro-biphenyl-2-carboxylic acid | 14 |
| 31 | 4-[4-(3-Methoxy-phenyl)-thiazol-2-yl]-2'-nitro-biphenyl-2-carboxylic acid | 18 |
| 32 | 4-[4-(4-Methoxy-phenyl)-thiazol-2-yl]-2'-nitro-biphenyl-2-carboxylic acid | 8.3 |
| 33 | 4-[4-(4-Methanesulfonyl-phenyl)-thiazol-2-yl]-2'-nitro-biphenyl-2-carboxylic acid | >80 |
| 34 | 4-[4-(2,3-Dihydro-benzo[1,4]dioxin-6-yl)-thiazol-2-yl]-2'-nitro-biphenyl-2-carboxylic acid | 33 |
| 35 | 4-[4-(3-Cyano-phenyl)-thiazol-2-yl]-2'-nitro-biphenyl-2-carboxylic acid | 28 |
| 36 | 4-[4-(4-Cyano-phenyl)-thiazol-2-yl]-2'-nitro-biphenyl-2-carboxylic acid | 30 |
| 37 | 2'-Nitro-4-(4-pyridin-2-yl-thiazol-2-yl)-biphenyl-2-carboxylic acid | >80 |
| 38 | 2'-Nitro-4-(4-pyridin-3-yl-thiazol-2-yl)-biphenyl-2-carboxylic acid | >80 |
| 39 | 2'-Nitro-4-(4-pyridin-4-yl-thiazol-2-yl)-biphenyl-2-carboxylic acid | >80 |
| 40 | 4-[4-(2,4-Dimethyl-phenyl)-thiazol-2-yl]-2'-nitro-biphenyl-2-carboxylic acid | 4.2 |

-continued

| Example | Name | IC$_{50}$ (uM) |
|---|---|---|
| 41 | 2'-Nitro-4-(4-p-tolyl-thiazol-2-yl)-biphenyl-2-carboxylic acid | 13 |
| 42 | 2'-Nitro-4-(4-thiophen-3-yl-thiazol-2-yl)-biphenyl-2-carboxylic acid | 18 |
| 43 | 2'-Nitro-4-(4-phenyl-thiazol-2-yl)-biphenyl-2-carboxylic acid | 26 |
| 44 | 2'-Nitro-4-(4-thiophen-2-yl-thiazol-2-yl)-biphenyl-2-carboxylic acid | 12 |
| 45 | 4-[4-(3,4-Dichloro-phenyl)-thiazol-2-yl]-4'-nitro-biphenyl-2-carboxylic acid | 4.1 |
| 46 | 4-[4-(3,4-Dichloro-phenyl)-thiazol-2-yl]-3'-nitro-biphenyl-2-carboxylic acid | 3.8 |
| 47 | 4-[4-(3,4-Dichloro-phenyl)-thiazol-2-yl]-4'-(3-diethylamino-propylcarbamoyl)-biphenyl-2-carboxylic acid | >80 |
| 48 | 4-[4-(3,4-Dichloro-phenyl)-thiazol-2-yl]-4'-(3-dimethylamino-propylcarbamoyl)-biphenyl-2-carboxylic acid | >80 |
| 49 | 4-[4-(3,4-Dichloro-phenyl)-thiazol-2-yl]-4'-(2-dimethylamino-ethylcarbamoyl)-biphenyl-2-carboxylic acid | >80 |
| 50 | 4-[4-(3,4-Dichloro-phenyl)-thiazol-2-yl]-4'-[(2-methyl-2H-pyrazol-3-ylmethyl)-carbamoyl]-biphenyl-2-carboxylic acid | 7.8 |
| 51 | 4-[4-(3,4-Dichloro-phenyl)-thiazol-2-yl]-4'-(1-methyl-piperidin-4-ylcarbamoyl)-biphenyl-2-carboxylic acid | >80 |
| 52 | 4'-(1-Acetyl-piperidin-4-ylcarbamoyl)-4-[4-(3,4-dichloro-phenyl)-thiazol-2-yl]-biphenyl-2-carboxylic acid | 10 |
| 53 | 4-[4-(3,4-Dichloro-phenyl)-thiazol-2-yl]-4'-(4-methyl-piperazine-1-carbonyl)-biphenyl-2-carboxylic acid | >80 |
| 54 | 4'-(4-Acetyl-piperazine-1-carbonyl)-4-[4-(3,4-dichloro-phenyl)-thiazol-2-yl]-biphenyl-2-carboxylic acid | 21 |
| 55 | 4-[4-(3,4-Dichloro-phenyl)-thiazol-2-yl]-4'-(4-hydroxy-piperidine-1-carbonyl)-biphenyl-2-carboxylic acid | 15 |
| 56 | 4-[4-(3,4-Dichloro-phenyl)-thiazol-2-yl]-4'-(morpholine-4-carbonyl)-biphenyl-2-carboxylic acid | 15 |
| 57 | 4-[4-(3,4-Dichloro-phenyl)-thiazol-2-yl]-4'-(pyrrolidine-1-carbonyl)-biphenyl-2-carboxylic acid | 4.3 |
| 58 | 4-[4-(3,4-Dichloro-phenyl)-thiazol-2-yl]-4'-(3-morpholin-4-yl-propylcarbamoyl)-biphenyl-2-carboxylic acid | >80 |
| 59 | 4-[4-(3,4-Dichloro-phenyl)-thiazol-2-yl]-4'-(2-morpholin-4-yl-ethylcarbamoyl)-biphenyl-2-carboxylic acid | >80 |
| 60 | 4-[4-(3,4-Dichloro-phenyl)-thiazol-2-yl]-4'-[(tetrahydro-pyran-4-ylmethyl)-carbamoyl]-biphenyl-2-carboxylic acid | 8.9 |
| 61 | 4-[4-(3,4-Dichloro-phenyl)-thiazol-2-yl]-4'[(tetrahydro-furan-2-ylmethyl)-carbamoyl]-biphenyl-2-carboxylic acid | 5.5 |
| 62 | 4-[4-(3,4-Dichloro-phenyl)-thiazol-2-yl]-4'-(tetrahydro-furan-3-ylcarbamoyl)-biphenyl-2-carboxylic acid | 7.7 |
| 63 | 4-[4-(3,4-Dichloro-phenyl)-thiazol-2-yl]-4'-(tetrahydro-pyran-4-ylcarbamoyl)-biphenyl-2-carboxylic acid | 5.7 |
| 64 | 4-[4-(3,4-Dichloro-phenyl)-thiazol-2-yl]-4'-(4-methoxy-benzylcarbamoyl)-biphenyl-2-carboxylic acid | 2 |
| 65 | 4-[4-(3,4-Dichloro-phenyl)-thiazol-2-yl]-4'-(3-methoxy-benzylcarbamoyl)-biphenyl-2-carboxylic acid | 1.3 |
| 66 | 4-[4-(3,4-Dichloro-phenyl)-thiazol-2-yl]-4'-(2-pyridin-3-yl-ethylcarbamoyl)-biphenyl-2-carboxylic acid | 9.6 |
| 67 | 4-[4-(3,4-Dichloro-phenyl)-thiazol-2-yl]-4'-phenethylcarbamoyl-biphenyl-2-carboxylic acid | 2.9 |
| 68 | 4-[4-(3,4-Dichloro-phenyl)-thiazol-2-yl]-4'-[(pyridin-3-ylmethyl)-carbamoyl]-biphenyl-2-carboxylic acid | 11 |
| 69 | 4-[4-(3,4-Dichloro-phenyl)-thiazol-2-yl]-4'-[(pyridin-4-ylmethyl)-carbamoyl]-biphenyl-2-carboxylic acid | 7.1 |
| 70 | 4-[4-(3,4-Dichloro-phenyl)-thiazol-2-yl]-4'-(3-methyl-benzylcarbamoyl)-biphenyl-2-carboxylic acid | 1.7 |
| 71 | 4-[4-(3,4-Dichloro-phenyl)-thiazol-2-yl]-4'-(3-trifluoromethyl-benzylcarbamoyl)-biphenyl-2-carboxylic acid | 3.2 |
| 72 | 4-[4-(3,4-Dichloro-phenyl)-thiazol-2-yl]-4'-(4-fluoro-benzylcarbamoyl)-biphenyl-2-carboxylic acid | 1.5 |
| 73 | 4-[4-(3,4-Dichloro-phenyl)-thiazol-2-yl]-4'-(3-fluoro-benzylcarbamoyl)-biphenyl-2-carboxylic acid | 2.1 |
| 74 | 4-[4-(3,4-Dichloro-phenyl)-thiazol-2-yl]-4'-(2-fluoro-benzylcarbamoyl)-biphenyl-2-carboxylic acid | 2.5 |
| 75 | 4-[4-(3,4-Dichloro-phenyl)-thiazol-2-yl]-4'-[(thiophen-2-ylmethyl)-carbamoyl]-biphenyl-2-carboxylic acid | 3.1 |
| 76 | 4'-Benzylcarbamoyl-4-[4-(3,4-dichloro-phenyl)-thiazol-2-yl]-biphenyl-2-carboxylic acid | 2.3 |
| 77 | 2-(2-Carbamoyl-pyridin-3-yl)-5-[4-(3,4-dichloro-phenyl)-thiazol-2-yl]-benzoic acid | 1.3 |
| 78 | 4'-Carbamoyl-4-[4-(3,4-dichloro-phenyl)-thiazol-2-yl]-2'-methyl-biphenyl-2-carboxylic acid | 1.9 |
| 79 | 4-[4-(3,4-Dichloro-phenyl)-thiazol-2-yl]-2'-methyl-biphenyl-2,4'-dicarboxylic acid | 5.4 |
| 80 | 4-[4-(3,4-Dichloro-phenyl)-thiazol-2-yl]-4'-(1-phenyl-ethylcarbamoyl)-biphenyl-2-carboxylic acid | 0.97 |

-continued

| Example | Name | IC$_{50}$ (uM) |
|---|---|---|
| 81 | 2'-Carbamoyl-4-[4-(3,4-dichloro-phenyl)-thiazol-2-yl]-biphenyl-2-carboxylic acid | 15 |
| 82 | 5-[4-(3,4-Dichloro-phenyl)-thiazol-2-yl]-2-(2-ethoxy-pyrimidin-5-yl)-benzoic acid | 3.6 |
| 83 | 5-[4-(3,4-Dichloro-phenyl)-thiazol-2-yl]-2-(2-methoxy-pyrimidin-5-yl)-benzoic acid | 14 |
| 84 | 5-[4-(3,4-Dichloro-phenyl)-thiazol-2-yl]-2-(2-hydroxy-pyrimidin-5-yl)-benzoic acid | 1.2 |
| 85 | 5-[4-(3,4-Dichloro-phenyl)-thiazol-2-yl]-2-(6-methoxy-pyridin-2-yl)-benzoic acid | 9.7 |
| 86 | 5-[4-(3,4-Dichloro-phenyl)-thiazol-2-yl]-2-(2-methoxy-pyridin-3-yl)-benzoic acid | 15 |
| 87 | 4-[4-(3,4-Dichloro-phenyl)-thiazol-2-yl]-4'-methoxy-2'-trifluoromethyl-biphenyl-2-carboxylic acid | 1.3 |
| 88 | 2'-Chloro-4-[4-(3,4-dichloro-phenyl)-thiazol-2-yl]-5'-trifluoromethoxy-biphenyl-2-carboxylic acid | 0.6 |
| 89 | 2'-Chloro-4-[4-(3,4-dichloro-phenyl)-thiazol-2-yl]-4'-ethoxy-biphenyl-2-carboxylic acid | 2 |
| 90 | 6'-Chloro-4-[4-(3,4-dichloro-phenyl)-thiazol-2-yl]-2'-methoxy-biphenyl-2-carboxylic acid | 1.8 |
| 91 | 4-[4-(3,4-Dichloro-phenyl)-thiazol-2-yl]-3'-methoxy-biphenyl-2-carboxylic acid | 5 |
| 92 | 4-[4-(3,4-Dichloro-phenyl)-thiazol-2-yl]-2'-methoxy-biphenyl-2-carboxylic acid | 4.8 |
| 93 | 2'-Chloro-4-[4-(3,4-dichloro-phenyl)-thiazol-2-yl]-5'-methoxy-biphenyl-2-carboxylic acid | 3 |
| 94 | 2'-Chloro-4-[4-(3,4-dichloro-phenyl)-thiazol-2-yl]-4'-methoxy-biphenyl-2-carboxylic acid | 1.5 |
| 95 | 2'-Chloro-4-[4-(3,4-dichloro-phenyl)-thiazol-2-yl]-5'-hydroxy-biphenyl-2-carboxylic acid | 3.4 |
| 96 | 5-[4-(3,4-Dichloro-phenyl)-thiazol-2-yl]-2-(4-isopropyl-pyrimidin-5-yl)-benzoic acid | 11 |
| 97 | 5-[4-(3,4-Dichloro-phenyl)-thiazol-2-yl]-2-pyrimidin-5-yl-benzoic acid | 16 |
| 98 | 5-[4-(3,4-Dichloro-phenyl)-thiazol-2-yl]-2-(2-methyl-pyridin-3-yl)-benzoic acid | 4 |
| 99 | 5-[4-(3,4-Dichloro-phenyl)-thiazol-2-yl]-2-(3-methyl-pyridin-4-yl)-benzoic acid | 12 |
| 100 | 5-[4-(3,4-Dichloro-phenyl)-thiazol-2-yl]-2-(5-fluoro-pyridin-2-yl)-benzoic acid | 3 |
| 101 | 5-[4-(3,4-Dichloro-phenyl)-thiazol-2-yl]-2-pyridin-3-yl-benzoic acid | 20 |
| 102 | 2-(5-Chloro-pyridin-3-yl)-5-[4-(3,4-dichloro-phenyl)-thiazol-2-yl]-benzoic acid | 5.4 |
| 103 | 5-[4-(3,4-Dichloro-phenyl)-thiazol-2-yl]-2-pyridin-4-yl-benzoic acid | 8.5 |
| 104 | 2-(6-Cyano-pyridin-2-yl)-5-[4-(3,4-dichloro-phenyl)-thiazol-2-yl]-benzoic acid | 12 |
| 105 | 4'-Cyano-4-[4-(3,4-dichloro-phenyl)-thiazol-2-yl]-2'-methyl-biphenyl-2-carboxylic acid | 1.3 |
| 106 | 4'-Cyano-4-[4-(3,4-dichloro-phenyl)-thiazol-2-yl]-biphenyl-2-carboxylic acid | 7.6 |
| 107 | 3'-Cyano-4-[4-(3,4-dichloro-phenyl)-thiazol-2-yl]-biphenyl-2-carboxylic acid | 3.2 |
| 108 | 2'-Chloro-5'-cyano-4-[4-(3,4-dichloro-phenyl)-thiazol-2-yl]-biphenyl-2-carboxylic acid | 3.5 |
| 109 | 5'-Carbamoyl-2'-chloro-4-[4-(3,4-dichloro-phenyl)-thiazol-2-yl]-biphenyl-2-carboxylic acid | 3.7 |
| 110 | 5'-Chloro-2'-cyano-4-[4-(3,4-dichloro-phenyl)-thiazol-2-yl]-biphenyl-2-carboxylic acid | 1.7 |
| 111 | 2'-Cyano-4-[4-(3,4-dichloro-phenyl)-thiazol-2-yl]-biphenyl-2-carboxylic acid | 30 |
| 112 | 2'-Cyano-4-[4-(3,4-dichloro-phenyl)-thiazol-2-yl]-biphenyl-2-carboxylic acid | 30 |
| 114 | 3'-Chloro-4'-cyano-4-[4-(3,4-dichloro-phenyl)-thiazol-2-yl]-biphenyl-2-carboxylic acid | 1.7 |
| 115 | 4'-Chloro-3'-cyano-4-[4-(3,4-dichloro-phenyl)-thiazol-2-yl]-biphenyl-2-carboxylic acid | 1.9 |
| 116 | 3'-Acetyl-4-[4-(3,4-dichloro-phenyl)-thiazol-2-yl]-biphenyl-2-carboxylic acid | 7.7 |
| 117 | 2'-Acetyl-4-[4-(3,4-dichloro-phenyl)-thiazol-2-yl]-biphenyl-2-carboxylic acid | 7.7 |
| 118 | 5'-Acetyl-2'-chloro-4-[4-(3,4-dichloro-phenyl)-thiazol-2-yl]-biphenyl-2-carboxylic acid | 1.5 |
| 119 | 2-(2-Acetyl-thiophen-3-yl)-5-[4-(3,4-dichloro-phenyl)-thiazol-2-yl]-benzoic acid | 9.6 |

-continued

| Example | Name | IC$_{50}$ (uM) |
|---|---|---|
| 120 | 4'-Acetyl-4-[4-(3,4-dichloro-phenyl)-thiazol-2-yl]-biphenyl-2-carboxylic acid | 3.8 |
| 121 | 4-[4-(3,4-Dichloro-phenyl)-thiazol-2-yl]-2'-fluoro-biphenyl-2,4'-dicarboxylic acid | 6.1 |
| 122 | 4-[4-(3,4-Dichloro-phenyl)-thiazol-2-yl]-2'-formyl-5'-methyl-biphenyl-2-carboxylic acid | 5.1 |
| 123 | 4-[4-(3,4-Dichloro-phenyl)-thiazol-2-yl]-2'-formyl-biphenyl-2-carboxylic acid | 5.5 |
| 124 | 4-[4-(3,4-Dichloro-phenyl)-thiazol-2-yl]-4'-fluoro-2'-trifluoromethyl-biphenyl-2-carboxylic acid | 0.8 |
| 125 | 4-[4-(3,4-Dichloro-phenyl)-thiazol-2-yl]-2',4'-bis-trifluoromethyl-biphenyl-2-carboxylic acid | 3 |
| 126 | 2'-Chloro-4-[4-(3,4-dichloro-phenyl)-thiazol-2-yl]-3'-trifluoromethyl-biphenyl-2-carboxylic acid | 2.8 |
| 127 | 2'-Chloro-4-[4-(3,4-dichloro-phenyl)-thiazol-2-yl]-4'-trifluoromethyl-biphenyl-2-carboxylic acid | 1.6 |
| 128 | 2'-Chloro-4-[4-(3,4-dichloro-phenyl)-thiazol-2-yl]-5'-trifluoromethyl-biphenyl-2-carboxylic acid | 1.1 |
| 129 | 4-[4-(3,4-Dichloro-phenyl)-thiazol-2-yl]-4'-fluoro-biphenyl-2-carboxylic acid | 2.6 |
| 130 | 2'-Chloro-4-[4-(3,4-dichloro-phenyl)-thiazol-2-yl]-5'-fluoro-biphenyl-2-carboxylic acid | 11 |
| 131 | 4-[4-(3,4-Dichloro-phenyl)-thiazol-2-yl]-2',5'-difluoro-biphenyl-2-carboxylic acid | 1.8 |
| 132 | 4-[4-(3,4-Dichloro-phenyl)-thiazol-2-yl]-2',4'-difluoro-biphenyl-2-carboxylic acid | 5.6 |
| 133 | 4-[4-(3,4-Dichloro-phenyl)-thiazol-2-yl]-2',3',5'-trifluoro-biphenyl-2-carboxylic acid | 1.6 |
| 134 | 2'-Chloro-4-[4-(3,4-dichloro-phenyl)-thiazol-2-yl]-4'-fluoro-biphenyl-2-carboxylic acid | 1.4 |
| 135 | 4'-Chloro-4-[4-(3,4-dichloro-phenyl)-thiazol-2-yl]-2'-fluoro-biphenyl-2-carboxylic acid | 55 |
| 136 | 6'-Chloro-4-[4-(3,4-dichloro-phenyl)-thiazol-2-yl]-2'-fluoro-biphenyl-2-carboxylic acid | 11 |
| 137 | 4-[4-(3,4-Dichloro-phenyl)-thiazol-2-yl]-2'-fluoro-biphenyl-2-carboxylic acid | 3.6 |
| 138 | 4-[4-(3,4-Dichloro-phenyl)-thiazol-2-yl]-2',3'-difluoro-biphenyl-2-carboxylic acid | 1.9 |
| 139 | 2'-Chloro-4-[4-(3,4-dichloro-phenyl)-thiazol-2-yl]-6'-fluoro-3'-methyl-biphenyl-2-carboxylic acid | 1.6 |
| 140 | 6'-Chloro-4-[4-(3,4-dichloro-phenyl)-thiazol-2-yl]-2'-fluoro-3'-methyl-biphenyl-2-carboxylic acid | 0.7 |
| 141 | 4-[4-(3,4-Dichloro-phenyl)-thiazol-2-yl]-2'-methyl-biphenyl-2-carboxylic acid | 5.9 |
| 142 | 5-[4-(3,4-Dichloro-phenyl)-thiazol-2-yl]-2-(4-methyl-thiophen-3-yl)-benzoic acid | 4.2 |
| 143 | 2'-Chloro-4-[4-(3,4-dichloro-phenyl)-thiazol-2-yl]-4'-methyl-biphenyl-2-carboxylic acid | 11 |
| 144 | 2'-Chloro-4-[4-(3,4-dichloro-phenyl)-thiazol-2-yl]-5'-methyl-biphenyl-2-carboxylic acid | 1.1 |
| 145 | 2-(2-Chloro-thiophen-3-yl)-5-[4-(3,4-dichloro-phenyl)-thiazol-2-yl]-benzoic acid | 2.2 |
| 146 | 2-(3-Chloro-thiophen-2-yl)-5-[4-(3,4-dichloro-phenyl)-thiazol-2-yl]-benzoic acid | 1.7 |
| 147 | 4'-Chloro-4-[4-(3,4-dichloro-phenyl)-thiazol-2-yl]-biphenyl-2-carboxylic acid | 1.7 |
| 148 | 2',5'-Dichloro-4-[4-(3,4-dichloro-phenyl)-thiazol-2-yl]-biphenyl-2-carboxylic acid | 1.7 |
| 149 | 2',3',5'-Trichloro-4-[4-(3,4-dichloro-phenyl)-thiazol-2-yl]-biphenyl-2-carboxylic acid | >80 |
| 150 | 2',4'-Dichloro-4-[4-(3,4-dichloro-phenyl)-thiazol-2-yl]-biphenyl-2-carboxylic acid | 1.4 |
| 151 | 4-[4-(3,4-Dichloro-phenyl)-thiazol-2-yl]-biphenyl-2-carboxylic acid | 5.9 |
| 152 | 2',3'-Dichloro-4-[4-(3,4-dichloro-phenyl)-thiazol-2-yl]-biphenyl-2-carboxylic acid | 2.1 |
| 153 | 2'-Chloro-4-[4-(3,4-dichloro-phenyl)-thiazol-2-yl]-biphenyl-2-carboxylic acid | 2.2 |

What is claimed is:
1. A compound of formula I:

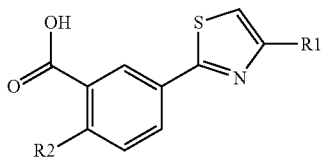

Formula I wherein R1 is selected from the group consisting of

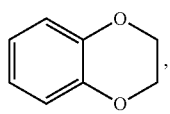, bromothienyl, thienyl, pyridyl and phenyl optionally substituted with one or two members selected from the group consisting of fluoro, chloro, bromo, methyl, methoxy, difluoromethoxy, trifluoromethyl, trifluoromethoxy, —S(O)$_2$-methyl, and cyano;
  R2 is selected from the group consisting of
  thienyl optionally substituted by a member selected from the group consisting of methyl, acetyl, and chloro;
  pyridyl optionally substituted by one or two members selected from the group consisting of amido, methoxy, methyl, fluoro, chloro, and cyano;
  pyrimidinyl optionally substituted with a member selected from the group consisting of ethoxy, methoxy, hydroxy, and isopropyl; and
  phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH,
  —C(O)—X1, wherein X1 is a member selected from the group consisting of

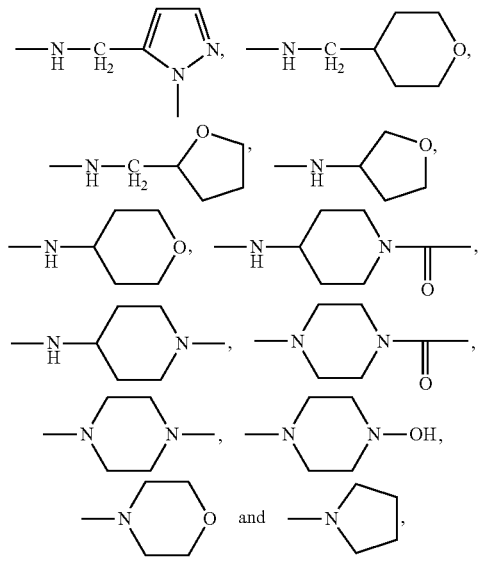

and
  —NH—X2, wherein X2 is a member selected from the group consisting of —CH(CH3)-phenyl and —(CH2)n-X4, wherein n is 1, 2 or 3 and X4 is a member selected from the group consisting of —N(methyl)$_2$, —N(ethyl)$_2$, pyridyl, thienyl, morpholinyl, and phenyl optionally substituted with a member selected from the group consisting of methyl, methoxy, fluoro, and trifluoromethyl;
or a pharmaceutically acceptable salt thereof.
2. The compound of claim 1
wherein R1 is selected from the group consisting of

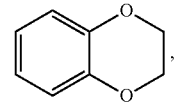, bromothienyl, thienyl, pyridyl, and phenyl optionally substituted with one or two members selected from the group consisting of fluoro, chloro, bromo, methyl, methoxy, difluoromethoxy, trifluoromethyl, trifluoromethoxy, and cyano;
wherein R2 is selected from the group consisting of:
thienyl optionally substituted by a member selected from the group consisting of methyl, acetyl, and chloro;
pyridyl optionally substituted by one or two members selected from the group consisting of amido, methoxy, methyl, fluoro, chloro, and cyano;
pyrimidinyl optionally substituted with a member selected from the group consisting of ethoxy, methoxy, hydroxy, and isopropyl; and
phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH,
—C(O)—X1, wherein X1 is a member selected from the group consisting of

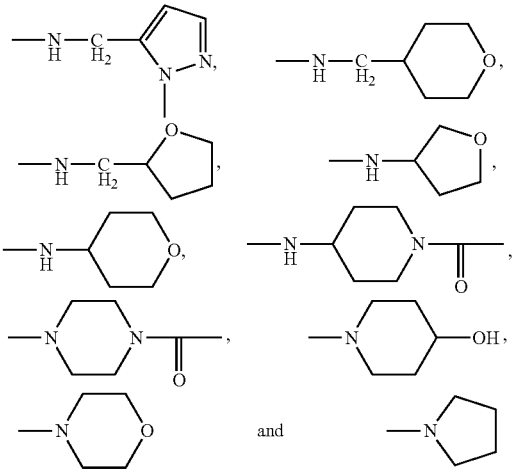

and
—NH—X2, wherein X2 is a member selected from the group consisting of —CH(CH3)-phenyl and —(CH2)n-X4, wherein n is 1 or 2 and X4 is a member selected from the group consisting of pyridyl, thienyl, and phenyl optionally substituted with a member selected from the group consisting of methyl, methoxy, fluoro, and trifluoromethyl;
and a pharmaceutically acceptable salt thereof.

3. The compound of claim 2, wherein R1 is phenyl optionally substituted with one or two members selected from the group consisting of fluoro, chloro, bromo, methyl, methoxy, difluoromethoxy, trifluoromethyl, trifluoromethoxy, and cyano.

4. The compound of claim 3, wherein R2 is phenyl optionally substituted with one to three members selected from the group consisting of methyl, cyano, hydroxy, acetyl, C(O)NH2, methoxy, ethoxy, trifluoromethoxy, C(O)H, chloro, fluoro, trifluoromethyl, nitro, —C(O)OH, —C(O)—X1, wherein X1 is a member selected from the group consisting of

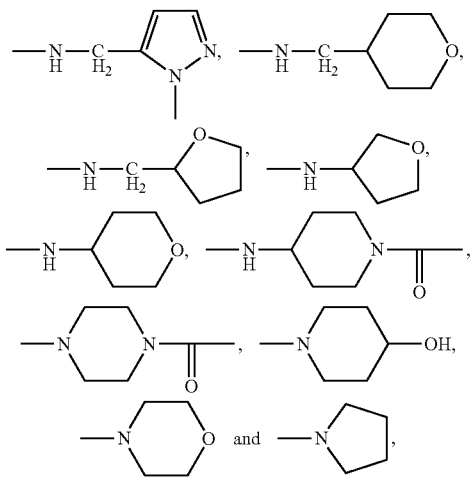

and

—NH—X2, wherein X2 is a member selected from the group consisting of —CH(CH3)-phenyl and —(CH2)n-X4, wherein n is 1 or 2 and X4 is a member selected from the group consisting of pyridyl, thienyl, and phenyl optionally substituted with a member selected from the group consisting of methyl, methoxy, fluoro, and trifluoromethyl.

5. The compound of claim 1, wherein R1 is selected from the group consisting of

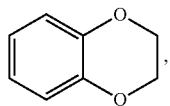

bromothienyl, thienyl, and pyridyl.

6. The compound of claim 1, wherein R2 is selected from the group consisting of:
   thienyl optionally substituted by a member selected from the group consisting of methyl, acetyl, and chloro;
   pyridyl optionally substituted by one or two members selected from the group consisting of amido, methoxy, methyl, fluoro, chloro, and cyano; and
   pyrimidinyl optionally substituted with a member selected from the group consisting of ethoxy, methoxy, hydroxy, and isopropyl.

7. The compound of claim 1, wherein R2 is nitrophenyl.

8. The compound of claim 1, wherein R1 is dichlorophenyl.

9. A compound of claim 1 selected from the group consisting of
   4-[4-(4-Fluoro-phenyl)-thiazol-2-yl]-2'-nitro-biphenyl-2-carboxylic acid,
   2'-Nitro-4-[4-(4-trifluoromethoxy-phenyl)-thiazol-2-yl]-biphenyl-2-carboxylic acid,
   4-[4-(4-Difluoromethoxy-phenyl)-thiazol-2-yl]-2'-nitro-biphenyl-2-carboxylic acid,
   2'-Nitro-4-[4-(2-trifluoromethyl-phenyl)-thiazol-2-yl]-biphenyl-2-carboxylic acid,
   2'-Nitro-4-[4-(3-trifluoromethyl-phenyl)-thiazol-2-yl]-biphenyl-2-carboxylic acid,
   2'-Nitro-4-[4-(4-trifluoromethyl-phenyl)-thiazol-2-yl]-biphenyl-2-carboxylic acid,
   4-[4-(4-Chloro-3-methyl-phenyl)-thiazol-2-yl]-2'-nitro-biphenyl-2-carboxylic acid,
   4-[4-(2-Chloro-phenyl)-thiazol-2-yl]-2'-nitro-biphenyl-2-carboxylic acid,
   4-[4-(4-Chloro-phenyl)-thiazol-2-yl]-2'-nitro-biphenyl-2-carboxylic acid,
   4-[4-(3-Chloro-phenyl)-thiazol-2-yl]-2'-nitro-biphenyl-2-carboxylic acid,
   4-[4-(3-Chloro-4-fluoro-phenyl)-thiazol-2-yl]-2'-nitro-biphenyl-2-carboxylic acid,
   4-[4-(2-Fluoro-phenyl)-thiazol-2-yl]-2'-nitro-biphenyl-2-carboxylic acid and
   4-[4-(3-Fluoro-phenyl)-thiazol-2-yl]-2'-nitro-biphenyl-2-carboxylic acid.

10. A compound of claim 1 selected from the group consisting of
   4-[4-(5-Bromo-thiophen-2-yl)-thiazol-2-yl]-2'-nitro-biphenyl-2-carboxylic acid,
   4-[4-(3-Bromo-phenyl)-thiazol-2-yl]-2'-nitro-biphenyl-2-carboxylic acid,
   4-[4-(4-Bromo-phenyl)-thiazol-2-yl]-2'-nitro-biphenyl-2-carboxylic acid,
   4-[4-(2-Fluoro-4-methoxy-phenyl)-thiazol-2-yl]-2'-nitro-biphenyl-2-carboxylic acid,
   4-[4-(2-Methoxy-phenyl)-thiazol-2-yl]-2'-nitro-biphenyl-2-carboxylic acid,
   4-[4-(3-Methoxy-phenyl)-thiazol-2-yl]-2'-nitro-biphenyl-2-carboxylic acid,
   4-[4-(4-Methoxy-phenyl)-thiazol-2-yl]-2'-nitro-biphenyl-2-carboxylic acid,
   4-[4-(4-Methanesulfonyl-phenyl)-thiazol-2-yl]-2'-nitro-biphenyl-2-carboxylic acid,
   4-[4-(3-Cyano-phenyl)-thiazol-2-yl]-2'-nitro-biphenyl-2-carboxylic acid,
   4-[4-(4-Cyano-phenyl)-thiazol-2-yl]-2'-nitro-biphenyl-2-carboxylic acid,
   2'-Nitro-4-(4-pyridin-2-yl-thiazol-2-yl)-biphenyl-2-carboxylic acid and
   2'-Nitro-4-(4-pyridin-3-yl-thiazol-2-yl)-biphenyl-2-carboxylic acid.

11. A compound of claim 1 selected from the group consisting of
   2'-Nitro-4-(4-pyridin-4-yl-thiazol-2-yl)-biphenyl-2-carboxylic acid,
   2'-Nitro-4-(4-p-tolyl-thiazol-2-yl)-biphenyl-2-carboxylic acid,
   2'-Nitro-4-(4-thiophen-3-yl-thiazol-2-yl)-biphenyl-2-carboxylic acid,
   2'-Nitro-4-(4-phenyl-thiazol-2-yl)-biphenyl-2-carboxylic acid,
   2'-Nitro-4-(4-thiophen-2-yl-thiazol-2-yl)-biphenyl-2-carboxylic acid, 4-[4-(3,4-Dichloro-phenyl)-thiazol-2-yl]-2'-methyl-biphenyl-2,4'-dicarboxylic acid,
4-[4-(3,4-Dichloro-phenyl)-thiazol-2-yl]-2'-fluoro-biphenyl-2,4'-dicarboxylic acid,
4-[4-(2,3-Dihydro-benzo[1,4]dioxin-6-yl)-thiazol-2-yl]-2'-nitro-biphenyl-2-carboxylic acid,
4-[4-(2,4-Dichloro-phenyl)-thiazol-2-yl]-2'-nitro-biphenyl-2-carboxylic acid,
4-[4-(2,4-Difluoro-phenyl)-thiazol-2-yl]-2'-nitro-biphenyl-2-carboxylic acid,
4-[4-(2,4-Dimethyl-phenyl)-thiazol-2-yl]-2'-nitro-biphenyl-2-carboxylic acid and
4-[4-(2,5-Dichloro-phenyl)-thiazol-2-yl]-2'-nitro-biphenyl-2-carboxylic acid.

12. A compound of claim 1 selected from the group consisting of
4-[4-(2,6-Difluoro-phenyl)-thiazol-2-yl]-2'-nitro-biphenyl-2-carboxylic acid,
4-[4-(3,4-Dichloro-phenyl)-thiazol-2-yl]-2'-nitro-5'-trifluoromethyl-biphenyl-2-carboxylic acid,
5'-Chloro-4-[4-(3,4-dichloro-phenyl)-thiazol-2-yl]-2'-nitro-biphenyl-2-carboxylic acid,
4-[4-(3,4-Dichloro-phenyl)-thiazol-2-yl]-2'-nitro-biphenyl-2-carboxylic acid,
4-[4-(3,4-Difluoro-phenyl)-thiazol-2-yl]-2'-nitro-biphenyl-2-carboxylic acid,
4-[4-(3,4-Dichloro-phenyl)-thiazol-2-yl]-4'-methoxy-2'-nitro-biphenyl-2-carboxylic acid,
4-[4-(3,4-Dichloro-phenyl)-thiazol-2-yl]-4'-nitro-biphenyl-2-carboxylic acid,
4-[4-(3,4-Dichloro-phenyl)-thiazol-2-yl]-3'-nitro-biphenyl-2-carboxylic acid,
4-[4-(3,4-Dichloro-phenyl)-thiazol-2-yl]-4'-(3-diethylamino-propylcarbamoyl)-biphenyl-2-carboxylic acid,
4-[4-(3,4-Dichloro-phenyl)-thiazol-2-yl]-4'-(3-dimethylamino-propylcarbamoyl)-biphenyl-2-carboxylic acid,
4-[4-(3,4-Dichloro-phenyl)-thiazol-2-yl]-4'-(2-dimethylamino-ethylcarbamoyl)-biphenyl-2-carboxylic acid and
4-[4-(3,4-Dichloro-phenyl)-thiazol-2-yl]-4'-[(2-methyl-2H-pyrazol-3-ylmethyl)-carbamoyl]-biphenyl-2-carboxylic acid.

13. A compound of claim 1 selected from the group consisting of
4-[4-(3,4-Dichloro-phenyl)-thiazol-2-yl]-4'-(1-methyl-piperidin-4-ylcarbamoyl)-biphenyl-2-carboxylic acid,
4'-(1-Acetyl-piperidin-4-ylcarbamoyl)-4-[4-(3,4-dichloro-phenyl)-thiazol-2-yl]-biphenyl-2-carboxylic acid,
4-[4-(3,4-Dichloro-phenyl)-thiazol-2-yl]-4'-(4-methyl-piperazine-1-carbonyl)-biphenyl-2-carboxylic acid,
4'-(4-Acetyl-piperazine-1-carbonyl)-4-[4-(3,4-dichloro-phenyl)-thiazol-2-yl]-biphenyl-2-carboxylic acid,
4-[4-(3,4-Dichloro-phenyl)-thiazol-2-yl]-4'-(4-hydroxy-piperidine-1-carbonyl)-biphenyl-2-carboxylic acid,
4-[4-(3,4-Dichloro-phenyl)-thiazol-2-yl]-4'-(morpholine-4-carbonyl)-biphenyl-2-carboxylic acid,
4-[4-(3,4-Dichloro-phenyl)-thiazol-2-yl]-4'-(pyrrolidine-1-carbonyl)-biphenyl-2-carboxylic acid,
4-[4-(3,4-Dichloro-phenyl)-thiazol-2-yl]-4'-(3-morpholin-4-yl-propylcarbamoyl)-biphenyl-2-carboxylic acid,
4-[4-(3,4-Dichloro-phenyl)-thiazol-2-yl]-4'-(2-morpholin-4-yl-ethylcarbamoyl)-biphenyl-2-carboxylic acid,
4-[4-(3,4-Dichloro-phenyl)-thiazol-2-yl]-4'-[(tetrahydro-pyran-4-ylmethyl)-carbamoyl]-biphenyl-2-carboxylic acid,
4-[4-(3,4-Dichloro-phenyl)-thiazol-2-yl]-4'-[(tetrahydro-furan-2-ylmethyl)-carbamoyl]-biphenyl-2-carboxylic acid and
4-[4-(3,4-Dichloro-phenyl)-thiazol-2-yl]-4'-(tetrahydro-furan-3-ylcarbamoyl)-biphenyl-2-carboxylic acid, and
4-[4-(3,4-Dichloro-phenyl)-thiazol-2-yl]-4'-(tetrahydro-pyran-4-ylcarbamoyl)-biphenyl-2-carboxylic acid.

14. A compound of claim 1 selected from the group consisting of
4-[4-(3,4-Dichloro-phenyl)-thiazol-2-yl]-4'-(4-methoxy-benzylcarbamoyl)-biphenyl-2-carboxylic acid,
4-[4-(3,4-Dichloro-phenyl)-thiazol-2-yl]-4'-(3-methoxy-benzylcarbamoyl)-biphenyl-2-carboxylic acid,
4-[4-(3,4-Dichloro-phenyl)-thiazol-2-yl]-4'-(2-pyridin-3-yl-ethylcarbamoyl)-biphenyl-2-carboxylic acid,
4-[4-(3,4-Dichloro-phenyl)-thiazol-2-yl]-4'-phenethylcarbamoyl-biphenyl-2-carboxylic acid,
4-[4-(3,4-Dichloro-phenyl)-thiazol-2-yl]-4'-[(pyridin-3-ylmethyl)-carbamoyl]-biphenyl-2-carboxylic acid,
4-[4-(3,4-Dichloro-phenyl)-thiazol-2-yl]-4'-[(pyridin-4-ylmethyl)-carbamoyl]-biphenyl-2-carboxylic acid,
4-[4-(3,4-Dichloro-phenyl)-thiazol-2-yl]-4'-(3-methyl-benzylcarbamoyl)-biphenyl-2-carboxylic acid,
4-[4-(3,4-Dichloro-phenyl)-thiazol-2-yl]-4'-(3-trifluoromethyl-benzylcarbamoyl)-biphenyl-2-carboxylic acid,
4-[4-(3,4-Dichloro-phenyl)-thiazol-2-yl]-4'-(4-fluoro-benzylcarbamoyl)-biphenyl-2-carboxylic acid,
4-[4-(3,4-Dichloro-phenyl)-thiazol-2-yl]-4'-(3-fluoro-benzylcarbamoyl)-biphenyl-2-carboxylic acid,
4-[4-(3,4-Dichloro-phenyl)-thiazol-2-yl]-4'-(2-fluoro-benzylcarbamoyl)-biphenyl-2-carboxylic acid,
4-[4-(3,4-Dichloro-phenyl)-thiazol-2-yl]-4'-[(thiophen-2-ylmethyl)-carbamoyl]-biphenyl-2-carboxylic acid and
4'-Benzylcarbamoyl-4-[4-(3,4-dichloro-phenyl)-thiazol-2-yl]-biphenyl-2-carboxylic acid.

15. A compound of claim 1 selected from the group consisting of
2-(2-Carbamoyl-pyridin-3-yl)-5-[4-(3,4-dichloro-phenyl)-thiazol-2-yl]-benzoic acid,
4'-Carbamoyl-4-[4-(3,4-dichloro-phenyl)-thiazol-2-yl]-2'-methyl-biphenyl-2-carboxylic acid,
4-[4-(3,4-Dichloro-phenyl)-thiazol-2-yl]-4'-(1-phenyl-ethylcarbamoyl)-biphenyl-2-carboxylic acid,
2'-Carbamoyl-4-[4-(3,4-dichloro-phenyl)-thiazol-2-yl]-biphenyl-2-carboxylic acid,
5-[4-(3,4-Dichloro-phenyl)-thiazol-2-yl]-2-(2-ethoxy-pyrimidin-5-yl)-benzoic acid,
5-[4-(3,4-Dichloro-phenyl)-thiazol-2-yl]-2-(2-methoxy-pyrimidin-5-yl)-benzoic acid,
5-[4-(3,4-Dichloro-phenyl)-thiazol-2-yl]-2-(2-hydroxy-pyrimidin-5-yl)-benzoic acid,
5-[4-(3,4-Dichloro-phenyl)-thiazol-2-yl]-2-(6-methoxy-pyridin-2-yl)-benzoic acid,
5-[4-(3,4-Dichloro-phenyl)-thiazol-2-yl]-2-(2-methoxy-pyridin-3-yl)-benzoic acid,
4-[4-(3,4-Dichloro-phenyl)-thiazol-2-yl]-4'-methoxy-2'-trifluoromethyl-biphenyl-2-carboxylic acid,
2'-Chloro-4-[4-(3,4-dichloro-phenyl)-thiazol-2-yl]-5'-trifluoromethoxy-biphenyl-2-carboxylic acid,
2'-Chloro-4-[4-(3,4-dichloro-phenyl)-thiazol-2-yl]-4'-ethoxy-biphenyl-2-carboxylic acid and
6'-Chloro-4-[4-(3,4-dichloro-phenyl)-thiazol-2-yl]-2'-methoxy-biphenyl-2-carboxylic acid.

16. A compound of claim 1 selected from the group consisting of
- 4-[4-(3,4-Dichloro-phenyl)-thiazol-2-yl]-3'-methoxy-biphenyl-2-carboxylic acid,
- 4-[4-(3,4-Dichloro-phenyl)-thiazol-2-yl]-2'-methoxy-biphenyl-2-carboxylic acid,
- 2'-Chloro-4-[4-(3,4-dichloro-phenyl)-thiazol-2-yl]-5'-methoxy-biphenyl-2-carboxylic acid,
- 2'-Chloro-4-[4-(3,4-dichloro-phenyl)-thiazol-2-yl]-4'-methoxy-biphenyl-2-carboxylic acid,
- 2'-Chloro-4-[4-(3,4-dichloro-phenyl)-thiazol-2-yl]-5'-hydroxy-biphenyl-2-carboxylic acid,
- 5-[4-(3,4-Dichloro-phenyl)-thiazol-2-yl]-2-(4-isopropyl-pyrimidin-5-yl)-benzoic acid,
- 5-[4-(3,4-Dichloro-phenyl)-thiazol-2-yl]-2-pyrimidin-5-yl-benzoic acid,
- 5-[4-(3,4-Dichloro-phenyl)-thiazol-2-yl]-2-(2-methyl-pyridin-3-yl)-benzoic acid,
- 5-[4-(3,4-Dichloro-phenyl)-thiazol-2-yl]-2-(3-methyl-pyridin-4-yl)-benzoic acid,
- 5-[4-(3,4-Dichloro-phenyl)-thiazol-2-yl]-2-(5-fluoro-pyridin-2-yl)-benzoic acid,
- 5-[4-(3,4-Dichloro-phenyl)-thiazol-2-yl]-2-pyridin-3-yl-benzoic acid,
- 2-(5-Chloro-pyridin-3-yl)-5-[4-(3,4-dichloro-phenyl)-thiazol-2-yl]-benzoic acid and
- 5-[4-(3,4-Dichloro-phenyl)-thiazol-2-yl]-2-pyridin-4-yl-benzoic acid.

17. A compound of claim 1 selected from the group consisting of
- 2-(6-Cyano-pyridin-2-yl)-5-[4-(3,4-dichloro-phenyl)-thiazol-2-yl]-benzoic acid,
- 4'-Cyano-4-[4-(3,4-dichloro-phenyl)-thiazol-2-yl]-2'-methyl-biphenyl-2-carboxylic acid,
- 4'-Cyano-4-[4-(3,4-dichloro-phenyl)-thiazol-2-yl]-biphenyl-2-carboxylic acid,
- 3'-Cyano-4-[4-(3,4-dichloro-phenyl)-thiazol-2-yl]-biphenyl-2-carboxylic acid,
- 2'-Chloro-5'-cyano-4-[4-(3,4-dichloro-phenyl)-thiazol-2-yl]-biphenyl-2-carboxylic acid,
- 5'-Carbamoyl-2'-chloro-4-[4-(3,4-dichloro-phenyl)-thiazol-2-yl]-biphenyl-2-carboxylic acid,
- 5'-Chloro-2'-cyano-4-[4-(3,4-dichloro-phenyl)-thiazol-2-yl]-biphenyl-2-carboxylic acid,
- 2'-Cyano-4-[4-(3,4-dichloro-phenyl)-thiazol-2-yl]-biphenyl-2-carboxylic acid,
- 3'-Chloro-4'-cyano-4-[4-(3,4-dichloro-phenyl)-thiazol-2-yl]-biphenyl-2-carboxylic acid,
- 4'-Chloro-3'-cyano-4-[4-(3,4-dichloro-phenyl)-thiazol-2-yl]-biphenyl-2-carboxylic acid,
- 3'-Acetyl-4-[4-(3,4-dichloro-phenyl)-thiazol-2-yl]-biphenyl-2-carboxylic acid,
- 2'-Acetyl-4-[4-(3,4-dichloro-phenyl)-thiazol-2-yl]-biphenyl-2-carboxylic acid and
- 5'-Acetyl-2'-chloro-4-[4-(3,4-dichloro-phenyl)-thiazol-2-yl]-biphenyl-2-carboxylic acid.

18. A compound of claim 1 selected from the group consisting of
- 2-(2-Acetyl-thiophen-3-yl)-5-[4-(3,4-dichloro-phenyl)-thiazol-2-yl]-benzoic acid,
- 4'-Acetyl-4-[4-(3,4-dichloro-phenyl)-thiazol-2-yl]-biphenyl-2-carboxylic acid,
- 4-[4-(3,4-Dichloro-phenyl)-thiazol-2-yl]-2'-formyl-5'-methyl-biphenyl-2-carboxylic acid,
- 4-[4-(3,4-Dichloro-phenyl)-thiazol-2-yl]-2'-formyl-biphenyl-2-carboxylic acid,
- 4-[4-(3,4-Dichloro-phenyl)-thiazol-2-yl]-4'-fluoro-2'-trifluoromethyl-biphenyl-2-carboxylic acid,
- 4-[4-(3,4-Dichloro-phenyl)-thiazol-2-yl]-2',4'-bis-trifluoromethyl-biphenyl-2-carboxylic acid,
- 2'-Chloro-4-[4-(3,4-dichloro-phenyl)-thiazol-2-yl]-3'-trifluoromethyl-biphenyl-2-carboxylic acid,
- 2'-Chloro-4-[4-(3,4-dichloro-phenyl)-thiazol-2-yl]-4'-trifluoromethyl-biphenyl-2-carboxylic acid,
- 2'-Chloro-4-[4-(3,4-dichloro-phenyl)-thiazol-2-yl]-5'-trifluoromethyl-biphenyl-2-carboxylic acid,
- 4-[4-(3,4-Dichloro-phenyl)-thiazol-2-yl]-4'-fluoro-biphenyl-2-carboxylic acid,
- 2'-Chloro-4-[4-(3,4-dichloro-phenyl)-thiazol-2-yl]-5'-fluoro-biphenyl-2-carboxylic acid,
- 4-[4-(3,4-Dichloro-phenyl)-thiazol-2-yl]-2',5'-difluoro-biphenyl-2-carboxylic acid and
- 4-[4-(3,4-Dichloro-phenyl)-thiazol-2-yl]-2',4'-difluoro-biphenyl-2-carboxylic acid.

19. A compound of claim 1 selected from the group consisting of
- 4-[4-(3,4-Dichloro-phenyl)-thiazol-2-yl]-2',3',5'-trifluoro-biphenyl-2-carboxylic acid,
- 2'-Chloro-4-[4-(3,4-dichloro-phenyl)-thiazol-2-yl]-4'-fluoro-biphenyl-2-carboxylic acid,
- 4'-Chloro-4-[4-(3,4-dichloro-phenyl)-thiazol-2-yl]-2'-fluoro-biphenyl-2-carboxylic acid,
- 6'-Chloro-4-[4-(3,4-dichloro-phenyl)-thiazol-2-yl]-2'-fluoro-biphenyl-2-carboxylic acid,
- 4-[4-(3,4-Dichloro-phenyl)-thiazol-2-yl]-2'-fluoro-biphenyl-2-carboxylic acid,
- 4-[4-(3,4-Dichloro-phenyl)-thiazol-2-yl]-2',3'-difluoro-biphenyl-2-carboxylic acid,
- 2'-Chloro-4-[4-(3,4-dichloro-phenyl)-thiazol-2-yl]-6'-fluoro-3'-methyl-biphenyl-2-carboxylic acid,
- 6'-Chloro-4-[4-(3,4-dichloro-phenyl)-thiazol-2-yl]-2'-fluoro-3'-methyl-biphenyl-2-carboxylic acid,
- 4-[4-(3,4-Dichloro-phenyl)-thiazol-2-yl]-2'-methyl-biphenyl-2-carboxylic acid,
- 5-[4-(3,4-Dichloro-phenyl)-thiazol-2-yl]-2-(4-methyl-thiophen-3-yl)-benzoic acid and
- 2'-Chloro-4-[4-(3,4-dichloro-phenyl)-thiazol-2-yl]-4'-methyl-biphenyl-2-carboxylic acid.

20. A compound of claim 1 selected from the group consisting of
- 2'-Chloro-4-[4-(3,4-dichloro-phenyl)-thiazol-2-yl]-5'-methyl-biphenyl-2-carboxylic acid,
- 2-(2-Chloro-thiophen-3-yl)-5-[4-(3,4-dichloro-phenyl)-thiazol-2-yl]-benzoic acid,
- 2-(3-Chloro-thiophen-2-yl)-5-[4-(3,4-dichloro-phenyl)-thiazol-2-yl]-benzoic acid,
- 4'-Chloro-4-[4-(3,4-dichloro-phenyl)-thiazol-2-yl]-biphenyl-2-carboxylic acid,
- 2',5'-Dichloro-4-[4-(3,4-dichloro-phenyl)-thiazol-2-yl]-biphenyl-2-carboxylic acid,
- 2',3',5'-Trichloro-4-[4-(3,4-dichloro-phenyl)-thiazol-2-yl]-biphenyl-2-carboxylic acid,
- 2',4'-Dichloro-4-[4-(3,4-dichloro-phenyl)-thiazol-2-yl]-biphenyl-2-carboxylic acid,
- 4-[4-(3,4-Dichloro-phenyl)-thiazol-2-yl]-biphenyl-2-carboxylic acid,
- 2',3'-Dichloro-4-[4-(3,4-dichloro-phenyl)-thiazol-2-yl]-biphenyl-2-carboxylic acid,
- 2'-Chloro-4-[4-(3,4-dichloro-phenyl)-thiazol-2-yl]-biphenyl-2-carboxylic acid,
- 4-[4-(3,5-Bis-trifluoromethyl-phenyl)-thiazol-2-yl]-2'-nitro-biphenyl-2-carboxylic acid, and 4-[4-(3,5-Difluoro-phenyl)-thiazol-2-yl]-2'-nitro-biphenyl-2-carboxylic acid,
or a pharmaceutically acceptable salt thereof.

21. A pharmaceutical composition comprising a compound of claim 1 and a therapeutically inert carrier.

* * * * *